US012122759B2

(12) United States Patent
Heimbach et al.

(10) Patent No.: US 12,122,759 B2
(45) Date of Patent: Oct. 22, 2024

(54) METHOD FOR THE SYNTHESIS OF CYCLIC DEPSIPEPTIDES

(71) Applicants: ELANCO ANIMAL HEALTH GMBH, Monheim am Rhein (DE); THE KITASATO INSTITUTE, Tokyo (JP)

(72) Inventors: Dirk Heimbach, Düsseldorf (DE); Satoshi Omura, Tokyo (JP); Toshiaki Sunazuka, Chiba (JP); Tomoyasu Hirose, Asao-ku (JP); Yoshihiko Noguchi, Tokyo (JP); Johannes Köbberling, Neuss (DE); Zhijie Wu, Zhejiang (CN); Shuibiao Fu, Zhejiang (CN); Wei Wu, Zhejiang (CN); Jinfeng Qiu, Zhejiang (CN); Liu He, Zhejiang (CN); Xudong Wei, Zhejiang (CN)

(73) Assignees: ELANCO ANIMAL HEALTH GMBH, Monheim am Rhein (DE); THE KITASATO INSTITUTE, Tokyo (JP)

( * ) Notice: Subject to any disclaimer, the term of this patent is extended or adjusted under 35 U.S.C. 154(b) by 0 days.

(21) Appl. No.: 16/762,068

(22) PCT Filed: Nov. 6, 2018

(86) PCT No.: PCT/EP2018/080333
§ 371 (c)(1),
(2) Date: May 6, 2020

(87) PCT Pub. No.: WO2019/091975
PCT Pub. Date: May 16, 2019

(65) Prior Publication Data
US 2021/0130315 A1 May 6, 2021

(30) Foreign Application Priority Data

Nov. 7, 2017 (EP) .................................... 17200415
Oct. 25, 2018 (CN) ........................ 201811254536.0

(51) Int. Cl.
C07D 325/00 (2006.01)
A61K 38/15 (2006.01)
(52) U.S. Cl.
CPC ............ *C07D 325/00* (2013.01); *A61K 38/15* (2013.01)
(58) Field of Classification Search
CPC .................................. C07C 273/00; C07D 325/00
See application file for complete search history.

(56) References Cited

U.S. PATENT DOCUMENTS 5,717,063 A   2/1998   Scherkenbeck et al.
5,747,448 A   5/1998   Ohyama et al.
5,777,075 A   7/1998   Scherkenbeck et al.
6,329,338 B1  12/2001  Sakanaka et al.
2007/0060509 A1  3/2007  Kanikanti
2008/0255037 A1  10/2008  Kanikanti
2009/0215678 A1  8/2009  Bach
2015/0166608 A1*  6/2015  Mitomi ................... A61P 33/14
                                                   514/2.3

FOREIGN PATENT DOCUMENTS

| EP | 0634408 A1 | 1/1995 | |
|----|------------|--------|---|
| EP | 2003104 A2 | 12/2008 | |
| EP | 2862872 A1 | 4/2015 | |
| JP | H05320148 A | 12/1993 | |
| JP | 2000044493 A | 2/2000 | |
| JP | 2017031060 A | 2/2017 | |
| WO | WO1993019053 A1 | 3/1993 | |
| WO | WO2005055973 A2 | 6/2005 | |
| WO | WO2006053641 A1 | 5/2006 | |
| WO | WO2006094664 A1 | 9/2006 | |
| WO | WO-2015093558 A1 * | 6/2015 | ............ A01N 43/72 |
| WO | WO-2016187534 A1 * | 11/2016 | ............ A01N 37/46 |
| WO | WO2017116702 A1 | 7/2017 | |
| WO | 2018/093920 | 5/2018 | |
| WO | 2019/040589 A1 | 2/2019 | |

OTHER PUBLICATIONS

Malesevic et al. Journal of Biotechnology 2004, 112, 73-77 (Year: 2004).*
Reichardt, C. Chem. Rev. 1994, 94, 2319-2358 (Year: 1994).*
Scherkenbeck et al. Eur. J. Org. Chem. 2012, 1546-1553 (Year: 2012).*
Dutton et al. Journal of Antibiotics 1994, 47, 1322-1327 (Year: 1994).*
Wissmann, Phosphorus and Sulfur, 1987, 30, 645-648 (Year: 1987).*
Basavaprabhu et al. Synthesis 2013, 45, 1569-1601 (Year: 2013).*
Andersson et al. Biopolymers, 2000, 55, 227-250 (Year: 2000).*
Von Samson-Himmelstjerna et al. Parasitol. Res. 2000, 86, 194-199 (Year: 2000).*
Kachi et al. Jpn. J. Pharmaceol. 1998, 77, 235-245 (Year: 1998).*
European Search Report mailed on May 4, 2018, for European Patent Application No. 17200415.2 filed on Nov. 7, 2017, six pages.
International Search Report and Written Opinion mailed on Feb. 19, 2019, for International Application No. PCT/EP/2018/080333 filed on Nov. 6, 2018, nine pages.
Okada, Y. et al. (2013). "Tag-Assisted Liquid-Phase Peptide Synthesis Using Hydrophobic Benzyl Alcohols as Supports," J. Org. Chem. 78:320-327.
Sivanathan, S. et al. (2014). "Cyclodepsipeptides: A Rich Source of Biologically Active Compounds for Drug Research," Molecules, 19:12368-12420.
Tamiaki, H. et al. (2001). "A Novel Protecting Group for Constructing Combinatorial Peptide Libraries," Bull. Chem. Soc. Jpn., 74:733-738.
Reichardt, C., "Empirical Parameters of Solvent Polarity as Linear Free-Energy Relationships", Angewandte Chemie International Edition English. 1979, vol. 18, pp. 98-110.

* cited by examiner

*Primary Examiner* — Matthew P Coughlin
(74) *Attorney, Agent, or Firm* — McBee Moore & Vanik, IP, LLC

(57) ABSTRACT

The present invention relates to a method for the synthesis of cyclic depsipeptides, in particular emodepside, from the open form.

13 Claims, 23 Drawing Sheets

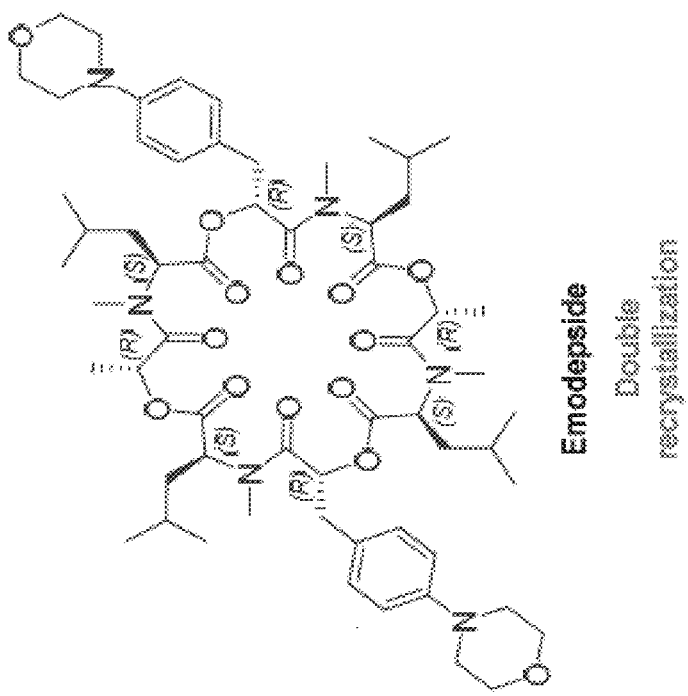

METHOD FOR THE SYNTHESIS OF CYCLIC DEPSIPEPTIDES

CROSS REFERENCE TO RELATED APPLICATIONS

This application is a national stage application under 35 U.S.C. § 371 of International Application No. PCT/EP2018/080333, filed internationally on Nov. 6, 2018, which claims the benefit of Chinese Application No. 201811254536.0, filed Oct. 25, 2018, and of European Application No. 17200415.2, filed Nov. 7, 2017.

FIELD OF INVENTION

The present invention relates to a method for the synthesis of cyclic depsipeptides, in particular emodepside, involving specific carboxylic acid group protecting tags.

BACKGROUND OF INVENTION

Emodepside (cyclo[(R)-lactoyl-N-methyl-L-leucyl-(R)-3-(p-morpholinophenyl)lactoyl-N-methyl-L-leucyl-(R)-lactoyl-N-methyl-L-leucyl-(R)-3-(p-morpholinophenyl)lactoyl-N-methyl-L-leucyl) is an anthelmintic drug that is effective against a number of gastrointestinal nematodes. Its molecular structure which is depicted below can be described as a cyclic octadepsipeptides, a depsipeptide being a peptide in which one or more of its amide groups are replaced by the corresponding ester groups. On a technical scale emodepside may be obtained by derivatization of the naturally occurring substance PF1022A in which two hydrogen atoms are exchanged for morpholine rings.

wherein A is benzyl group which has suitable substituent(s) or phenyl group which may have suitable substituent(s), Aa is benzyl group which may have suitable substituent(s) or phenyl group which may have suitable substituent(s), B and D are each lower alkyl, C is hydrogen or lower alkyl, and a pharmaceutically acceptable salt thereof.

WO 2005/055973 A2 discloses transdermally applicable agents containing cyclic depsipeptides and/or praziquantel, in addition to the production thereof and to the use thereof for fighting against endoparasites. Combinations of emodepside and praziquantel or epsiprantel and also 1,2-isopropylideneglycol as endoparasiticides are disclosed in WO 2006/094664 A1.

WO 2006/053641 A1 relates to the use of endoparasiticidal depsipeptides for producing pharmaceuticals for preventing vertical infection with endoparasites.

The total synthesis of, amongst others, PF1022A and its derivatization are discussed in the review article "Cyclodepsipeptides: A Rich Source of Biologically Active Compounds for Drug Research" by Sivatharushan Sivanathan and Jürgen Scherkenbeck, *Molecules* 2014, 19, 12368-12420; doi:10.3390/molecules190812368. For several cyclodepsipeptides total syntheses both in solution and on solid-phase have been established, allowing the production of combinatorial libraries. In addition, the biosynthesis of specific cyclodepsipeptides has been elucidated and used for the chemoenzymatic preparation of nonnatural analogues. The review article also summarizes the recent literature on cyclic tetra- to decadepsipeptides, composed exclusively of α-amino- and α-hydroxy acids.

In the synthesis of polypeptides a solid phase strategy has the advantage of easy separation of the reaction products,

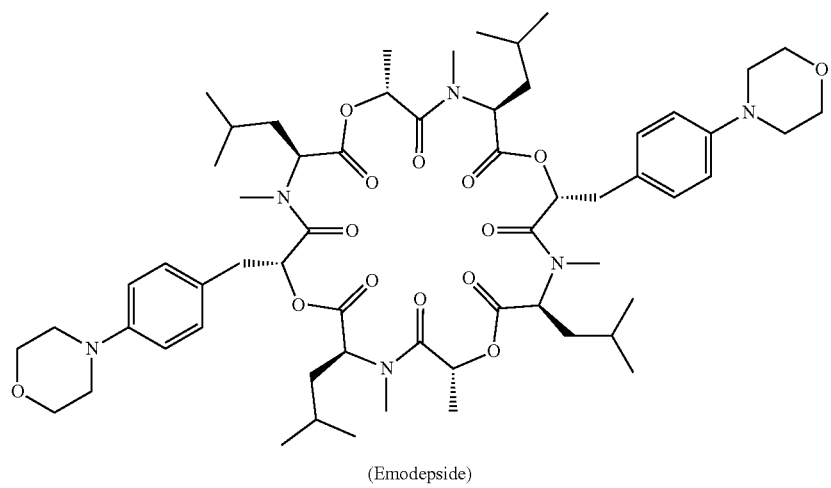 [SMILES: CC(C)C[C@H]1C(=O)O[C@H](Cc2ccc(N3CCOCC3)cc2)C(=O)N(C)[C@@H](CC(C)C)C(=O)O[C@H](C)C(=O)N(C)[C@@H](CC(C)C)C(=O)O[C@H](Cc2ccc(N3CCOCC3)cc2)C(=O)N(C)[C@@H](CC(C)C)C(=O)O[C@H](C)C(=O)N1C]

(Emodepside)

WO 93/19053 A1 (EP 0 634 408 A1) discloses a compound of the general formula:

whereas a liquid phase strategy has the advantage of homogenous reaction conditions. A hybrid approach is a tag-

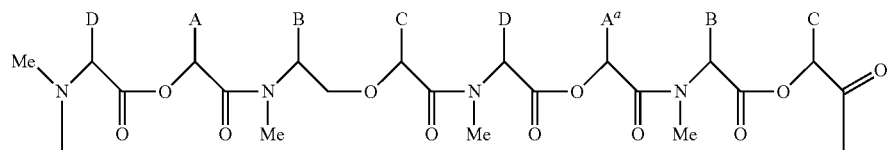

assisted strategy where compounds having a tag group are easily separated from untagged molecules.

In this respect, JP 2000/044493 A1 discloses a protecting group for synthesizing a compound library which consists of compounds capable of bonding with a compound to be protected in 1:1 ratio, having a single molecular structure and also having >=500 molecular weight, and consists of 3,4,5-tris-(n-octadecyloxy)benzyl alcohol, 3,4,5-tris-(n-octadecyloxy)benzyl chloride or methyl 3,4,5-tris-(n-octadecyloxy)benzoate.

EP 2 003 104 A2 relates to a reagent for organic synthesis with which a chemical reaction can be conducted in a liquid phase and unnecessary compound(s) can be easily separated at low cost from the liquid phase after completion of the reaction. The reagent for organic synthesis which is depicted below is reported to reversibly change from a liquid-phase state to a solid-phase state with changes in solution composition and/or solution temperature, and is for use in organic synthesis reactions.

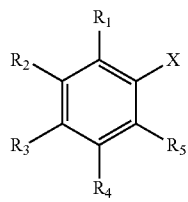

$R_1$ to $R_5$ may be the same or different, and represent hydrogen, halogen, alkyl group with a carbon number of 1 to 30 which may have a substituent group, alkoxyl group with a carbon number of 1 to 30 which may have a substituent group, aryl group with a carbon number of 1 to 30 which may have a substituent group, acyl group with a carbon number of 1 to 30 which may have a substituent group, thioalkyl group with a carbon number of 1 to 30 which may have a substituent group, dialkylamino group with a carbon number of 1 to 30 which may have a substituent group, nitro group, or amino group; and at least two of $R_1$ to R5 are groups with a carbon number of 18 to 30, and X represents a reagent active site having one or more atoms selected from the group consisting of a carbon atom, oxygen atom, sulfur atom, and nitrogen atom.

The publication "Tag-Assisted Liquid-Phase Peptide Synthesis Using Hydrophobic Benzyl Alcohols as Supports" by Yohei Okada, Hideaki Suzuki, Takashi Nakae, Shuji Fujita, Hitoshi Abe, Kazuo Nagano, Toshihide Yamada, Nobuyoshi Ebata, Shokaku Kim, and Kazuhiro Chiba, *The Journal of Organic Chemistry* 2013, 78, 320-327; doi: 10.1021/jo302127d; reports that a soluble tag-assisted liquid-phase peptide synthesis was successfully established based on simple hydrophobic benzyl alcohols, which can be easily prepared from naturally abundant materials. Excellent precipitation yields are reported to be obtained at each step, combining the best properties of solid-phase and liquid-phase techniques. This approach is reported to be able to be applied efficiently to fragment couplings, allowing chemical synthesis of several bioactive peptides.

The publication "A Novel Protecting Group for Constructing Combinatorial Peptide Libraries" by Hitoshi Tamiaki, Tomoyuki Obata, Yasuo Azefu and Kazunori Toma, *Bulletin of the Chemical Society of Japan* 2001, 74, 733-738; doi http://dx.doi.org/10.1246/bcsj.74.733; discloses 3,4,5-tris(octadecyloxy)benzyl alcohol, HO-Bzl $(OC_{18})_3$ which was prepared from gallic acid and stearyl bromide. Using conventional step-wise elongation, N,C-protected peptides, Fmoc-$AA_n$- . . . -$AA_1$-OBzl$(OC_{18})_3$, were synthesized. The substituted benzyl esters were selectively cleaved by a treatment with 4 M hydrogen chloride in ethyl acetate to give Fmoc-$AA_n$- . . . -$AA_1$-OH and HO-Bzl $(OC_{18})_3$. Thus, the substituted benzyl group is reported to be effective for the protection of C-terminal carboxyl groups in liquid-phase peptide synthesis. Because the substituted benzyl group has a moderately high molecular weight, Fmoc-$AA_n$- . . . -$AA_1$-OBzl$(OC_{18})_3$ is reported to be easily purified by size-exclusion chromatography; all protected peptides were reported to be eluted in the void fraction of a Sephadex LH-20 gel-filtration column. The combination of the carboxyl-protecting group Bzl$(OC_{18})_3$ with simple purification by the gel-filtration is reported to give a novel route for constructing combinatorial peptide libraries in the solution phase.

WO 2017/116702 A1 relates to a cyclic depsipeptide compound or a pharmaceutically or veterinarily acceptable salt of the following formula:

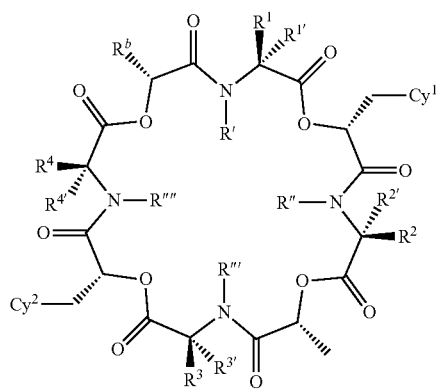

By way of example, a compound with the designation 7-34A as depicted below shows an $EC_{50}$ value between 0.1 µM and 1.0 µM in an in vitro test against microfilaria of *Dirofilaria immitis*:

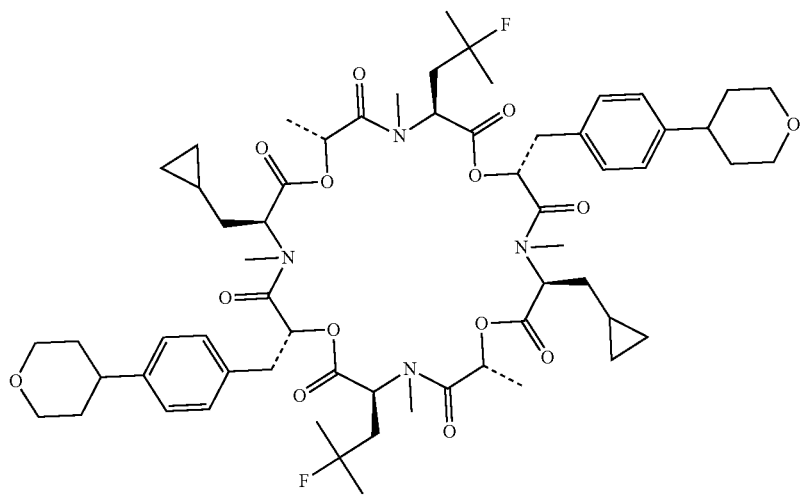

(7-34A of WO 2017/116702 A1)

The present invention has the object of providing an improved synthetic route to emodepside and related cyclic depsipeptides. Another object of the invention is to provide novel depsipeptides which may be synthesized using this route.

DETAILED DESCRIPTION

Figure 1:
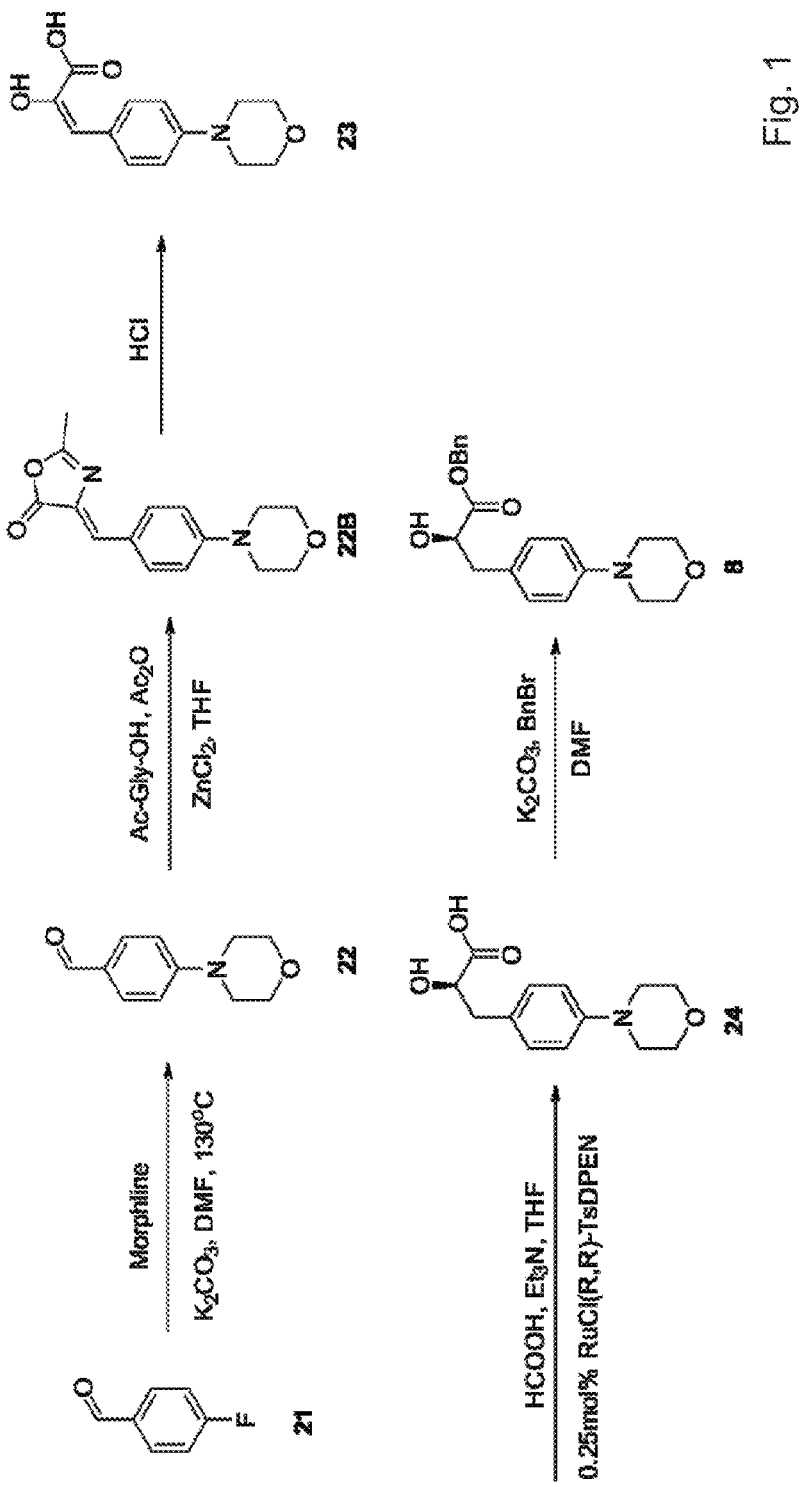
FIG. 1 Emodepside Synthesis—Preparation of Benzyl (R)-2-hydroxy-3-(4-morpholinophenyl) propanoate (EMD-8)
Figure 2A:
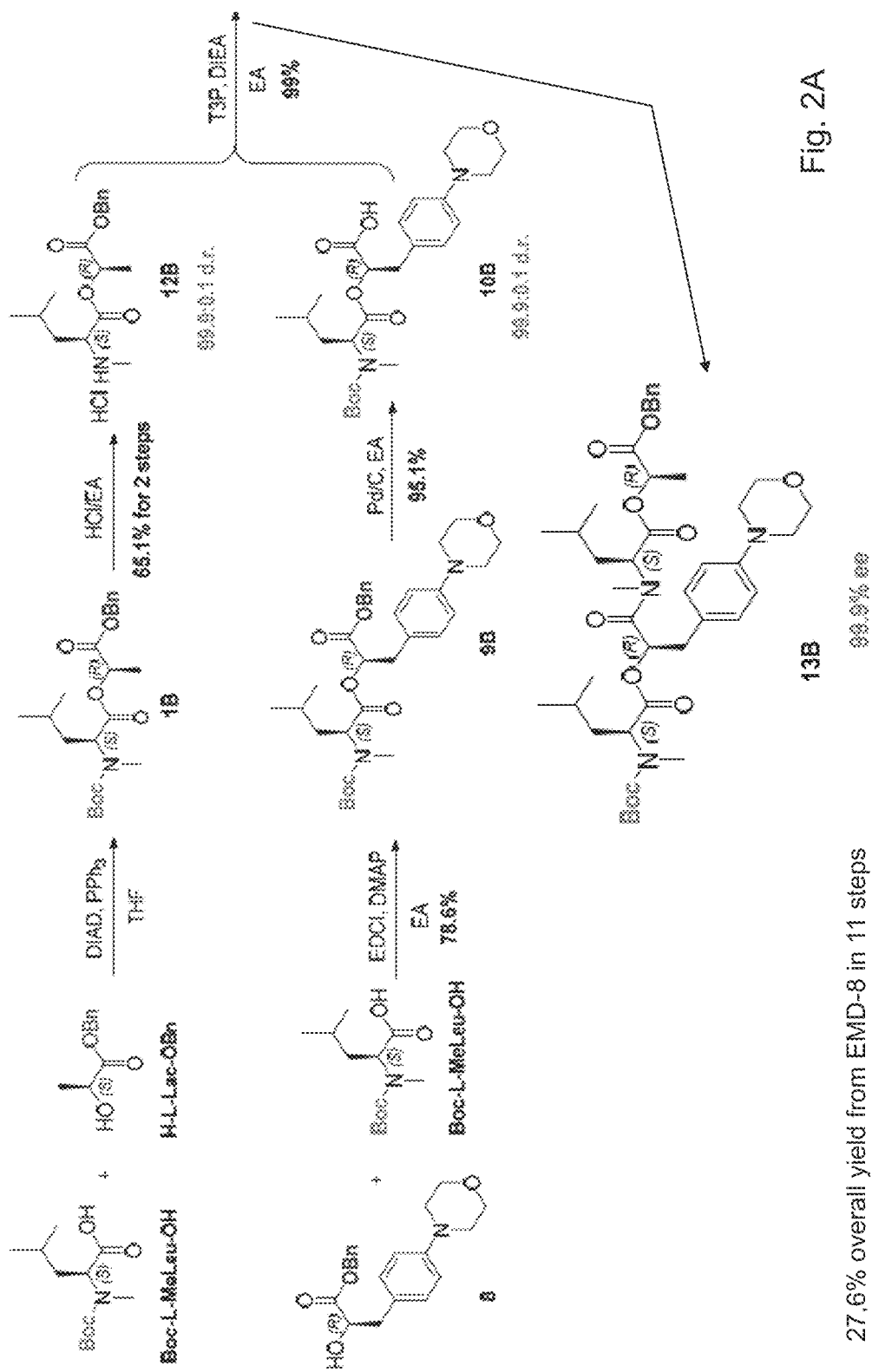
FIG. 2A Emodepside Synthesis—Preparation of EMD-13B
Figure 2B:
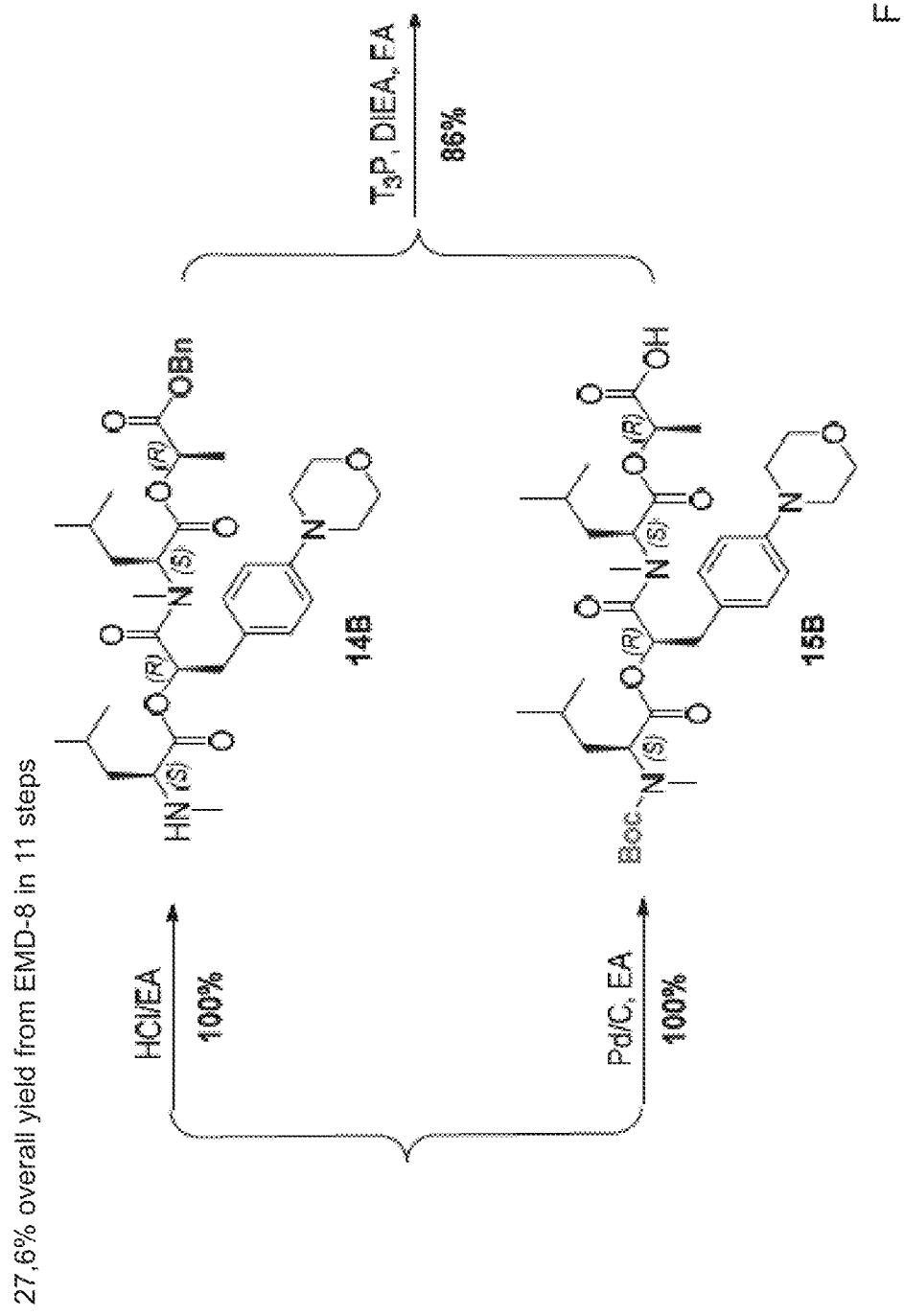
FIG. 2B Emodepside Synthesis—Preparation of EMD-14B and EMD-15B and reaction conditions for the preparation of EMD-16B FIG. 2C Emodepside Synthesis—Structure of EMD-16B and reaction conditions for the preparation of EMD-20B FIG. 2D Emodepside Synthesis—Structure of EMD-20B and reaction conditions for the preparation of EMD-18B FIG. 2E Emodepside Synthesis—Structure of EMD-18B and reaction conditions for the preparation of Emodepside FIG. 2F Emodepside Synthesis—Structure of Emodepside FIG. 3A PF1022A Synthesis (Method 1)-Preparation of 2
Figure 2C:
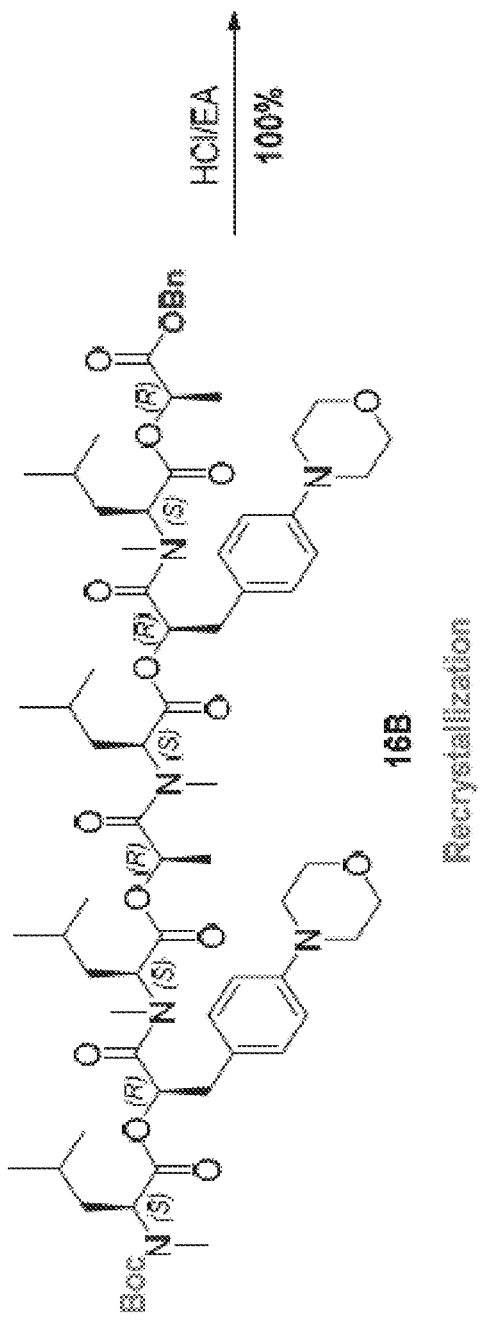
Figure 2D:
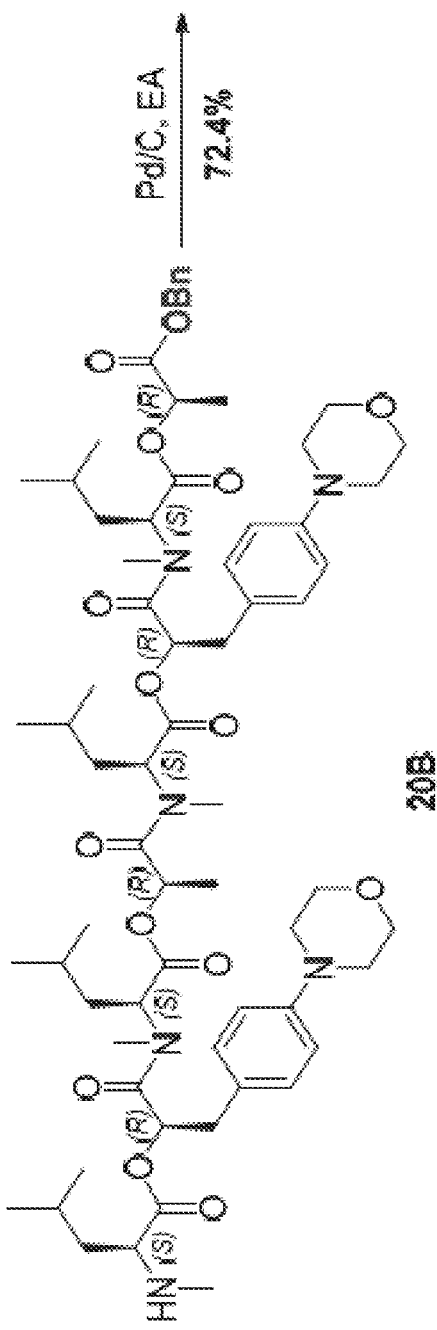
Figure 2E:
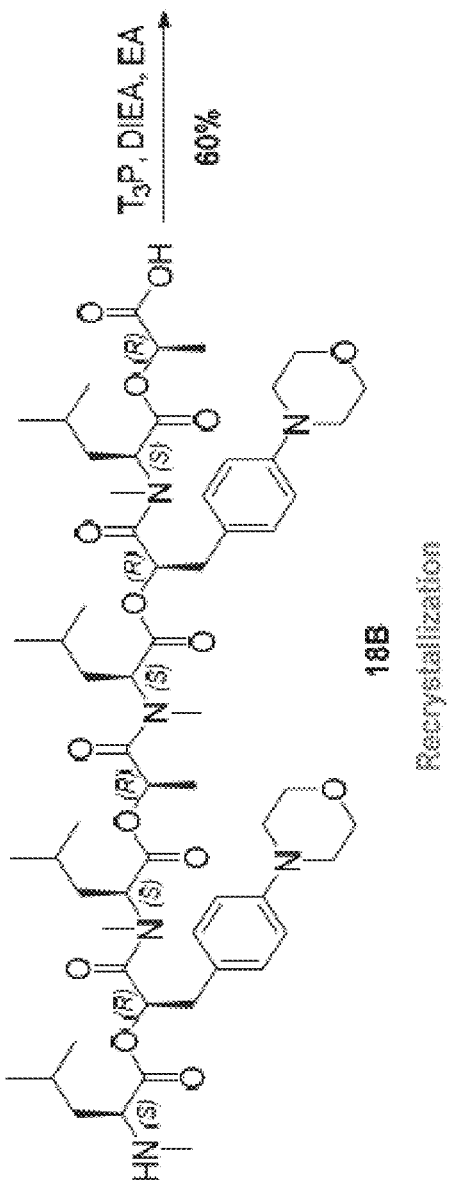

This object is achieved by a method of synthesizing a depsipeptide of formula (IIa) from formula (IV) and formula (III);

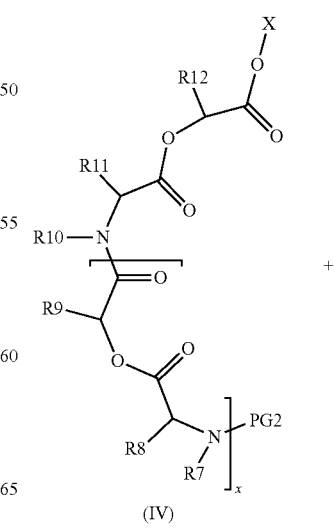

(IV)

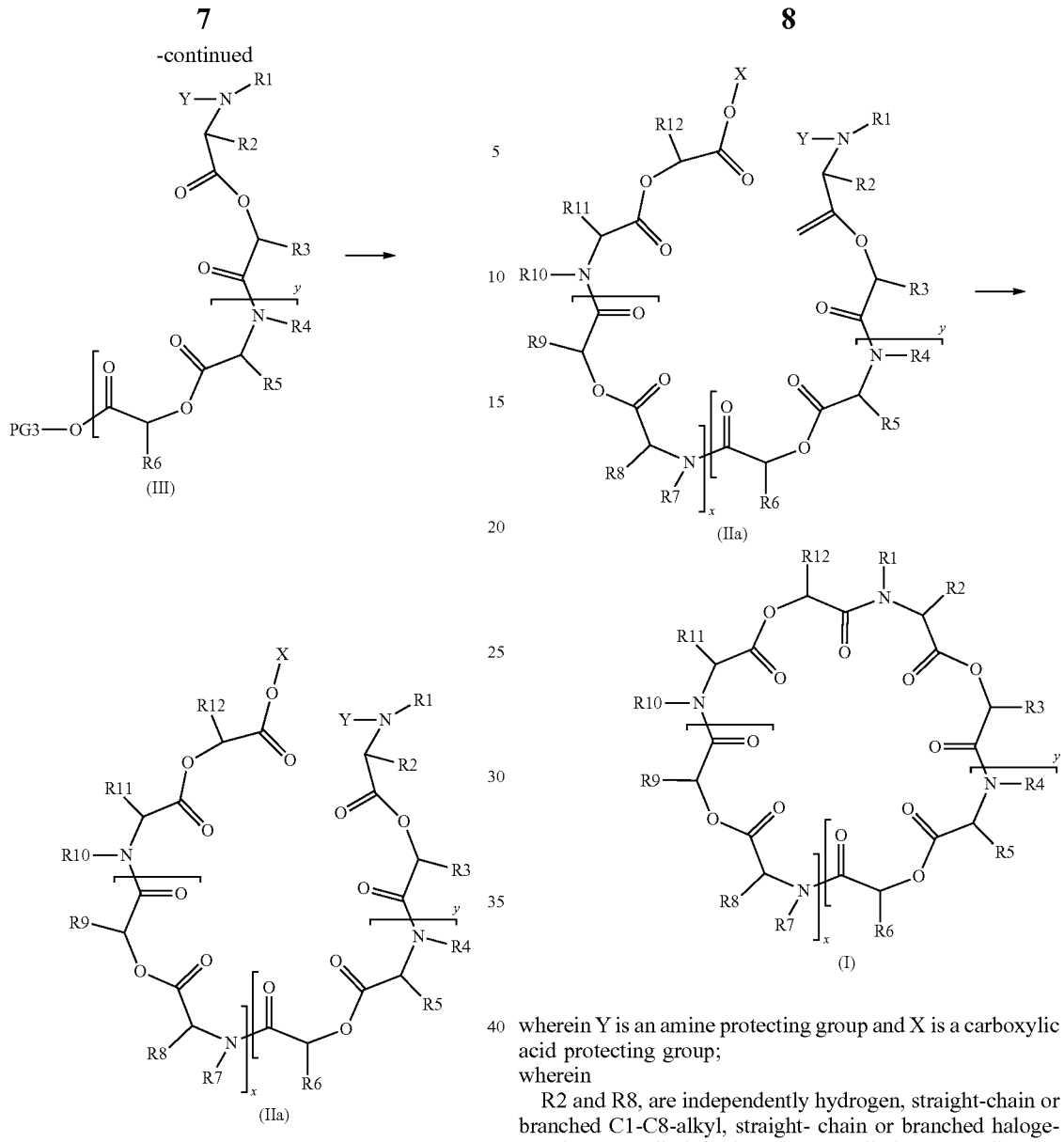

wherein PG2 is an amine protecting group and PG3 is a carboxylic acid protecting group, and by:

deprotecting the amine group that is protected by PG2 in the formula (IV) in the presence of a base to obtain a deprotected amine group;

deprotecting the carboxylic acid that is protected by the group PG3 in the formula (III) in the presence of an acid to obtain a deprotected carboxylic acid group; and condensing the deprotected amine group and the carboxylic acid group to obtain the depsipeptide of formula (IIa); and further synthesizing a cyclic depsipeptide of formula (I) from the depsipeptide of formula (IIa):

wherein Y is an amine protecting group and X is a carboxylic acid protecting group;

wherein

R2 and R8, are independently hydrogen, straight-chain or branched C1-C8-alkyl, straight- chain or branched halogenated C1-C8 alkyl, hydroxy-C1-C6-alkyl, C1-C4-alkanoyloxy- C1-C6-alkyl, C1-C4-alkoxy-C1-C6-alkyl, aryl-C1-C4-alkyloxy-C1-C6-alkyl, mercapto-C1- C6-alkyl, C1-C4-alkylthio-C1-C6-alkyl, C1-C4-alkylsulphinyl-C1-C6-alkyl, C1-C4- alkylsulphonyl-C1-C6-alkyl, carboxy-C1-C6-alkyl, C1-C4-alkoxycarbonyl-C1-C6-alkyl, C1- C4-arylalkoxycarbonyl-C1-C6-alkyl, carbamoyl-C1-C6-alkyl, amino-C1-C6-alkyl, C1-C4- alkylamino-C1-C6-alkyl, C1-C4-dialkylamino-C1-C6-alkyl, quanidino-C1-C6-alkyl, C1-C4-alkoxycarbonylamino-C1-C6-alkyl, 9-fluorenylmethoxycarbonyl (Fmoc) amino-C1-C6- alkyl, C2-C8-alkenyl, C3-C7-cycloalkyl, C3-C7-cycloalkyl-C1-C4-alkyl, benzyl, substituted benzyl, phenyl, or phenyl-C1-C4-alkyl which may optionally be substituted by halogen; wherein x is 1, y is 1, R1, R4, R7 and R10 are each methyl, R6 and R12 are each methyl, R5 and R11 are each independently a straight-chain or branched C1-C4-alkyl or a straight-chain or branched halogenated C1-C4-alkyl, and R3 and R9 are each independently benzyl or substituted benzyl; wherein synthesizing a cyclic depsipeptide of formula (I) from the depsipeptide of formula (IIa) comprises:

deprotecting the amine group that is protected by Y in the presence of an acid to obtain a deprotected amine group;

deprotecting the carboxylic acid that is protected by X via hydrogenolysis to obtain a deprotected carboxylic acid group; and condensing the deprotected amine group and the deprotected carboxylic acid group by a coupling agent to obtain the cyclic depsipeptide of formula (I),
wherein the coupling agent is BOP ((Benzotriazol-1-yloxy) tris (dimethylamino) phosphonium hexafluorophosphate), EDCI (1-Ethyl-3-(3-dimethylaminopropyl) carbodiimide), DEPBT (3- (diethoxyphosphoryloxy)-1,2,3-benzotriazin-4 (3H)-one), HATU (1- [Bis (dimethylamino) methylene]-1H-1,2,3-triazolo [4,5-b] pyridinium 3-oxid hexafluorophosphate), HBTU (2-(1H-benzotriazol-1-yl)-1,1,3,3-tetramethyluronium hexafluorophosphate) or Propylphosphonic anhydride (2,4,6-Tripropyl-1,3,5,2,4,6-trioxatriphosphorinane-2,4,6-trioxide, PPACA)
and depsipeptides of formula (IIa) selected from the group consisting of:

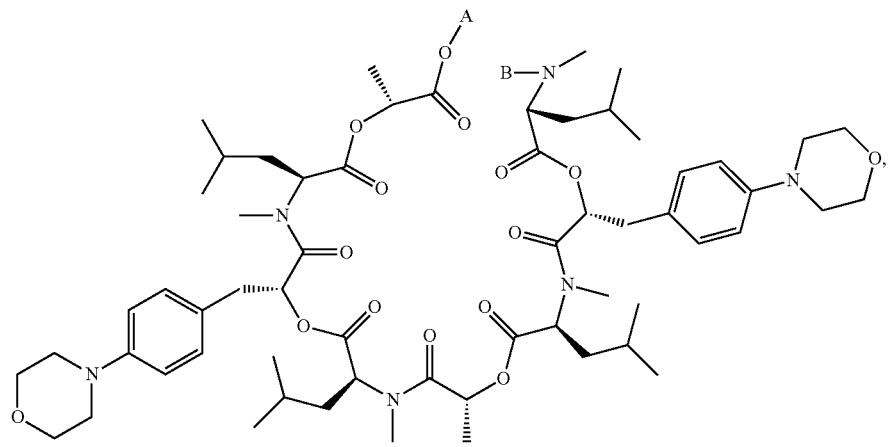

(II-1a)

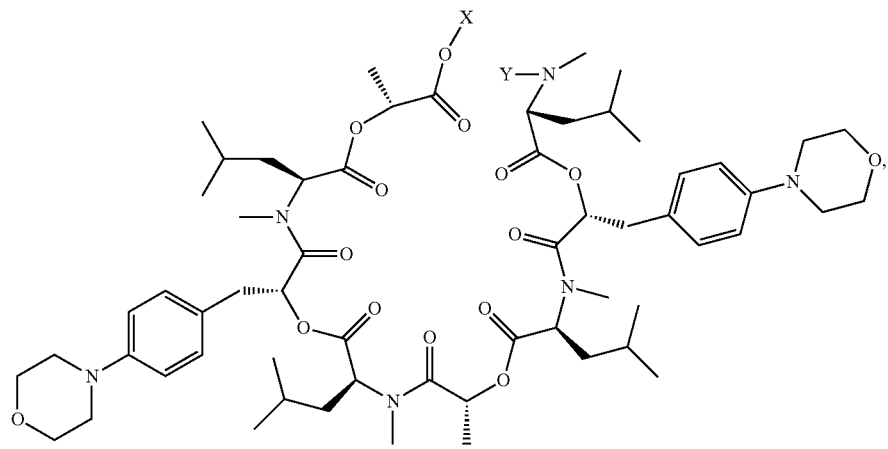

(II-1b)

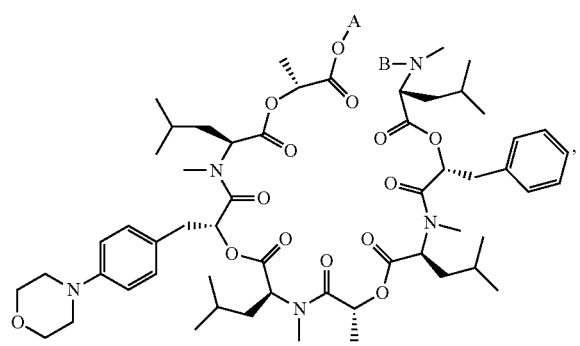

(II-2a)

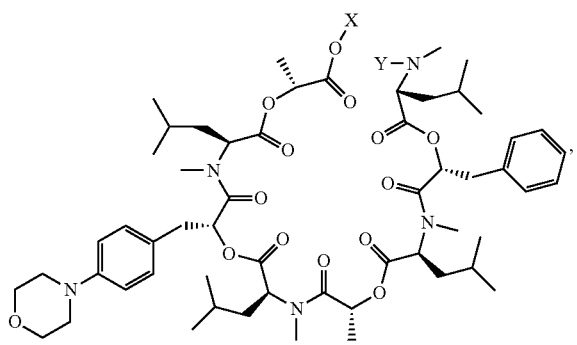

(II-2b)

-continued
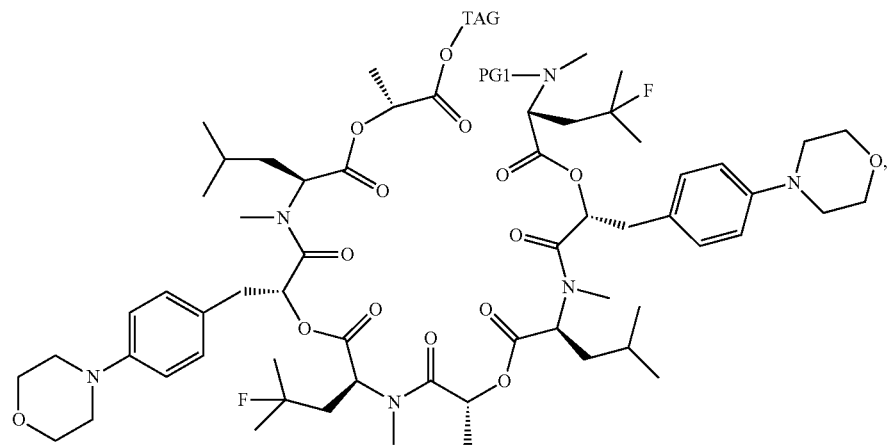
(II-3)
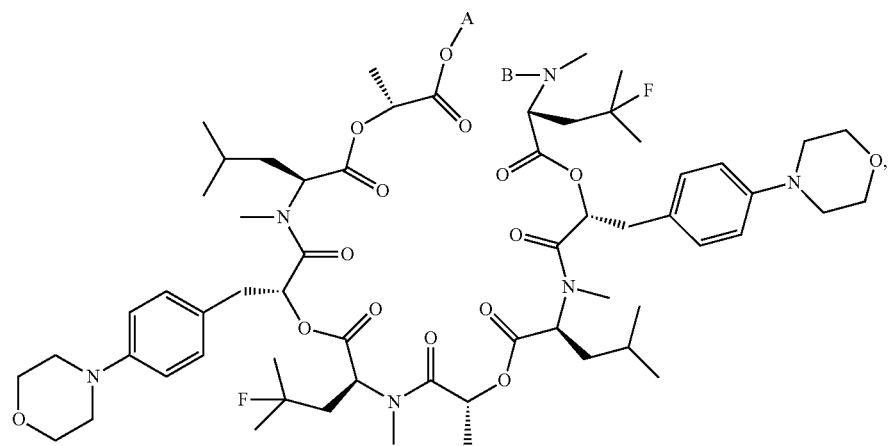
(II-3a)
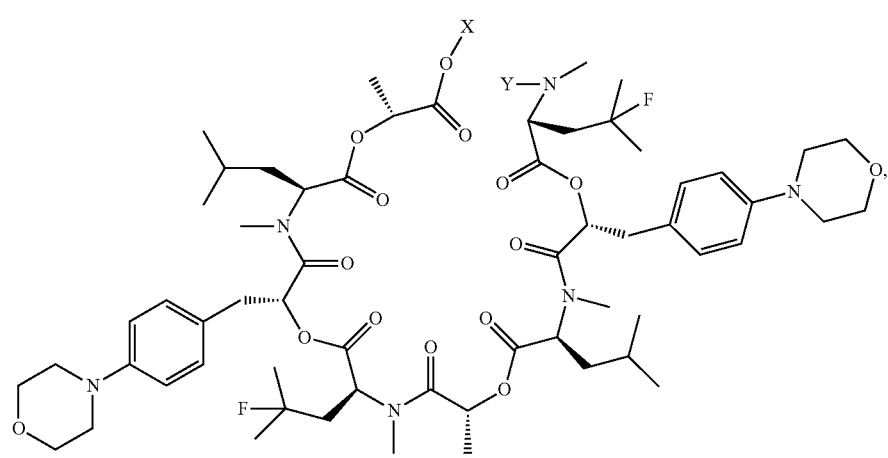
(II-3b)

-continued
(II-4a)
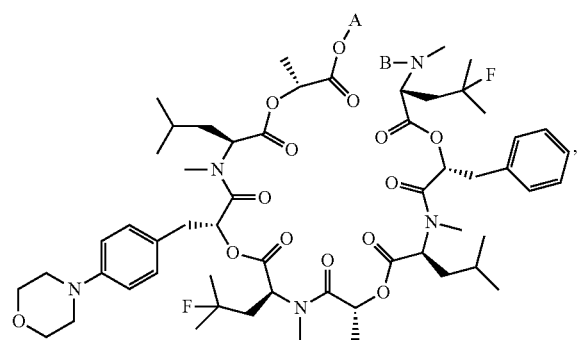
(II-4b)
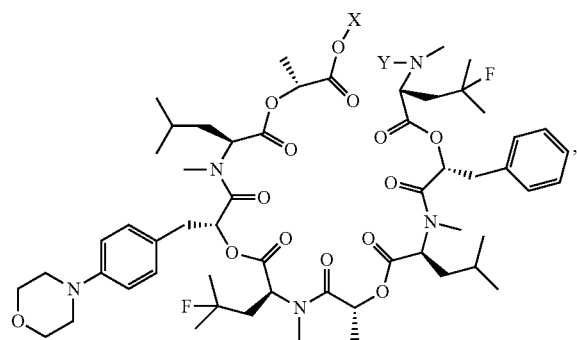
(II-5a)
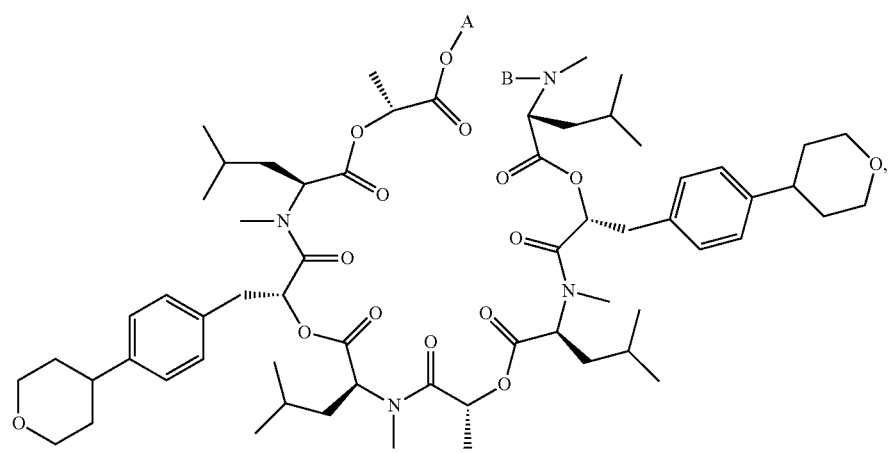
(II-5b)
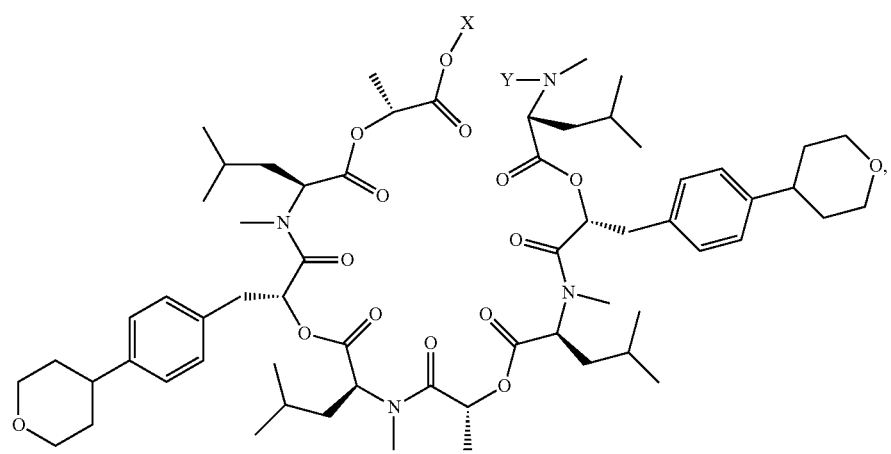

-continued
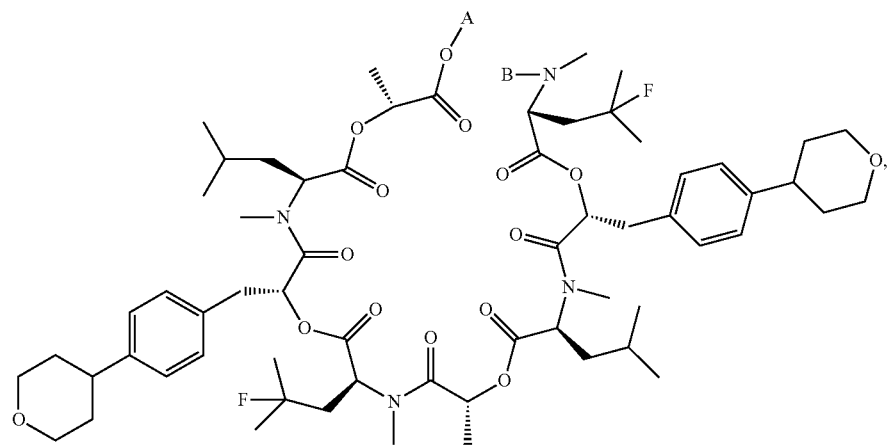
(II-6a)
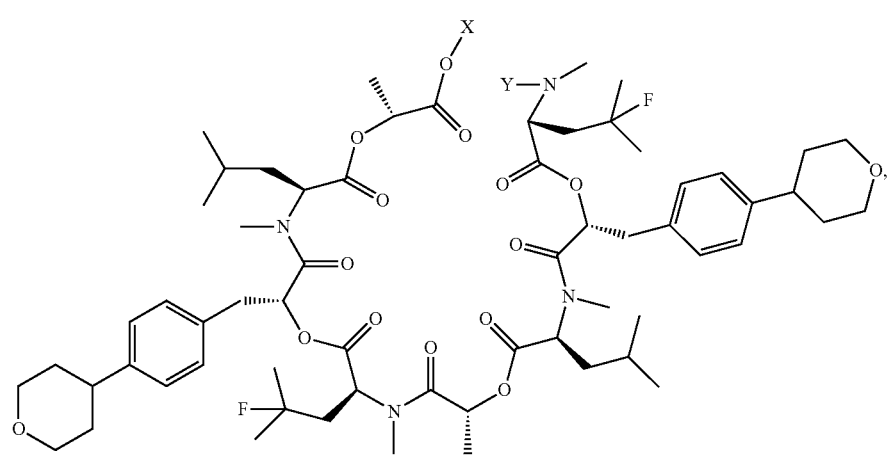
(II-6b)
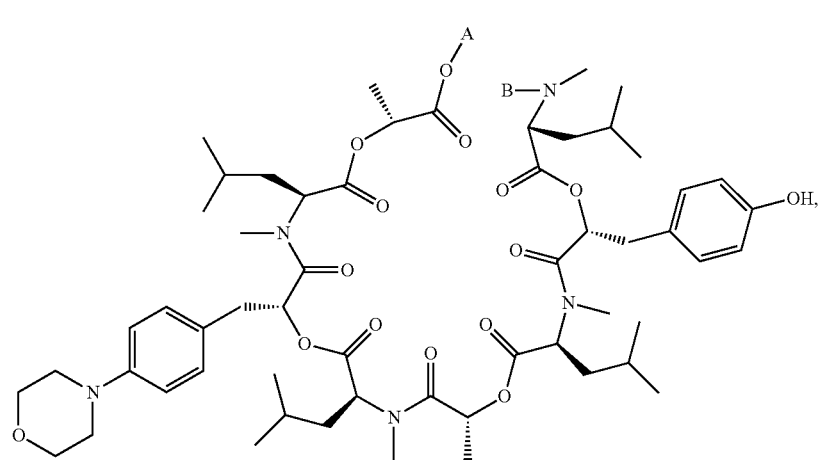
(II-7a)

-continued
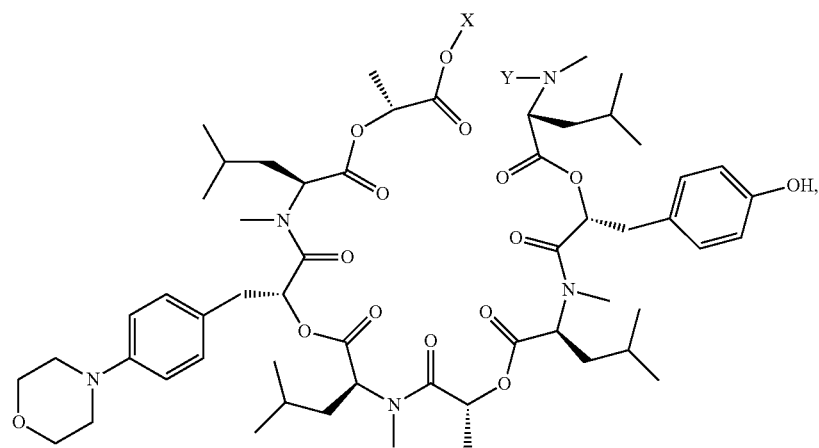
(II-7b)
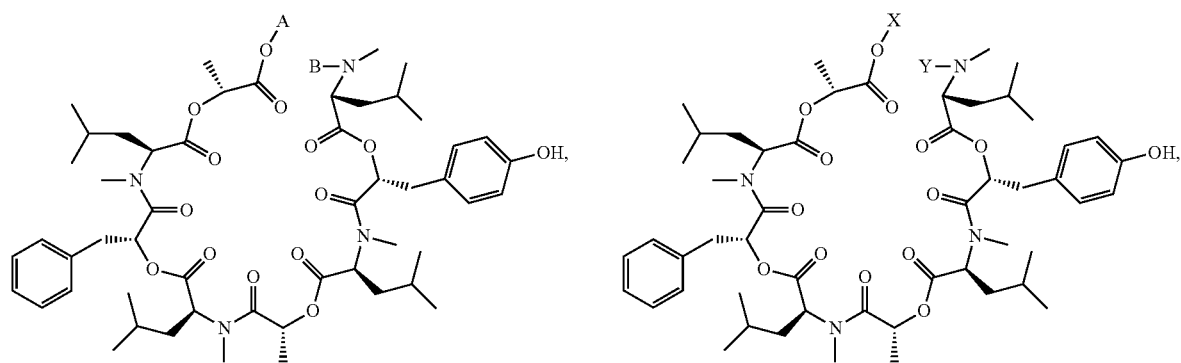
(II-8a) (II-8b)
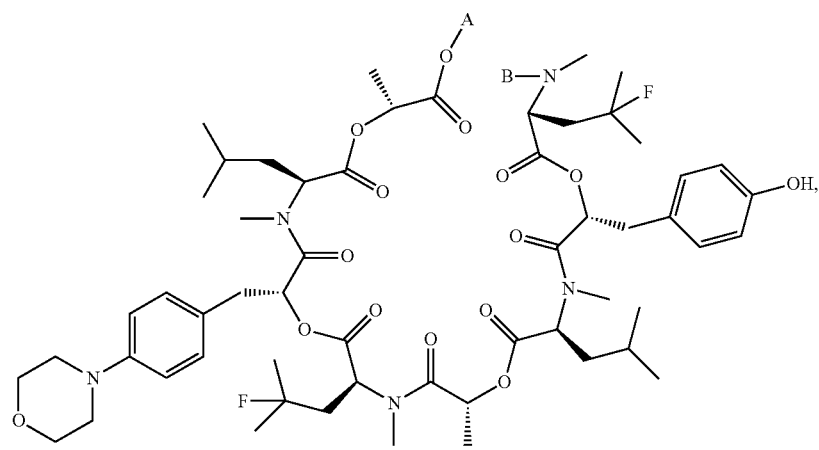
(II-9a)

(II-9b)
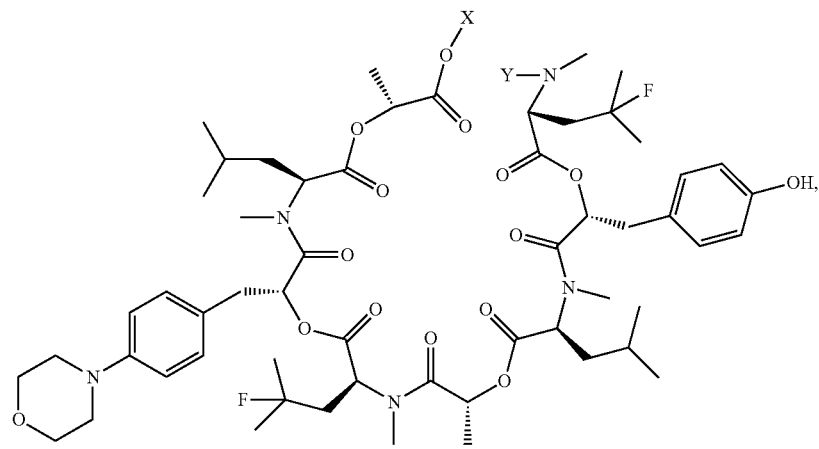
(II-10a) (II-10b)
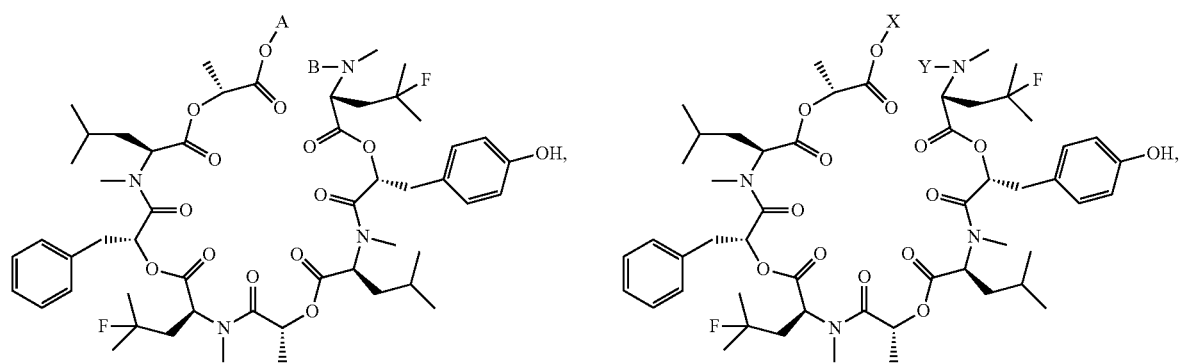
(II-11a)
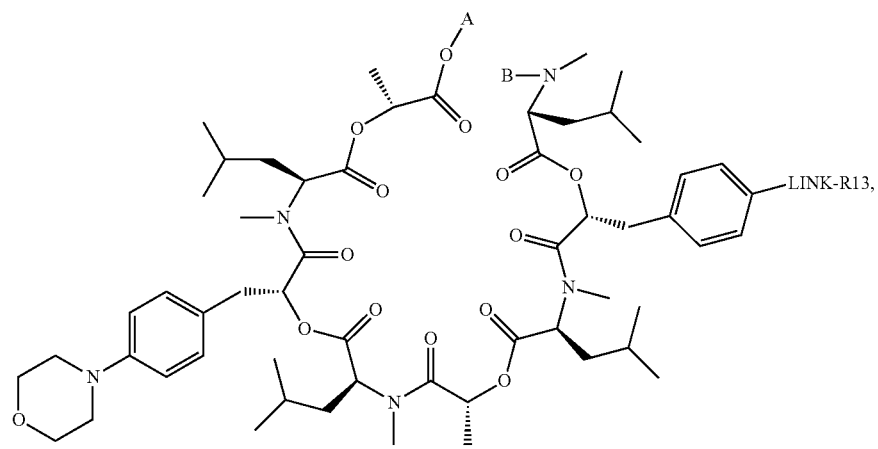

-continued
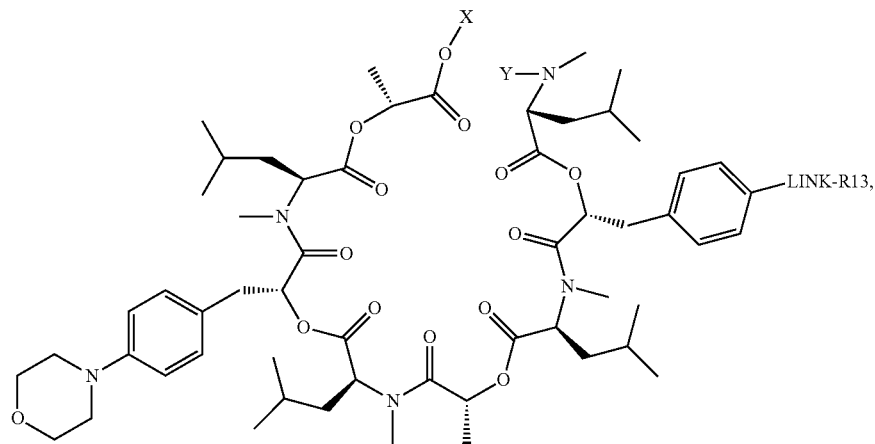
(II-11b)
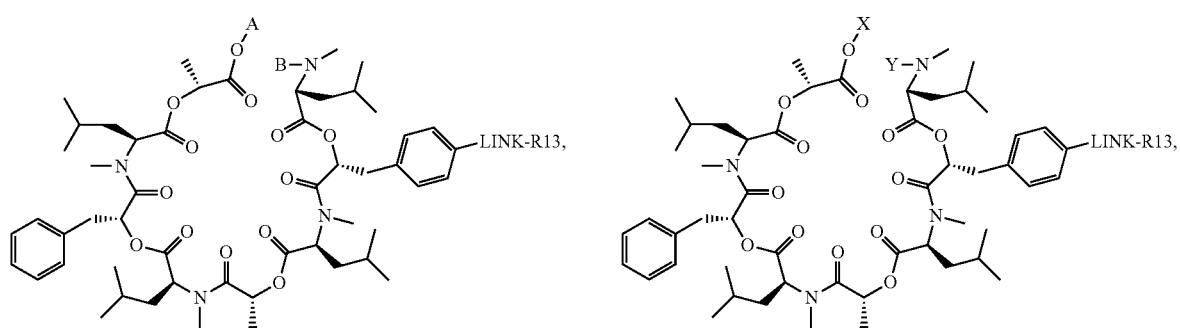
(II-12a)  (II-12b)
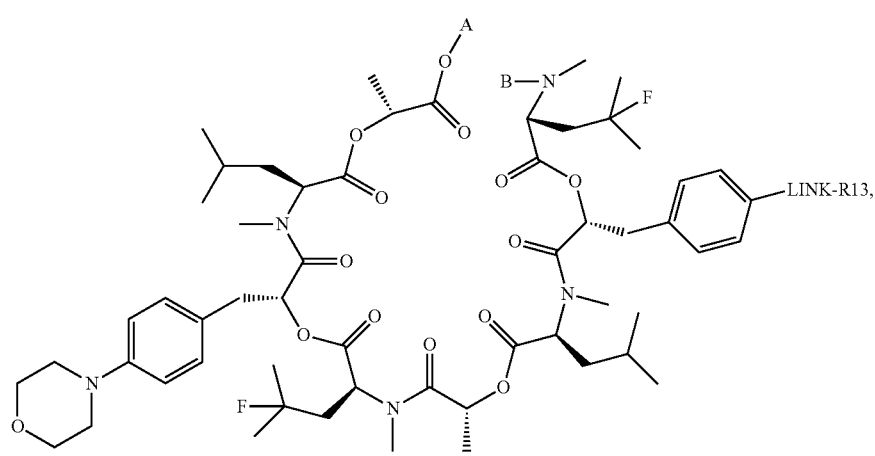
(II-13a)

-continued
(II-13b)
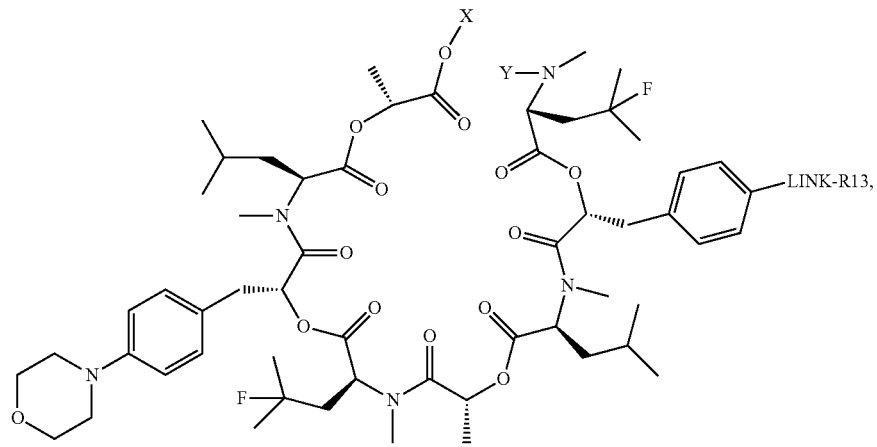
(II-14a)
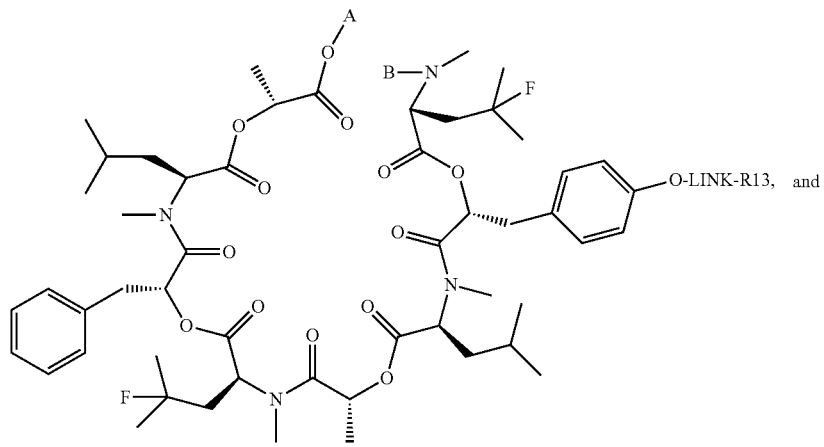
(II-14b)
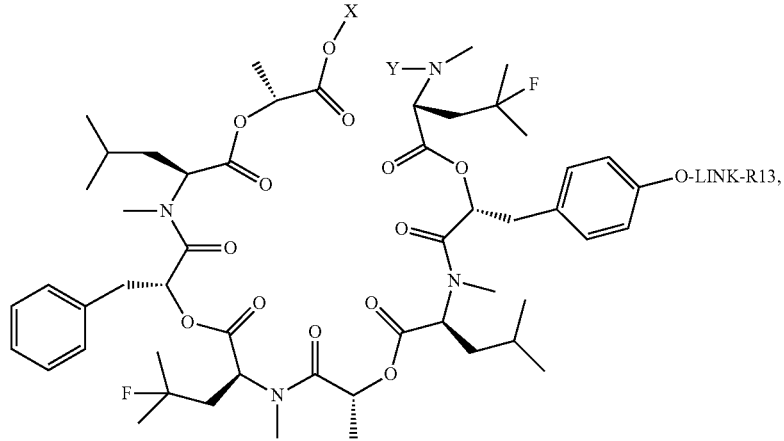
wherein in formulas (II-11a) to (II-14a), and (II-11b) to (II-14b)-LINK-is selected from the group consisting of:
-continued
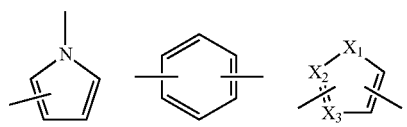
wherein X1 can be C, N, S, or O, X2 and X3 can be C or N;

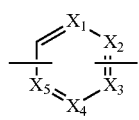

wherein X1 can be C, N, S, or O, X2, X3 and X4 can be C or N; and

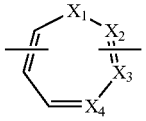

wherein X1, X2, X3 and X4 can be C or N;
and wherein R13 is selected from $SO_2NH(CH_3)$, $SO_2NH_2$, $OC(O)CH_3$, $CF_3$ or one the following lactone structures:

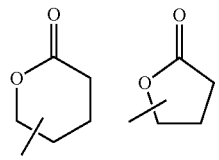

Y is an amine protecting group and X is a carboxylic acid protecting group;

B is an amine protecting group and A is a carboxylic acid protecting group;

PG1 is an amine protecting group and TAG is a carboxylic acid protecting group. Advantageous embodiments are the subject of the dependent claims. They may be combined freely unless the context clearly indicates otherwise.

Accordingly, the present invention provides a method for the synthesis of cyclic depsipeptides according to the general formula (I) from depsipeptides according to the general formula (II):

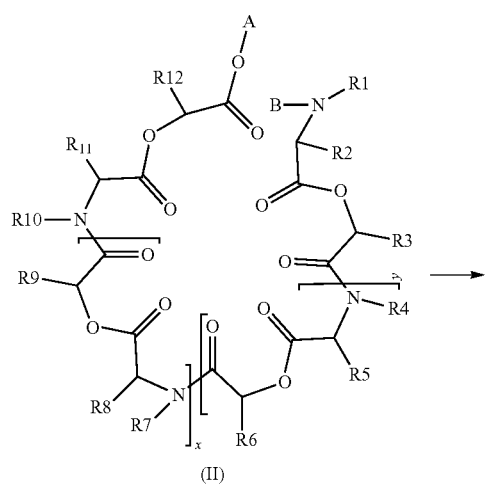

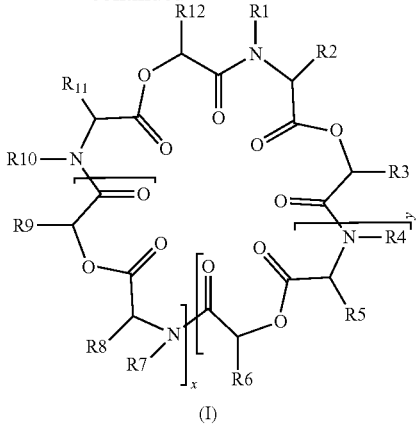

wherein B is an amine protecting group and A is a carboxylic acid protecting group, the method comprising the steps of:
deprotecting the amine group which is protected by the B group, thereby obtaining a deprotected amine group;
deprotecting the carboxylic acid which is protected by the A group, thereby obtaining a deprotected carboxylic acid group;
condensation of the deprotected amine and carboxylic acid groups, thereby obtaining the cyclic depsipeptide (I)

whereby x and y are, independent of each other, 0, 1 or 2 with the proviso that x+y≥1 (preferably, x and y are 1) and R1, R2, R3, R4, R5, R6, R7, R8, R9, R10, R11 and R12 each, independent of each other, represent hydrogen, straight-chain or branched C1-C8-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, straight-chain or branched halogenated C1-C8 alkyl, in particular fluorinated sec-butyl, hydroxy-C1-C6-alkyl, in particular hydroxymethyl, 1-hydroxyethyl, C1-C4-alkanoyloxy-C1-C6-alkyl, in particular acetoxymethyl, 1-acetoxyethyl, C1-C4-alkoxy-C1-C6-alkyl, in particular methoxymethyl, 1-methoxyethyl, aryl-C1-C4-alkyloxy-C1-C6-alkyl, in particular benzyloxymethyl, 1-benzyloxyethyl, mercapto-C1-C6-alkyl, in particular mercaptomethyl, C1-C4-alkylthio-C1-C6-alkyl, in particular methylthioethyl, C1-C4-alkylsulphinyl-C1-C6-alkyl, in particular methylsulphinylethyl, C1-C4-alkylsulphonyl-C1-C6-alkyl, in particular methylsulphonylethyl, carboxy-C1-C6-alkyl, in particular carboxymethyl, carboxyethyl, C1-C4-alkoxycarbonyl-C1-C6-alkyl, in particular methoxycarbonylmethyl, ethoxycarbonylethyl, C1-C4-arylalkoxycarbonyl-C1-C6-alkyl, in particular benzyloxycarbonylmethyl, carbamoyl-C1-C6-alkyl, in particular carbamoylmethyl, carbamoylethyl, amino-C1-C6-alkyl, in particular aminopropyl, aminobutyl, C1-C4-alkylamino-C1-C6-alkyl, in particular methylaminopropyl, methylaminobutyl, C1-C4-dialkylamino-C1-C6-alkyl, in particular dimethylaminopropyl, dimethylaminobutyl, guanidino-C1-C6-alkyl, in particular guanidinopropyl, C1-C4-alkoxycarbonylamino-C1-C6-alkyl, in particular tert-butoxycarbonylaminopropyl, tert-butoxycarbonylaminobutyl, 9-fluorenylmethoxycarbonyl-(Fmoc)amino-C1-C6-alkyl, in particular 9-fluorenylmethoxycarbonyl(Fmoc)aminopropyl, 9-fluorenylmethoxycarbonyl(Fmoc)aminobutyl, C2-C8-alkenyl, in particular vinyl, allyl, butenyl, C3-C7-cycloalkyl, in particular cyclopentyl, cyclohexyl, cycloheptyl, C3-C7-cycloalkyl-C1-C4-alkyl, in particular cyclopentylmethyl, cyclohexylmethyl, cycloheptylmethyl, benzyl, substituted benzyl, phenyl, phenyl-C1-C4-alkyl, in particular phenylmethyl which may optionally be substituted by radicals from the group consisting of halogen, in particular fluorine, chlorine, bromine or iodine, hydroxyl, C1-C4-alkoxy, in particular methoxy or ethoxy, C1-C4-alkyl, in particular methyl.

The protective groups A and B may be orthogonal in that way that when the B group is deprotected, the A group is stable; however, it is also an embodiment of the present invention that A and B are deprotected simultaneously.

In the method according to the invention it has surprisingly been found that cyclic depsipeptides (I), in particular emodepside and closely related structures, can be synthesized in high overall yields.

After deprotection the amine and carboxylic acid groups are reacted to form a peptide bond. Suitable coupling agents together with a base such as N,N-Diisopropylethylamine include PyBOP (benzotriazol-1-yl-oxytripyrrolidinophosphonium hexafluorophosphate), BOP ((Benzotriazol-1-yloxy)tris(dimethylamino)phosphonium hexafluorophosphate), BOP-Cl (Bis(2-oxo-3-oxazolidinyl)phosphinic chloride), EDCI (1-Ethyl-3-(3-dimethylaminopropyl)carbodiimide), DEPBT (3-(diethoxyphosphoryloxy)-1,2,3-benzotriazin-4(3H)-one), HATU (1-[Bis(dimethylamino)methylene]-1H-1,2,3-triazolo[4,5-b]pyridinium 3-oxid hexafluorophosphate), HBTU (2-(1H-benzotriazol-1-yl)-1,1,3,3-tetramethyluronium hexafluorophosphate) and, most preferred, T3P® (Propylphosphonic anhydride, 2,4,6-Tripropyl-1,3,5,2,4,6-trioxatriphosphorinane-2,4,6-trioxide, PPACA).

In one embodiment of the method according to the invention x is 1, y is 1, R1, R4, R7 and R10 are methyl, R6 and R12 are methyl, R5 and R11 are, independent of each other, straight-chain or branched C1-C4-alkyl or straight-chain or branched halogenated C1-C4-alkyl and R3 and R9 are, independent of each other, benzyl or substituted benzyl. According to one embodiment of the preferred invention, R3 and/or R9 are p-morpholino substituted benzyl.

According to an embodiment of the present invention, A is acid-labile whereas B is labile to hydrogenolysis. Accordingly, it is an embodiment of the present invention to provide a method for the synthesis of cyclic depsipeptides according to the general formula (I) from depsipeptides according to the general formula (IIa):

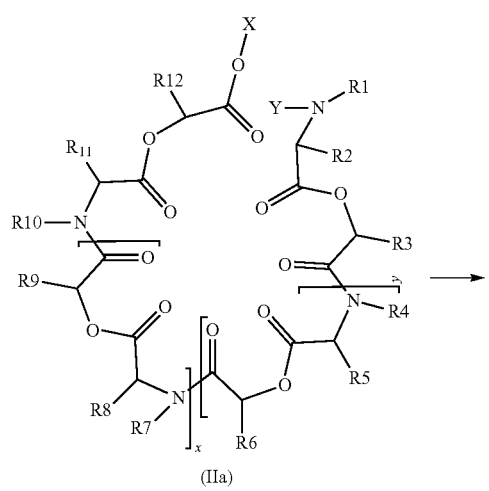

(IIa)

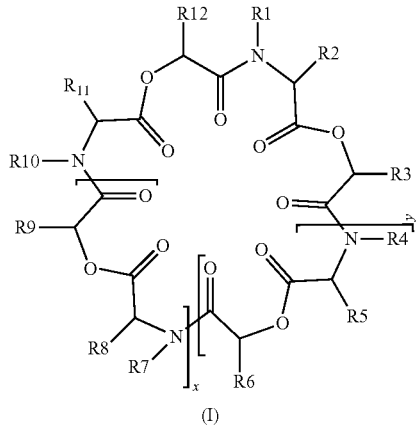

(I)

wherein Y is an amine protecting group and X is a carboxylic acid protecting group, the method comprising the steps of:

deprotecting the amine group which is protected by the Y group in the presence of an acid, thereby obtaining a deprotected amine group;

deprotecting the carboxylic acid which is protected by the X group via hydrogenolysis, thereby obtaining a deprotected carboxylic acid group;

condensation of the deprotected amine and carboxylic acid groups, thereby obtaining the cyclic depsipeptide (I)

In the method according to this embodiment it has surprisingly been found that cyclic depsipeptides (I), in particular emodepside and closely related structures, can be synthesized in high overall yields.

The term "hydrogenolysis" is to be understood in its broadest sense and is explicitly not limited to a reaction with gaseous and/or molecular hydrogen, although this is one embodiment of the present invention. Suitable catalysis are Pd, Pd/C, Pt, Pt/C. The term "hydrogenolysis" is also ment to include reactions where hydrogen is formed in situ or only formal and where hydrogenolysis reactants such as hydrazine or diimid etc. are employed.

In one embodiment of the present invention, X is a substituted or unsubstituted —CH$_2$-Aryl group. According to one embodiment, X is selected out of the group benzoyl (Bn), 4-methoxy-benzoyl (PMB), 3,4-dimethoxybenzoyl (DPMB), 4-phenyl-benzoyl (PPB), 2-naphthylmethyl (Nap), Benzyloxymethyl acetal (BOM).

In one embodiment of the present invention, Y is t.-butyloxycarbonyl (Boc), trityl (Trt), p-methoxybenzyl carbamate (Moz) or p-Nitrobenzyl carbamate (PNZ). Most preferred Y is Boc.

In another embodiment of the method according to the invention the depsipeptide according to the general formula (IIa) is obtained from precursors according to the general formulas (IV) and (III):

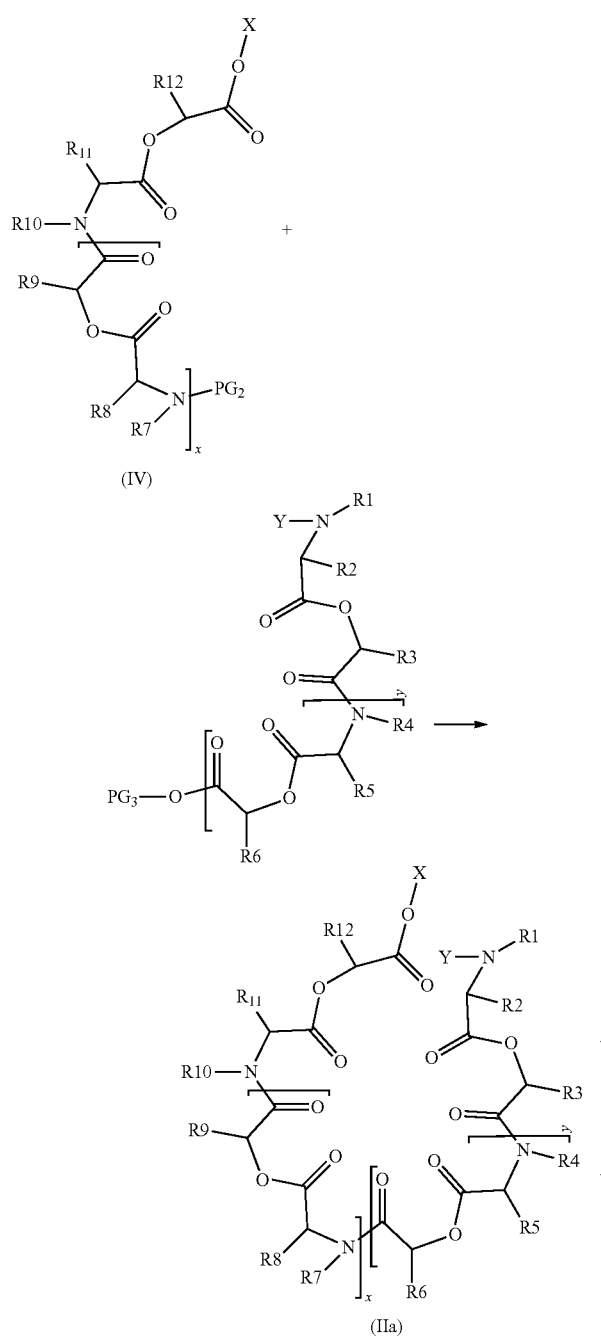

(IV)

(IIa)

by:
in precursor (IV), deprotecting the amine group which is protected by the PG2 group in the presence of a base, thereby obtaining a deprotected amine group;
in precursor (III), deprotecting the carboxylic acid which is protected by the PG3 group in the presence of an acid, thereby obtaining a deprotected carboxylic acid group;
condensation of the deprotected amine and carboxylic acid groups, thereby obtaining the depsipeptide (IIa);
wherein R1 to R12, X, Y, x, and y have a meaning as defined above (in particular, x and y may be 1), PG2 is an amine protecting group and PG3 is a carboxylic acid protecting group. The deprotection and condensation methods may be the same as outlined in connection with the reaction of compounds (IIa) to (I) above.

Preferably the precursor according to the general formula (IV) is obtained from precursors according to the general formulas (VI) and (V):

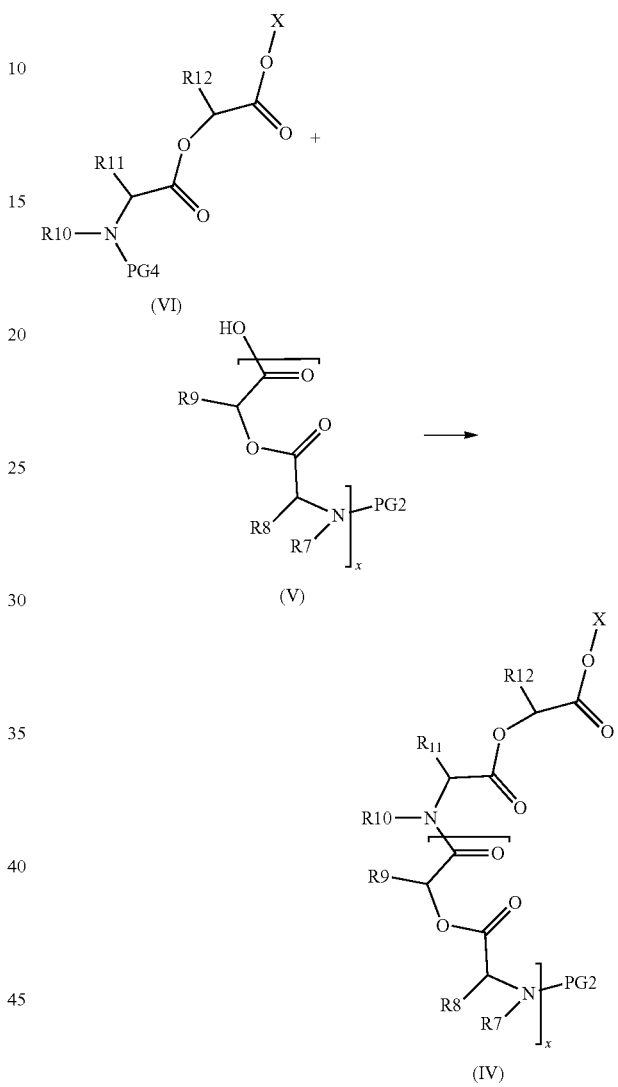

(VI)

(V)

(IV)

by:
in precursor (VI), deprotecting the amine group which is protected by the PG4 group in the presence of a base, thereby obtaining a deprotected amine group;
condensation of the deprotected amine group of precursor (VI) and carboxylic acid group of precursor (V), thereby obtaining the precursor (IV);
wherein R7 to R12, X and x have a meaning as defined above (in particular, x may be 1), PG2 has a meaning as defined above and PG4 is an amine protecting group. The deprotection and condensation methods may be the same as outlined in connection with the reaction of compounds (II) to (I) above.

It is also preferred that the precursor according to the general formula (III) is obtained from precursors according to the general formulas (VIII) and (VII):

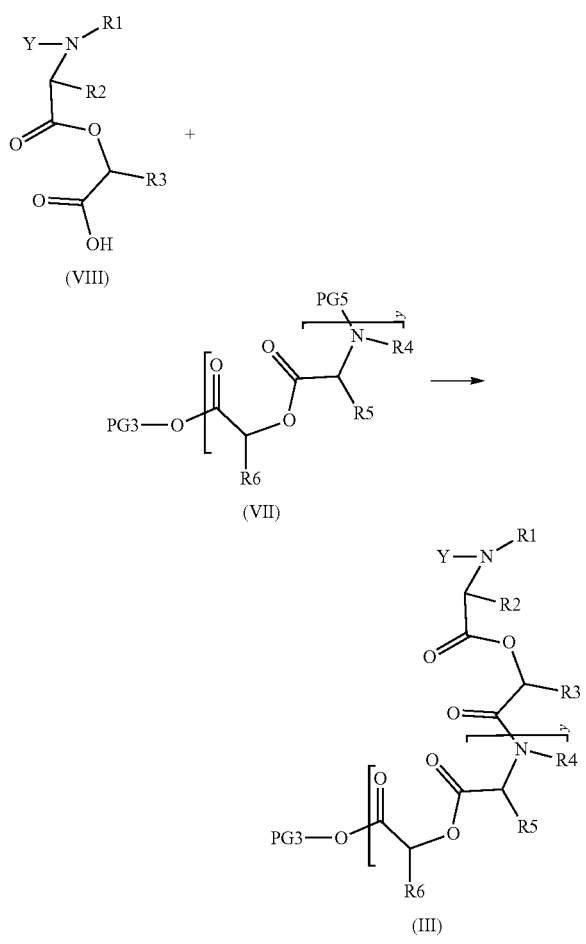

(VIII)

(VII)

(III)

by:
  in precursor (VII), deprotecting the amine group which is protected by the PG5 group in the presence of a base, thereby obtaining a deprotected amine group;
  condensation of the deprotected amine group of precursor (VII) and carboxylic acid group of precursor (VIII), thereby obtaining the precursor (III);
  wherein R1 to R6, Y and y have a meaning as defined above (in particular, y may be 1), PG3 has a meaning as defined above and PG5 is an amine protecting group. The deprotection and condensation methods may be the same as outlined in connection with the reaction of compounds (II) to (I) above.

It is also preferred that the precursor according to the general formula (VI) is obtained from the esterification of a precursor according to the general formula (IX) with X-LG:

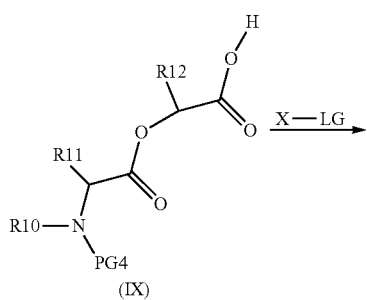

(IX)

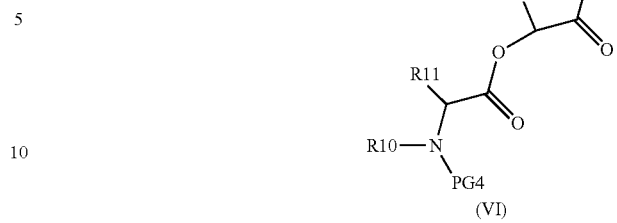

(VI)

wherein R10 to R12 and X have a meaning as defined above and PG4 has a meaning also as defined above and LG is a leaving group. The protection or tagging of the carboxylic acid group in (IX) may be effected using standard procedures, LG will often be halogenide, especially chloride.

Alternatively LG can be —OH, then standard condensation protocols will often apply.

It is also preferred that the precursor according to the general formula (VII) is obtained from the esterification of a precursor according to the general formula (X) with PG3-OH:

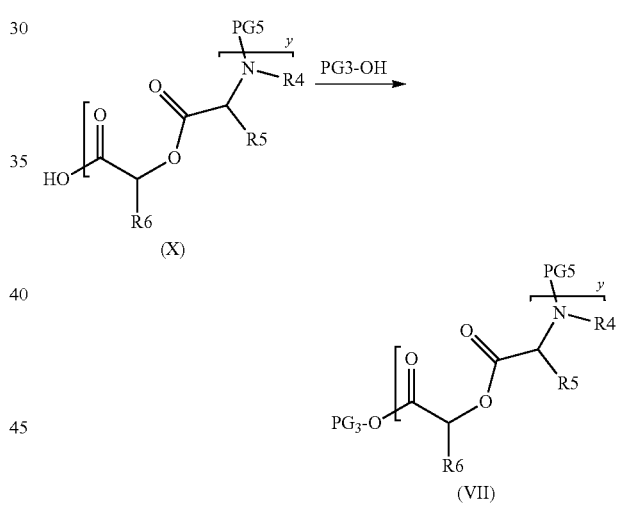

(X)

(VII)

wherein R4 to R6 and y have a meaning as defined above, PG3 also has a meaning as defined above and PG5 also has a meaning as defined above.

It is also preferred that precursors (III) and (IV) are identical.

It is also preferred that R3 and R9 are identical, R1 and R7 are identical, R2 and R8 are identical, R4 and R10 are identical, R5 and R11 are identical and R6 and R12 are identical.

According to an alternative embodiment of the present invention, A is base-labile whereas B is acid-labile. Therefore accordingly an alternative embodiment of the present invention present invention provides a method for the synthesis of cyclic depsipeptides according to the general formula (I) from depsipeptides according to the general formula (IIb):

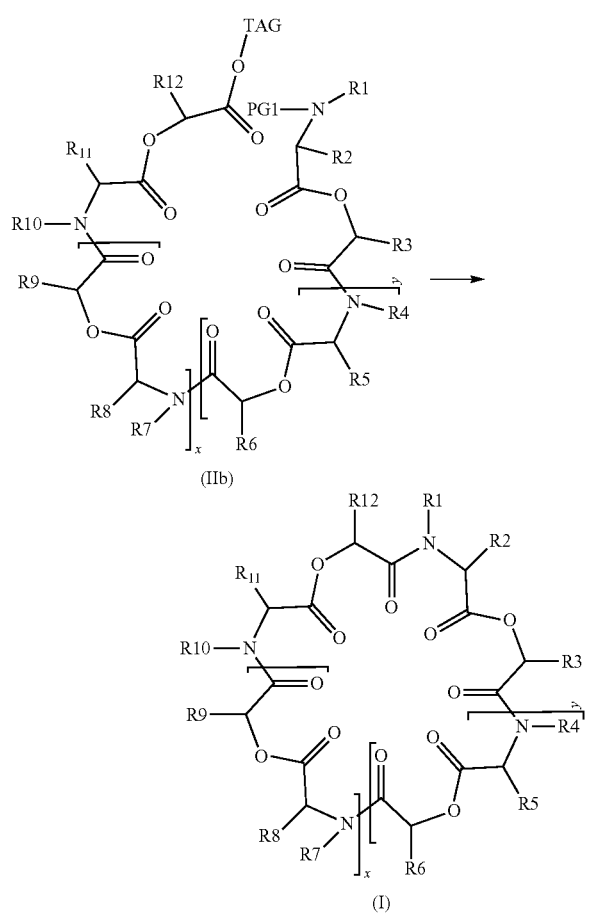

(IIb)

(I)

wherein PG1 is an amine protecting group and TAG is a carboxylic acid protecting group, the method comprising the steps of:
deprotecting the amine group which is protected by the PG1 group in the presence of a base, thereby obtaining a deprotected amine group;
deprotecting the carboxylic acid which is protected by the TAG group in the presence of an acid, thereby obtaining a deprotected carboxylic acid group;
condensation of the deprotected amine and carboxylic acid groups, thereby obtaining the cyclic depsipeptide (I)

The TAG group comprises a moiety Aryl-O—$(CH_2)_n$— with Aryl representing an aromatic moiety and n being ≥13, x and y are, independent of each other, 0, 1 or 2 with the proviso that x+y≥1 (preferably, x and y are 1) and R1, R2, R3, R4, R5, R6, R7, R8, R9, R10, R11 and R12 each, independent of each other, represent hydrogen, straight-chain or branched C1-C8-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, straight-chain or branched halogenated C1-C8 alkyl, in particular fluorinated sec-butyl, hydroxy-C1-C6-alkyl, in particular hydroxymethyl, 1-hydroxyethyl, C1-C4-alkanoyloxy-C1-C6-alkyl, in particular acetoxymethyl, 1-acetoxyethyl, C1-C4-alkoxy-C1-C6-alkyl, in particular methoxymethyl, 1-methoxyethyl, aryl-C1-C4-alkyloxy-C1-C6-alkyl, in particular benzyloxymethyl, 1-benzyloxyethyl, mercapto-C1-C6-alkyl, in particular mercaptomethyl, C1-C4-alkylthio-C1-C6-alkyl, in particular methylthioethyl, C1-C4-alkylsulphinyl-C1-C6-alkyl, in particular methylsulphinylethyl, C1-C4-alkylsulphonyl-C1-C6-alkyl, in particular methylsulphonylethyl, carboxy-C1-C6-alkyl, in particular carboxymethyl, carboxyethyl, C1-C4-alkoxycarbonyl-C1-C6-alkyl, in particular methoxycarbonylmethyl, ethoxycarbonylethyl, C1-C4-arylalkoxycarbonyl-C1-C6-alkyl, in particular benzyloxycarbonylmethyl, carbamoyl-C1-C6-alkyl, in particular carbamoylmethyl, carbamoylethyl, amino-C1-C6-alkyl, in particular aminopropyl, aminobutyl, C1-C4-alkylamino-C1-C6-alkyl, in particular methylaminopropyl, methylaminobutyl, C1-C4-dialkylamino-C1-C6-alkyl, in particular dimethylaminopropyl, dimethylaminobutyl, guanidino-C1-C6-alkyl, in particular guanidinopropyl, C1-C4-alkoxycarbonylamino-C1-C6-alkyl, in particular tert-butoxycarbonylaminopropyl, tert-butoxycarbonylaminobutyl, 9-fluorenylmethoxycarbonyl (Fmoc)amino-C1-C6-alkyl, in particular 9-fluorenylmethoxycarbonyl(Fmoc)aminopropyl, 9-fluorenylmethoxycarbonyl(Fmoc)aminobutyl, C2-C8-alkenyl, in particular vinyl, allyl, butenyl, C3-C7-cycloalkyl, in particular cyclopentyl, cyclohexyl, cycloheptyl, C3-C7-cycloalkyl-C1-C4-alkyl, in particular cyclopentylmethyl, cyclohexylmethyl, cycloheptylmethyl, benzyl, substituted benzyl, phenyl, phenyl-C1-C4-alkyl, in particular phenylmethyl which may optionally be substituted by radicals from the group consisting of halogen, in particular fluorine, chlorine, bromine or iodine, hydroxyl, C1-C4-alkoxy, in particular methoxy or ethoxy, C1-C4-alkyl, in particular methyl.

In the method according to the invention it has surprisingly been found that cyclic depsipeptides (I), in particular emodepside and closely related structures, can be synthesized in high overall yields using hydrophobic carboxylic acid protecting groups TAG. These groups can render the molecules to which they are bound ("tagged" molecules) insoluble in polar solvents such as methanol. Hence, the tagged molecules can be precipitated out of a reaction mixture and the tagging group itself, after deprotection, can also be separated using this technique. Furthermore, the hydrophobic tagging group allows tagged molecules to be soluble in unpolar solvents such as dichloromethane.

The deprotection of the amine group by removing the protection group PG1 can be performed using standard base-assisted procedures such as treatment with a piperidine solution in dichloromethane. Likewise, the deprotection of the carboxylic acid group by removing the TAG group can be performed using protocols for removing a benzyl group such as treatment with a solution of trifluoroacetic acid (TFA) in dichloromethane.

In another embodiment of the method according to the invention PG1 is 9-fluorenylmethoxycarbonyl (Fmoc), t-butyl carbamate (Boc), benzyl carbamate (Z), acetamide, trifluoroacetamide, phthalimide, benzyl (Bn), triphenylmethyl (Tr), benzylidene or p-toluenesulfonamide (Ts)
and TAG is:

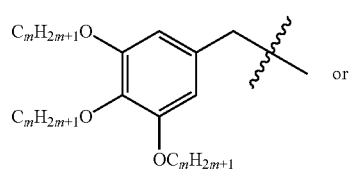 or

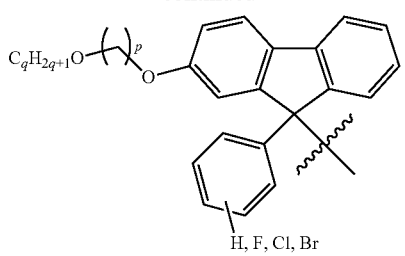

wherein m is ≥15 to ≤25, p is ≥8 to ≤18 and q is ≥15 to ≤25. Preferably, m is 18, 19, 20, 21 or 22, p is 11, 12 or 13 and q is 21, 22 or 23.

In another embodiment of the method according to the invention the depsipeptide according to the general formula (IIb) is obtained from precursors according to the general formulas (IVb) and (IIIb):

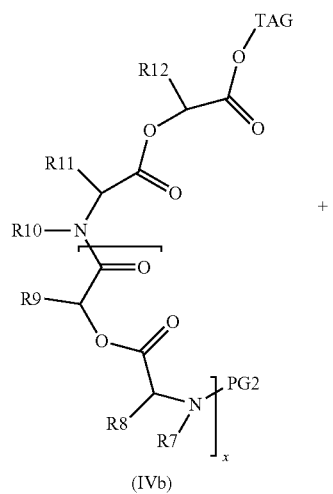

(IVb)

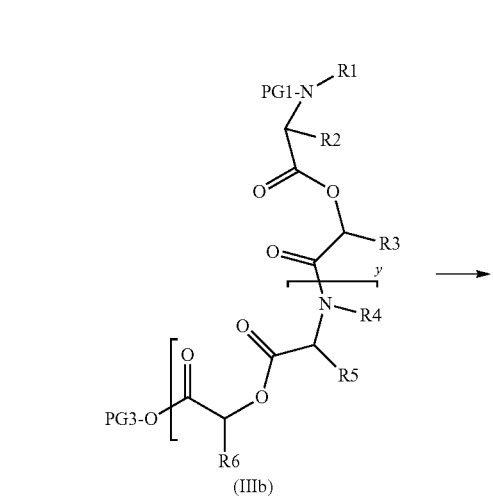

(IIIb)

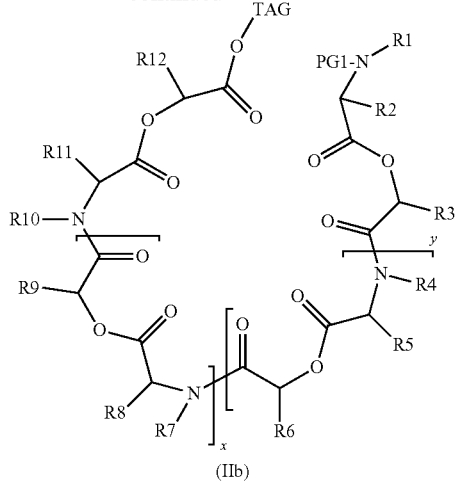

(IIb)

by:

in precursor (IVb), deprotecting the amine group which is protected by the PG2 group in the presence of a base, thereby obtaining a deprotected amine group;

in precursor (IIIb), deprotecting the carboxylic acid which is protected by the PG3 group in the presence of an acid, thereby obtaining a deprotected carboxylic acid group;

condensation of the deprotected amine and carboxylic acid groups, thereby obtaining the depsipeptide (IIb);

wherein R1 to R12, TAG, PG1, x, and y have a meaning as defined above (in particular, x and y may be 1), PG2 is an amine protecting group and PG3 is a carboxylic acid protecting group. The deprotection and condensation methods may be the same as outlined in connection with the reaction of compounds (II) to (I) above.

Preferably the precursor according to the general formula (IVb) is obtained from precursors according to the general formulas (Vb) and (Vb):

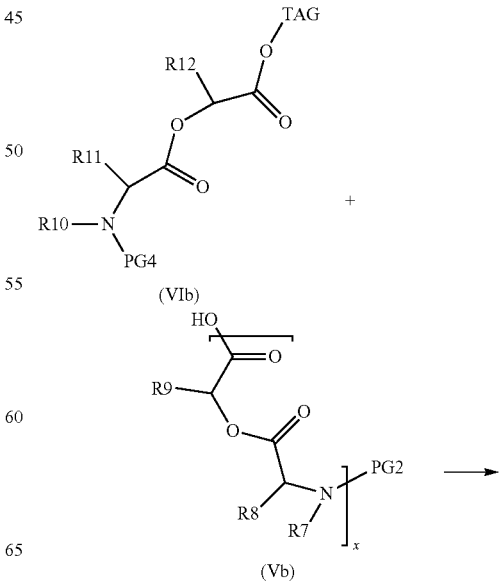

(VIb)

(Vb)

-continued

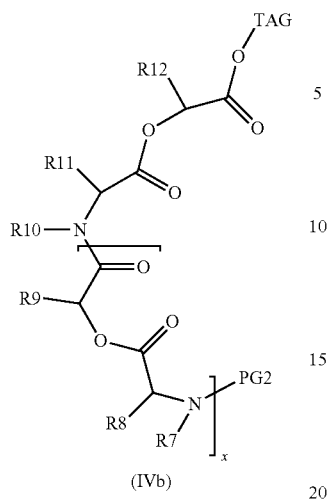

(IVb)

by:
in precursor (VIb), deprotecting the amine group which is protected by the PG4 group in the presence of a base, thereby obtaining a deprotected amine group;
condensation of the deprotected amine group of precursor (VIb) and carboxylic acid group of precursor (Vb), thereby obtaining the precursor (IVb);

wherein R7 to R12, TAG and x have a meaning as defined above (in particular, x may be 1), PG2 has a meaning as defined above and PG4 is an amine protecting group. The deprotection and condensation methods may be the same as outlined in connection with the reaction of compounds (IIb) to (I) above.

It is also preferred that the precursor according to the general formula (IIIb) is obtained from precursors according to the general formulas (VIIIb) and (VIIb):

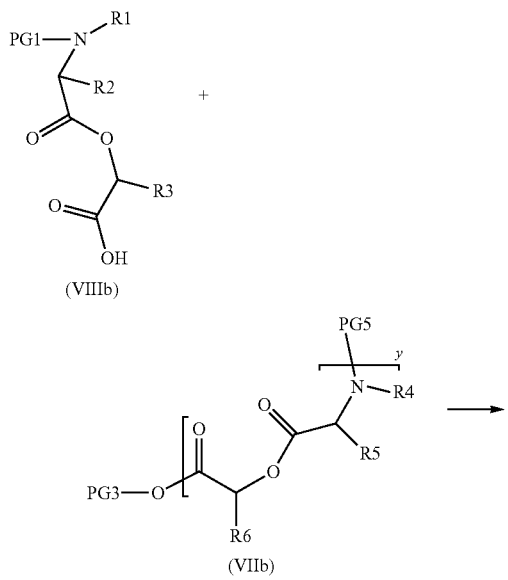

-continued

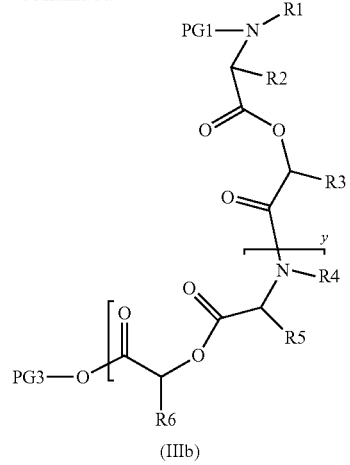

(IIIb)

by:
in precursor (VIIb), deprotecting the amine group which is protected by the PG5 group in the presence of a base, thereby obtaining a deprotected amine group;
condensation of the deprotected amine group of precursor (VIIb) and carboxylic acid group of precursor (VIIIb), thereby obtaining the precursor (IIIb);

wherein R1 to R6, PG1 and y have a meaning as defined above (in particular, y may be 1), PG3 has a meaning as defined above and PG5 is an amine protecting group. The deprotection and condensation methods may be the same as outlined in connection with the reaction of compounds (IIb) to (I) above.

It is also preferred that the precursor according to the general formula (VIb) is obtained from the esterification of a precursor according to the general formula (IXb) with TAG-OH:

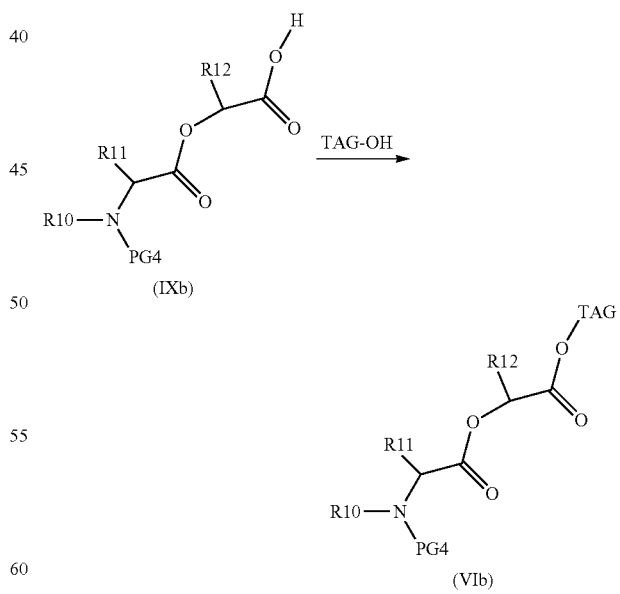

wherein R10 to R12 and TAG have a meaning as defined above and PG4 has a meaning also as defined above. The protection or tagging of the carboxylic acid group in (IXb) may be effected using a standard condensation system such as DCC/DMAP.

It is also preferred that the precursor according to the general formula (VIIb) is obtained from the esterification of a precursor according to the general formula (X) with PG3-OH:

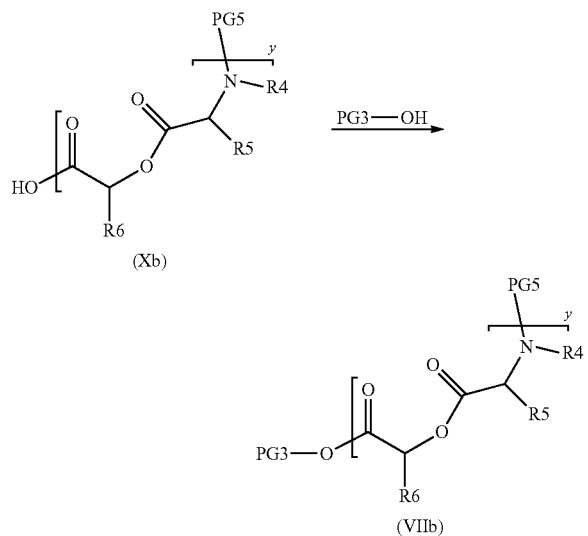

wherein R4 to R6 and y have a meaning as defined above, PG3 also has a meaning as defined above and PG5 also has a meaning as defined above.

It is also preferred that PG3 is TAG as defined above.

In another embodiment of the method according to the invention at least one reaction step of the reaction steps resulting in a TAG-bearing molecule is followed by precipitation of crude reaction product in methanol, thereby purifying the crude reaction product.

In another embodiment of the method according to the invention at least one step of the reaction steps in which TAG-protected carboxylic acid groups are deprotected is followed by precipitation of cleaved TAG-OH in methanol and removal of the precipitate by filtration, thereby purifying the crude reaction product.

It is also preferred that precursors (IIIb) and (IVb) are identical.

It is also preferred that R3 and R9 are different from each other, R1 and R7 are identical, R2 and R8 are identical, R4 and R10 are identical, R5 and R11 are identical and R6 and R12 are identical.

In another embodiment of the method according to the invention the depsipeptide is selected from one of the general formulas (II-1) to (II-14b):

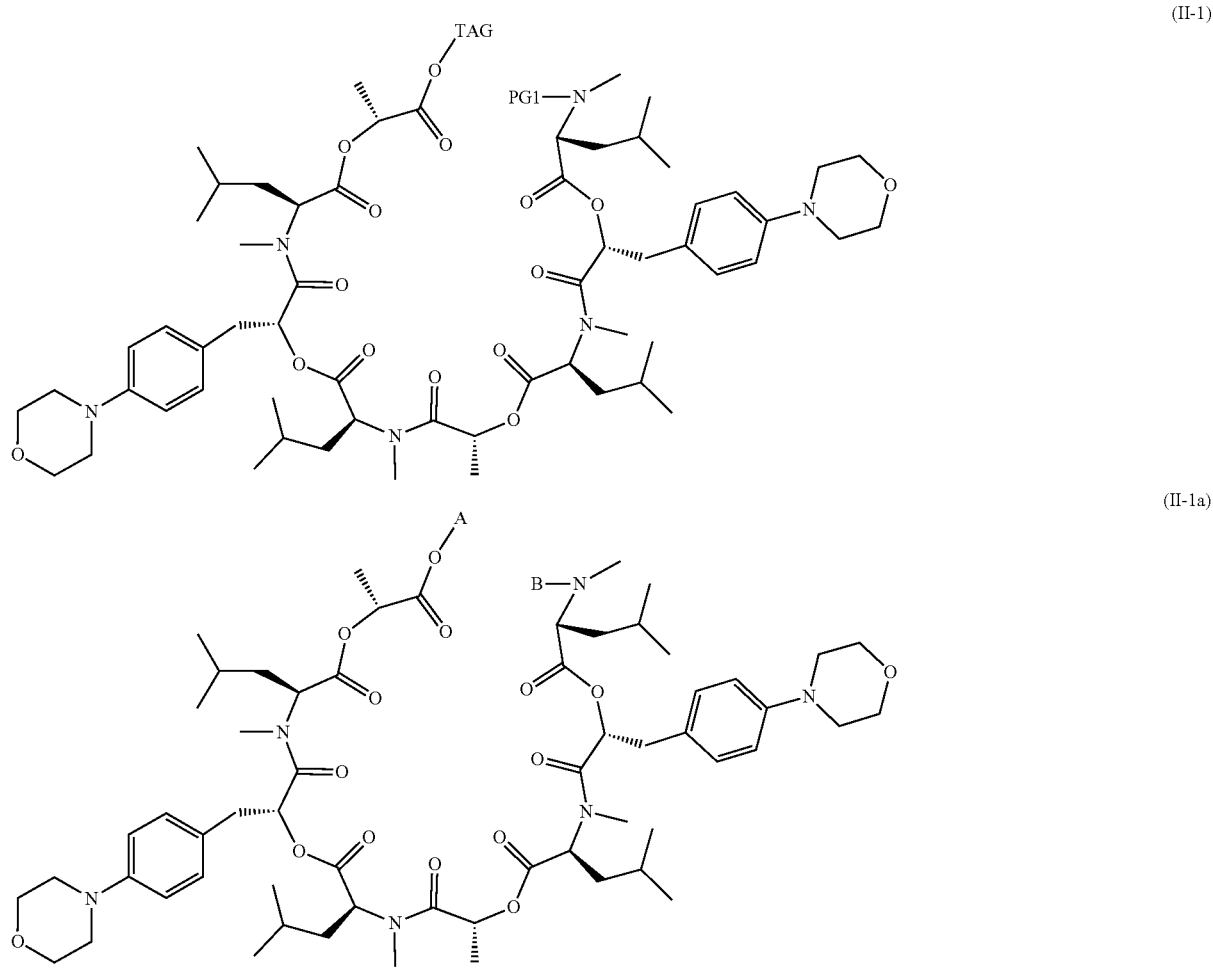

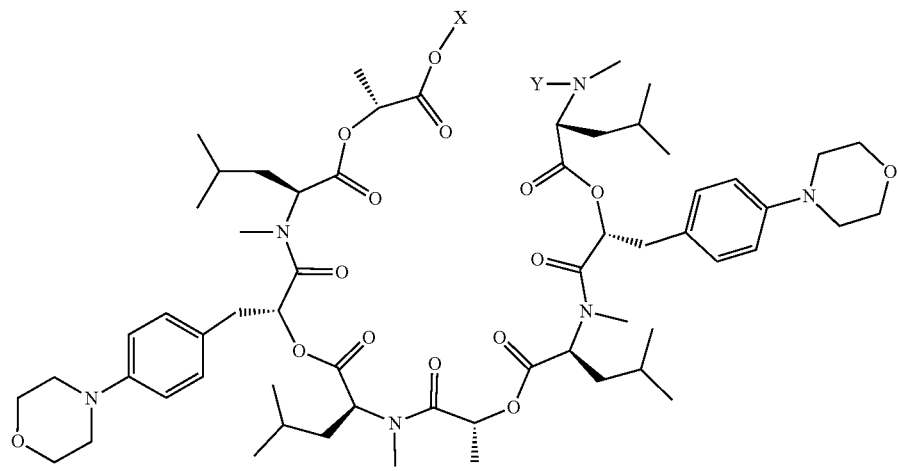
(II-1b)
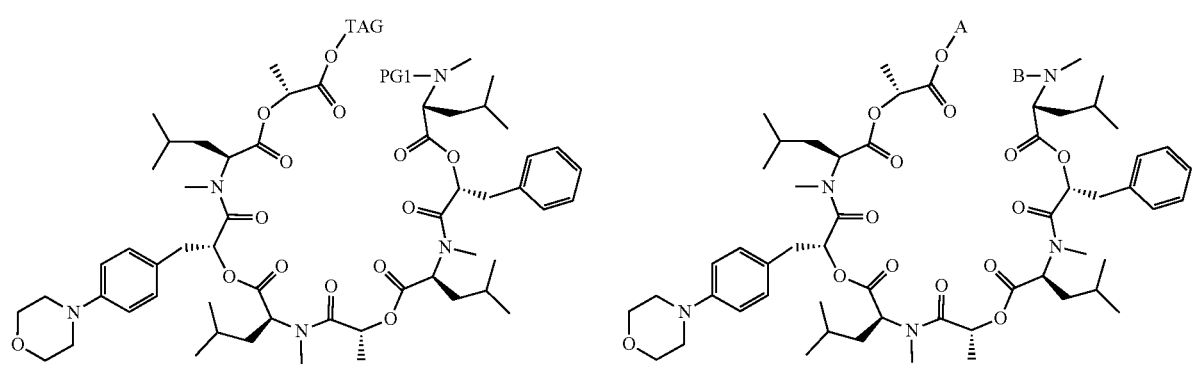
(II-2) (II-2a)
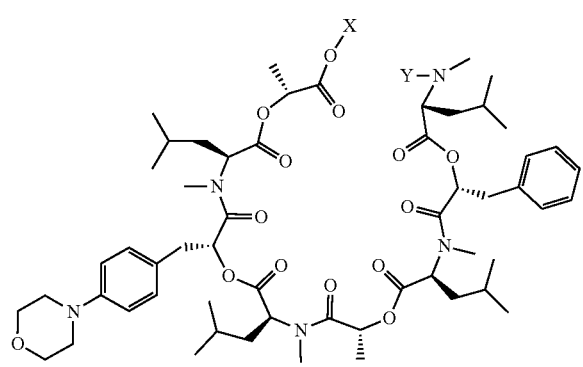
(II-2b)

-continued
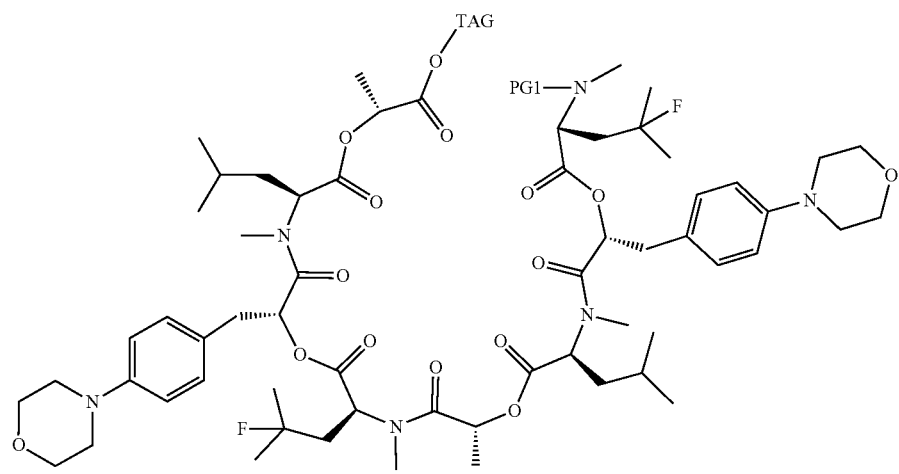
(II-3)
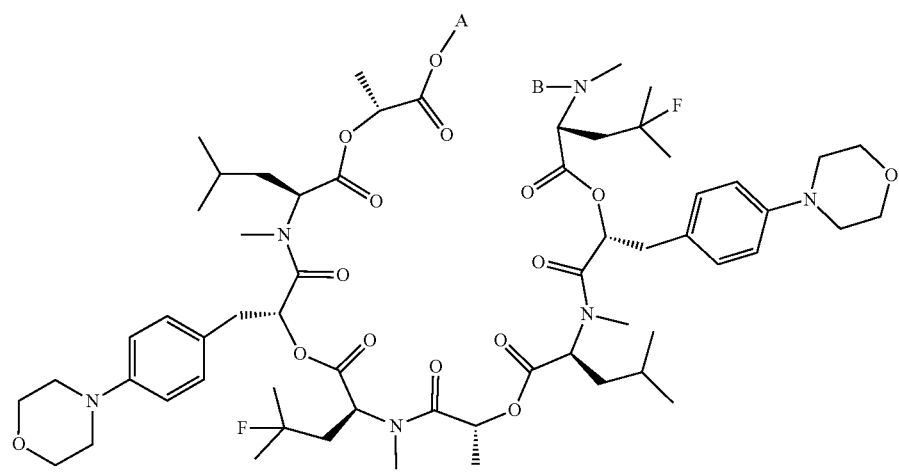
(II-3a)
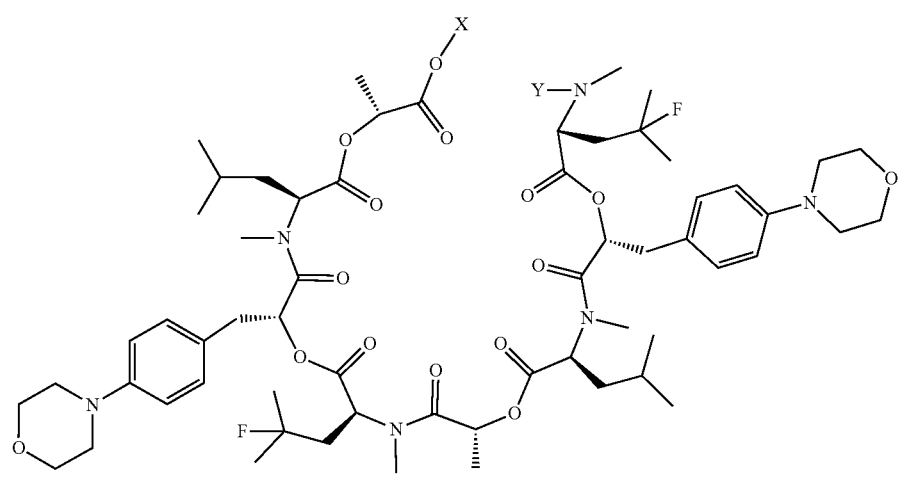
(II-3b)

(II-4) 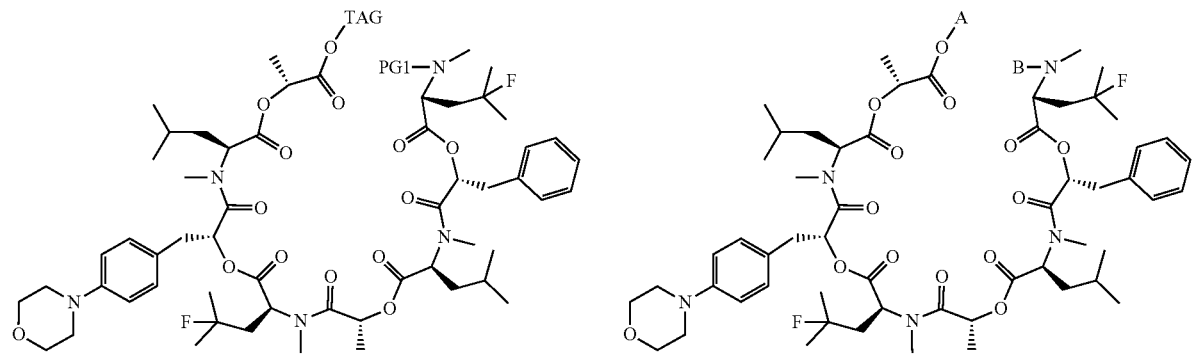 (II-4a)
(II-4b) 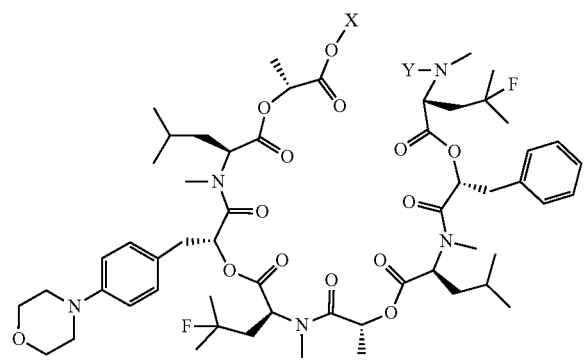
(II-5) 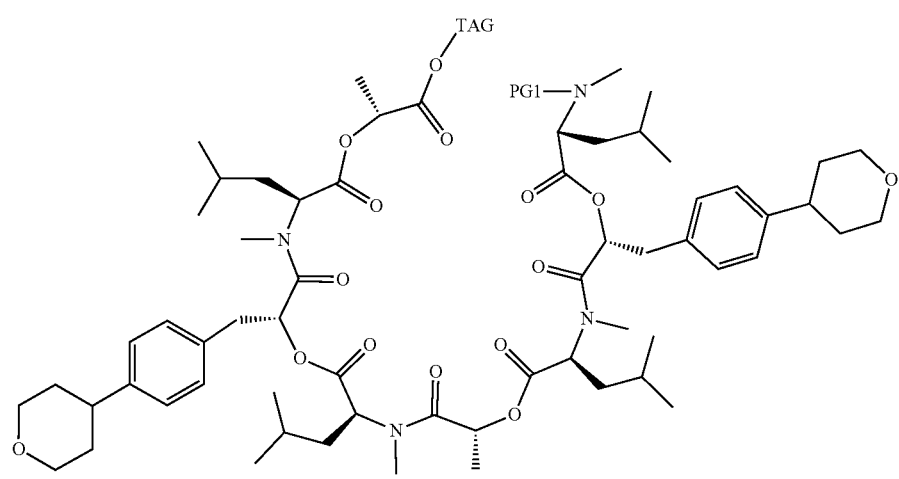

-continued
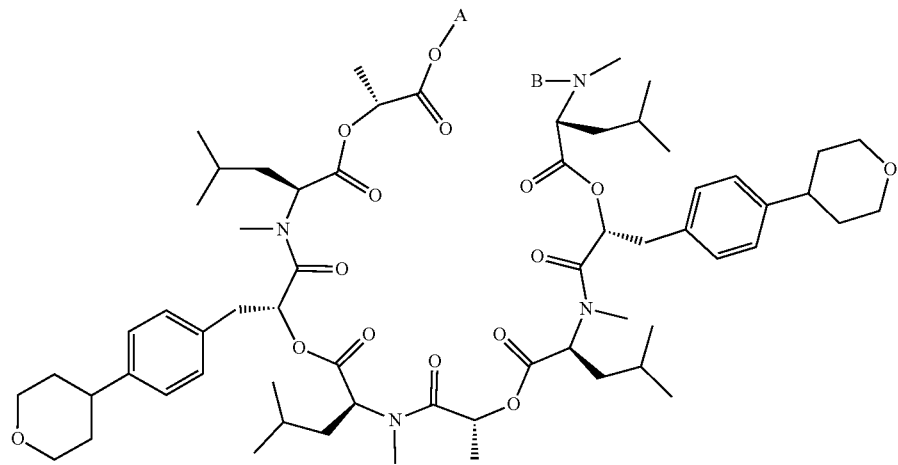
(II-5a)
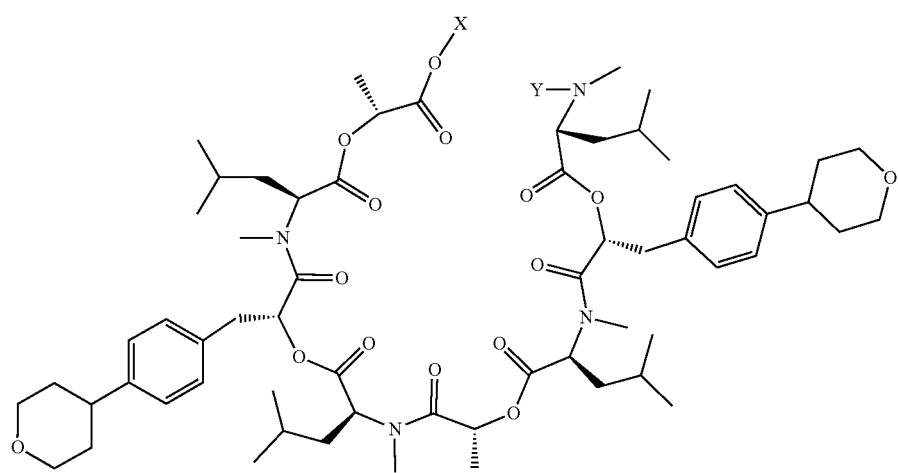
(II-5b)
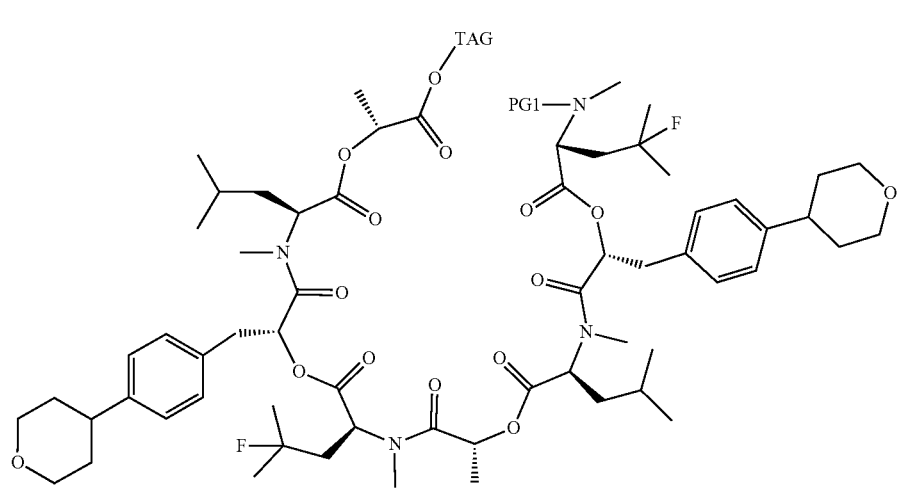
(II-6)

-continued
(II-6a)
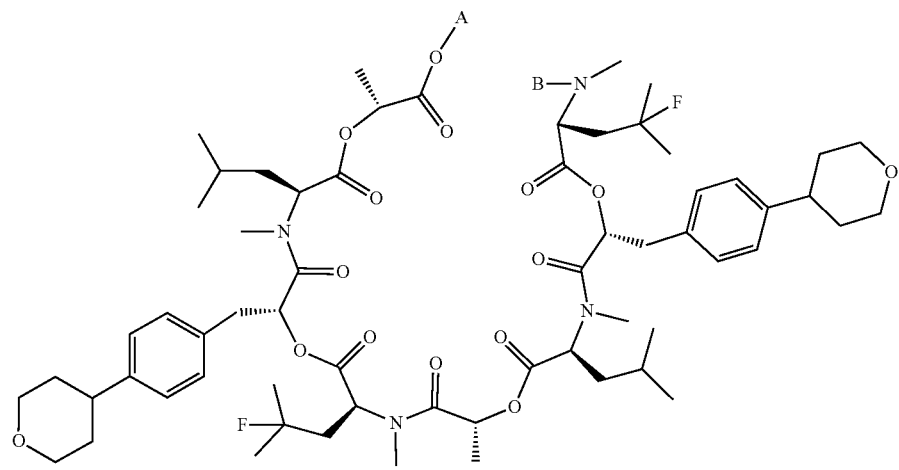
(II-6b)
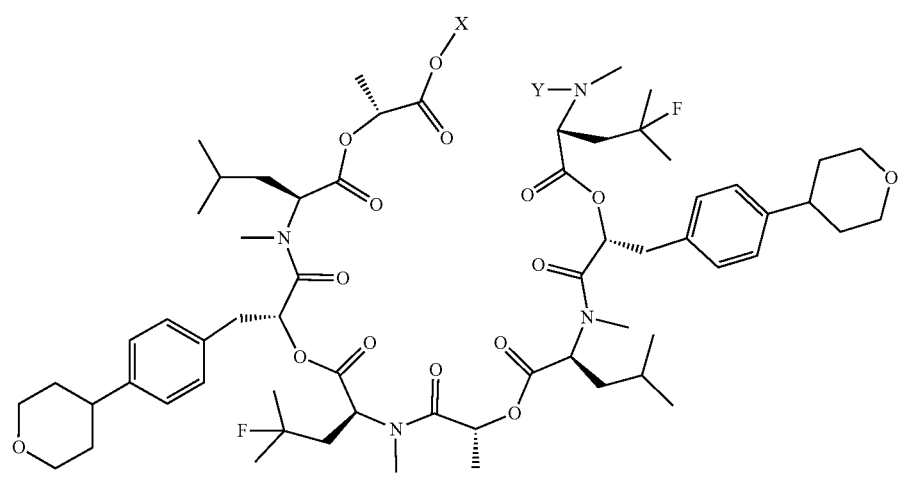
(II-7)
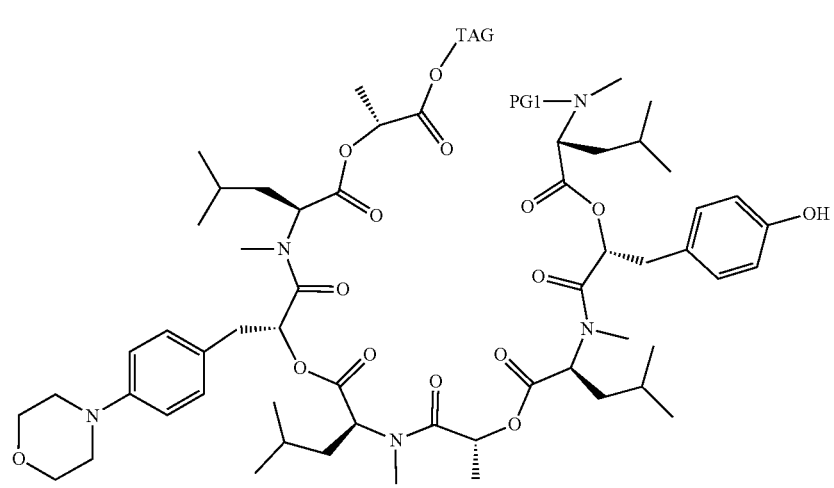

(II-7a)
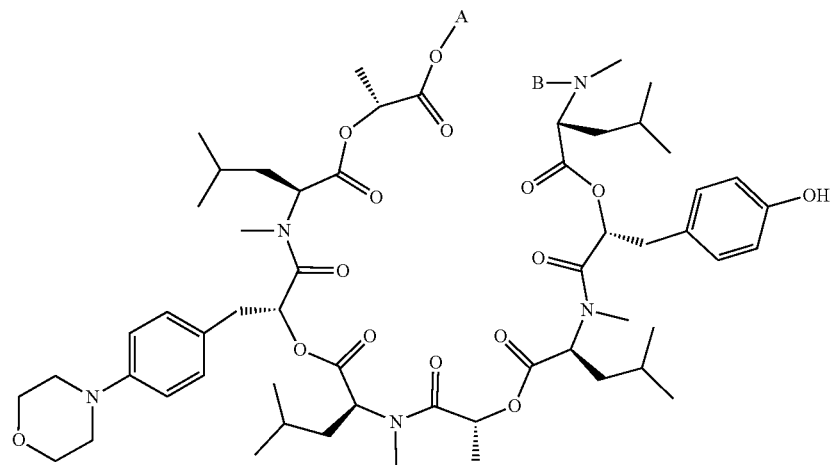
(II-7b)
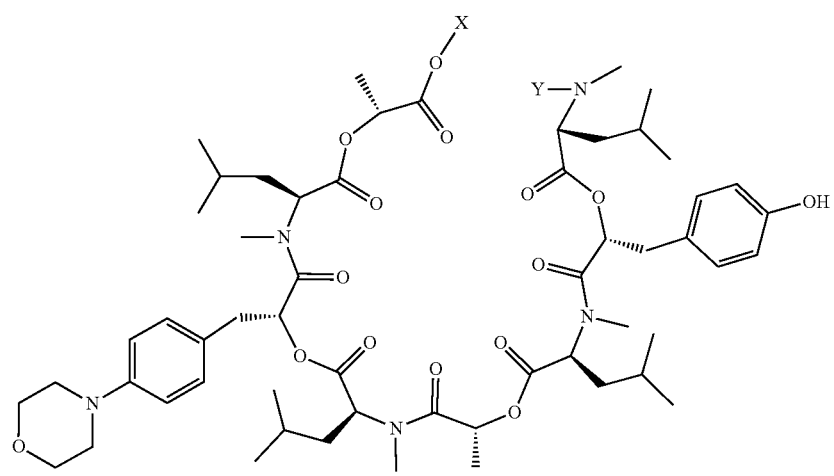
(II-8) (II-8a)
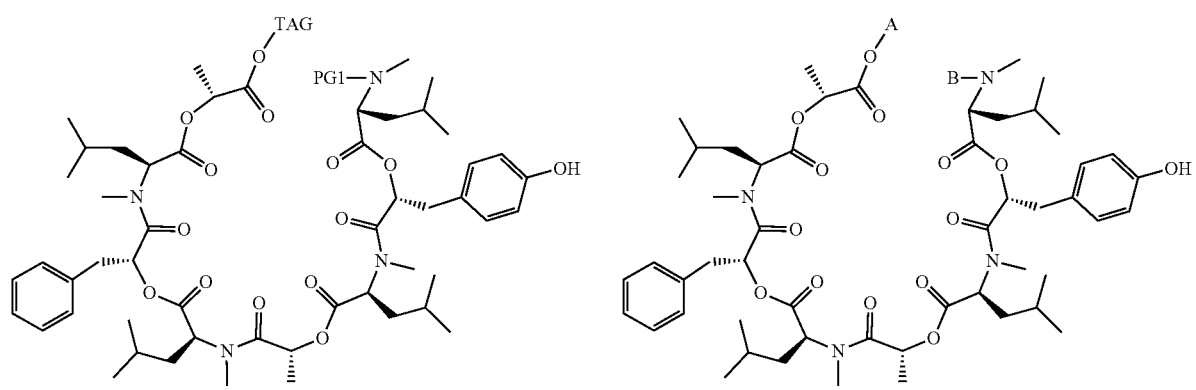

(II-8b)
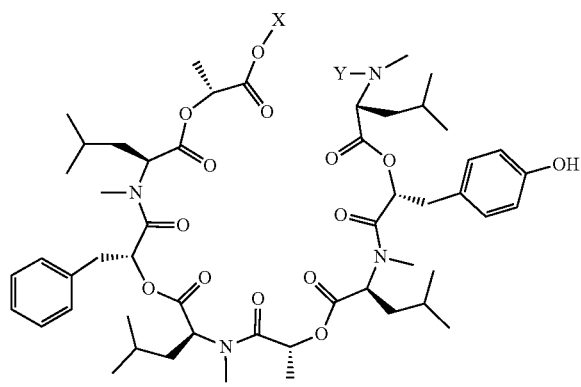
(II-9)
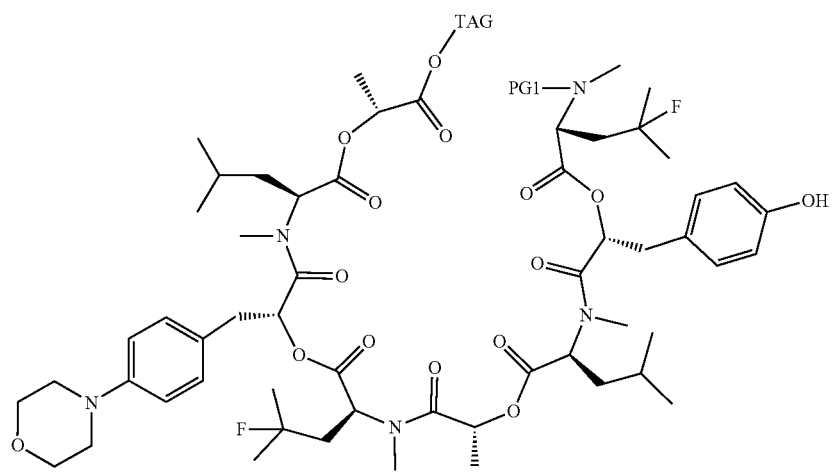
(II-9a)
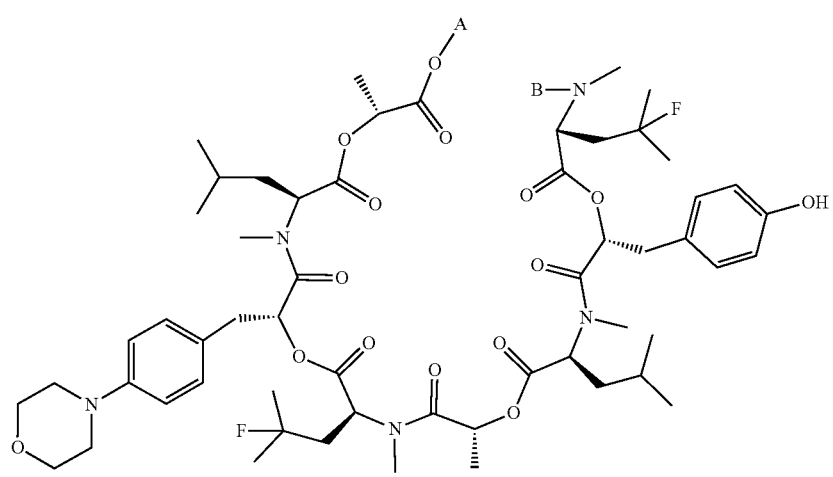

-continued
(II-9b)
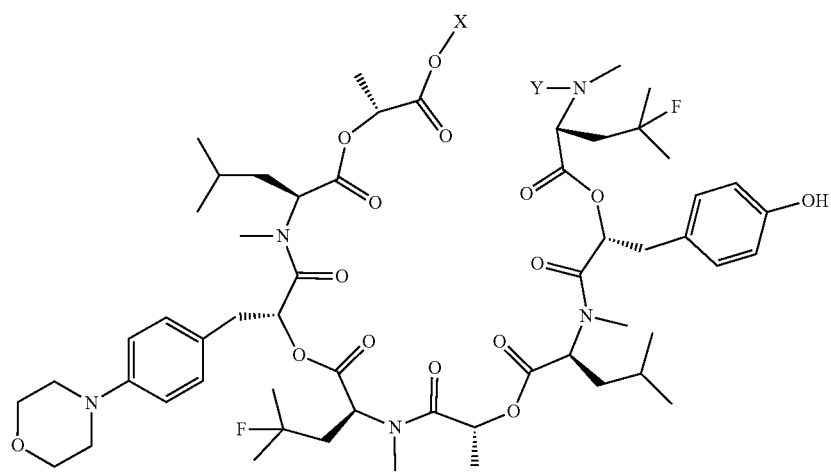
(II-10)
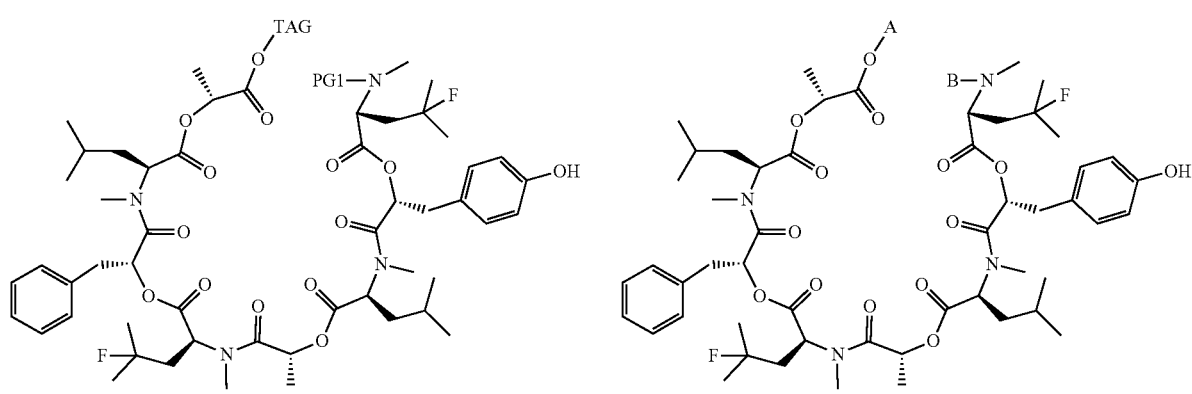
(II-10a)
(II-10b)
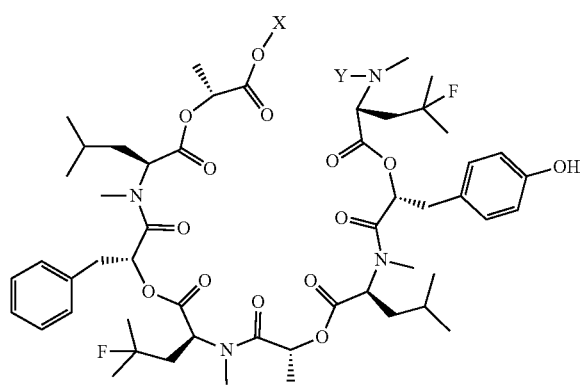

-continued
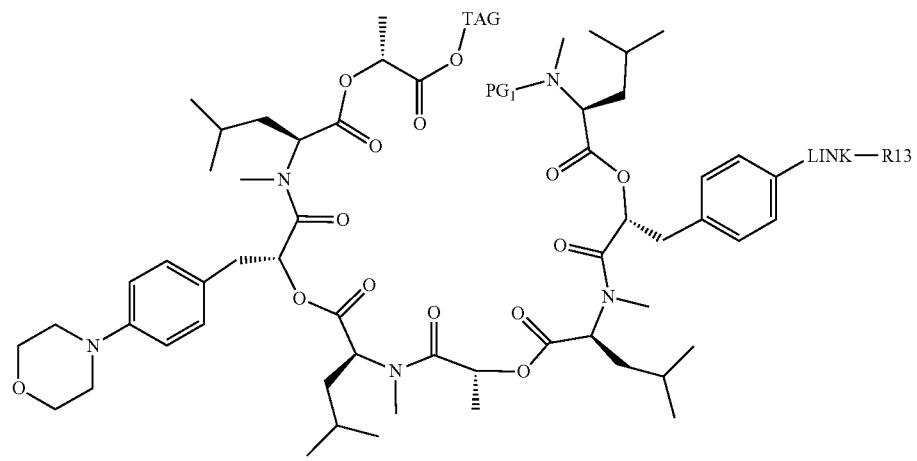
(II-11)
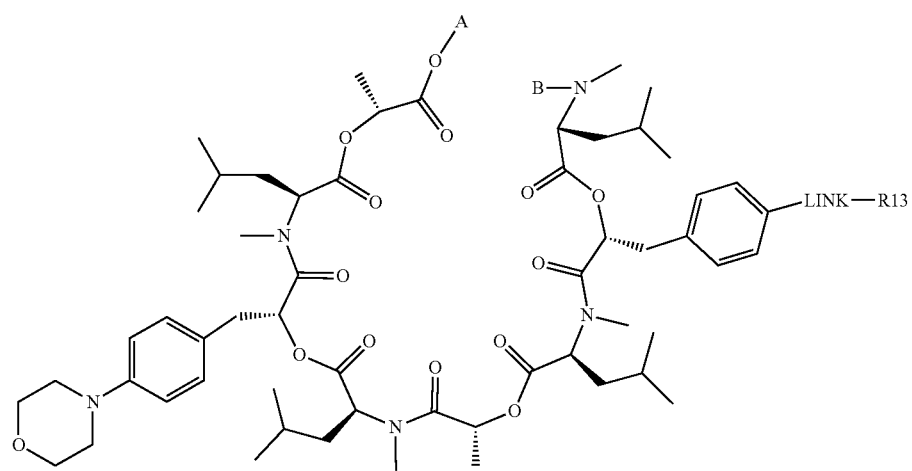
(II-11a)
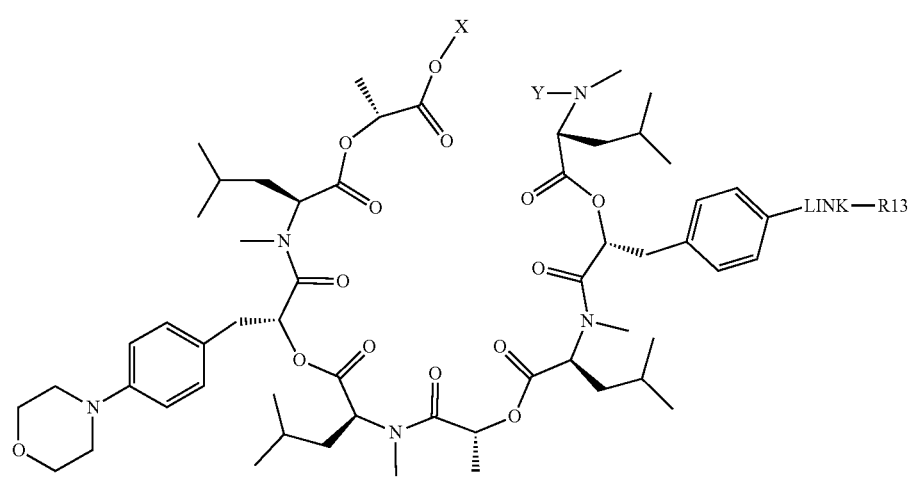
(II-11b)

(II-12)
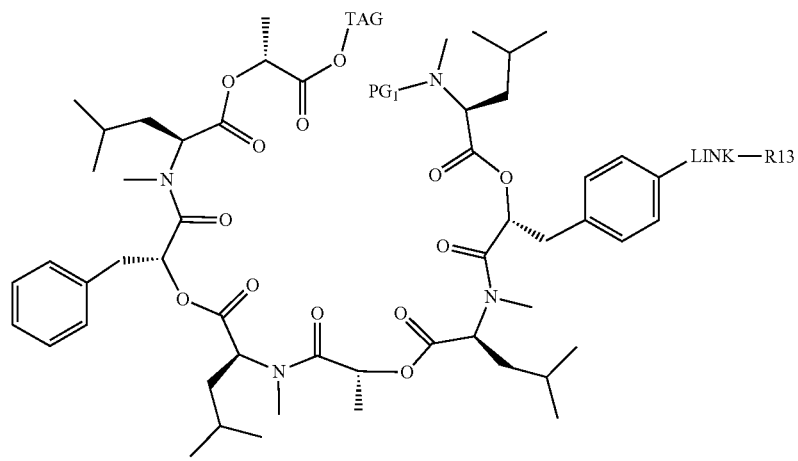
(II-12a)
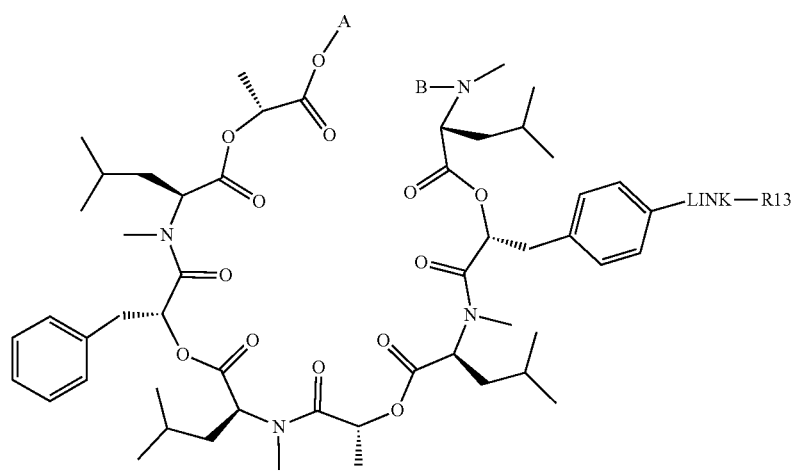
(II-12b)
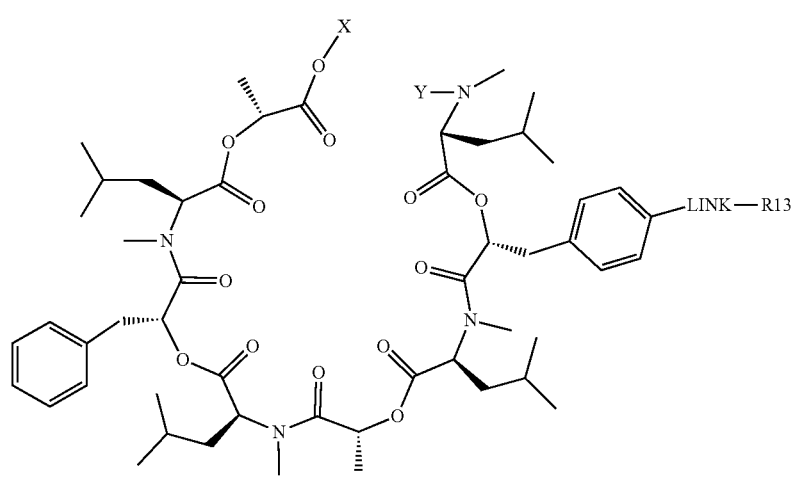

-continued
(II-13)
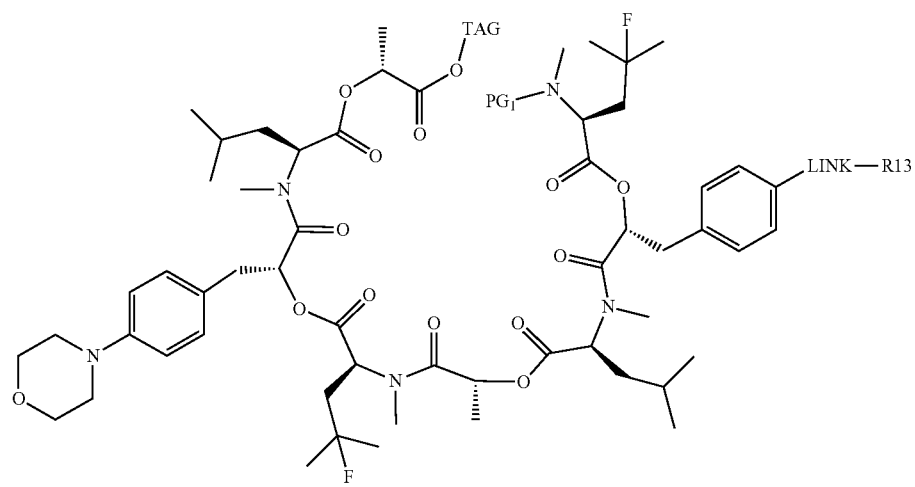
(II-13a)
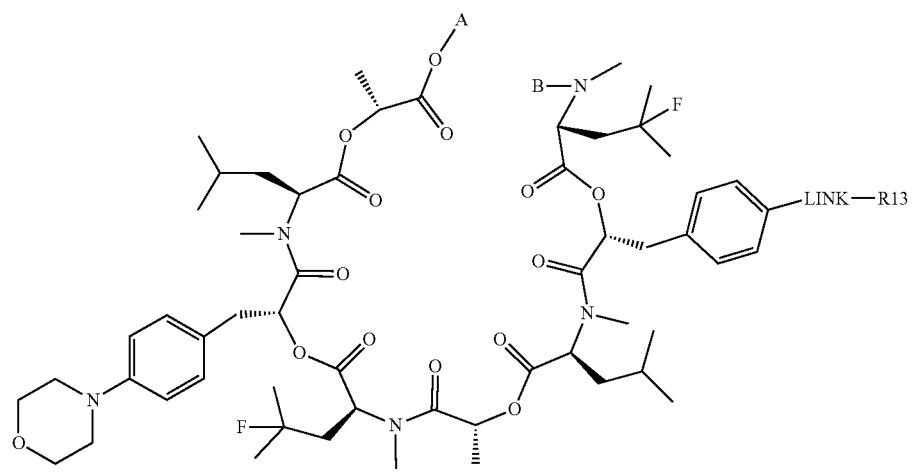
(II13-b)
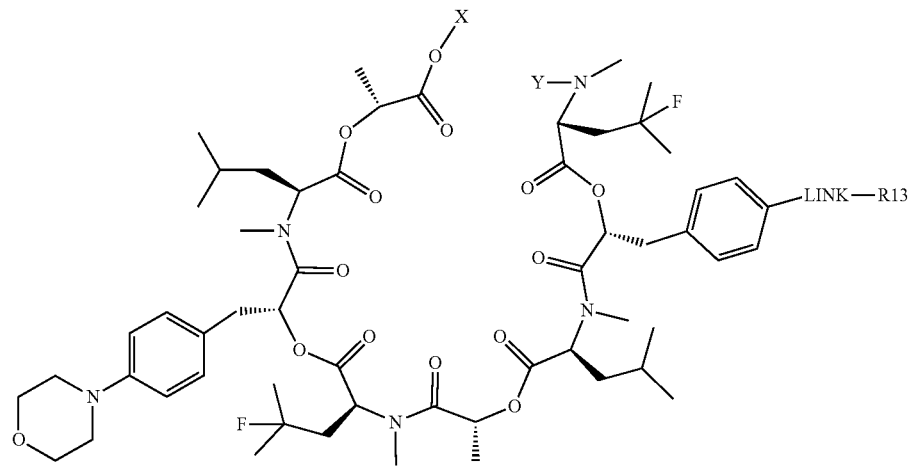

(II-14)
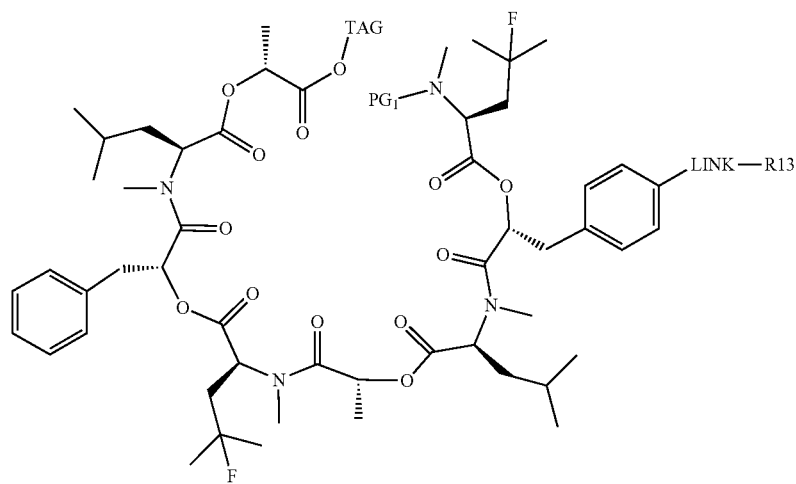
(II-14a)
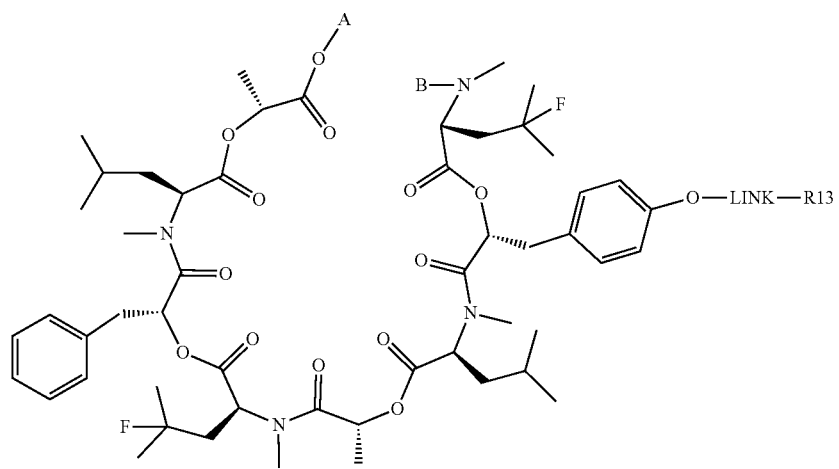
(II-14b)
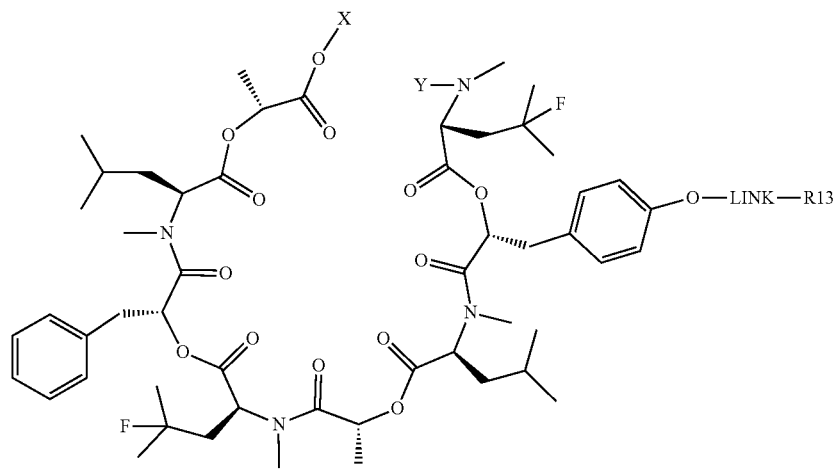

wherein in formulas (II-11) to (II-14)-LINK- is selected from:

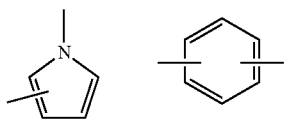

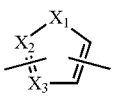

wherein X1 can be C, N, S, O, X2 and X3 can be C or N;

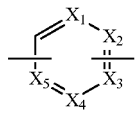

wherein X1 can be C, N, S, O, X2, X3 and X4 can be C or N;

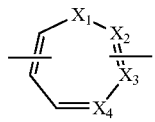

wherein X1, X2, X3 and X4 can be C or N;

and wherein R13 is selected from $SO_2NH(CH_3)$, $SO_2NH_2$, $OC(O)CH_3$, $CF_3$ or one the following lactone structures:

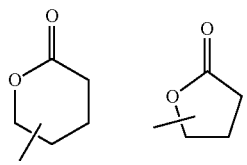

The present invention furthermore provides a method for the synthesis of cyclic depsipeptides according to the general formula (1) from depsipeptides according to the general formula (IIb):

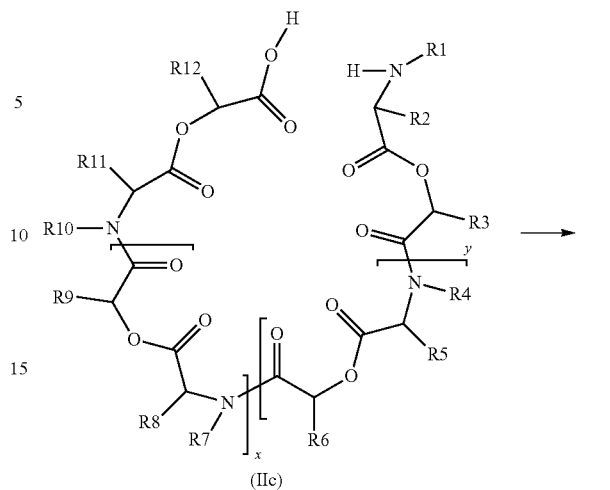

(IIc)

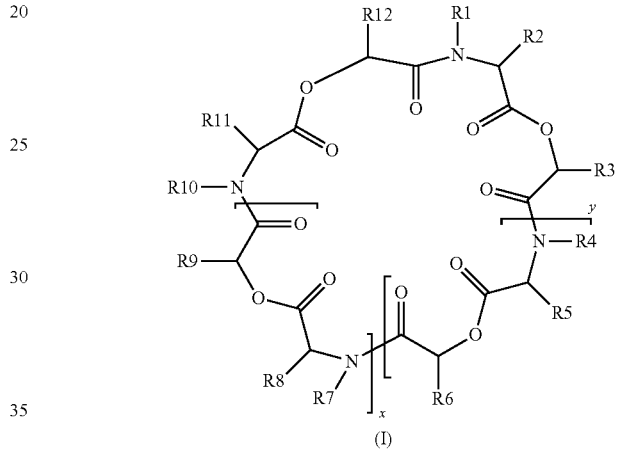

(I)

comprising the steps of
Providing a mixture of compound (IIc) and a base in a solvent having an $E_T(30)$-value of ≥30 and ≤43
Slow, preferably dropwise addition of a solution of a coupling agent in the solvent to form the cyclic depsipeptide (I)
whereby x and y are, independent of each other, 0, 1 or 2 with the proviso that x+y≥1 (preferably, x and y are 1) and R1, R2, R3, R4, R5, R6, R7, R8, R9, R10, R11 and R12 each, independent of each other, represent hydrogen, straight-chain or branched C1-C8-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, straight-chain or branched halogenated C1-C8 alkyl, in particular fluorinated sec-butyl, hydroxy-C1-C6-alkyl, in particular hydroxymethyl, 1-hydroxyethyl, C1-C4-alkanoyloxy-C1-C6-alkyl, in particular acetoxymethyl, 1-acetoxyethyl, C1-C4-alkoxy-C1-C6-alkyl, in particular methoxymethyl, 1-methoxyethyl, aryl-C1-C4-alkyloxy-C1-C6-alkyl, in particular benzyloxymethyl, 1-benzyloxyethyl, mercapto-C1-C6-alkyl, in particular mercaptomethyl, C1-C4-alkylthio-C1-C6-alkyl, in particular methylthioethyl, C1-C4-alkylsulphinyl-C1-C6-alkyl, in particular methylsulphinylethyl, C1-C4-alkylsulphonyl-C1-C6-alkyl, in particular methylsulphonylethyl, carboxy-C1-C6-alkyl, in particular carboxymethyl, carboxyethyl, C1-C4-alkoxycarbonyl-C1-C6-alkyl, in particular methoxycarbonylmethyl, ethoxycarbonylethyl, C1-C4-arylalkoxycarbonyl-C1-C6-alkyl, in particular benzyloxycarbonylmethyl, carbamoyl-C1-C6-alkyl, in particular carbamoylmethyl, carbamoylethyl, amino-C1-C6-alkyl, in particular aminopropyl, aminobutyl, C1-C4-alkylamino-C1-C6-alkyl, in particular methylaminopropyl, methylaminobutyl, C1-C4-dialkylamino-C1-C6-alkyl, in particular dimethylaminopropyl, dimethylaminobutyl, guanidino-C1-C6-alkyl, in particular guanidinopropyl, C1-C4-alkoxycarbonylamino-C1-C6-alkyl, in particular tert-butoxycarbonylaminopropyl, tert-butoxycarbonylaminobutyl, 9-fluorenylmethoxycarbonyl(Fmoc)amino-C1-C6-alkyl, in particular 9-fluorenylmethoxycarbonyl(Fmoc)aminopropyl, 9-fluorenylmethoxycarbonyl(Fmoc)aminobutyl, C2-C8-alkenyl, in particular vinyl, allyl, butenyl, C3-C7-cycloalkyl, in particular cyclopentyl, cyclohexyl, cycloheptyl, C3-C7-cycloalkyl-C1-C4-alkyl, in particular cyclopentylmethyl, cyclohexylmethyl, cycloheptylmethyl, benzyl, substituted benzyl, phenyl, phenyl-C1-C4-alkyl, in particular phenylmethyl which may optionally be substituted by radicals from the group consisting of halogen, in particular fluorine, chlorine, bromine or iodine.

The term "slow" especially means and/or includes that the solution of coupling agent is added at a rate of ≤2 (mol)-% per minute, preferably ≤1 (mol)-% per minute more preferred ≤0.5 (mol)-% per minute.

In the method according to the invention it has surprisingly been found that cyclic depsipeptides (I), in particular emodepside and closely related structures, can be synthesized in high overall yields. Without being bound to any theory, the inventors believe that this is due to the poor solubility of the cyclic depsipeptide (I) in the solvent in contrast to the open form (IIb).

The term "$E_T(30)$-value" refers to the $E_T(30)$ according Reichardt, Angew. Chem. 1979, 119-131, where both a method to determine such values as well as measured values for many standard solvents are listed.

According to one embodiment of the present invention, the $E_T(30)$-value of the solvent is ≥34 and ≤39.

The term "solvent" in the sense of the present invention shall also include a mixture of solvents.

According to one embodiment of the present invention, the solvent comprises ethyl acetate, according to one embodiment of the present invention, the solvent is ethyl acetate.

Suitable coupling agents which are embodiments of the present invention are given above. According to one embodiment of the present invention, the coupling agent comprises T3P, according to one embodiment of the present invention, the coupling agent is T3P.

According to one embodiment, the ratio of coupling agent to compound (IIc) prior to the reaction (in mol:mole) is ≥1:1 to ≤5:1, preferably ≥2:1 to ≤3:1.

According to one embodiment, the ratio of base to compound (IIb) prior to the reaction (in mol:mole) is ≥2:1 to ≤10:1, preferably ≥4:1 to ≤6:1.

Suitable bases which insofar are embodiments of the present invention comprise N,N-diisopropylethylamine (DIEA), Triethylamine, Dimethylaminopyridine (DMAP), N-methylmorpholine, pyridine, 1,8-diazabicyclo[5.4.0]undec-7-ene (DBU), 1,5-diazabicyclo[4.3.0]non-5-ene (DBN) or mixtures thereof. Most preferred is N,N-diisopropylethylamine.

According to one embodiment, the temperature during the addition of the coupling agent is ≤25° C.

In one embodiment of the method according to the invention x is 1, y is 1, R1, R4, R7 and R are methyl, R6 and R12 are methyl, R5 and R11 are, independent of each other, straight-chain or branched C1-C4-alkyl or straight-chain or branched halogenated C1-C4-alkyl and R3 and R9 are, independent of each other, benzyl or substituted benzyl. According to one embodiment of the preferred invention, R3 and/or R9 are p-morpholino substituted benzyl.

In one embodiment of the method according to the invention R3 and R9 are identical, R1 and R7 are identical, R2 and R8 are identical, R4 and R1 are identical, R5 and R11 are identical and R6 and R12 are identical.

According to a preferred embodiment of the present invention, the compound IIb is synthesized from compound II or IIa by deprotecting the protective groups A and B or X and Y respectively. Compound IIb can be isolated or used in situ to synthesize the depsipeptide (I).

The present invention is also directed towards a linear or cyclic depsipeptide selected from one of the general formulas (II-1) to (II-14b) or (I-1) to (I-9) as depicted below or a pharmaceutically or veterinarily acceptable salt thereof:

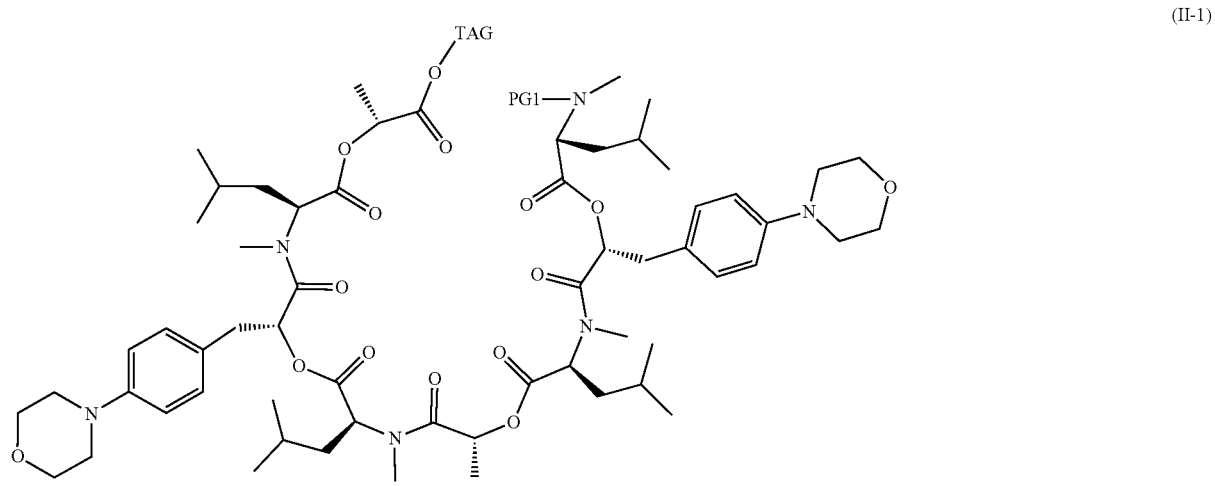

(II-1)

(II-1a)
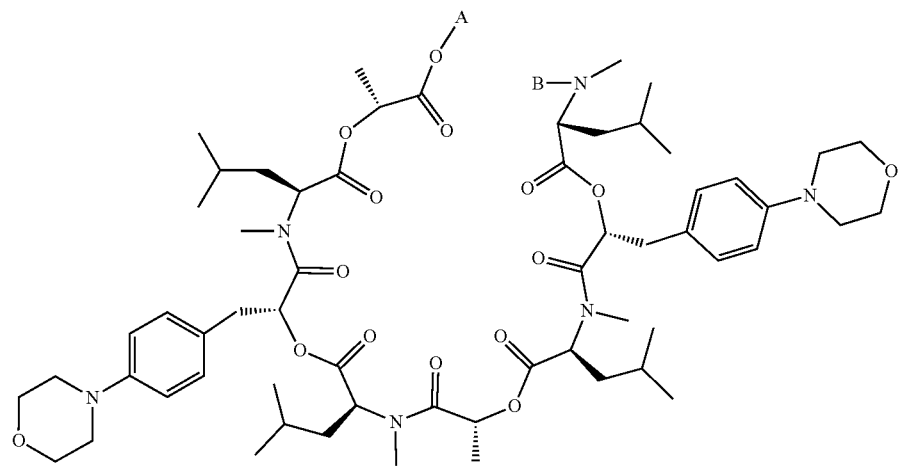
(II-1b)
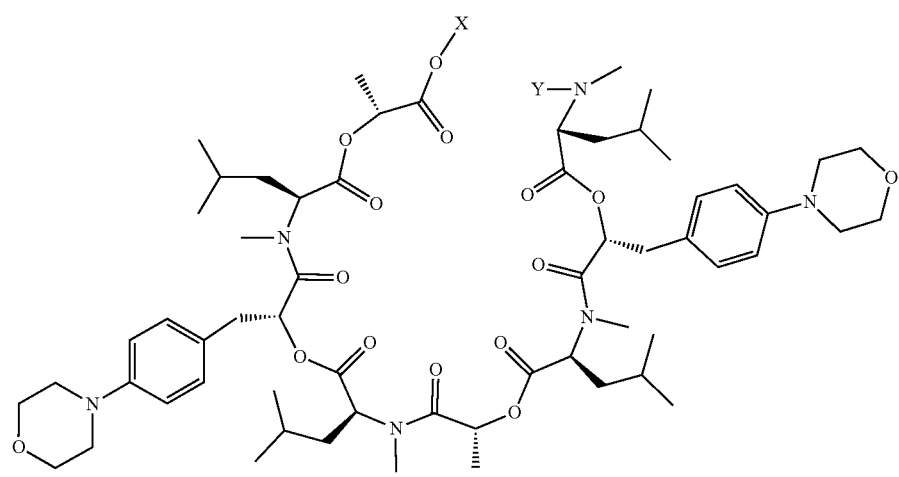
(II-2)
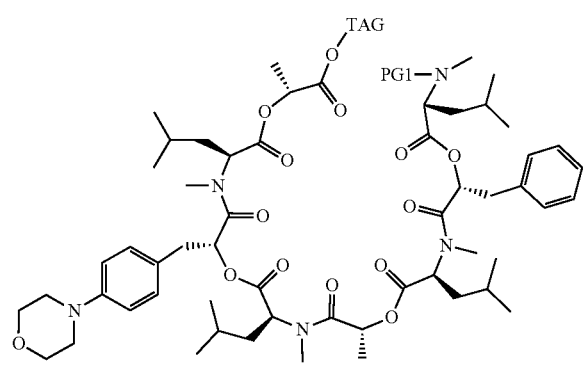
(II-2a)
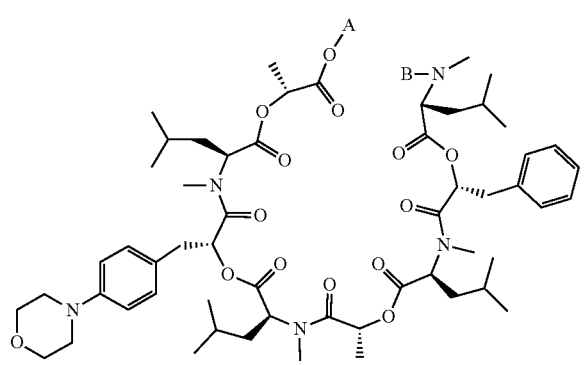

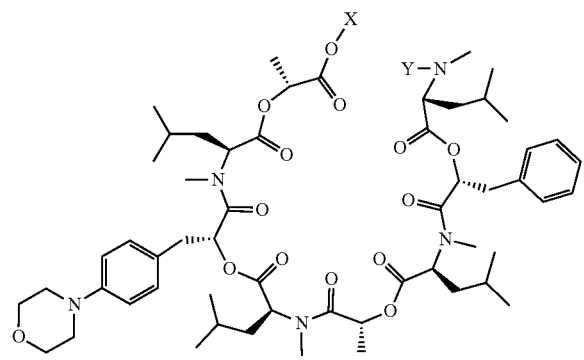
(II-2b)
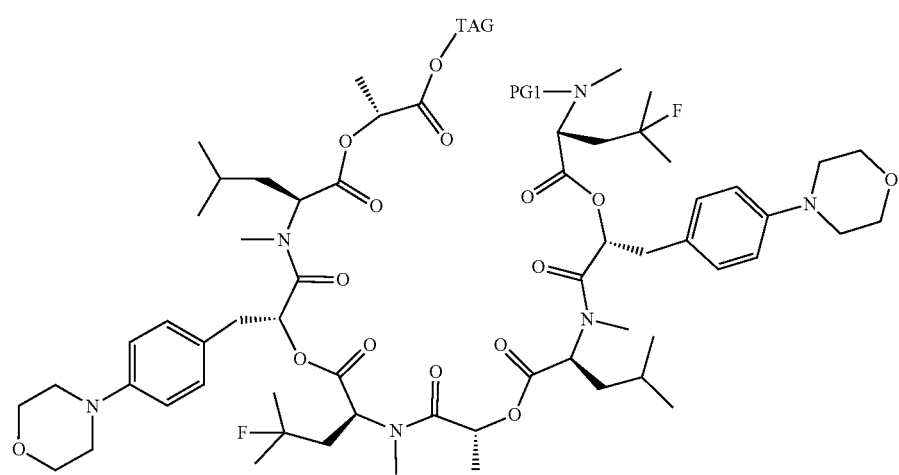
(II-3)
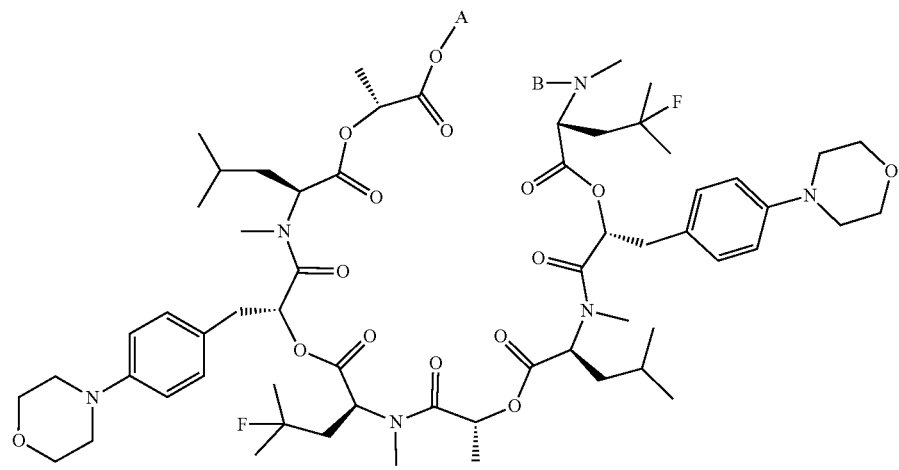
(II-3a)

(II-3b)
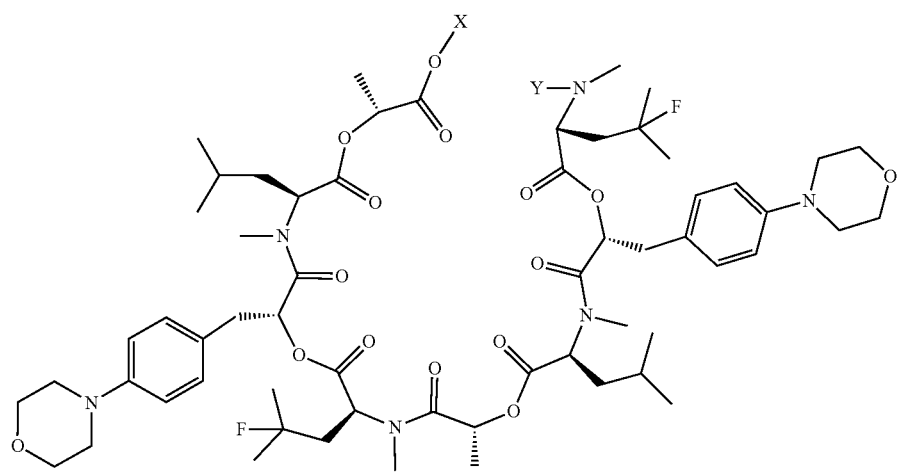
(II-4)
(II-4a)
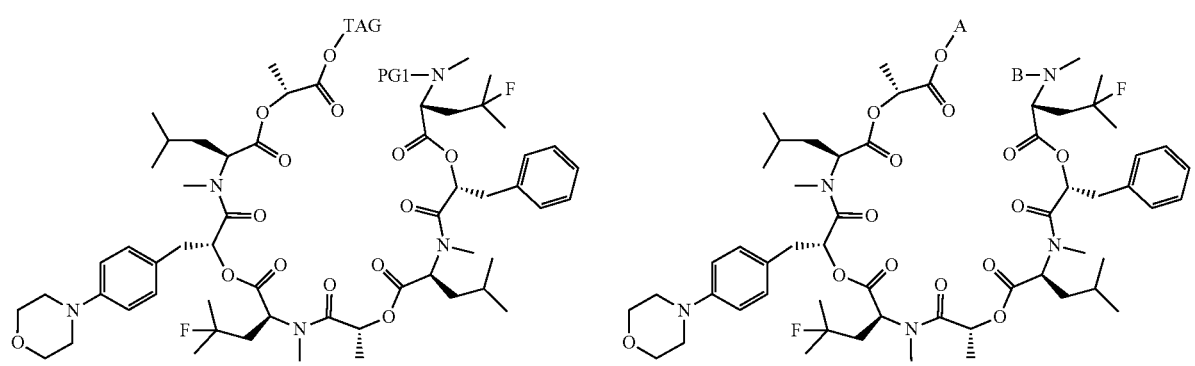
(II-4b)
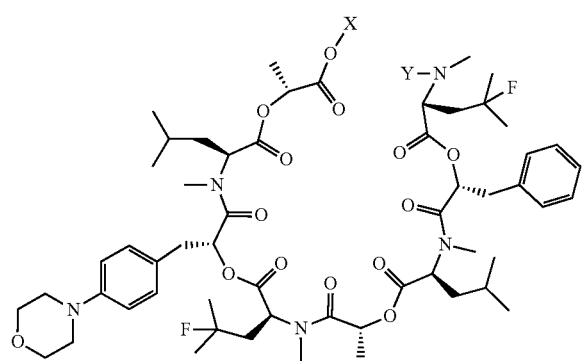

(II-5)
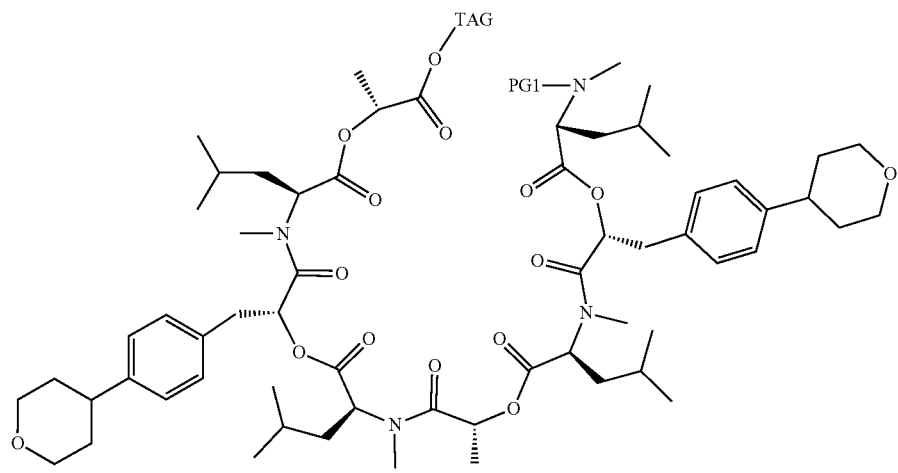
(II-5a)
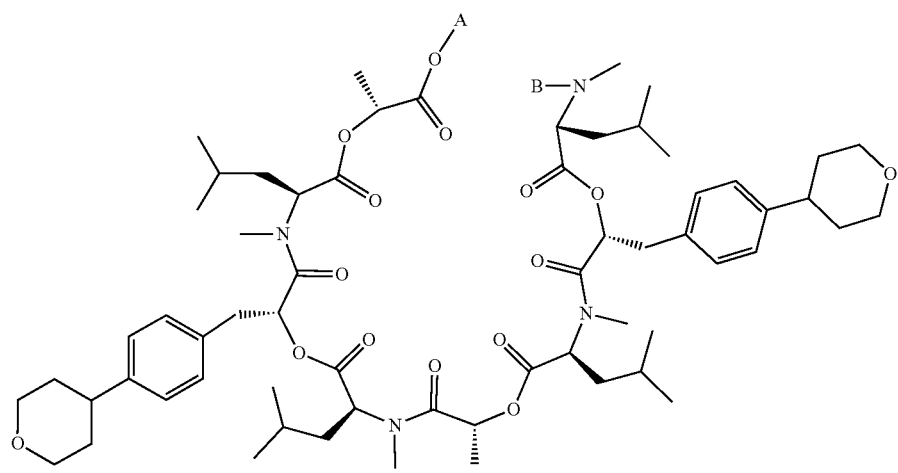
(II-5b)
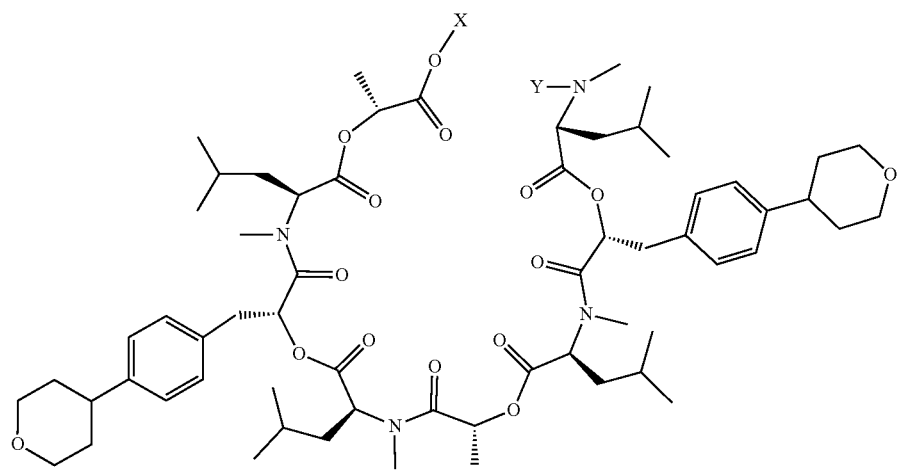

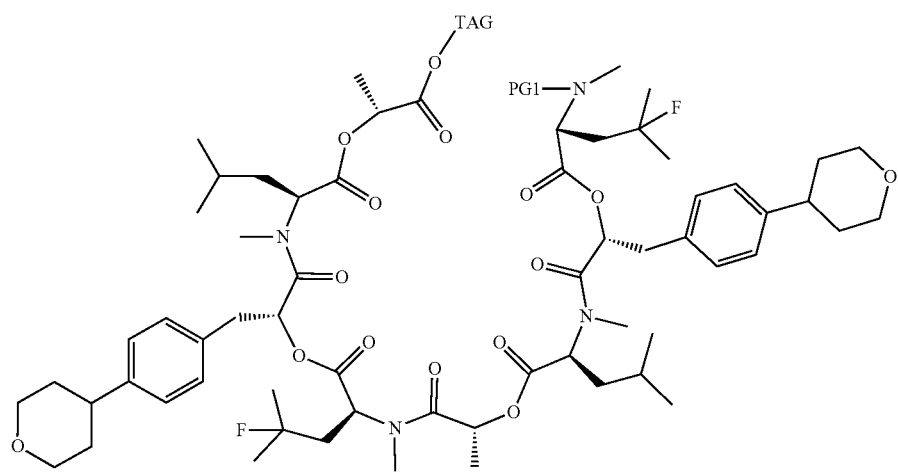
(II-6)
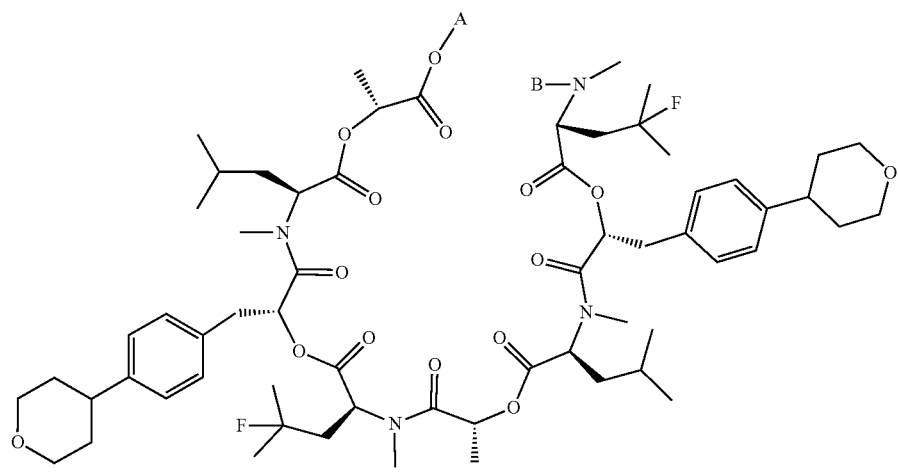
(II-6a)
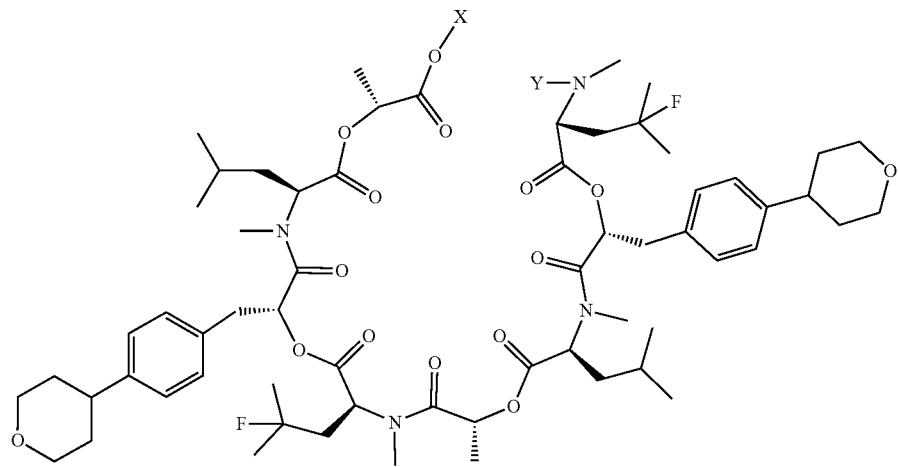
(II-6b)

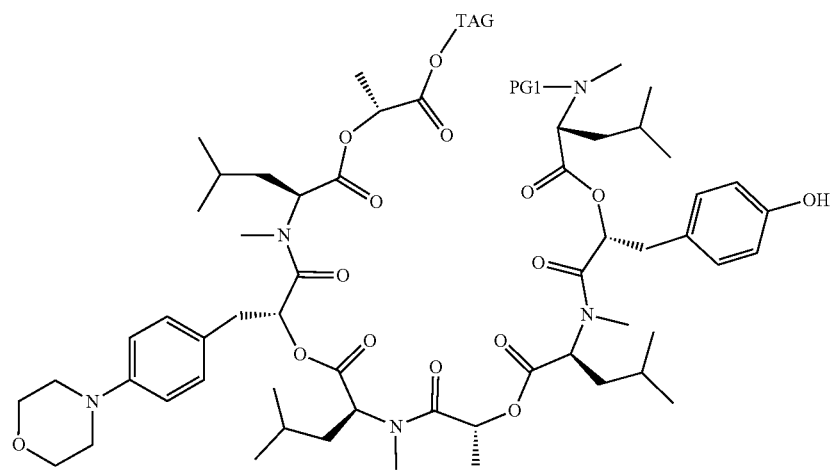
(II-7)
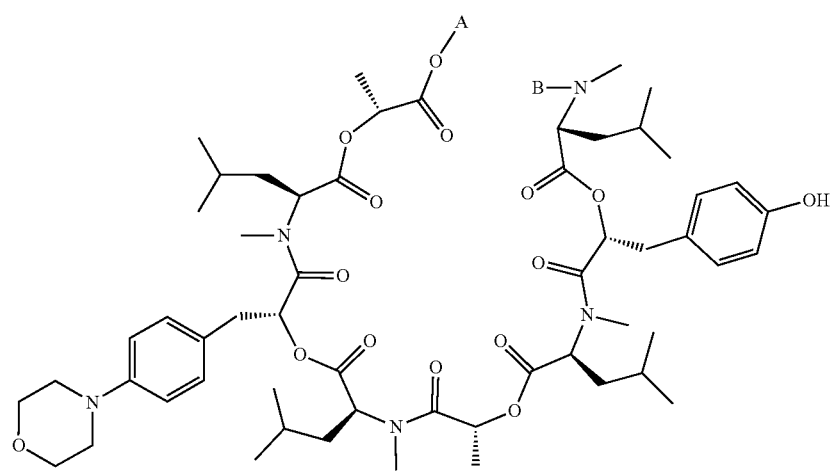
(II-7a)
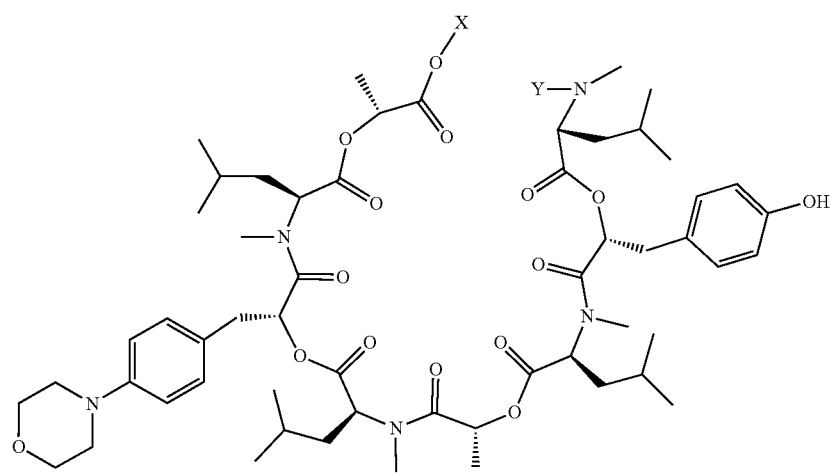
(II-7b)

(II-8)
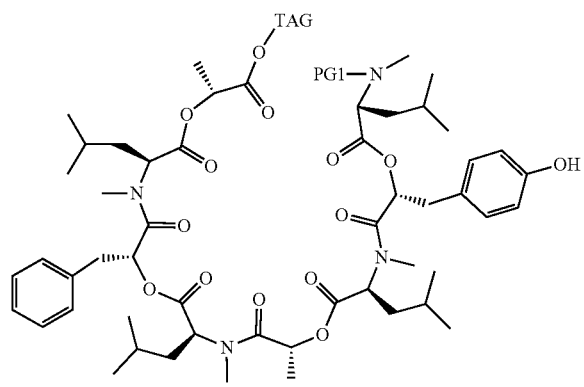
(II-8a)
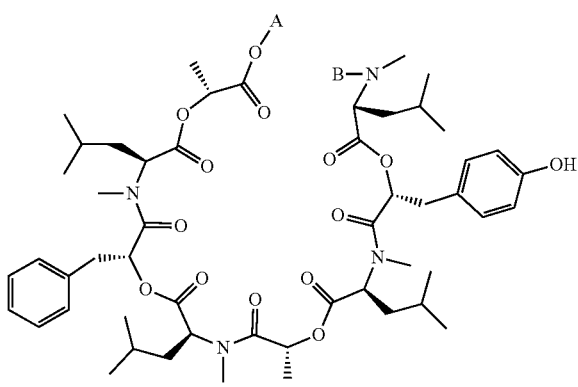
(II-8b)
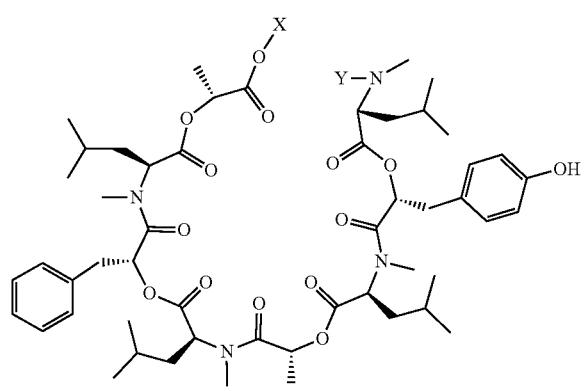
(II-9)
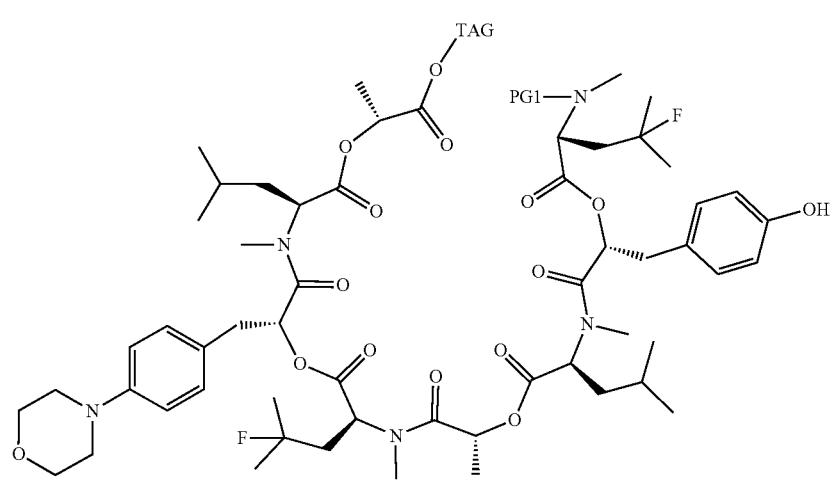

(II-9a)
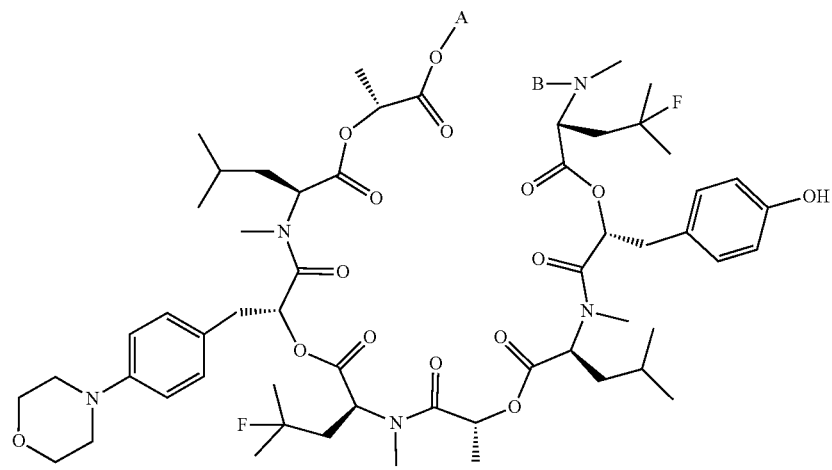
(II-9b)
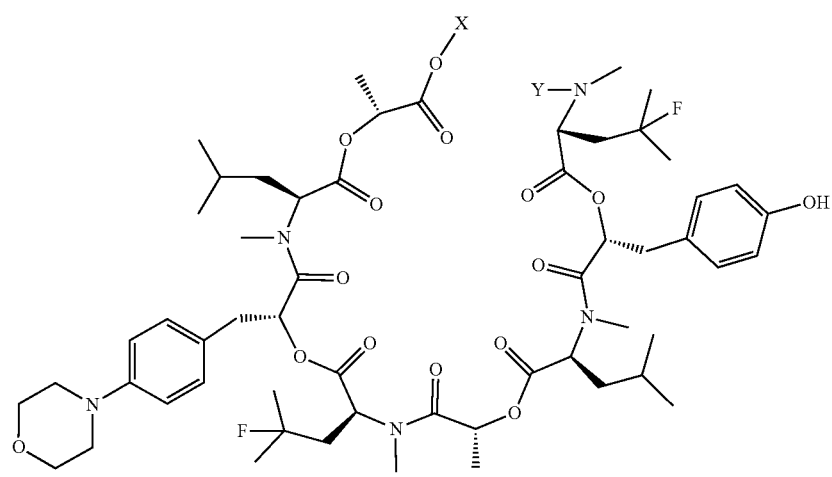
(II-10) (II-10a)
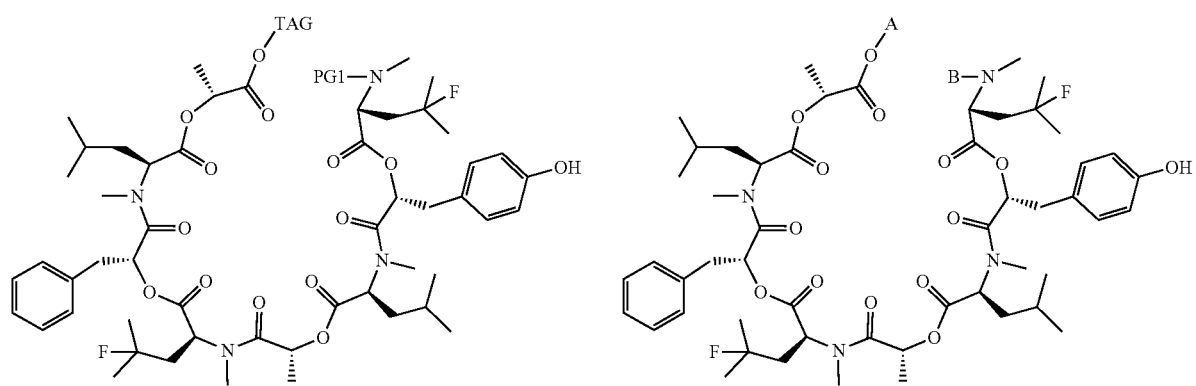

(II-10b)
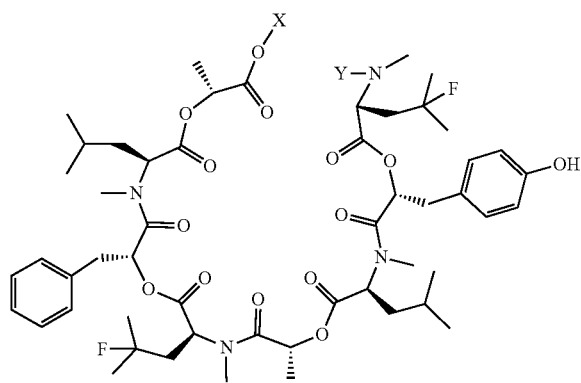
(II-11)
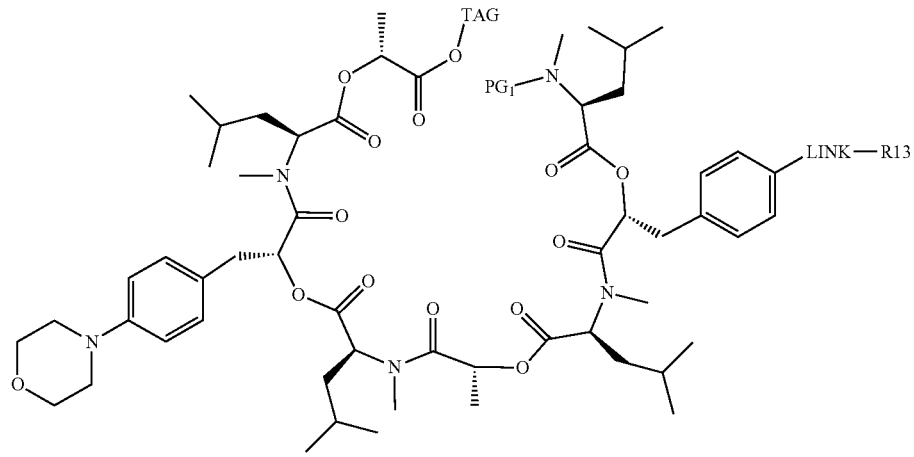
(II-11a)
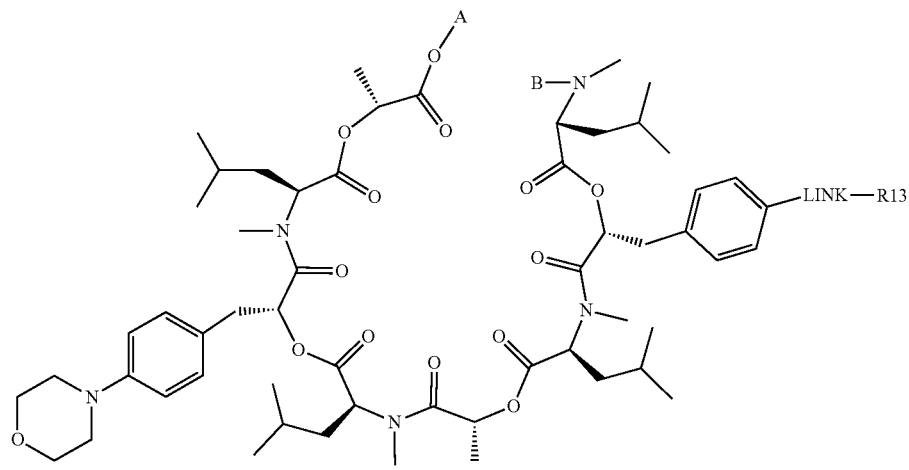

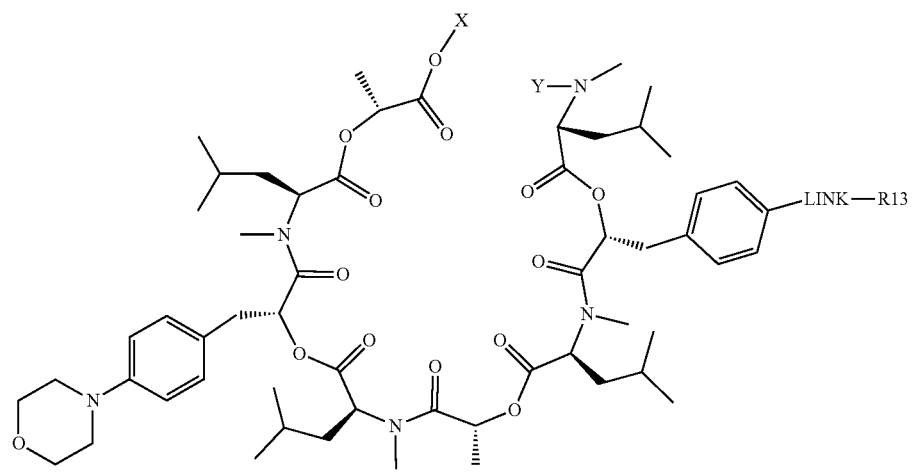
(II-11b)
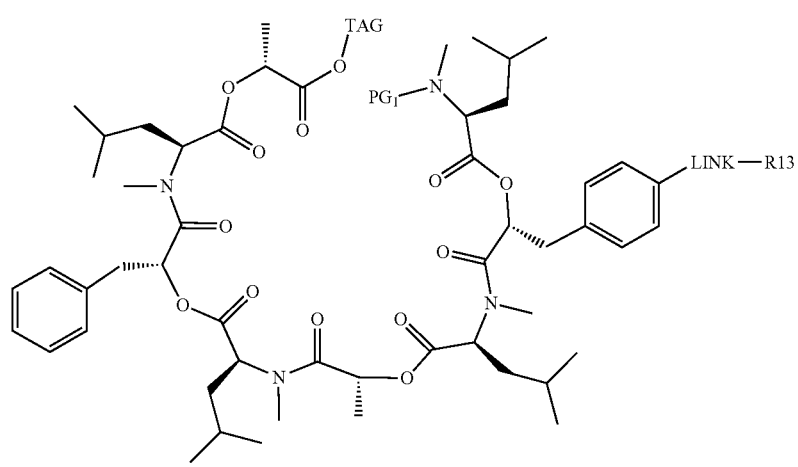
(II-12)
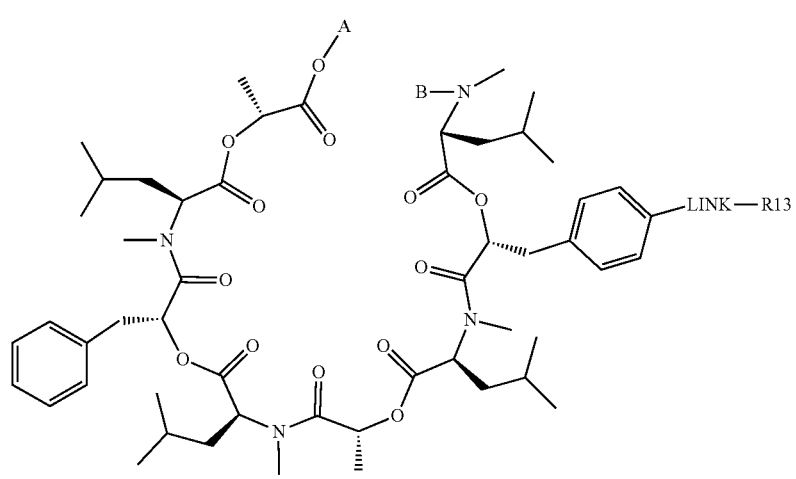
(II-12a)

(II-12b)
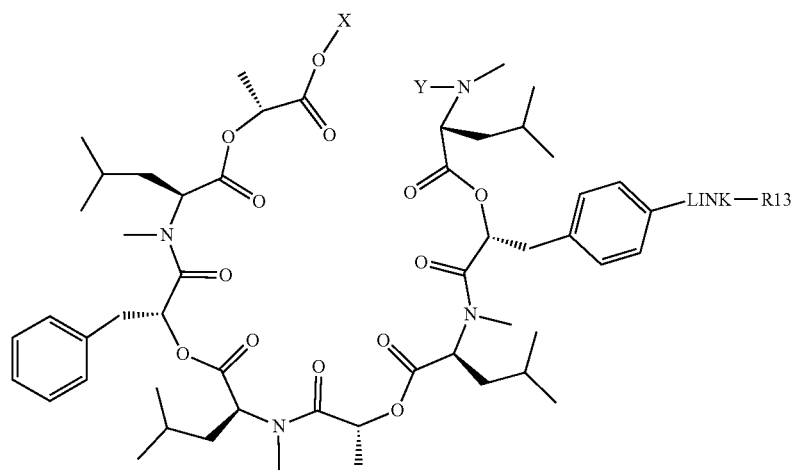
(II-13)
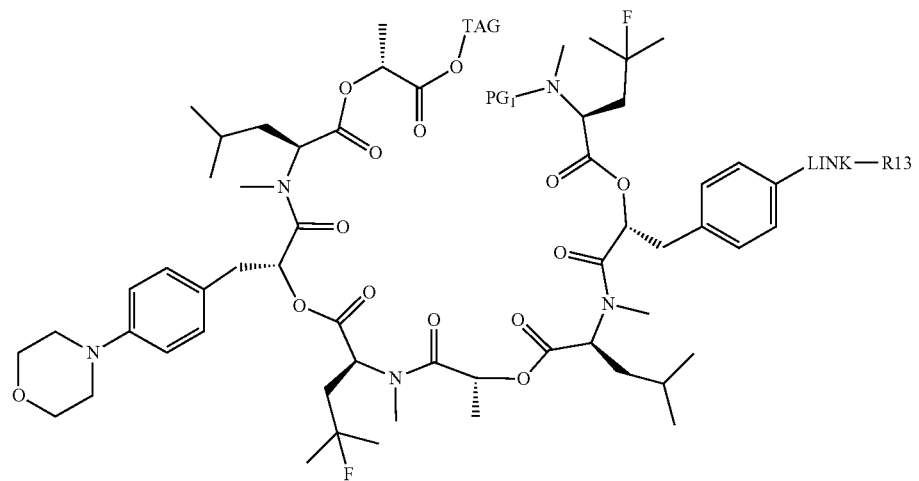
(II-13a)
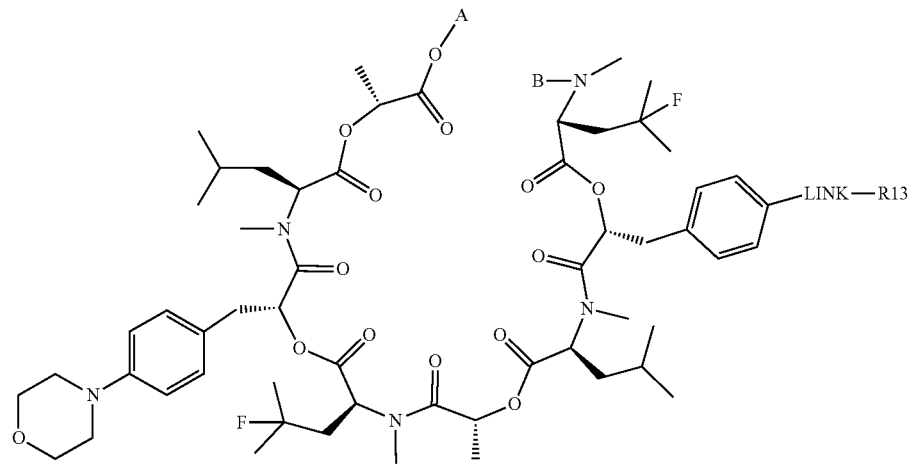

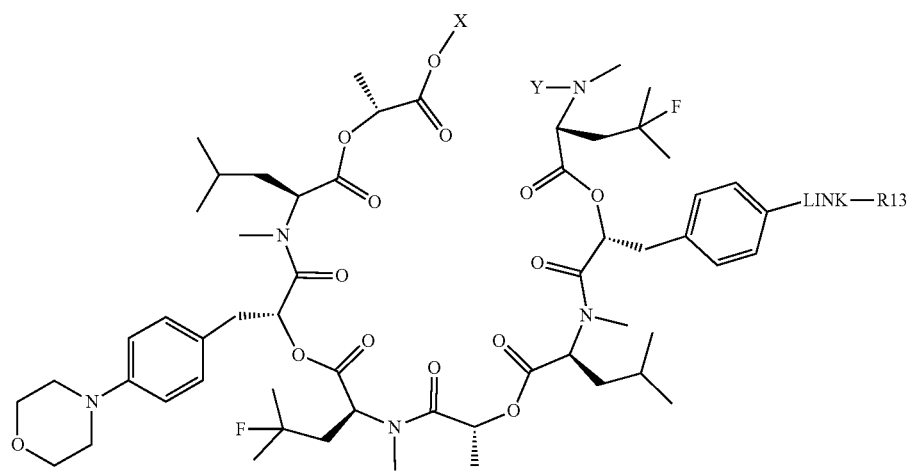
(II13-b)
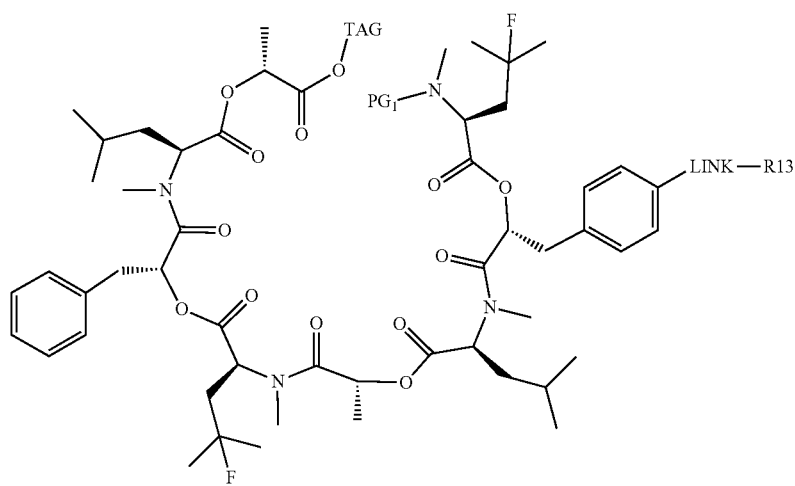
(II-14)
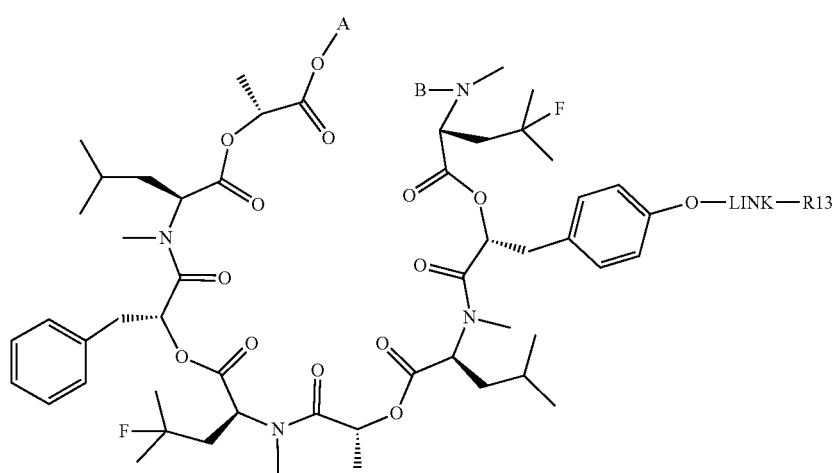
(II-14a)

-continued
(II-14b)
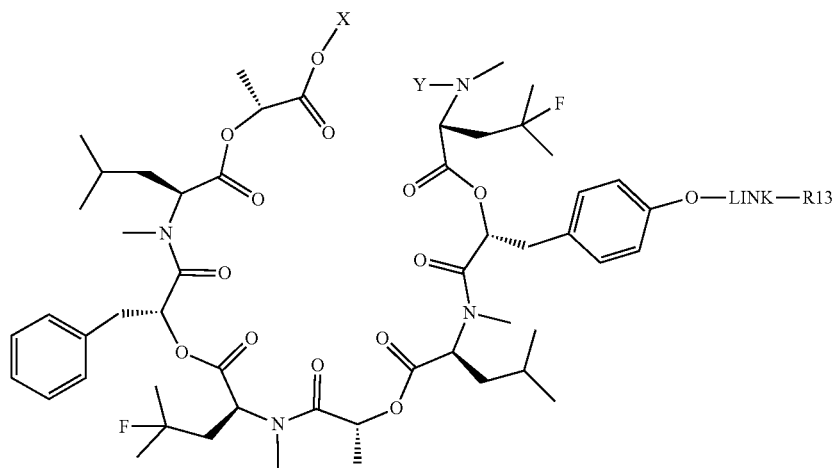
(I-1)
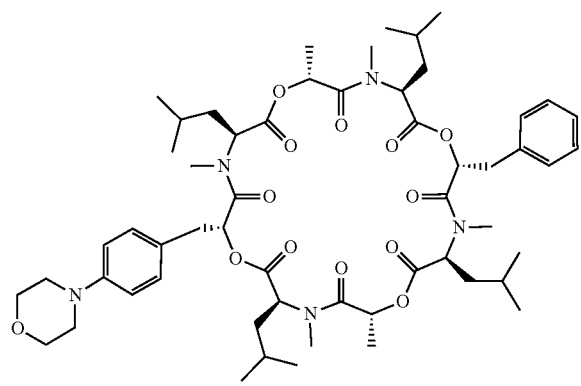
(I-2)
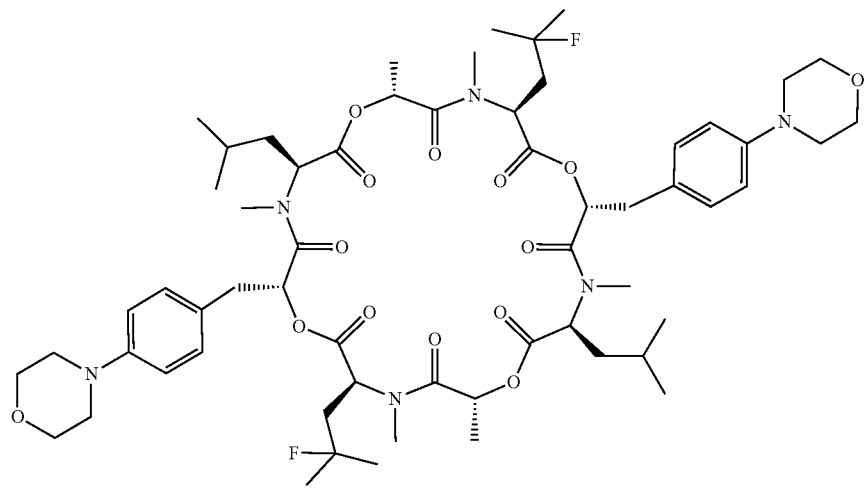

(I-3)
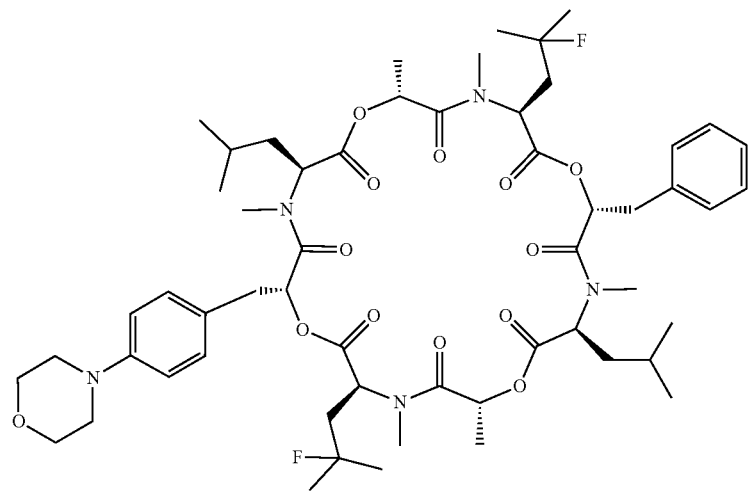
(I-4)
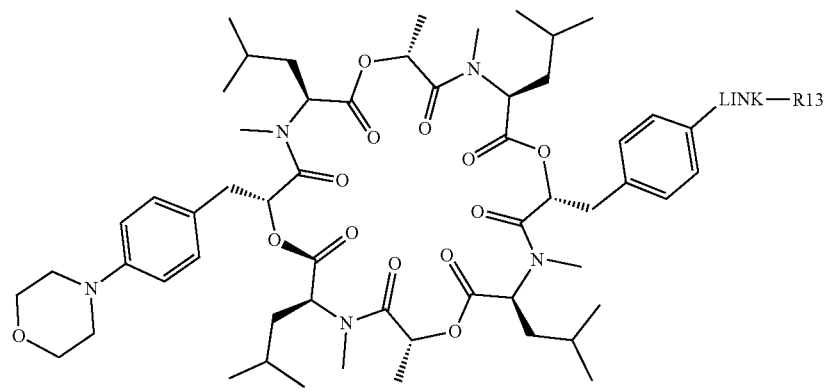
(I-5)
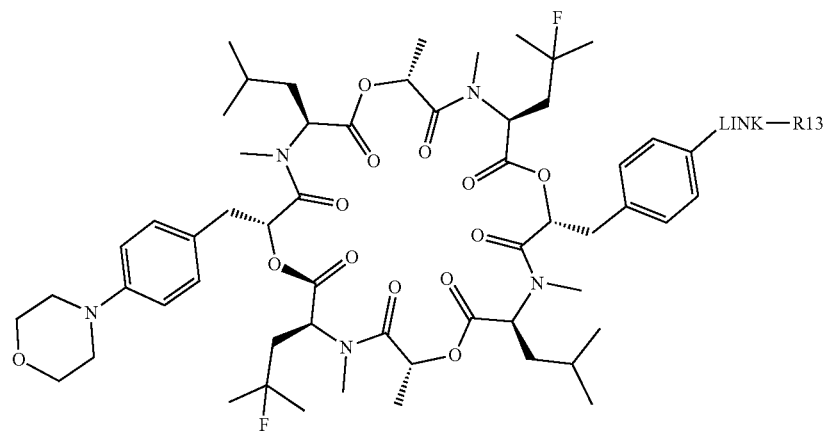

-continued (I-6)

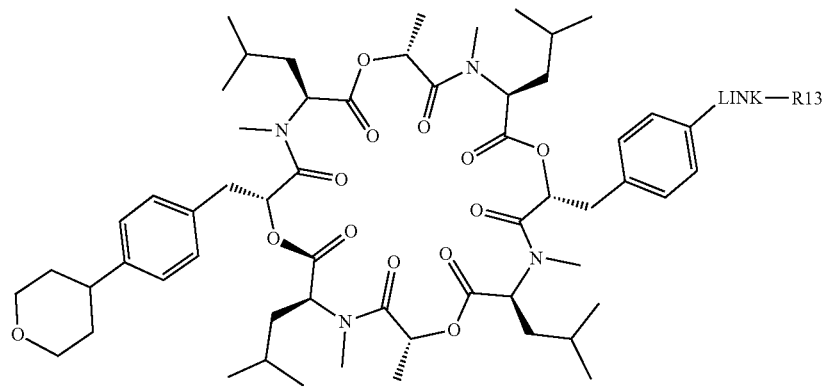

(I-7)

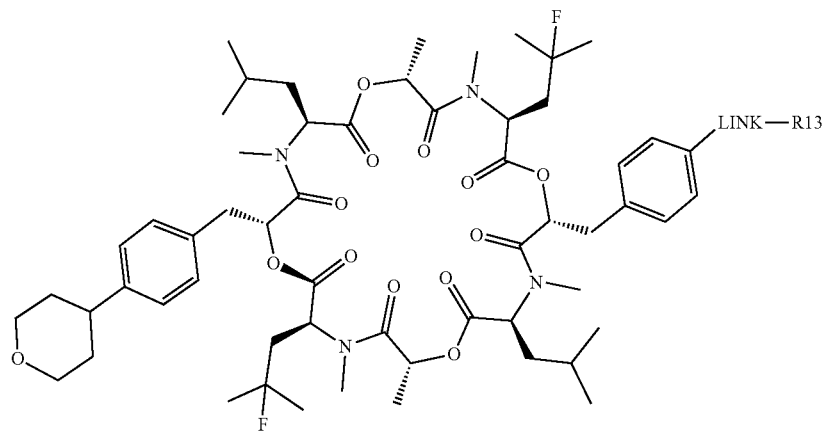

(I-9)

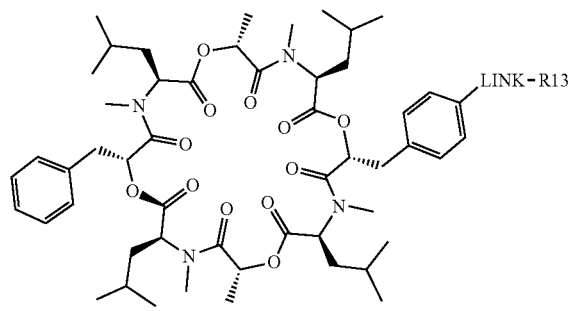

(I-8)

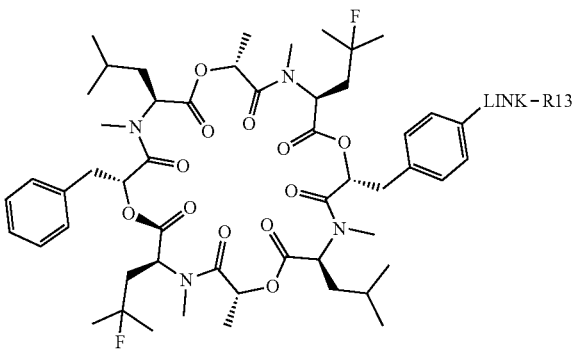

wherein in formulas (II-11) to (II-14) and (I-1) to (I-9), respectively:

A, B, X and Y are defined as above,

-LINK- is selected from:

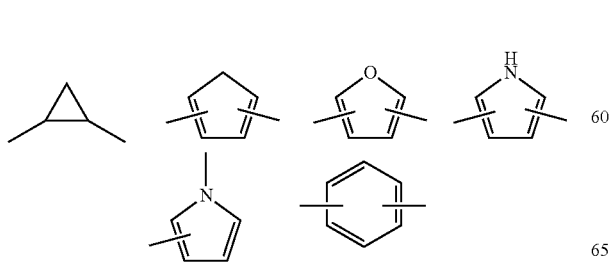

and R13 is selected from $SO_2NH(CH_3)$, $SO_2NH_2$, $OC(O)$ $CH_3$, $CF_3$ or one the following lactone structures:

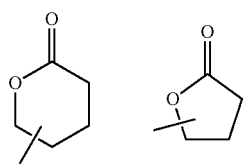

The terms "veterinarily acceptable salt" and "pharmaceutically acceptable salt" are used throughout the specification to describe any salts of the compounds that are acceptable for administration for pharmaceutical or veterinary applications, and which provides the active compound upon administration.

Veterinarily acceptable salts include those derived from veterinarily acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations as well as substituted ammonium cations, in which one or more of the hydrogen atoms are replaced by alkyl or aryl groups are encompassed by the invention. Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compounds of the invention.

EXAMPLES

The present invention will be further described with reference to the following examples without wishing to be limited by them.

1. General Method

The starting building blocks were prepared from commercial available reagents. Unless otherwise noted, reagents and solvents were purchased at highest commercial quality and used without further purification. Methanol and dry toluene, $CH_2Cl_2$ were purchased from Kanto Chemical Co., Inc. All reactions were monitored by thin-layer chromatography (TLC) using Merck silica gel 60 F254 pre-coated plates (0.25 mm). Flash chromatography was carried out with Kanto Chemical silica gel (Kanto Chemical, silica gel 60N, spherical neutral, 0.040-0.050 mm, Cat.-No. 37563-84). $^1H$ and $^{13}C$ NMR spectra were recorded on JEOL JNM-ECA-500 (500 MHz for $^1$H-NMR and 125 MHz for $^{13}$C-NMR). Chemical shifts are expressed in ppm downfield from the internal solvent peaks for $CDCl_3$ ($^1$H; δ=7.26 ppm, $^{13}$C; δ=77.0 ppm), $CD_3OD$ ($^1$H; δ=3.31 ppm, $^{13}$C; δ=49.0 ppm) and J values are given in Hertz. The following abbreviations were used to explain the multiplicities: s=singlet, d=doublet, t=triplet, q=quartet, dd=double doublet, ddd=double double doublet, dt=double triplet, dq=double quartet, m=multiplet, br=broad. All infrared spectra were measured on a Horiba FT-210 spectrometer. High- and Low-resolution mass spectra were measured on a JEOL JMS-AX505 HA, JEOL JMS-700 MStation and JEOL JMS-T100LP. Optical rotations were measured by using JASCO P-1010 polarimeter. Melting points were measured on a YANACO MP-500P or OptiMelt (Stanford Research Systems) apparatus.

General Method for Fmoc Deprotection

Fmoc protected substrate was dissolved into 5% piperidine/$CH_2Cl_2$ (generally 0.05 M for substrate) at room temperature and solution was stirred for 3 h. The reaction mixture was subsequently cooled to −5° C. and MeOH was added (five times excess of reaction solution). The resulting heterogeneous solution was stirred for further 30 min at −5° C., and the colorless precipitate was filtered and washed with additional MeOH to afford corresponding amine as a colorless powder.

General Method for the Cleavage of TAGa Function

Tagged substrates with TAGa dissolved into 50% TFA/CH2Cl2 (0.05 M for substrate) at room temperature and solution was stirred for generally 1 h. The reaction mixture was subsequently concentrated with toluene (×3) to remove TFA. To a flask was then added CH2Cl2 at −5° C., followed MeOH was added (five times excess of CH2Cl2). The resulting heterogeneous solution was stirred for further 30 min at −5° C., and the colorless precipitate was filtered off and washed with additional MeOH. The combined filtrates were concentrated in vacuo. To the resulting product was added 4 M HCl/Dioxane (0.05 M for product) and concentrated with toluene (×3) to afford corresponding carboxylic acid as a generally brown oil. The crude was used next reaction without further purification.

product) and concentrated with toluene (×3) to afford corresponding carboxylic acid as a generally brown oil. The crude was used next reaction without further purification.

2. Synthesis of Emodepside

In the following the synthesis of emodepside is described, using the compound Benzyl (R)-2-hydroxy-3-(4-morpholinophenyl)propanoate (named EMD-8) which is synthesized from p-fluroro benzaldehyd according to the scheme of FIG. 1. Using this compound, emodepside is synthesized according to the scheme of FIGS. 2A, 2B, 2C, 2D, 2E and 2F.

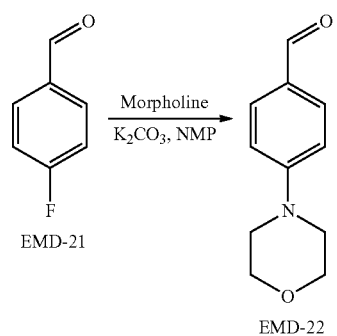 [SMILES: O=Cc1ccc(F)cc1 ; O=Cc1ccc(N2CCOCC2)cc1]

4-Morpholinobenzaldehyde (EMD-22): Into a 100 L reactor, was placed a solution of 4-fluorobenzaldehyde (EMD-21, 3.6 kg, 29.0 mol, 1.0 eq) in 1-methyl-2-pyrrolidine (36 L, 10.0V), morphline (7.6 kg, 87 mol, 3.0 eq), $K_2CO3$ (10.0 kg, 72.5 mol, 2.5 eq). The resulting mixture was stirred at least for 6 h at 125~130° C. The reaction was monitored by TLC until no EMD-21. The reaction mixture was diluted with ethyl acetate (18 L, 5 V), $H_2O$ (72 L, 20 V), and separated. The water phase was extracted with ethyl acetate (18 L×2) and combined the organic phase, and washed with $H_2O$ (36.0 L×3). The organic extracts were concentrated under vacuum at below 45° C. until no distillate drops out.

The residue was eluted with heptane/ethyl acetate (5:1, v/v, 7.2 L) and concentrated under vacuum at below 45° C. Then, to the above residue was added heptane/ethyl acetate (5:1, v/v, 21.6 L) at 20~25° C. The solution was stirred at 20~25° C. for 16 h. The mixture was filtered, and the filter cake was washed with heptane (7.3 L). The solids were dried under vacuum at 40~45° C. This resulted in 4.67 kg (84.8%) of 4-Morpholinobenzaldehyde (EMD-22) as a yellow solid. MS (ES, m/z): 192 (M+H); $^1$H NMR (DMSO-$d_6$, 300 MHz) 9.74 (s, 1H), 7.74 (d, J=8.1 Hz, 2H), 7.07 (d, J=8.4 Hz, 2H), 3.75-3.74 (m, 4H), 3.35-3.33 (m, 4H).

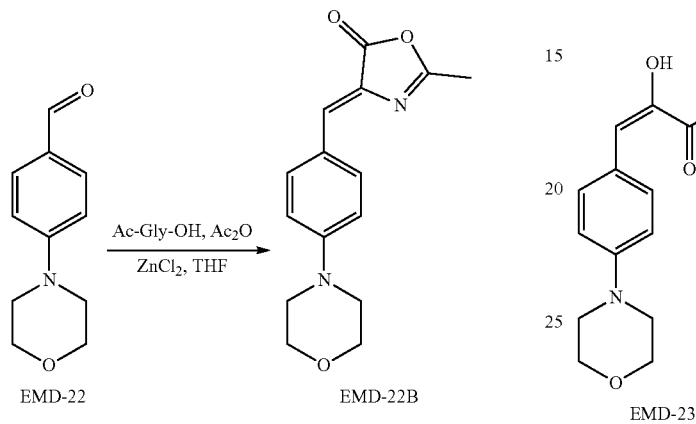

(Z)-2-methyl-4-(4-morpholinobenzylidene)oxazol-5 (4H)-one (EMD-22B): Into a 100 L reactor, was placed a solution of N-acetylglycine (1.22 kg, 10.46 mol, 1.0 eq) in tetrahydrofuran (20 L, 10 V), acetic anhydride (3.2 kg, 31.38 mol, 3.0 eq), zinc(II) chloride (1.48 kg, 10.46 mol, 1.0 eq). The resulting mixture was stirred at 70° C. for 1 h and EMD-22 (2.0 kg, 10.46 mol, 1.0 eq) was added. Then, the mixture was stirred at 70° C. for another 16 h and monitored by LCMS. After cooling to 20~25° C., H$_2$O (40 L) was added. Then, the mixture was stirred at 0~5° C. for 3 h and filtered. The filter cake was washed with H$_2$O (10 L), and dried under vacuum at 40~45° C. This resulted in 2.29 kg (80.4%) of (Z)-2-methyl-4-(4-morpholinobenzylidene)oxazol-5(4H)-one (EMD-22B) as a brown solid. MS (ES, m/z): 273 (M+H); $^1$H NMR (DMSO-$d_6$, 300 MHz) 7.84 (s, 1H), 7.47 (d, J=9.0 Hz, 2H), 7.02 (d, J=9.1 Hz, 2H), 3.74-3.71 (m, 4H), 3.32-3.27 (m, 4H).

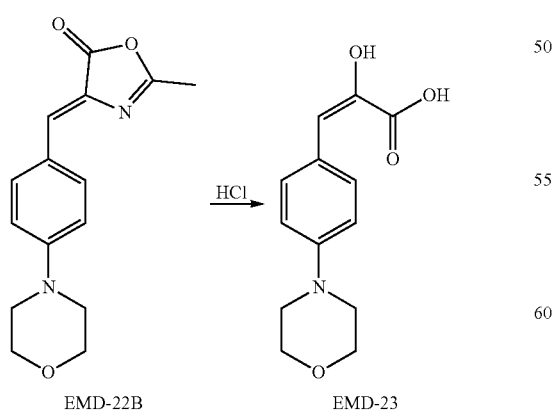

(E)-2-hydroxy-3-(4-morpholinophenyl)acrylic acid (EMD-23): Into a 50 L reactor, was placed a solution of EMD-22B (2.2 kg, 8.08 mol, 1.0 eq) in 1,4-dioxane (8.8 L, 4.0 V), HCl (8.8 L, 4.0 V) at 20~25° C. The resulting mixture was stirred at 80° C. for 3 h and monitored by LCMS. After cooling to 0~10° C., the mixture was stirred at 0~10° C. for 16 h and filtered. The fiter cake was dried under vacuum at 40~45° C., The crude product was eluted with H$_2$O (4.4 L) and stirred at 0~10° C. for 2 h. The mixture was fitered, and the filter cake was dried under vacuum at 40~45° C. This resulted in 1.17 kg (56.0%) of (E)-2-hydroxy-3-(4-morpholinophenyl)acrylic acid (EMD-23) as a slater solid. MS (ES, m/z): 250 (M+H); $^1$H NMR (DMSO-$d_6$, 300 MHz) 7.66 (d, J=8.5 Hz, 2H), 6.97 (d, J=8.6 Hz, 2H), 6.35 (s, 1H), 4.05 (s, 1H, —OH), 3.77-3.74 (m, 4H), 3.19-3.16 (m, 4H).

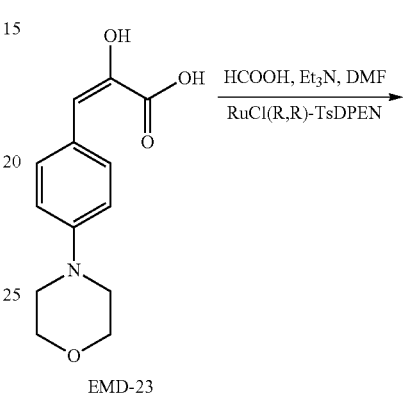

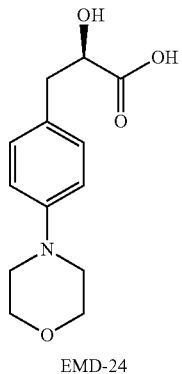

(R)-2-hydroxy-3-(4-morpholinophenyl)propanoic acid (EMD-24): Into a 2 L round-bottom flask purged and maintained with an inert atmosphere of nitrogen, was placed a solution of EMD-23 (66.0 g, 0.26 mol, 1.0 eq) in N,N-dimethylformamide (660 mL, 10.0 V), Et$_3$N (107.2 g, 1.06 mol, 4.0 eq), RuCl(R,R)-TsDPEN (1.69 g, 0.0026 mol, 0.01 eq) at 20~25° C. To the above mixture was added formic acid (36.59 g, 0.79 mol, 3.0 eq) dropwise for 2 h at 20~25° C. under N$_2$ atmosphere. Then, the mixture was stirred at 20~25° C. and monitored by LCMS. The reaction was noted for M1, which was used for next step without further purification.

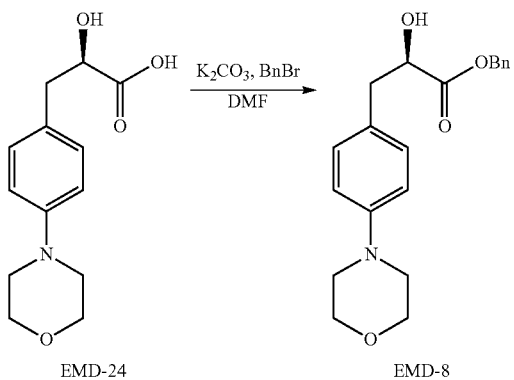

EMD-24 → EMD-8

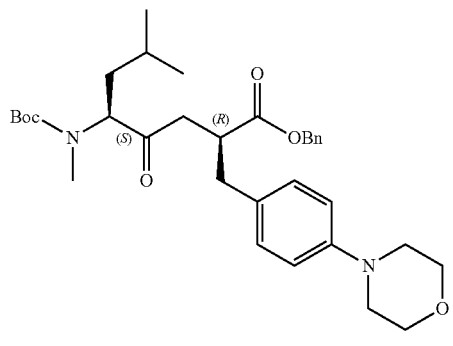

EMD-9B

Benzyl (R)-2-hydroxy-3-(4-morpholinophenyl)propanoate (EMD-8): To a mixture (M1) was added K$_2$CO$_3$ (109.0 g, 0.78 mol, 3.0 eq) and dropwise benzyl bromide (54.0 g, 0.32 mol, 1.2 eq) at 20~25° C. for 1 h. Then, the mixture was stirred at 55~60° C. for another 16 h. The reaction mixture was diluted with ethyl acetate (330 mL, 5 V), H$_2$O (1.2 L, 20 V), and separated. The water phase was extracted with ethyl acetate (330 mL×2) and combined the organic phase, and washed with H$_2$O (660 mL×3). The organic extracts were concentrated under vacuum at below 45° C. until no distillate drops out. The residue was eluted with heptane/ethyl acetate (3:1, v/v, 132 mL) and concentrated under vacuum at below 45° C. Then, to the above residue was added heptane/ethyl acetate (3:1, v/v, 264 mL) at 20~25° C. The mixture was filtered, and the filter cake was washed with heptane (132 mL). The solids were dried under vacuum at 40~45° C. This resulted in 52 g (58%) of benzyl (R)-2-hydroxy-3-(4-morpholinophenyl)propanoate (EMD-8) as a yellow solid. MS (ES, m/z): 342 (M+H); $^1$H NMR (DMSO-d$_6$, 300 MHz) 7.40-7.27 (m, 5H), 7.05 (d, J=8.1 Hz, 2H), 6.82 (d, J=8.1 Hz, 2H), 5.17 (s, 2H), 4.24 (t, J=7.5 Hz, 1H), 3.74-3.71 (m, 4H), 3.06-3.03 (m, 4H), 2.90-2.73 (m, 2H).

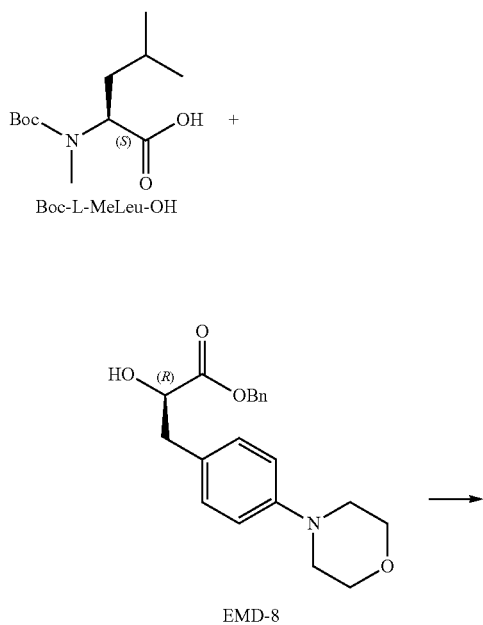

(R)-1-(benzyloxy)-3-(4-morpholinophenyl)-1-oxopropan-2-yl-N-(tert-butoxycarbonyl)-N-methyl-L-leucinate (EMD-9B): Into a 50 L reactor purged and maintained with an inert atmosphere of nitrogen, was placed a solution of EMD-8 (1.96 kg, 5.75 mol, 1.0 eq) in dichloromethane (14.1 L, 10.V), N-(tert-butoxycarbonyl)-N-methyl-L-leucine (1.41 kg, 5.75 mol, 1.0 eq), DMAP (0.77 kg, 6.32 mol, 1.1 eq), EDCI (1.21 kg, 6.32 mol, 1.1 eq) at 20~25° C. The mixture was stirred at this temperature for at least 3 h and monitored by LCMS. The mixture was concentrated at below 40° C. until no distillate drops out. The residue was dissolved in MTBE (14.1 L) and HCl (aq, 1N, 14.1 L) and filtered. The organic was washed with HCl (aq, 1N, 14.1 L), NaHCO$_3$ (sat, 14.1 L×2), and concentrated at below 40° C. until no distillate drops out. Then the residue was resolved in heptane/MTBE (28.2 L, 8:1, v/v), and concentrated at below 40° C. until no distillate drops out. To the above residue was added heptane/MTBE (15.5 L, 8:1, v/v) at 20~25° C. and seed crystal (0.2%, w/w), and kept stirring for overnight at 20~25° C. The mixture was filtered; the filter cake was washed with heptane (7.0 L). The solids were dried under vacuum at 4045° C. This resulted in 2.56 kg (78.3%) of (R)-1-(benzyloxy)-3-(4-morpholinophenyl)-1-oxopropan-2-yl-N-(tertbutoxycarbonyl)-N-methyl-L-leucinate (EMD-9B) as a light yellow solid. MS (ES, m/z): 569 (M+H); $^1$H NMR (DMSO-d$_6$, 300 MHz) 7.38-7.26 (m, 5H), 7.10 (d, J=8.2 Hz, 2H), 6.96 (d, J=8.1 Hz, 2H), 5.25-5.22 (m, 1H), 5.12-5.10 (m, 2H), 4.07-3.99 (m, 1H), 3.79-3.76 (m, 4H), 3.19-2.97 (m, 6H), 2.57 (s, 3H), 1.42-1.34 (m, 11H), 1.24-1.15 (m, 1H), 0.88-0.82 (m, 6H).

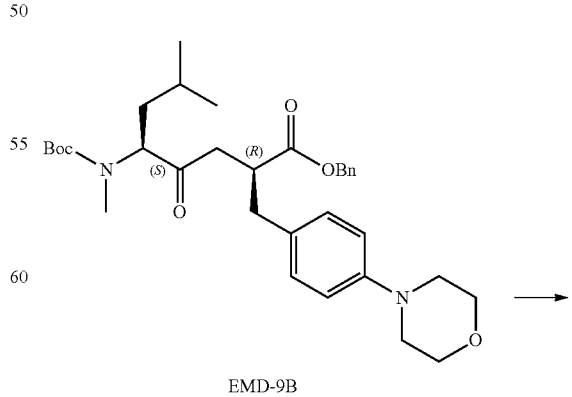

EMD-9B

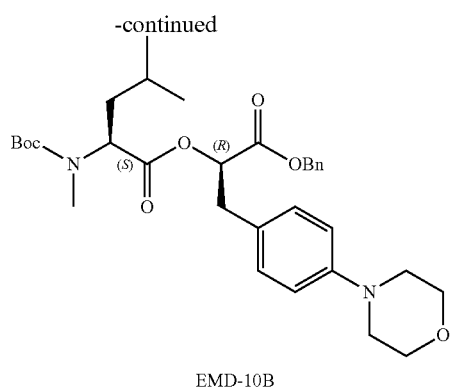

EMD-10B (R)-2-((N-(tert-butoxycarbonyl)-N-methyl-L-leucyl)oxy)-3-(4-morpholinophenyl)propanoic acid (EMD-10B): Into a 50 L reactor purged and maintained with an inert atmosphere of nitrogen, was placed a solution of EMD-9B (400 g, 0.7 mol, 1.0 eq) in EtOH (4.0 L, 10.0V) at 20~25° C., The reactor was evacuated and flushed with nitrogen for three times and Pd/C (28.0 g, 7% w/w) was added. Then the reactor was evacuated and flushed with nitrogen for three times again, and kept hydrogen bubbling underneath the reaction mixture surface. The mixture was stirring for at least for 4 h at 20~25° C. and monitored by HPLC. After the reaction completing, the hydrogen bubbling was cut off. The mixture was filtered through celite (2.0 kg) and filter cake was rinsed with EA (0.8 L), and the filtrate was concentrated at below 40° C. until no distillate drops out. This resulted in 317.7 g (94.4%) of (R)-2-((N-(tert-butoxycarbonyl)-N-methyl-L-leucyl)oxy)-3-(4-morpho-linophenyl)propanoic acid (EMD-10B) as a dark yellow oil; MS (ES, m/z): 479 (M+H); $^1$H NMR (DMSO-$d_6$, 300 MHz) 7.10 (d, J=8.4 Hz, 2H), 6.85 (d, J=8.7 Hz, 2H), 5.03-5.02 (m, 1H), 4.81-4.53 (m, 1H), 3.73 (t, J=7.2 Hz, 4H), 3.05 (t, J=7.2 Hz, 4H), 2.96-2.90 (m, 1H), 2.63 (s, 3H), 1.42-1.16 (m, 12H), 0.89-0.84 (m, 6H).

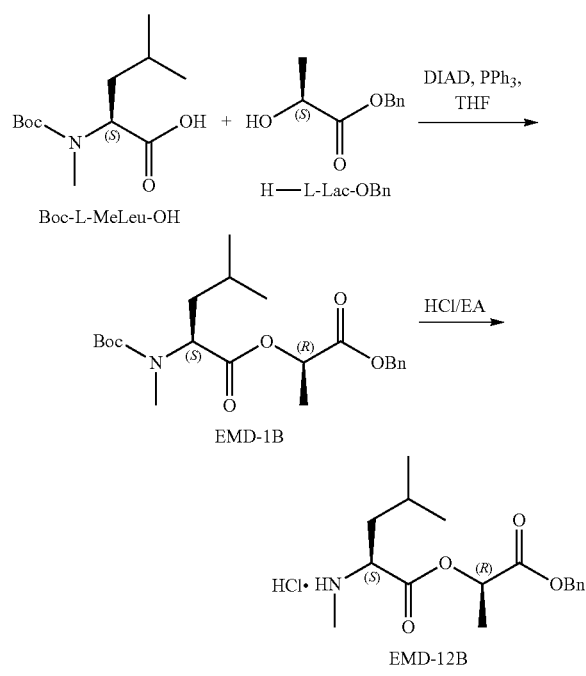

(R)-1-(benzyloxy)-1-oxopropan-2-yl methyl-L-leucinate (EMD-12B): Into a 10 L reactor purged and maintained with an inert atmosphere of nitrogen, was placed a solution of N-(tert-butoxycarbonyl)-N-methyl-L-leucine (240.3 g, 0.98 mol, 1.0 eq) in THF (3.9 L, 16 v), benzyl (S)-2-hydroxypropanoate (176.5 g, 0.98 mol, 1.0 eq), triphenylphosphine (385.1 g, 1.47 mol, 1.5 eq) at 20~25° C. After cooling to below 10° C., diisopropyl azodiformate (297 g, 1.47 mol, 1.5 eq) was added dropwise with stirring at below 10° C. Then, warming up to 20~25° C. and stirring for at least 2 h. The reaction was monitored by HPLC until benzyl (S)-2-hydroxypropanoate less than or equal to 0.5%. The resulting mixture was diluted with ethyl acetate (3.9 L) and washed with NaHCO$_3$ (sat, 3.9 L×2), brine (3.9 L×2). The organic phase was concentrated at below 40° C. until no distillate drops out. The residue was exchanged with tert-Butyl methyl ether (240 mL×2), concentrated below 40° C. until no distillate drops out, and slurryed with tert-butyl methyl ether (960 mL) for at least 3 h. The mixture was filtered and the filter cake was washed with tert-butyl methyl ether (240 mL). The filtrate was concentrated at below 40° C. until no distillate drops out. This resulted in crude product of (R)-1-(benzyloxy)-1-oxopropan-2-yl N-(tert-butoxycarbonyl)-N-methyl-L-leucinate (EMD-1B) as a yellow oil, which was used for next step without further purification.

Into a 10 L reactor purged and maintained with an inert atmosphere of nitrogen, was placed a solution of EMD-1B in HCl/EA (1.2 L, 5.0 eq) below 25° C. The mixture was stirred for at least 1 h at 20~25° C. and monitored by HPLC until EMD-1B less than or equal to 0.5%. The solution was concentrated at below 40° C. until no distillate drops out. The residue was exchanged with tert-Butyl methyl ether (240 mL×2), concentrated below 40° C. until no distillate drops out, and resolved with tert-butyl methyl ether (1.92 L). Then, the seed crystal (0.1%, w/w) was added and stirred for at least 5 h at 20~25° C. The mixture was filtered and the filter cake was washed with tert-butyl methyl ether (0.24 L). The solid was dried under vacuum at 40±5° C. and 270 g of crude product was obtained as a white solid. The solid was dissolved in ethyl acetate (810 mL) by warming up to 40±5° C. and tert-butyl methyl ether (4.05 L) was added. Subsequently, cooling down to 20~25° C. and the seed crystal (0.1%. w/w) was added. The mixture was stirred for at least 5 h at 20~25° C., filtered, the filter cake was washed with tert-butyl methyl ether (0.24 L). The solid was dried under vacuum at 40±5° C. This resulted in 226.7 g (67.3%, two steps) of (R)-1-(benzyloxy)-1-oxopropan-2-yl methyl-L-leucinate (EMD-12B) as a white solid. MS (ES, m/z): 308 (M+H); $^1$H NMR (DMSO-$d_6$, 300 MHz) 7.41-7.35 (m, 5H), 5.28 (q, J=7.1 Hz, 1H), 5.20 (s, 2H), 2.51 (s, 3H), 1.77-1.71 (m, 3H), 1.50-1.48 (m, 3H), 0.90-0.87 (m, 6H).

-continued

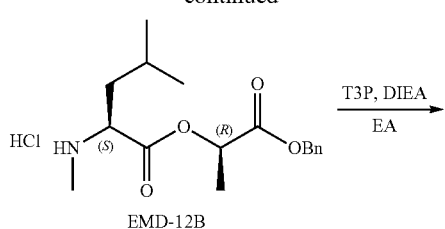

EMD-12B

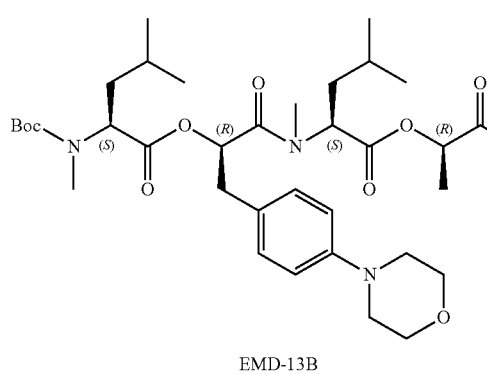

EMD-13B (R)-1-(benzyloxy)-1-oxopropan-2-yl N—((R)-2-((N-(tert-butoxycarbonyl)-N-methyl-L-leucyl)oxy)-3-(4-morpholinophenyl)propanoyl)-N-methyl-L-leucinate (EMD-13B): Into a 10 L reactor purged and maintained with an inert atmosphere of nitrogen, was placed a solution of EMD-10B (275.0 g, 0.57 mol, 1.0 eq) in ethyl acetate (2.2 L, 8.0 V), EMD-12B (197.7 g, 0.57 mol, 1.0 eq), N,N-diisopropylethylamine (372.2 g, 2.88 mol, 5.0 eq) at 20~25° C. After cooling to 10~20° C., propylphosphonic anhydride (916.4 g, 1.44 mol, 2.5 eq) was added dropwise with stiring at below 25° C. Then, the mixture was stirred at 20~25° C. for at least 2.5 h and monitored by HPLC until EMD-12B less than or equal to 1.0%. The solution was diluted with heptane (2.75 L) at 0~10° C. and quenched slowly with HCl (aq, 1.0N, 2.75 L). The organic phase was washed HCl (aq, 1.0N, 2.75 L), NaHCO₃ (sat, 2.75 L×2), and concentrated at below 40° C. until no distillate drops out. This resulted in 429.8 g (97.4%) of (R)-1-(benzyloxy)-1-oxopropan-2-yl N—((R)-2-((N-(tert-butoxycarbonyl)-N-methyl-L-leucyl)oxy)-3-(4-morpholinophenyl)propanoyl)-N-methyl-L-leucinate (EMD-13B) as a yellow thick oil. MS (ES, m/z): 768 (M+H);

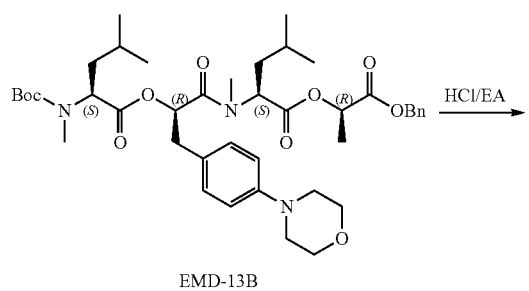

EMD-13B

-continued

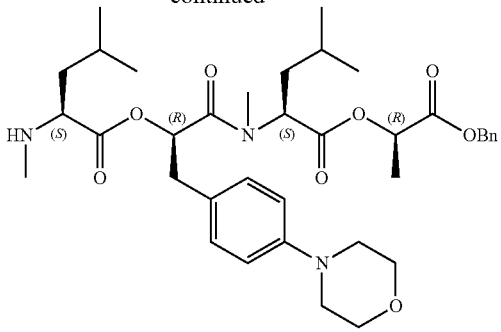

EMD-14B (R)-1-(benzyloxy)-1-oxopropan-2-yl-N-methyl-N—((R)-2-((methyl-L-leucyl)oxy)-3-(4-morphol-inophenyl)propanoyl)-L-leucinate (EMD-14B): Into a 5 L reactor purged and maintained with an inert atmosphere of nitrogen, was placed a solution of EMD-13B (245 g, 0.32 mol, 1.0 eq) in HCl/EA (735, 3.0 V) below 25° C. The mixture was stirred for at least 1 h at 20~25° C. and monitored by HPLC until EMD-13B was less than or equal to 0.5%. The resulting solution was concentrated at below 40° C. until no distillate drops out and exchanged with ethyl acetate (245 mL×2) at below 40° C. The residue was dissolved in ethyl acetate (735 mL) and N,N-diisopropylethylamine (245 g) was added at 20~25° C. The mixture was washed with NaHCO₃ (sat, 735 mL×2). The organic was concentrated at below 40° C. until no distillate drops out. This resulted in 186.9 g (89.9%) of (R)-1-(benzyloxy)-1-oxopropan-2-yl-N-methyl-N—((R)-2-((methyl-L-leucyl)oxy)-3-(4-morphol-inophenyl)propanoyl)-L-leucinate (EMD-14B) as a yellow oil. MS (ES, m/z): 668 (M+H); ¹H NMR (DMSO-d₆, 300 MHz) 7.41-7.32 (m, 5H), 7.17 (d, J=8.5 Hz, 2H), 6.86 (d, J=8.6 Hz, 2H), 5.50-5.47 (m, 1H), 5.20-5.04 (m, 4H), 4.23-3.99 (m, 1H), 3.74-3.72 (m, 4H), 3.09-2.76 (m, 10H), 2.22-1.99 (m, 3H), 1.63-1.35 (m, 5H), 1.29-1.16 (m, 4H), 0.97-0.70 (m, 12H).

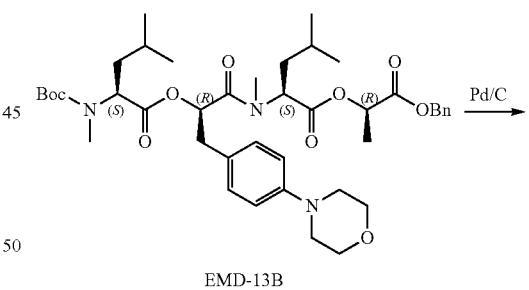

EMD-13B

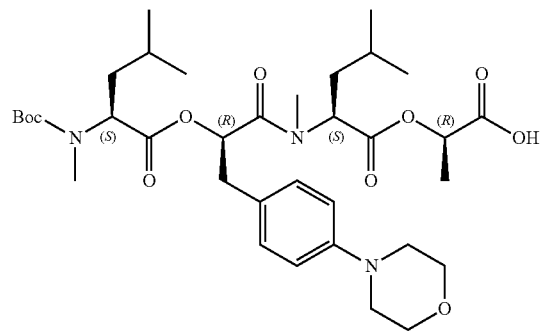

EMD-15B (6S,9R,12S,15R)-6,12-diisobutyl-2,2,5,11,15-pentamethyl-9-(4-morpholinobenzyl)-4,7,10,13-tetraoxo-3,8,14-trioxa-5,11-diazahexadecan-16-oic acid (EMD-15B): Into a 10 L reactor purged and maintained with an inert atmosphere of nitrogen, was placed a solution of EMD-13B (274.2 g, 0.36 mol, 1.0 eq) in EtOH (2.8 L, 10.0V) at 20~25° C., The reactor was evacuated and flushed with nitrogen for three times and Pd/C (19.2 g, 7% w/w) was added. Then the reactor was evacuated and flushed with nitrogen for three times again, and kept hydrogen bubbling underneath the reaction mixture surface. The mixture was stirring for at least for 4 h at 20~25° C. and monitored by HPLC. After the reaction completing, the hydrogen bubbling was cut off. The mixture was filtered through celite (2.0 kg) and filter cake was rinsed with ethyl acetate (0.56 L), and the filtrate was concentrated at below 40° C. until no distillate drops out. This resulted in 237.4 g (98.0%) of (6S,9R,12S,15R)-6,12-diisobutyl-2,2,5,11,15-pentamethyl-9-(4-morpholinobenzyl)-4,7,10,13-tetraoxo-3,8,14-trioxa-5,11-diazahexadecan-16-oic acid (EMD-15B) as a yellow oil; MS (ES, m/z): 678 (M+H); $^1$H NMR (DMSO-$d_6$, 300 MHz) 7.15 (d, J=8.4 Hz, 2H), 6.85 (d, J=8.3 Hz, 2H), 5.52-5.40 (m, 1H), 5.09-5.02 (m, 1H), 4.91-4.53 (m, 2H), 3.74-3.72 (m, 4H), 3.15-3.04 (m, 5H), 2.94-2.86 (m, 4H), 2.65-2.64 (m, 3H), 1.43-1.28 (m, 16H), 0.93-0.77 (m, 12H).

(R)-1-(benzyloxy)-1-oxopropan-2-yl N-methyl-N-((6S,9R,12S,15R,18S,21R)-6,12,18-triiso butyl-2,2,5,11,15,17-hexamethyl-9,21-bis(4-morpholinobenzyl)-4,7,10,13,16,19-hexaoxo-3,8,14,20-tetraoxa-5,11,17-triazadocosan-22-oyl)-L-leucinate (EMD-16B): Into a 10 L reactor purged and maintained with an inert atmosphere of nitrogen, was placed a solution of EMD-15B (147.6 g, 0.22 mol, 1.0 eq) in ethyl acetate (2.2 L, 8.0 V), EMD-14B (145.5 g, 0.22 mol, 1.0 eq), N,N-diisopropylethylamine (139.6 g, 1.08 mol, 5.0 eq) at 20~25° C. After cooling to 10~20° C., propylphosphonic anhydride (346.4 g, 0.54 mol, 2.5 eq) was added dropwise with stirring at below 25° C. Then, the mixture was stirred at 20~25° C. for at least 2.5 h and monitored by HPLC until EMD-12B less than or equal to 0.5%. The solution was diluted with heptane (2.2 L) at 0~10° C. and quenched slowly with HCl (aq, 1.0 N, 2.2 L). The organic phase was washed HCl (aq, 1.0N, 2.2 L), NaHCO$_3$ (sat, 2.2 L×2), concentrated at below 40° C. until no distillate drops out, and exchanged with heptane/MTBE (0.44 L, 1.5:1, v/v) at below 40° C. The residue was dissolved in heptane/MTBE (1.65 L, 1.5:1, v/v) and seed crystal (0.1%, w/w) was added at 20~25° C. The mixture was stirred for at least 16 h at 20~25° C. and filtered. The filter cake was washed with heptane (0.66 L), dried under vacuum at 40~45° C. This resulted in 242.4 g (83.4%) of (R)-1-(benzyloxy)-1-oxopropan-2-yl N-methyl-N-((6S,9R,12S,15R,18S,21R)-6,12,18-triiso-butyl-2,2,5,11,15,17-hexamethyl-9,21-bis(4-morpholinobenzyl)-4,7,10,13,16,19-hexaoxo-3,8,14,20-tetraoxa-5,11,17-triazadocosan-22-oyl)-L-leucinate (EMD-16B) as a white solid: MS (ES, m/z): 1328 (M+H);

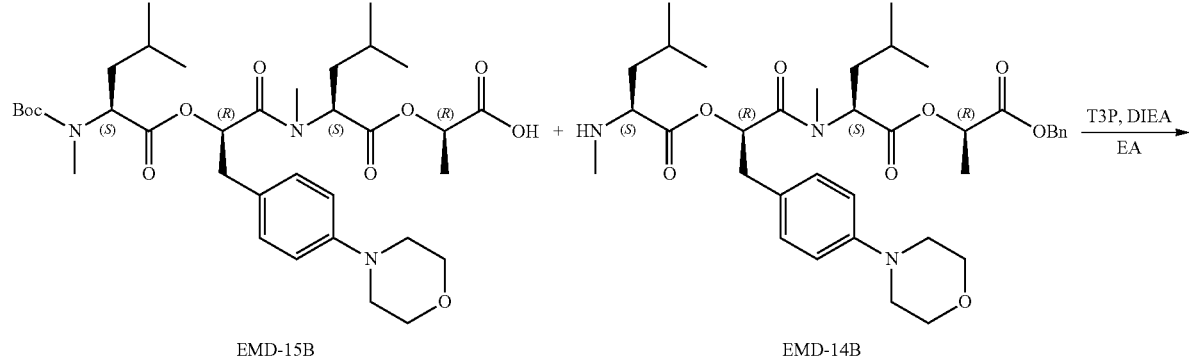

EMD-15B + EMD-14B

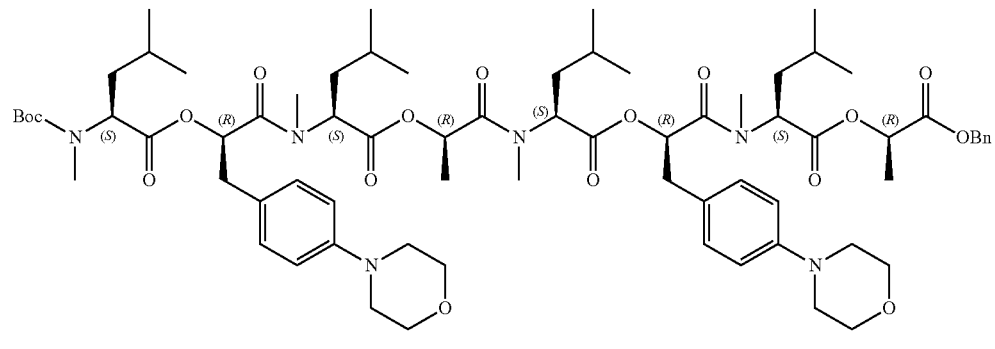

EMD-16B

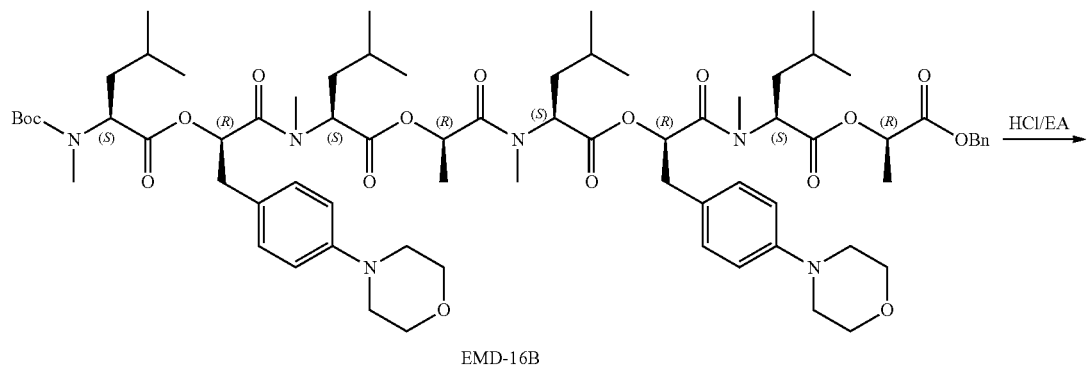

EMD-16B

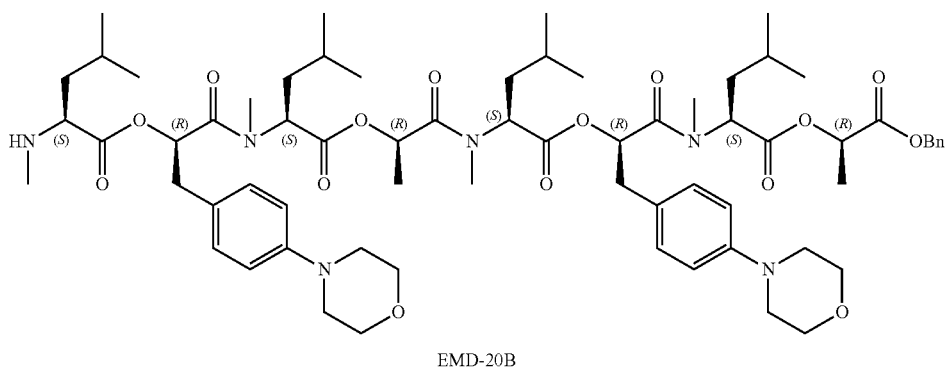

EMD-20B (R)-1-(benzyloxy)-1-oxopropan-2-yl N-((2R,5S,8R,11S, 14R,17S)-5,11-diisobutyl-6,8,12,19-tetramethyl-17-(methylamino)-2,14-bis(4-morpholinobenzyl)-4,7,10,13,16-pentaoxo-3,9,15-trioxa-6,12-diazaicosanoyl)-N-methyl-L-leucinate (EMD-20B): Into a 5 L reactor purged and maintained with an inert atmosphere of nitrogen, was placed a solution of EMD-16B (376.4 g, 0.28 mol, 1.0 eq) in HC/EA (1128 mL, 3.0 V) below 25° C. The mixture was stirred for at least 1 h at 20~25° C. and monitored by HPLC until EMD-16B was less than or equal to 0.5%. The resulting solution was concentrated at below 40° C. until no distillate drops out and exchanged with ethyl acetate (376.4 mL×2) at below 40° C. The residue was dissolved in ethyl acetate (1128 mL) and N,N-diisopropylethylamine (376.4 g) was added at 20~25° C. The mixture was washed with NaHCO3 (sat, 1128 mL×2). The organic was concentrated at below 40° C. until no distillate drops out. This resulted in 313.56 g (90.1%) of (R)-1-(benzyloxy)-1-oxopropan-2-yl N-((2R, 5S,8R,11S,14R,17S)-5,11-diisobutyl-6,8,12,19-tetramethyl-17-(methylamino)-2,14-bis(4-morpholinobenzyl)-4,7,10, 13,16-pentaoxo-3,9,15-trioxa-6,12-diazaicosanoyl)-N-methyl-L-leucinate (EMD-20B) as a yellow oil; MS (ES, m/z): 1228 (M+H);

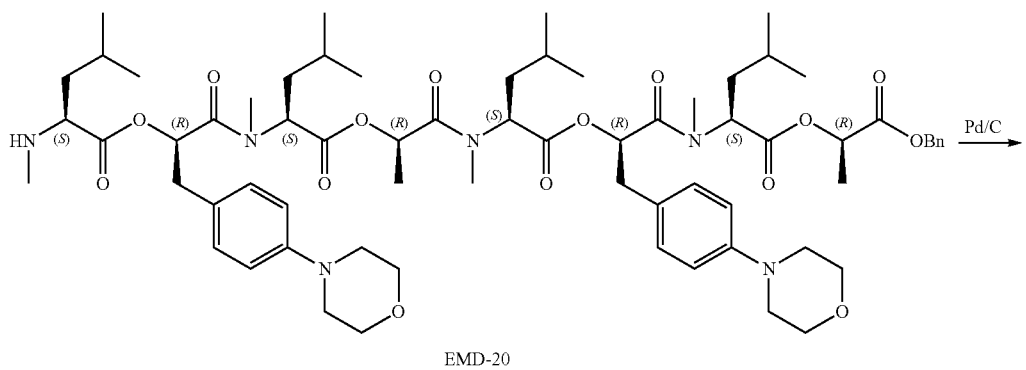

EMD-20

-continued

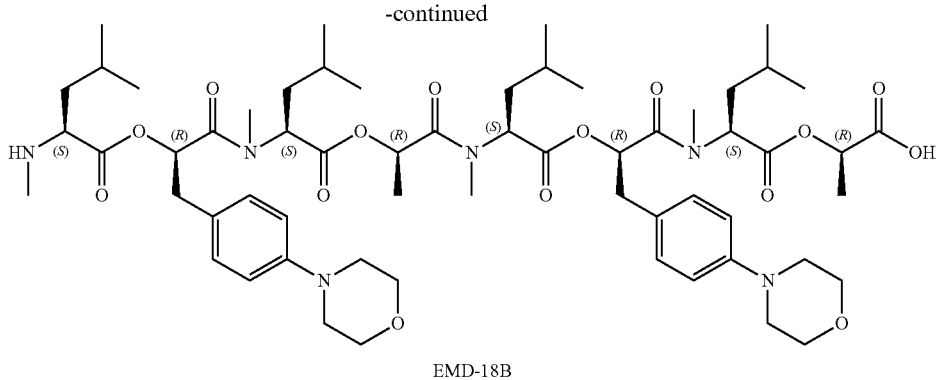

EMD-18B (3S,6R,9S,12R,15S,18R,21S,24R)-3,9,15,21-tetraisobutyl-8,12,14,20,24-pentamethyl-6,18-bis(4-morpholinobenzyl)-4,7,10,13,16,19,22-heptaoxo-5,11,17,23-tetraoxa-2,8,14,20-tetraazapentacosan-25-oic acid (EMD-18B): Into a 10 L reactor purged and maintained with an inert atmosphere of nitrogen, was placed a solution of EMD-20B (313.56 g, 0.26 mol, 1.0 eq) in EtOH (3.2 L, 10.0V) at 20~25° C., The reactor was evacuated and flushed with nitrogen for three times and Pd/C (21.95 g, 7% w/w) was added. Then the reactor was evacuated and flushed with nitrogen for three times again, and kept hydrogen bubbling underneath the reaction mixture surface. The mixture was stirring for at least for 4 h at 20-25° C. and monitored by HPLC until EMD-20B was less than or equal to 1.0%. After the reaction completing, the hydrogen bubbling was cut off. The mixture was filtered through celite (2.0 kg) and filter cake was rinsed with ethyl acetate (0.64 L×3), and the filtrate was concentrated at below 40° C. until no distillate drops out. The residue was slurred with ethyl acetate (0.7 L) for at least 3 h and filtered; the filter cake was rinsed with ethyl acetate (0.32 L×2). The solid was dried under vacuum at 40~45° C. This resulted in 234.2 g (80.6%) of (3S,6R,9S,12R,15S,18R,21S,24R)-3,9,15,21-tetraisobutyl-8,12,14,20,24-pentamethyl-6,18-bis(4-morpholinobenzyl)-4,7,10,13,16,19,22-heptaoxo-5,11,17,23-tetraoxa-2,8,14,20-tetraazapentacosan-25-oic acid (EMD-18B) as an off white solid; MS (ES, m/z): 1138 (M+H); $^1$H NMR (DMSO-$d_6$, 300 MHz) 7.34-7.16 (m, 8H), 5.68-5.28 (m, 3H), 5.11-5.04 (m, 3H), 4.93-4.86 (m, 1H), 4.03-3.99 (m, 1H), 3.85-3.82 (m, 8H), 3.23-3.22 (m, 8H), 3.23-2.76 (m, 13H), 2.49 (s, 2H), 2.07 (s, 2H), 1.66-1.45 (m, 8H), 1.43-1.16 (m, 10H), 0.99-0.64 (m, 24H).

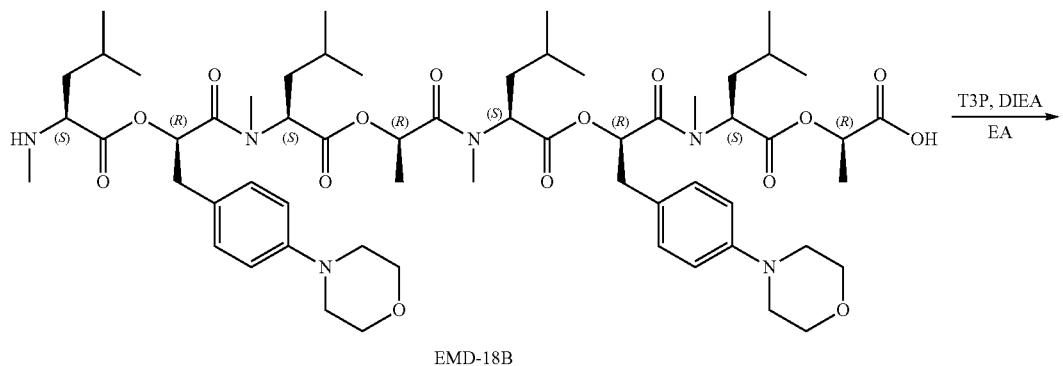

EMD-18B

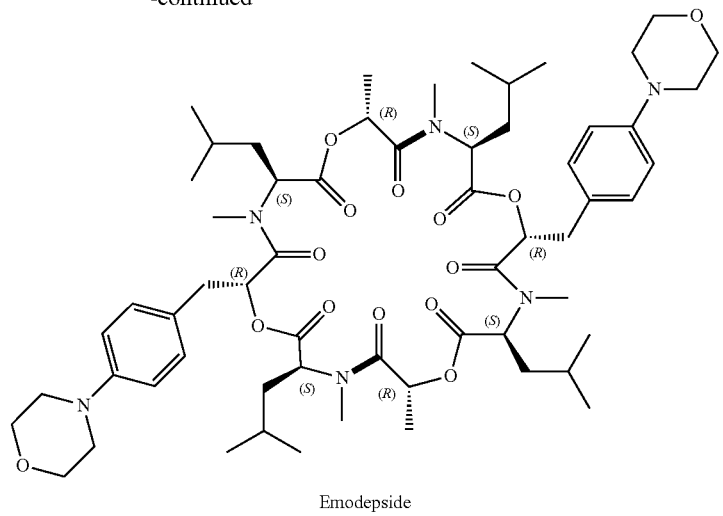

Emodepside (3S,6R,9S,12R,15S,18R,21S,24R)-3,9,15,21-tetraisobutyl-4,6,10,16,18,22-hexamethyl-12,24-bis(4-morpholinobenzyl)-1,7,13,19-tetraoxa-4,10,16,22-tetraazacyclotetracosan-2,5,8,11,14,17,20,23-octaone (Emodepside): Into a 10 L reactor purged and maintained with an inert atmosphere of nitrogen, was placed a solution of EMD-18B (234.2 g, 0.21 mol, 1.0 eq) in ethyl acetate (3.8 L, 16.0 V), N,N-diisopropylethylamine (131.84 g, 1.02 mol, 5.0 eq) at 20~25° C. After cooling to 10~20° C., propylphosphonic anhydride (324.5 g, 0.51 mol, 2.5 eq) was added dropwise with stiring at below 25° C. Then, the mixture was stirred at 20~25° C. for at least 2.5 h and monitored by HPLC until EMD-18B less than or equal to 0.5%. The mixture was diluted with heptane (2.38 L) at 0~10° C. and quenched slowly with HCl (aq, 1.0 N, 2.38 L). The organic phase was washed HCl (aq, 1.0N, 2.38 L), NaHCO₃ (sat, 2.38 L×2), concentrated at below 40° C. until no distillate drops out, and exchanged with EtOH (0.48 L×2) at below 40° C. The residue was dissolved in EtOH (0.72 L) at 45~55° C. and seed crystal (0.1%, w/w) was added at 20~25° C. The mixture was stirred for at least 16 h at 20~25° C. and filtered. The filter cake was rinse with EtOH (0.24 L). The solid was dried under vacuum at 40±5° C. The crude product was recrystallized with ethyl acetate. This resulted in 118.24 g (51.3%) of (3S,6R,9S,12R,15S,18R,21S,24R)-3,9,15,21-tetraisobutyl-4,6,10,16,18,22-hexamethyl-12,24-bis(4-morpholinobenzyl)-1,7,13,19-tetraoxa-4,10,16,22-tetraazacyclotetracosan-2,5,8,11,14,17,20,23-octaone (Emodepside) as a white solid; MS (ES, m/z): 1120 (M+H); $^1$H NMR (DMSO-d₆, 300 MHz) 7.16 (d, J=8.71 Hz, 4H), 6.87 (d, J=8.2 Hz, 4H), 5.68 (q, J=8.0 Hz, 1H), 5.51-4.04 (m, 7H), 3.74-3.71 (m, 8H), 3.08-3.04 (m, 8H), 2.99-2.96 (m, 4H), 2.90-2.88 (m, 4H), 2.83-2.82 (m, 4H), 2.78 (s, 2H), 2.70 (s, 2H), 1.78-1.38 (m, 8H), 1.31-1.14 (m, 6H), 0.97-0.69 (m, 28H).

Figure 3A:
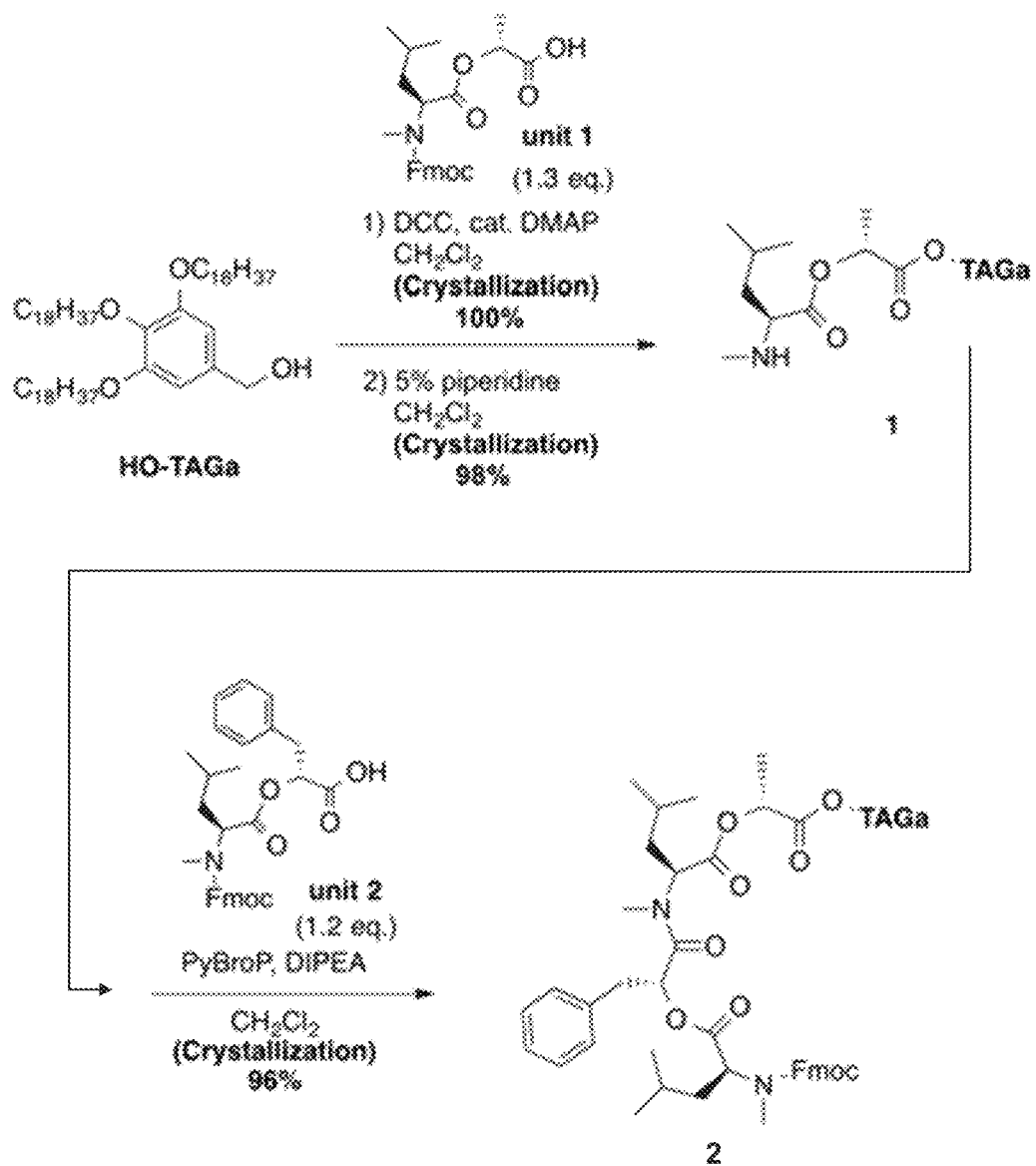
FIG. 3B PF1022A Synthesis (Method 1)-Preparation of 3 and 4 and reaction conditions for the preparation of 5
FIG. 3C PF1022A Synthesis (Method 1)-Preparation of PF1022A
Figure 3B:
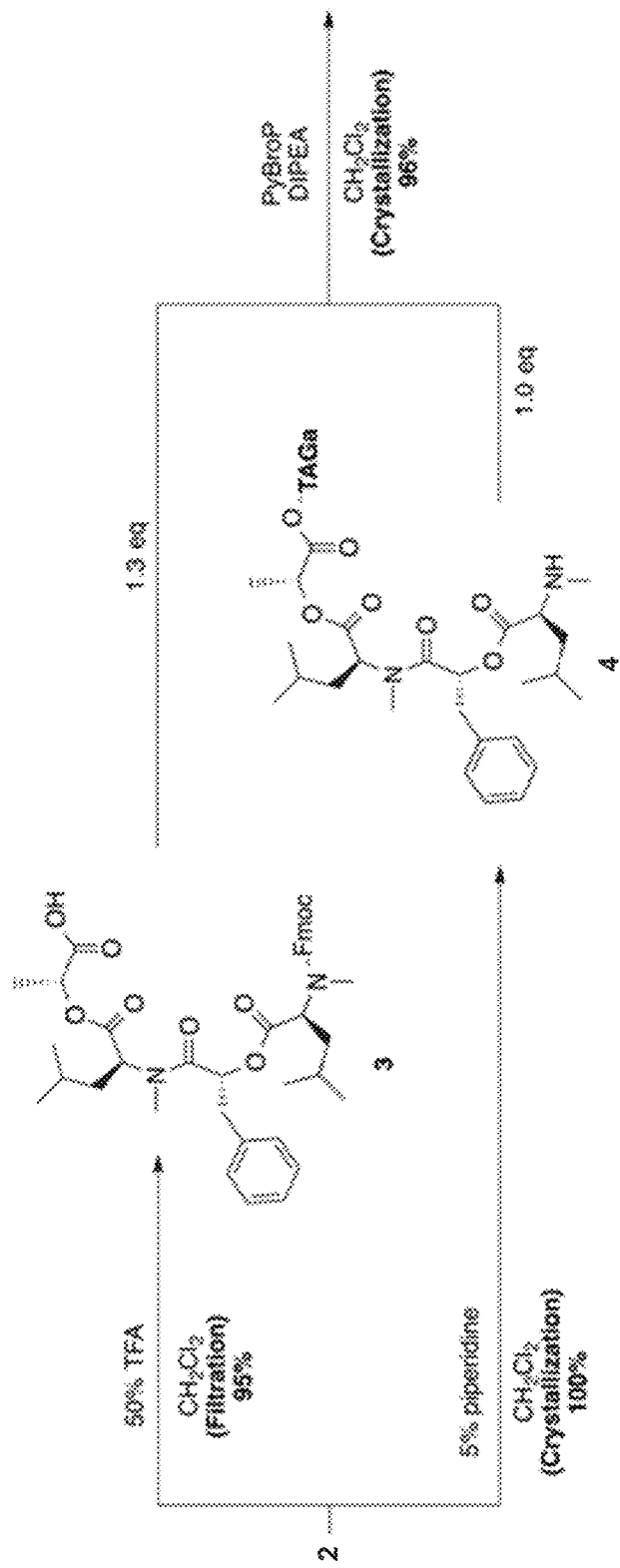
Figure 3C:
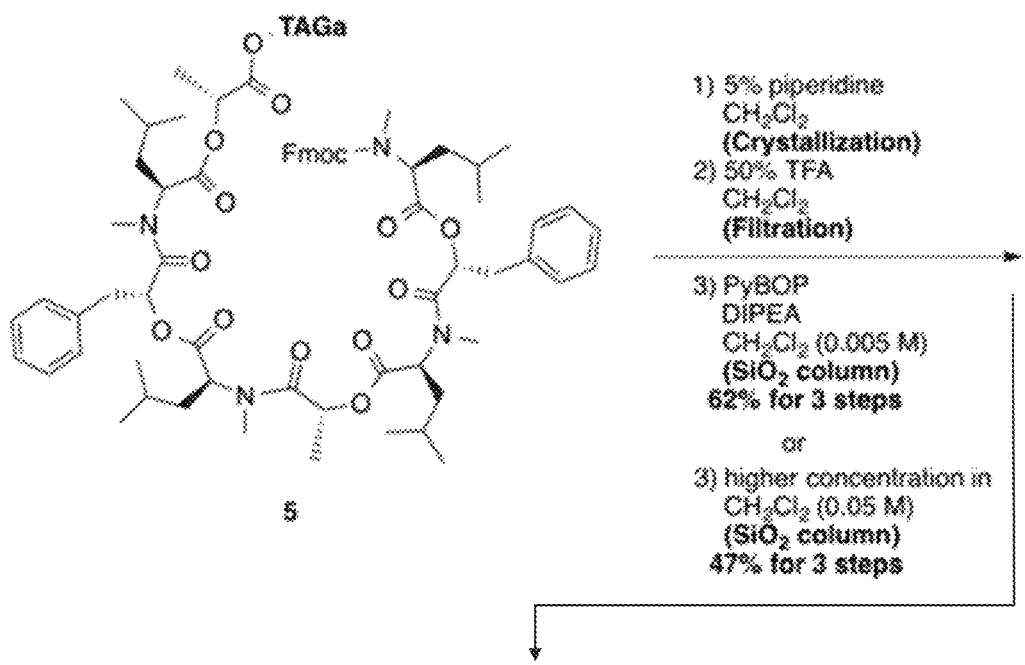
Figure 3C:
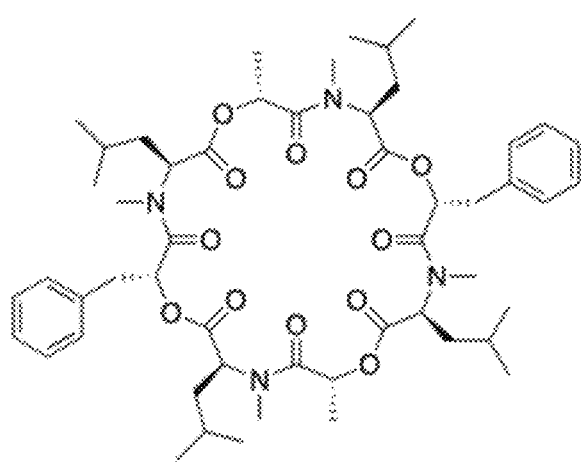
Figure 4:
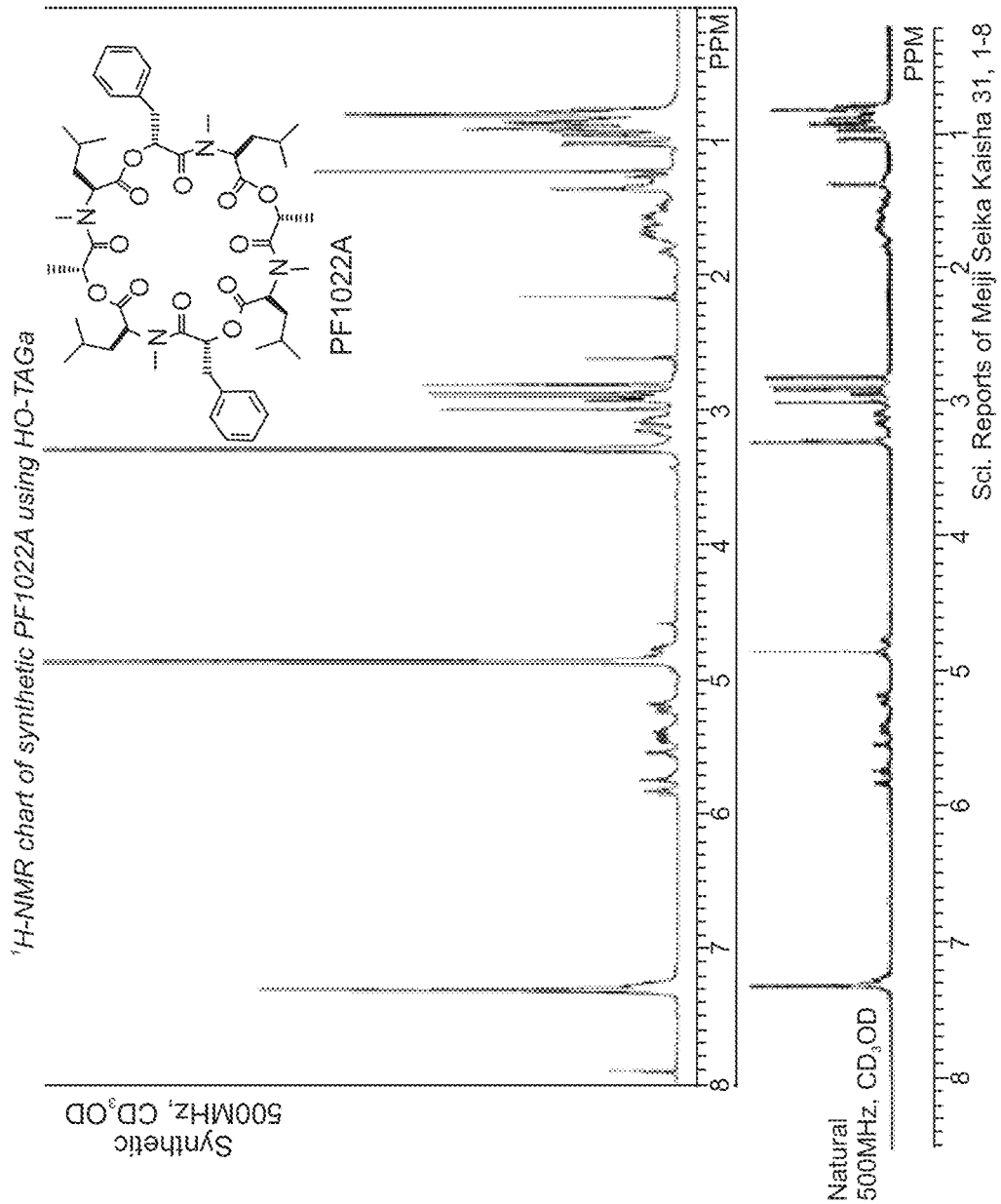
FIG. 4 $^1$H NMR spectra of PF1022A

3. Preparation of PF1022A (Method 1; Cf. Reaction Scheme in FIGS. 3A, 3B, and 3C and NMR Spectra in FIG. 4)
3-1. Synthetic Procedure N-Fmoc-N-MeLeu-D-Lac-O-TAGa

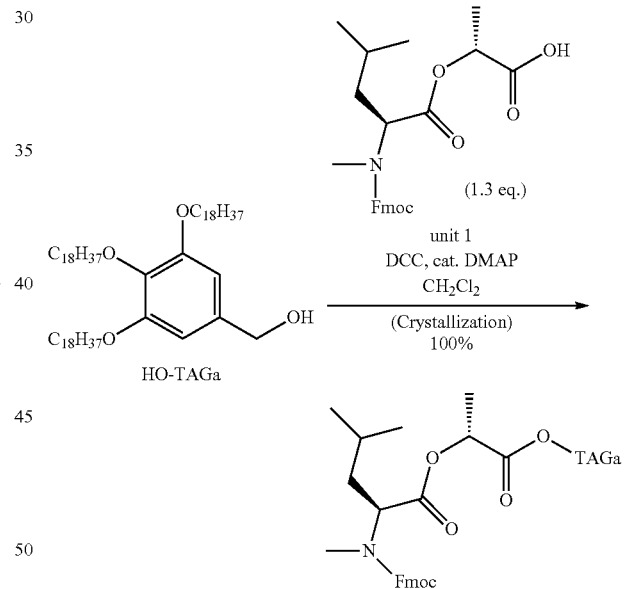

To a stirred solution of HO-TAGa (1.69 g, 1.85 mmol) in CH₂Cl2 (37 mL) was added 0.2 M toluene solution of unit 1 (12.0 mL, 2.40 mmol), 4-dimethylaminopyridine (12 mg, 93.0 μmol), and N,N'-dicyclohexylcarbodiimide (1.30 g, 2.78 mmol) at room temperature under N₂ atmosphere. After stirring for 2 h, the reaction mixture was then cooled to −5° C., and MeOH (185 mL) was added. The resulting heterogeneous solution was stirred for further 15 min at −5° C., and the colorless precipitate was filtered and washed with additional MeOH (500 mL) to afford N-Fmoc-N-MeLeu-D-Lac-O-TAGa (2.46 g, 100%) as a colorless powder.
mp: 44-45° C.
$[\alpha]_D^{24}$: −10.2 (c 1.0, CHCl₃)
$^1$H-NMR (500 MHz, CDCl₃) δ: 7.78-7.74 (complex m, 2H), 7.60-7.56 (complex m, 2H), 7.39 (m, 2H), 7.29 (m, 2H), 6.50 (s, 4/3H), 6.48 (s, 2/3H), 5.12-5.00 (complex-m, 4H), 4.67 (dd, J=6.3, 9.7 Hz, 3/10H), 4.58 (dd, J=6.3 Hz, 10.9 Hz, 4/10H), 4.50 (dd, J=6.9 Hz, 10.3 Hz, 6/10H), 4.38-4.34 (complex m, 9/10H), 4.30 (m, 5/10H), 4.23 (t, J=6.3 Hz, 3/10H), 3.93 (m, 6H), 2.86 (s, 2H), 2.83 (s 1H), 1.76 (m, 6H), 1.64-1.42 (complex m, 9H), 1.31-1.14 (complex m, 87H), 0.96-0.87 (complex m, 14H), 0.78 (d, J=6.9 Hz, 1H).

HRMS (FAB, NBA matrix) m/z: 1334.0748 (M+, calcd for $C_{86}H_{143}NO_9$: 1334.0763)

N-MeLeu-D-Lac-O-TAGa (1)

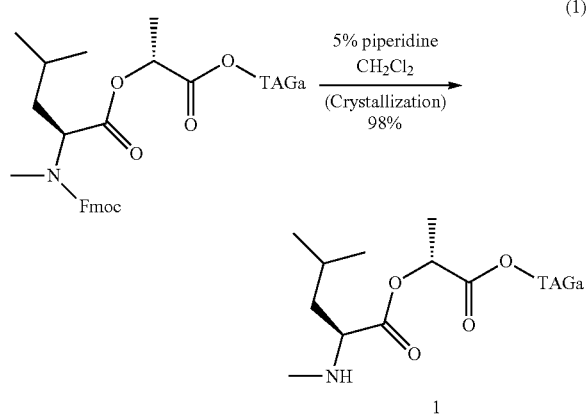

Following the procedure described for general procedure of Fmoc deprotection, N-Fmoc-N-MeLeu-D-Lac-O-TAGa (1.00 g, 0.749 mmol) was converted to 1 (816 mg, 98%) as a colorless powder.

$^1$H-NMR (500 MHz, CDCl$_3$) δ: 6.50 (s, 2H), 5.16 (q, J=6.9 Hz, 1H), 5.08 (d, J=12.0 Hz, 1H), 5.04 (d, J=12.0 Hz, 1H), 3.93 (m, 6H), 3.30 (t, J=7.5 Hz, 1H), 2.37 (s, 3H), 1.75 (m, 6H), 1.53-1.42 (complex m, 10H), 1.32-1.25 (complex m, 86H), 0.93-0.86 (complex m, 15H).

$^{13}$C-NMR (125 MHz, CDCl$_3$) δ: 170.6, 153.3, 138.4, 130.2, 106.4, 73.5, 69.2, 68.9, 67.6, 61.4, 42.2, 34.5, 32.0, 30.4, 29.8 (×2), 29.5 (×2), 26.2, 25.0, 22.8, 22.6, 22.5, 17.1, 14.2.

HRMS (FAB, NBA matrix) m/z: 1113.0151 [(M+H)+, calcd for $C_{71}H_{34}NO_7$: 1113.0160]

N-Fmoc-N-MeLeu-D-PhLac-N-MeLeu-D-LacO-TAGa (2)

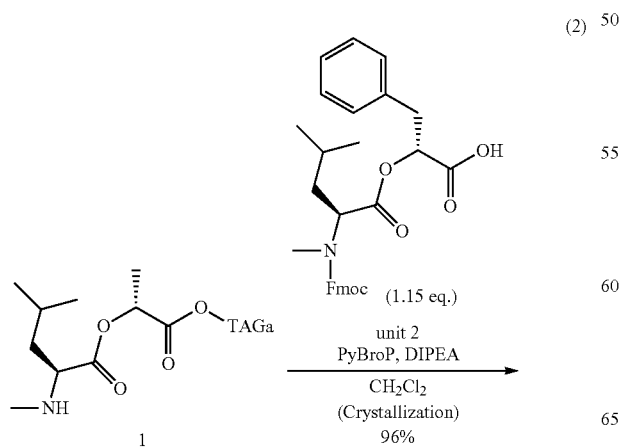

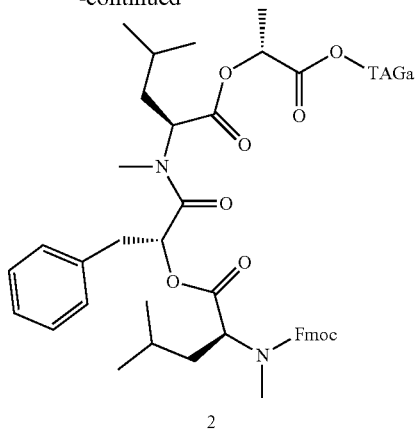

To a stirred solution of 1 (800 mg, 0.719 mmol) in CH$_2$C12 (25 mL) was added unit 2 (426 mg, 0.827 mmol), N,N-diisopropylethylamine (0.429 mL, 2.52 mmol), and PyBroP (496 mg, 1.222 mmol) at room temperature. After stirring for 88 h, the reaction mixture was crystallized by the procedure described in synthesis of N-Fmoc-N-MeLeu-D-Lac-O-TAGa to afford 2 (1.11 g, 96%) as a colorless powder.

$^1$H-NMR (500 MHz, CDCl$_3$) δ: 7.76-7.72 (complex m, 2H), 7.62-7.40 (complex m, 2H), 7.39-7.17 (complex m, 9H), 6.47 (m, 2H), 5.47-5.27 (complex m, 2H), 5.15-4.97 (complex m, 4H), 4.69-4.13 (complex m, 3H), 3.92 (complex m, 6H), 3.07 (m, 2H), 2.85 (complex, 6H), 1.80-1.25 (complex m, 105H), 1.02-0.72 (complex m, 21H).

HRMS (FAB, NBA matrix) m/z: 1632.2163 [(M+Na)+, calcd for $C_{102}H_{164}N_2O_{12}Na$: 1632.2182]

N-MeLeu-D-PhLac-N-MeLeu-D-Lac-OH (3)

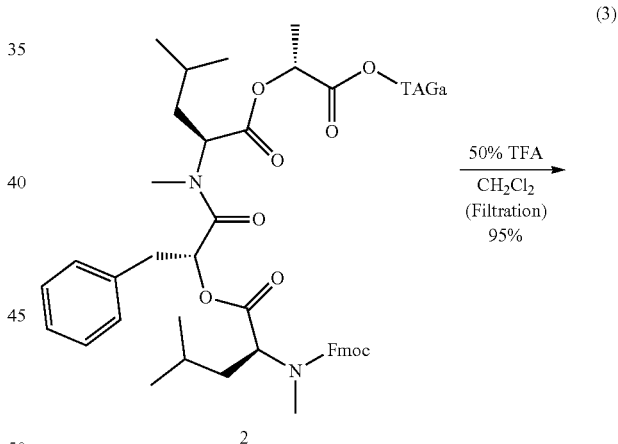

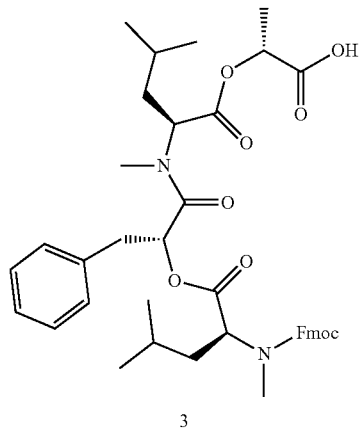

Following the procedure described for general procedure of TAGa cleavage, 2 (614 mg, 0.381 mmol) was converted to 3 (261 mg, 95%) as an yellow oil, which was used next reaction without further purification.

N-MeLeu-D-PhLac-N-MeLeu-D-Lac-O-TAGa (4)

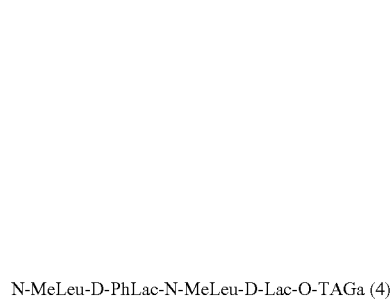

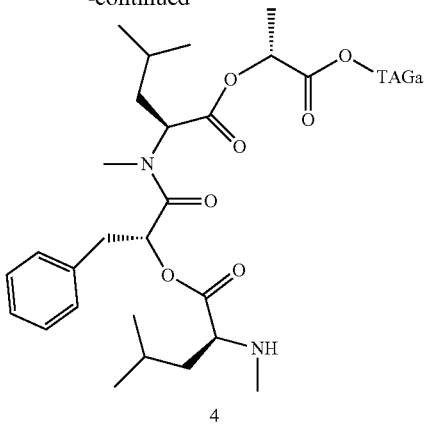

Following the procedure described for general procedure of Fmoc deprotection, 2 (472 mg, 0.293 mmol) was converted to 4 (404 mg, 100%) as a colorless powder.

$^1$H-NMR (500 MHz, CDCl$_3$) δ: 7.27 (m, 5H), 6.49 (s, 2H), 5.50 (dd, J=5.7, 8.6 Hz, 1H), 5.32 (dd, J=4.6, 10.9 Hz, 1H), 5.09-5.00 (complex m, 3H), 3.93 (m, 6H), 3.28 (t, J=6.9 Hz, 1H), 3.09 (m, 2H), 2.92 (s, 3H), 2.27 (s, 3H), 1.82-1.25 (complex m, 105H), 0.89-0.77 (complex m, 21H).
$^{13}$C-NMR (125 MHz, CDCl$_3$) δ: 175.6, 175.1, 175.0, 174.8, 170.9, 170.5 (×2), 170.4, 169.8, 169.7, 166.7, 165.1, 153.3, 138.5, 138.3, 135.8 (×2), 130.2, 129.5, 129.3, 128.7, 128.6, 128.5 (×2), 127.2, 107.0, 106.9, 105.4, 78.1, 73.5, 71.9, 71.6, 69.4, 69.2, 68.9, 67.7, 67.5, 66.9, 65.6, 61.3, 61.2, 59.7, 57.7, 54.7, 42.3, 42.2, 42.1, 40.0, 38.8, 37.5, 36.9, 34.4, 34.3, 32.8, 32.0, 31.3, 30.4, 29.8 (×2), 29.6, 29.5 (×2), 26.2, 25.0, 24.8, 24.7, 24.6, 23.4, 22.9, 22.8, 22.5 (×2), 22.4 (×2), 21.9, 21.4, 20.5, 17.0, 16.9, 16.8, 14.2.
HRMS (FAB, NBA matrix) m/z: 1388.1664 [(M+H)$^+$, calcd for C$_{87}$H$_{155}$N$_2$O$_{10}$: 1388.1682]

N-Fmoc-N-MreLeu-D-PhLac-N-MeLeu-D-Lac-N-MeLeu-D-PhLac-N-MeLeu-D-Lac-O-TAGa (5)

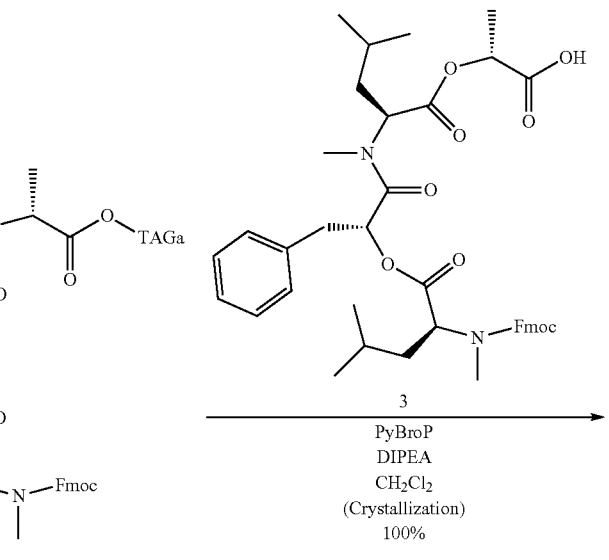

-continued

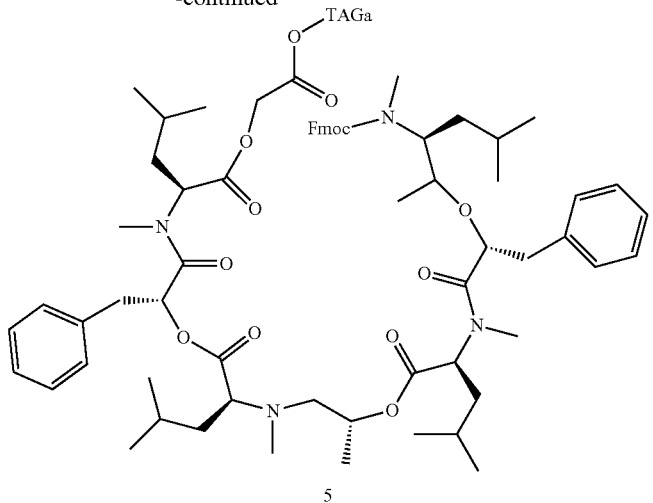

5

To a stirred solution of 2 (330 mg, 0.238 mmol) in CH$_2$Cl$_2$ (4.8 mL) was added 3 (221 mg, 0.309 mmol), N,N-diisopropylethylamine (0.150 mL, 0.881 mmol), and PyBroP (197 mg, 0.428 mmol) at room temperature. After stirring for 42 h, the reaction mixture was crystallized by the procedure described in synthesis of N-Fmoc-N-MeLeu-D-Lac-O-TAGa to afford 5 (477 mg, 96%) as a colorless powder.

$^1$H-NMR (500 MHz, CDCl$_3$) δ: 7.74 (m, 2H), 7.53 (m, 2H), 7.38 (m, 2H), 7.32-7.15 (complex m, 12H), 6.48 (m, 2H), 5.51-4.96 (complex m, 10H), 4.70-4.12 (complex m, 3H), 3.93 (m, 6H), 3.23 (dd, J=6.9, 13.7 Hz, 1H), 3.08-2.70 (complex m, 15H), 1.80-1.25 (complex m, 114H), 0.95-0.78 (complex m, 33H).

HRMS (FAB, NBA matrix) m/z: 2106.4949 [(M+Na)$^+$, calcd for C$_{128}$H$_{202}$N$_4$O$_{18}$Na$_1$: 2106.4912]

N-MeLeu-D-PhLac-N-MeLeu-D-Lac-N-MeLeu-D-PhLac-N-MeLeu-D-Lac-O-TAGa

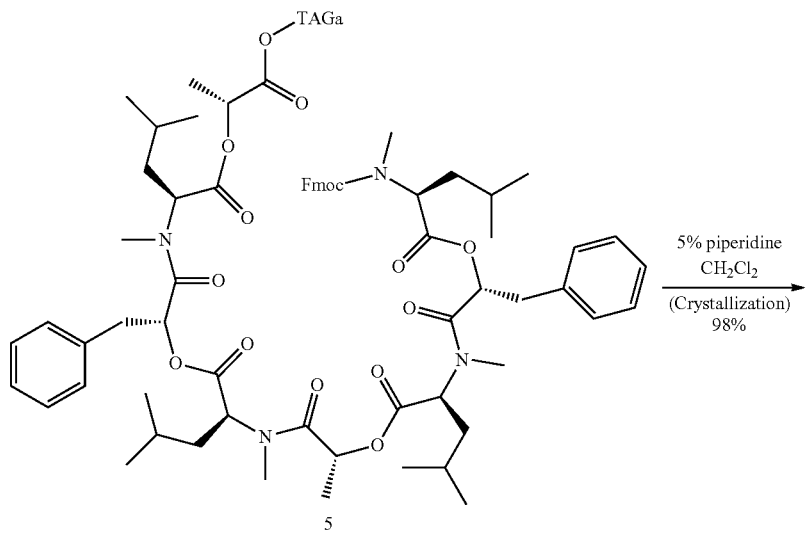

5

5% piperidine
CH$_2$Cl$_2$
(Crystallization)
98%

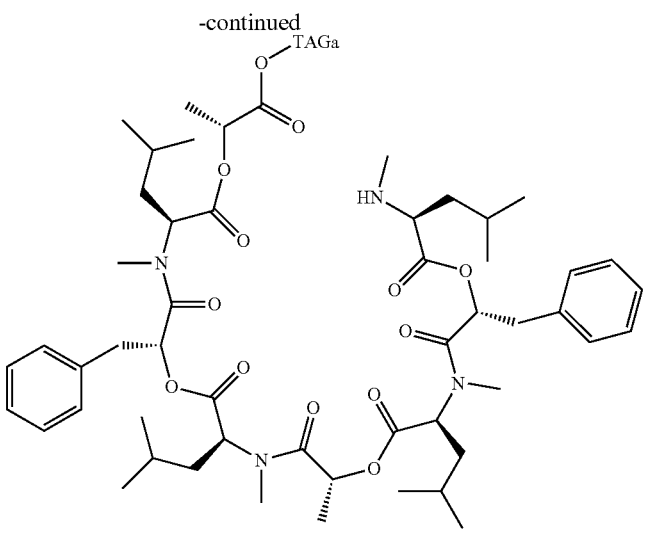

Following the procedure described for general procedure of Fmoc deprotection, 5 (450 mg, 0.206 mmol) was converted to the corresponding amine (398 mg, 98%) as a colorless powder.

$^1$H-NMR (500 MHz, CDCl$_3$) δ: 7.25 (m, 10H), 6.48 (s, 2H), 5.57-4.99 (complex m, 9H), 3.93 (m, 6H), 3.26-2.78 (complex m, 14H), 2.24 (s, 3H), 1.80-1.25 (complex m, 114H), 0.90-0.78 (complex m, 33H).

$^{13}$C-NMR (125 MHz, CDCl$_3$) δ: 175.6, 175.2 (×2), 171.5, 171.1, 170.8 (×2), 170.6, 170.5 (×2), 170.3, 153.3, 138.5 (×2), 138.3, 136.1, 135.9, 135.5, 130.2, 130.1, 130.0, 129.8, 129.7, 129.6, 129.4 (×2), 128.8, 128.7, 128.6, 128.5, 127.4 (×2), 127.2, 127.1, 126.9, 126.8, 107.0 (×2), 106.9, 73.5, 72.5, 72.2, 71.7, 71.6, 69.8, 69.4, 69.2, 68.1, 68.0, 67.8, 67.5 (×2), 66.9, 61.4, 57.4, 55.2, 54.8, 54.6 (×2), 38.8, 37.7, 37.6, 37.4 (×2), 37.1 (×2), 37.0, 36.9, 34.7, 34.6, 32.2, 32.0, 31.9, 31.7, 31.6, 31.4, 31.3, 31.2, 30.4, 29.8 (×2), 29.6, 29.5 (×2), 26.2, 24.9, 24.8 (×2), 24.7, 24.6, 24.5, 23.5, 23.4, 23.3, 23.1 (×2), 23.0, 22.8, 22.7, 22.5, 22.4, 22.3, 22.0, 21.5, 21.4, 21.3 (×2), 20.5, 16.9, 16.8, 16.6, 14.2.

HRMS (FAB, NBA matrix) m/z: 1862.4425 [(M+H)$^+$, calcd for C$_{113}$H$_{193}$N$_4$O$_{16}$: 1862.4412]

N-MeLeu-D-PhLac-N-MeLeu-D-Lac-N-MeLeu-D-PhLac-N-MeLeu-D-Lac-OH

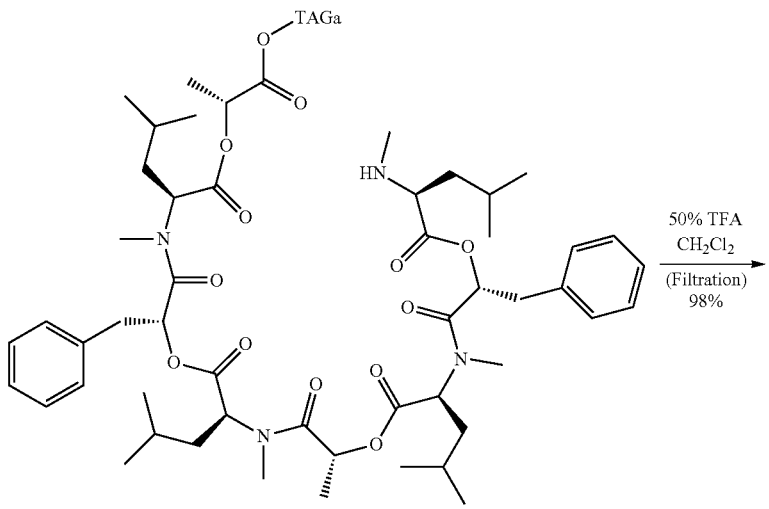

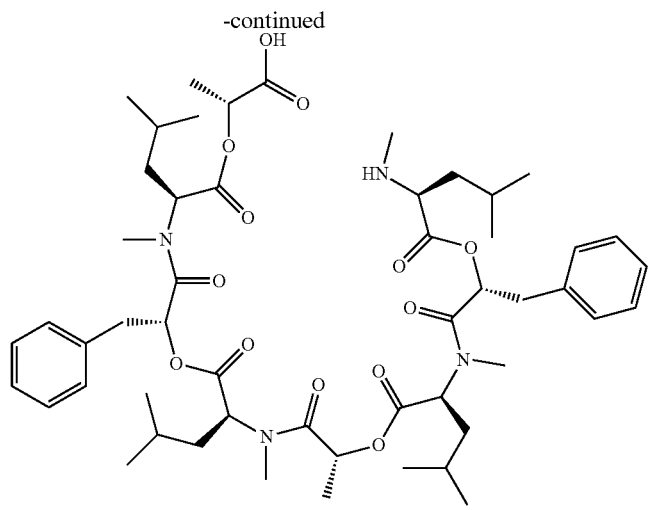

Following the procedure described for general procedure of TAGa cleavage, N-MeLeu-D-PhLac-N-MeLeu-D-Lac-N-MeLeu-D-PhLac-N-MeLeu-D-LacO-TAGa (380 mg, 0.204 mmol) was converted to the corresponding carboxylic acid (198 mg, 98%) as a yellow oil, which was used next reaction without further purification.

Reaction for 0.005M Concentration of Substrate

A crude of previous reaction (90 mg, 0.0895 mmol) was dissolved in $CH_2Cl_2$ (18 mL, 0.005 M). The reaction mixture was added N,N-diisopropylethylamine (76 μL, 4.48 mmol) and PyBOP (93 mg, 0.179 mmol) at room temperature. After being stirred for 48 h, the reaction mixture was quenched

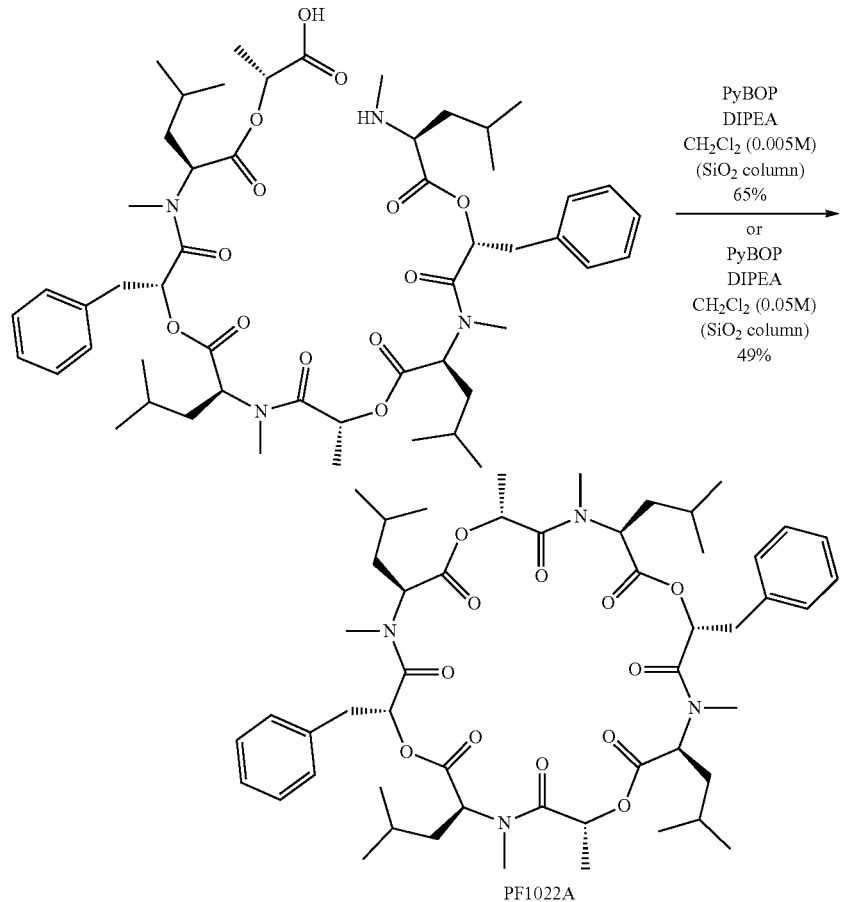

with saturated aqueous NaHCO$_3$ (18 mL) at 0° C. and this mixture was extracted with CHCl$_3$ (20 mL×2). The combined organic layers were washed with 10% aqueous NaHSO$_4$ (60 mL) and brine (60 mL), dried over Na$_2$SO$_4$, filtered and concentrated in vacuo. The crude was purified by column chromatography on silica gel (CHCl3:MeOH=400:1 to 40:1) to provide PF1022A (55 mg, 65%) as a colorless solid.

Reaction for 0.05M Concentration of Substrate

According to the procedure for cyclization mentioned above, a crude of previous reaction (90 mg, 0.0895 mmol) was cyclized in CH$_2$Cl$_2$ (1.8 ml, 0.05 M) with N,N-diisopropylethylamine (76 µL, 4.48 mmol) and PyBOP (93 mg, 0.179 mmol) at room temperature for 48 h to provide PF1022A (40 mg, 49%) as a colorless solid.

mp: 100-103° C.

[α]$^{22}_D$: −99.4° C. (c 0.06, MeOH)

IR (KBr) ṽ: 1743, 1666, 1466, 1412, 1265, 1188, 1126, 1080, 1026, 748, 701

$^1$H-NMR (500 MHz, CD$_3$OD) δ: 7.29 (m, 10H), 5.82 (t, J=7.5 Hz, 1H), 5.72 (m, 2H, rotamer), 5.54 (q, J=6.9 Hz, 1H), 5.44 (dd, J=4.6, 11.7 Hz, 1H), 5.40 (dd, J=4.6, 11.7 Hz, 1H, rotamer), 5.23 (dd, J=4.6, 11.7 Hz, 1H), 5.18 (q, J=6.9 Hz, 1H, rotamer), 4.77 (dd, J=3.4, 11.2 Hz, 1H), 3.14 (m, 4H), 3.00 (s, 5/2H, rotamer), 2.91 (m, 7H, rotamer), 2.82 (s, 5/2H, rotamer), 1.84 (m, 1H), 1.77-1.47 (complex m, 11H), 1.39 (d, J=6.3 Hz, 3H), 1.05 (d, J=6.3 Hz, 3H), 0.98 (d, J=6.9 Hz, 3H), 0.80 (d, J=6.3 Hz, 3H), 0.95-0.82 (complex m, 18H).

$^{13}$C-NMR (125 MHz, CD$_3$OD) δ: 174.4, 173.5, 173.1, 173.1, 172.3, 172.0, 171.0, 170.7, 136.4, 136.2, 130.8, 130.7, 130.7, 129.8, 129.7, 129.7, 128.4, 128.3, 72.5, 72.3, 69.9, 68.5, 58.6, 55.7, 55.5, 55.4, 39.0, 38.9, 38.6, 38.6, 37.8, 37.3, 32.0, 31.3, 31.1, 30.0, 26.2, 26.1, 25.5, 25.2, 23.9, 23.7, 23.7, 23.6, 21.7, 21.6, 21.4, 21.1, 17.5, 17.2.

HRMS (FAB, NBA matrix) m/z: 971.5353 [(M+Na)$^+$, calcd for C$_{52}$H$_{76}$N$_4$O$_{12}$Na$_1$: 971.5357]

*Literature (J. Antibiot., 1992, 45, 692-697)

mp: 104-106° C.

[α]$^{22}_D$: −102° C. (c 0.1, MeOH)

$^1$H-NMR (400 MHz, CD$_3$OD) δ: 7.30-7.20 (PhH, 10H), 5.80 and 5.75 (C$_α$H-PhLac, 1H×2), 5.54 and 5.16 (C$_α$H-Lac, 1H×2), 5.43, 5.42, 5.22 and 4.78 (C$_α$H-Leu, 1H×4), 3.22-3.15 (C$_β$H$_2$-PhLac, 2H×2), 3.00, 2.90, 2.88 and 2.80 (N-MeLeu, 3H×4), 1.87-1.50 (C$_β$H$_2$-Leu, 2H×4), 1.40 (C$_γ$H-Leu, 1H×4), 1.38 (C$_β$H$_3$-Lac, 3H), 1.02-0.75 (C$_δ$H$_3$-Leu, 6H×4), 0.88 (C$_β$H$_3$-Lac, 3H).

$^{13}$C-NMR (100 MHz, CD$_3$OD) δ: 174.4, 173.4, 172.4, 172.4, 172.1, 172.1, 171.0, 170.8, 136.5, 136.2, 130.7, 130.7, 130.7, 130.7, 129.7, 129.7, 129.7, 129.7, 128.3, 128.2, 72.5, 72.3, 69.9, 68.4, 58.6, 55.7, 55.5, 55.4, 39.0, 38.9, 38.6, 38.6, 37.9, 37.4, 32.0, 31.3, 31.1, 29.9, 26.2, 26.1, 25.6, 25.2, 23.6, 23.6, 23.5, 23.5, 21.7, 21.6, 21.4, 21.0, 17.5, 17.2.

Figure 5A:
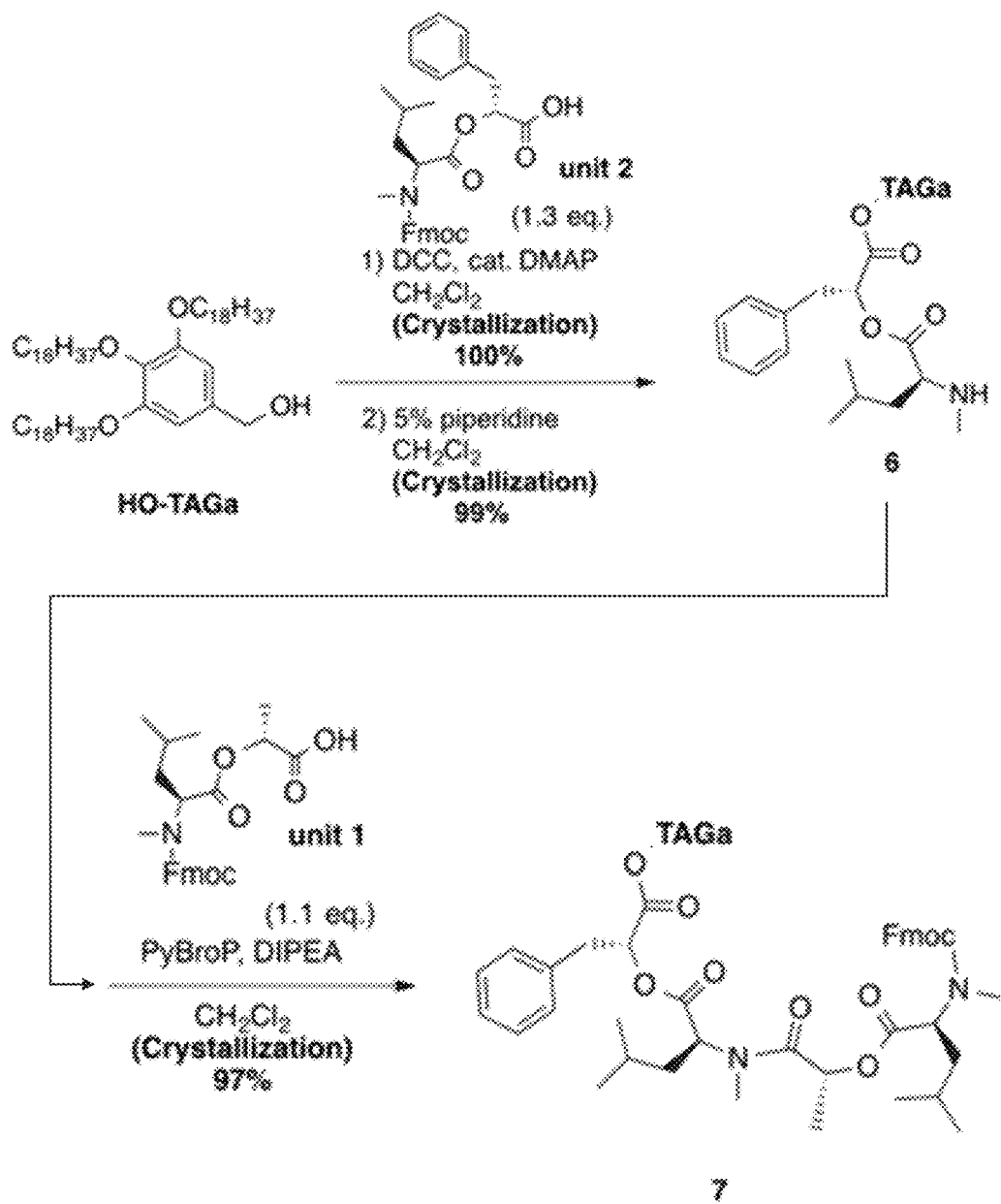
FIG. 5A PF1022A Synthesis (Method 2)-Preparation of 7
Figure 5B:
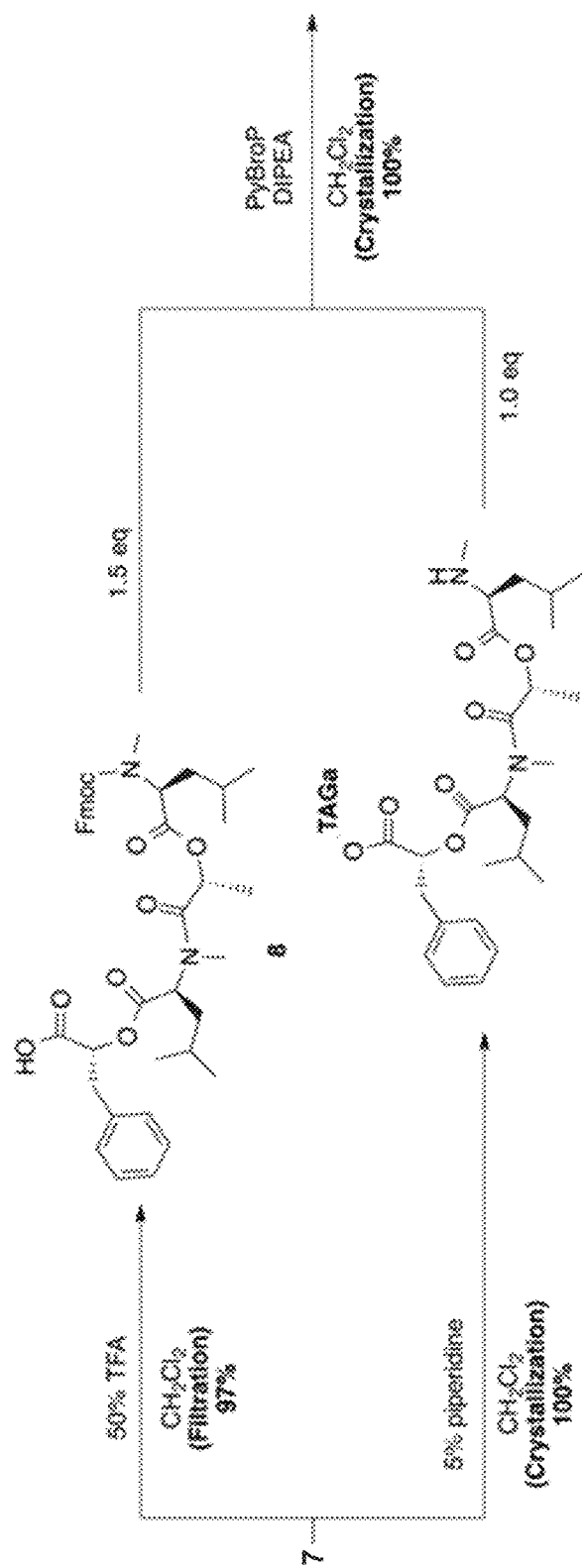
FIG. 5B PF1022A Synthesis (Method 2)-Preparation of 8 and 9 and reaction conditions for the preparation of 10
Figure 5C:
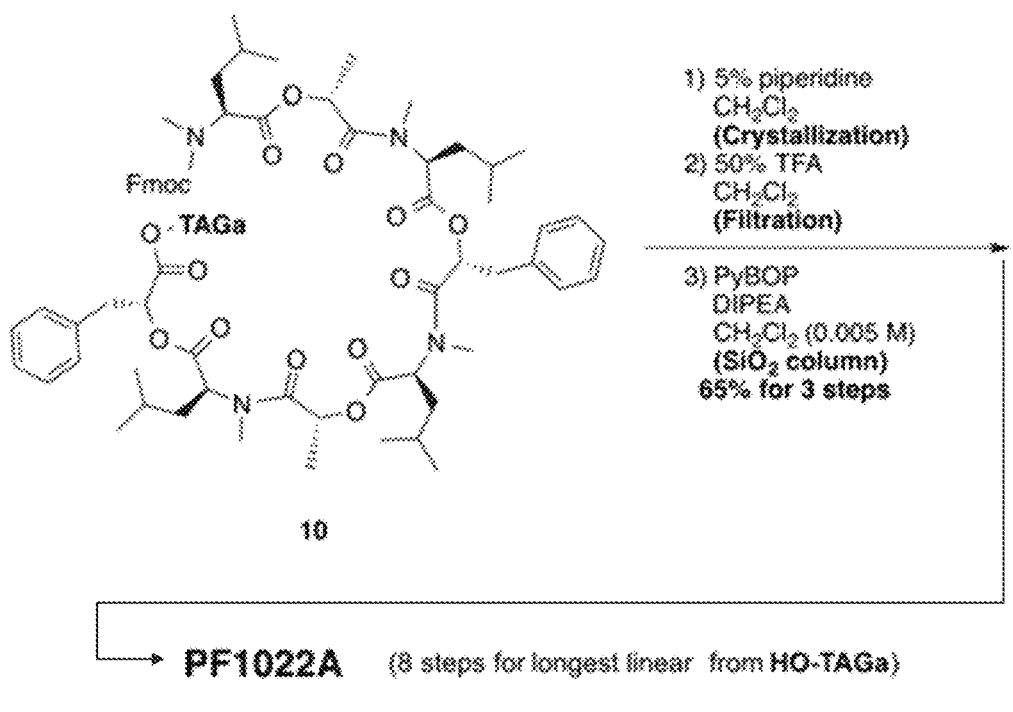
FIG. 5C PF1022A Synthesis (Method 2)-Preparation of PF1022A
Figure 5C:
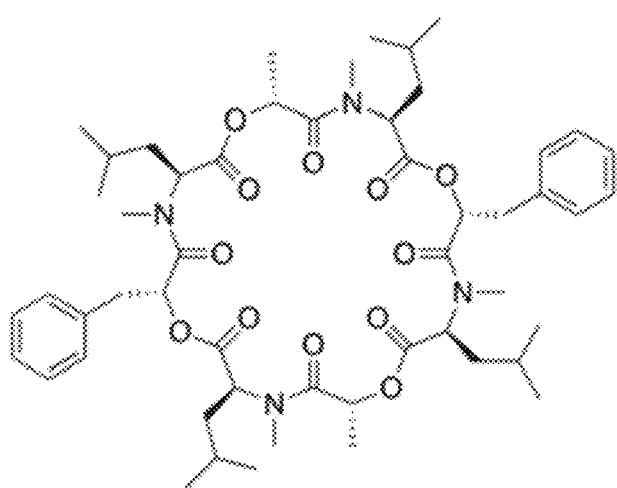
Figure 6A:
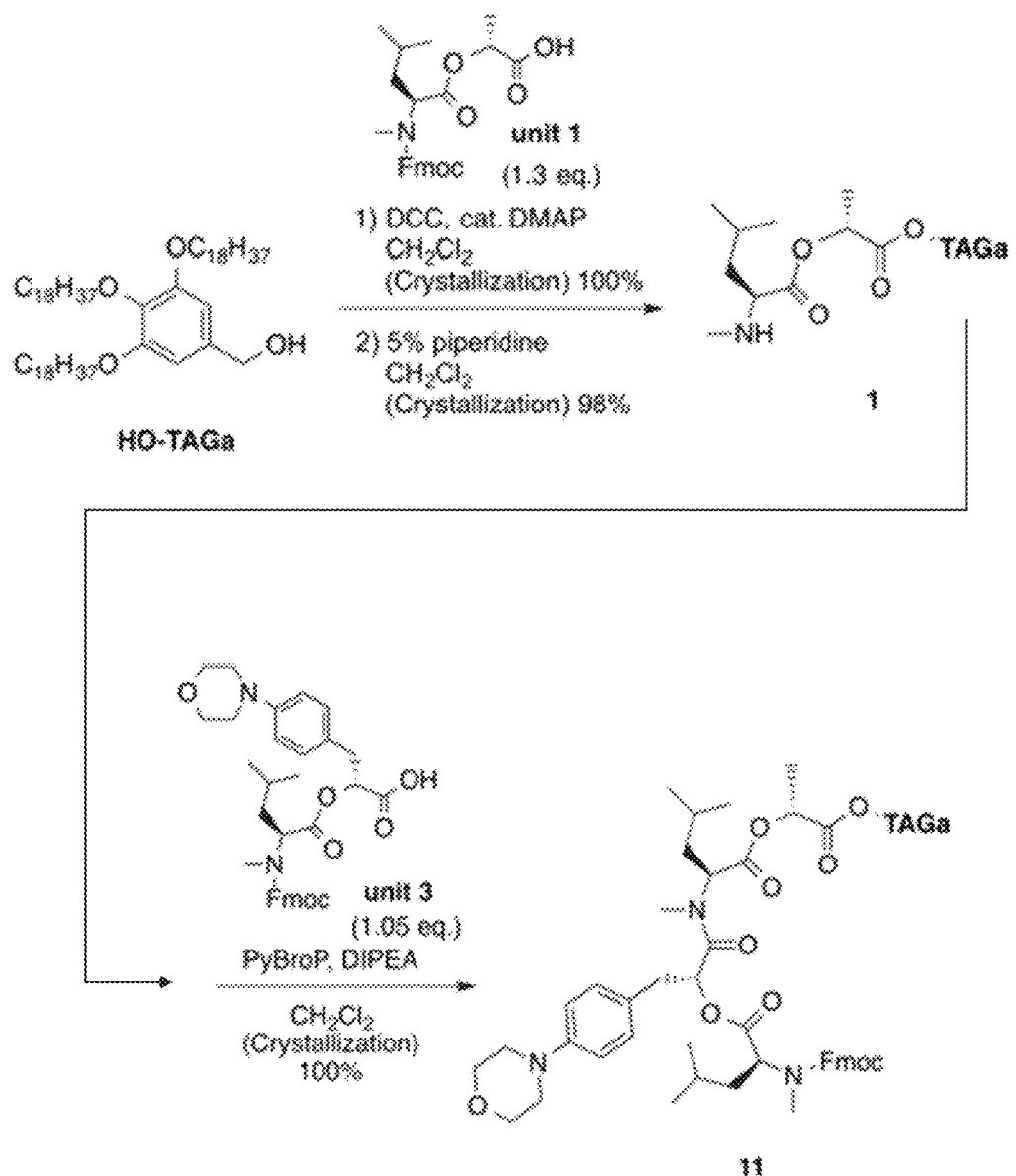
FIG. 6A Emodepside Synthesis (Method 1)-Preparation of 11
Figure 6B:
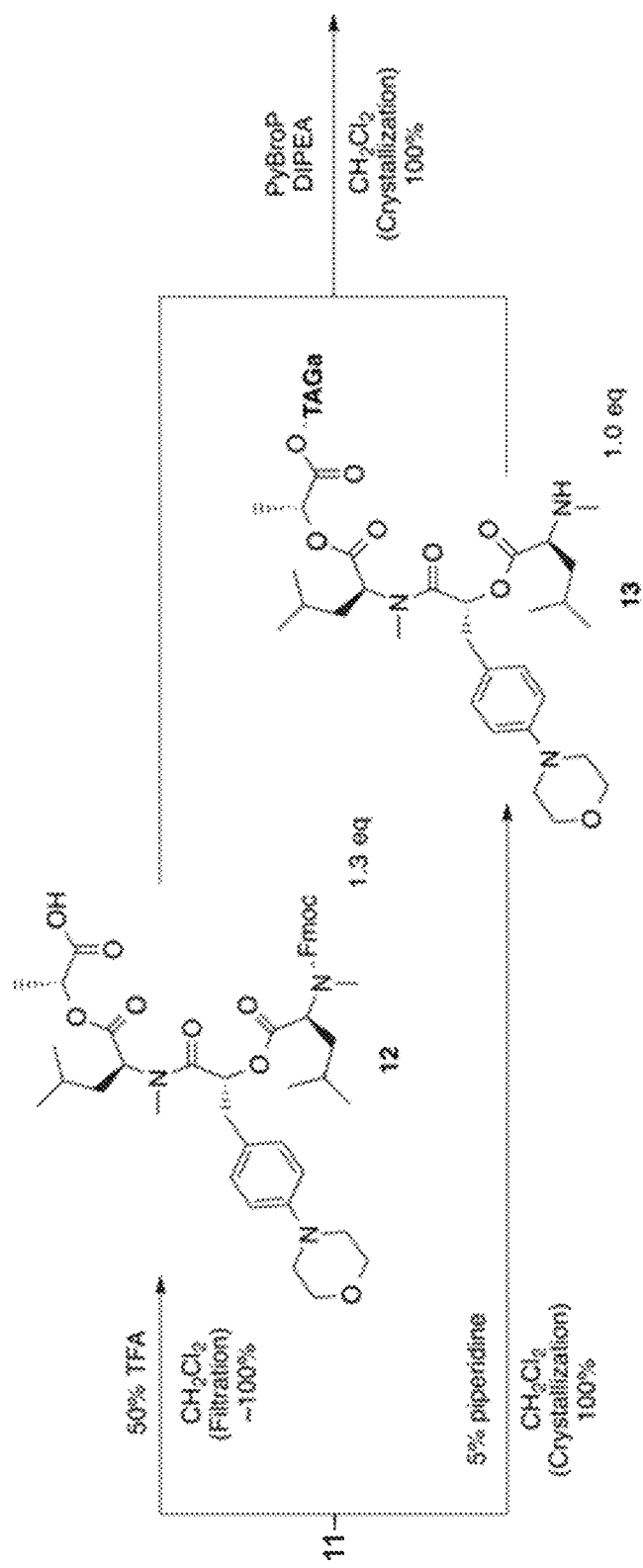
FIG. 6B Emodepside Synthesis (Method 1)-Preparation of 12 and 13 and reaction conditions for the preparation of 14
Figure 6C:
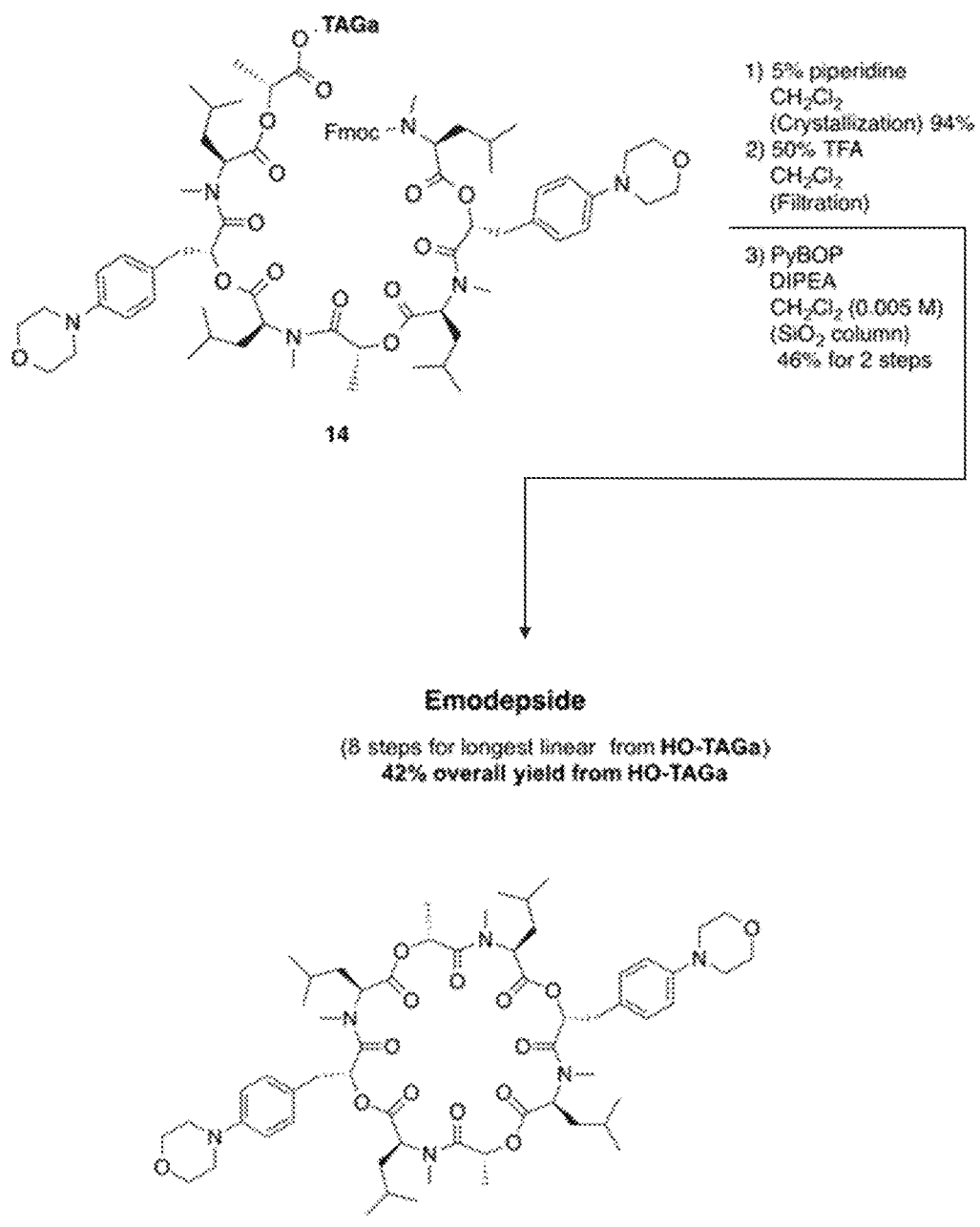
FIG. 6C Emodepside Synthesis (Method 1)-Preparation of Emodepside
Figure 6D:
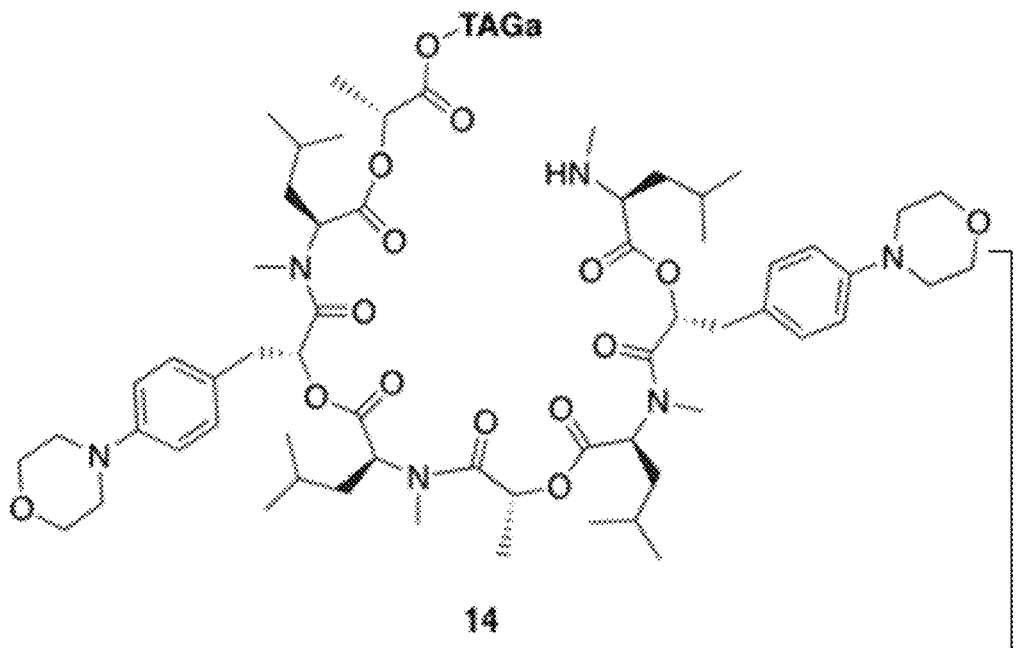
FIG. 6D Emodepside Synthesis (Method 1)-Improved preparation of Emodepside

4. Preparation of PF1022A (Method 2; Cf. Reaction Scheme in FIGS. 5A, 5B, and 5C)

4-1. Synthetic Procedure

N-Fmoc-N-MeLeu-D-PhLac-O-TAGa

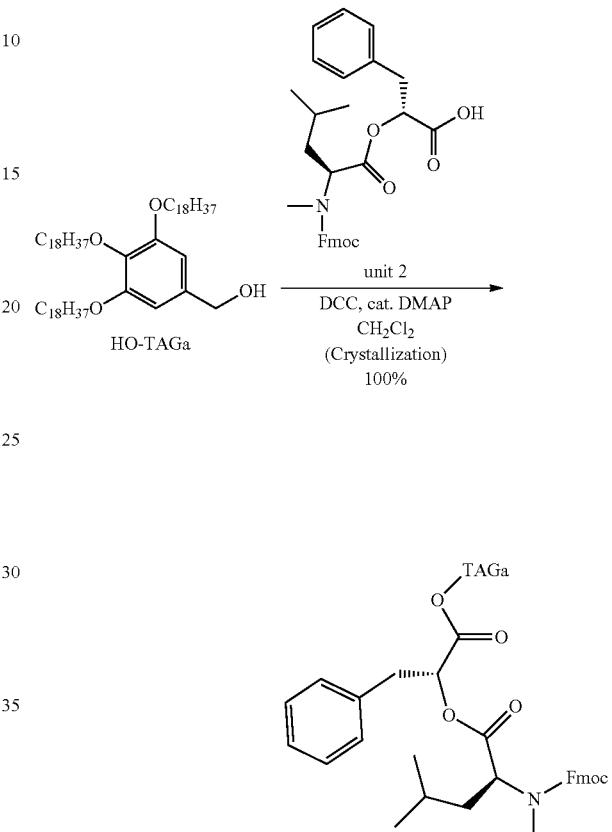

To a stirred solution of HO-TAGa (170 mg, 0.186 mmol) in CH$_2$C2 (3.7 mL) was added 0.1 M toluene solution of unit 2 (2.42 mL, 0.242 mmol), 4-dimethylaminopyridine (1.1 mg, 9.30 µmol), and N,N'-dicyclohexylcarbodiimide (58 mg, 0.279 mmol) at room temperature under N$_2$ atmosphere. After stirring for 1 h, the reaction mixture was crystallized by the procedure described in synthesis of N-Fmoc-N-MeLeu-D-Lac-O-TAGa to afford N-Fmoc-N-MeLeu-D-PhLac-O-TAGa (266 mg, 100%) as a colorless powder.

mp: 44-45° C.

[α]$_D^{27}$: −6.1 (c 1.74, CHCl$_3$)

$^1$H-NMR (500 MHz, CDCl$_3$) δ: 7.76 (complex m, 2H), 7.54 (m, 2H), 7.39 (m, 2H), 7.30 (m, 1H), 7.26-7.14 (complex m, 4H), 7.08 (m, 2H) 6.44 (m, 2H), 5.20 (m, 1H), 5.04-4.94 (complex m, 3H), 4.61-4.15 (complex m, 3H), 3.92 (m, 6H), 3.10 (m, 2H), 2.72 (s, 3H), 1.76 (m, 6H), 1.60-1.25 (complex m, 93H), 0.90-0.71 (complex m, 15H).

$^{13}$C-NMR (125 MHz, CDCl$_3$) δ: 177.2, 175.2, 169.5, 153.3, 138.4, 135.9, 130.0, 129.6, 129.3, 128.6, 128.4, 127.1, 107.5, 107.2, 73.5, 73.1, 69.2, 67.8, 61.6, 42.5, 37.4, 34.5, 32.0, 30.4, 29.8 (×2), 29.6, 29.5, 26.2, 24.8, 22.8, 22.6, 22.5, 14.2.

HRMS (FAB, NBA matrix) m/z: 1410.1063 [(M+H)$^+$, calcd for C$_{92}$H$_{147}$NO$_9$: 1410.1076]

N-MeuLeu-D-PhLac-O-TAGa

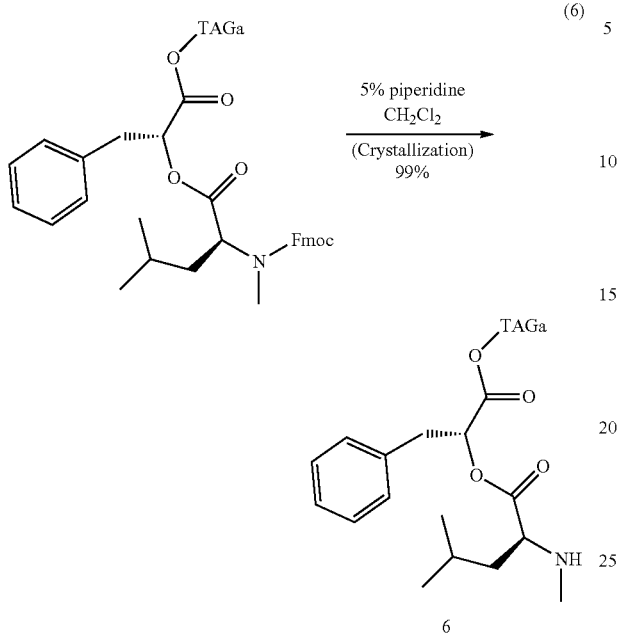

Following the procedure described for general procedure of Fmoc deprotection, N-Fmoc-N-MeLeu-D-PhLac-O-TAGa (457 mg, 0.324 mmol) was converted to 6 (378 mg, 99%) as a colorless powder.

mp: 48-49° C.

$[\alpha]_D^{26}$: +4.2 (c1.10, CHCl$_3$)

$^1$H-NMR (500 MHz, CDCl$_3$) δ: 7.22 (m, 5H), 6.48 (s, 2H), 5.28 (dd, J=4.0, 10.3 Hz, 1H), 5.08 (d, J=12.0 Hz, 1H), 5.04 (d, J=12.0 Hz, 1H), 3.93 (m, 6H), 3.24 (dd, J=4.0 Hz, 14.3 Hz, 1H), 3.17 (t, J=6.9 Hz, 1H), 3.07 (dd, J=9.7, 14.3 Hz, 1H), 2.18 (s, 3H), 1.76 (m, 6H), 1.48-1.25 (complex m, 93H), 0.90-0.76 (complex m, 15H).

HRMS (FAB, NBA matrix) m/z: 1189.0458 [(M+H)$^+$, calcd for C$_{77}$H$_{138}$NO$_7$: 1189.0473]

To a stirred solution of 6 (358 mg, 0.301 mmol) in CH$_2$Cl$_2$ (6.0 ml) was added 0.1 M toluene solution of unit 1 (3.31 mL, 0.331 mmol), N,N-diisopropylethylamine (0.15 mL, 0.903 mmol), and PyBroP (211 mg, 0.452 mm) at room temperature. After stirring for 13 h, reaction mixture was crystallized by the procedure described in synthesis of N-Fmoc-N-MeLeu-D-Lac-O-TAGa to afford 7 (468 mg, 97%) as a colorless powder.

mp: 47-48° C.

$[\alpha]_D26$: −13.9 (c 1.10, CHCl$_3$)

$^1$H-NMR (500 MHz, CDCl$_3$) δ:7.75 (m, 2H), 7.59 (m, 2H), 7.39 (m, 2H), 7.30-7.09 (complex m, 7H), 6.44 (m, 2H), 5.36-4.96 (complex m, 6H), 4.71-4.24 (complex m, 3H), 3.93 (t, J=6.5 Hz, 6H), 3.14 (m, 2H), 2.90-2.81 (complex s, 6H), 1.80-1.25 (complex m, 105H), 0.96-0.76 (complex m, 21H).

$^{13}$C-NMR (125 MHz, CDCl$_3$) δ: 171.6, 171.2, 171.1, 170.9, 169.3, 157.0, 153.3, 144.3, 143.9, 141.4 (×2), 138.4, 135.9, 130.0, 129.9, 129.8, 129.7, 129.6, 129.5, 129.3, 128.7, 128.5, 128.4, 127.7, 127.6, 127.0, 125.3, 125.1, 125.0, 124.9, 120.0, 107.5, 107.2, 74.1, 74.0, 73.9, 73.8, 73.5, 71.3, 69.2, 67.9, 67.7, 57.4, 57.2, 56.7, 56.6 (×2), 54.5 (×2), 47.4 (×2), 47.3, 37.6, 37.3, 37.2, 37.1, 37.0, 32.0, 31.1, 30.7, 30.6 (×2), 30.5, 30.4, 30.3, 30.2, 29.8 (×2), 29.6, 29.5 (×2), 26.2, 24.9, 24.8, 24.7, 24.6, 24.4, 23.4, 23.2, 22.9, 22.8, 22.1, 21.4, 21.2, 16.8, 14.2.

HRMS (FAB, NBA matrix) m/z: 1609.2274 (M$^+$, calcd for C$_{102}$H$_{168}$N$_2$O$_{12}$: 1609.2284)

N-MeLeu-D-Lac-N-MeLeu-D-PhLacOH (8)

-continued

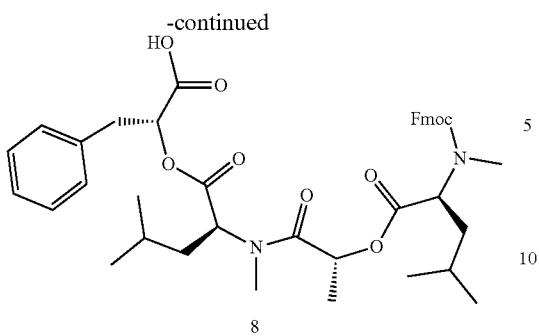

8

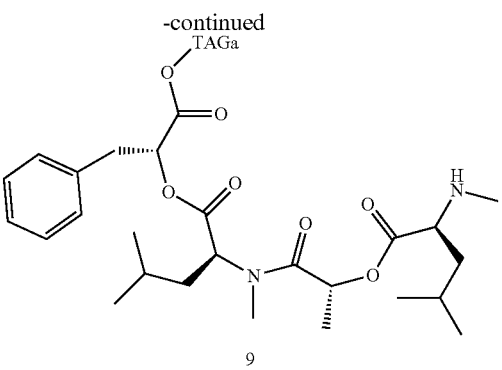

9

Following the procedure described for general procedure of TAGa cleavage, 7 (244 mg, 0.152 mmol) was converted to 8 (106 mg, 97%) as a yellow oil, which was used next reaction without further purification.

N-MeLeu-D-Lac-N-MeLeu-D-PhLacO-TAGa (9)

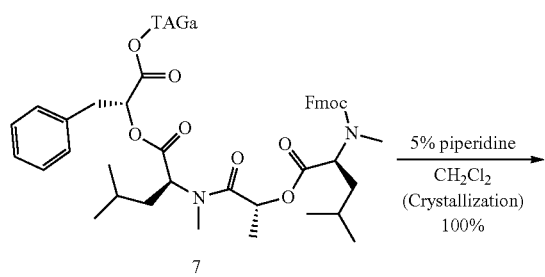

Following the procedure described for general procedure of Fmoc deprotection, 7 (204 mg, 0.127 mmol) was converted to 9 (176 mg, 100%) as a colorless powder.

mp: 47-48° C.
$[\alpha]_D^{26}$: −2.1 (c 1.1, CHCl$_3$)
$^1$H-NMR (500 MHz, CDCl$_3$) δ: 7.19 (m, 5H), 6.45 (s, 2H), 5.45 (q, J=6.9 Hz, 1H), 5.31 (ddd, J=4.6, 11.2, 19.6 Hz, 1H), 5.22 (dd, J=5.2, 6.9 Hz, 1H), 5.03 (m, 2H), 3.94 (m, 6H), 3.33-2.95 (complex m, 3H), 2.80 (s, 3H), 2.38 (s, 3H), 1.82-1.25 (complex m, 105H), 0.96-0.75 (complex m, 21H).
$^{13}$C-NMR (125 MHz, CDCl$_3$) δ: 175.0, 171.1, 171.0, 169.2, 153.3, 130.0, 129.8, 129.7, 129.3, 128.7, 128.6, 128.5, 127.4, 127.1, 126.9, 107.5, 107.2, 73.8, 73.5, 71.3, 69.2, 67.9, 67.7, 67.4, 67.3, 61.2, 57.5, 54.6, 42.3, 42.2, 37.3, 37.2, 37.0, 34.6, 32.0, 31.1, 30.4, 29.8 (×2), 29.6, 29.5 (×2), 26.2, 25.0, 24.8, 23.4, 23.0, 22.8, 22.7, 22.4, 22.1, 21.3, 16.9, 16.8, 14.2.
HRMS (FAB, NBA matrix) m/z: 1388.1676 [(M+H)$^+$, calcd for C$_{87}$H$_{155}$N$_2$O$_{10}$: 1388.1682]

N-Fmoc-N-MeLeu-D-Lac-N-MeLeu-D-PhLac-N-MeLeu-D-Lac-N-MeLeu-D-PhLac-O-TAGa (10)

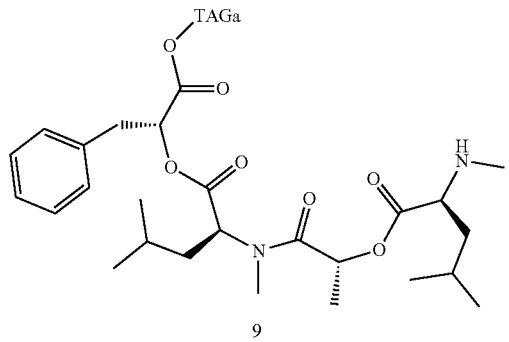

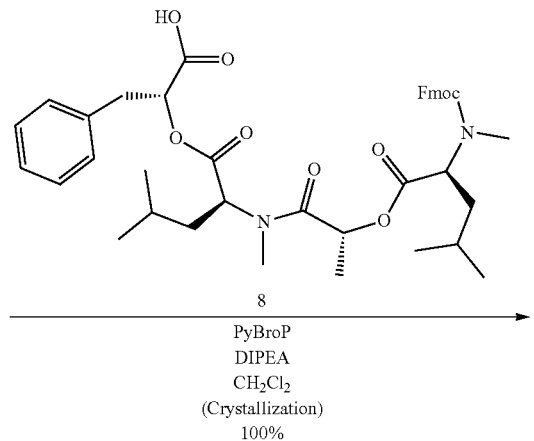

-continued

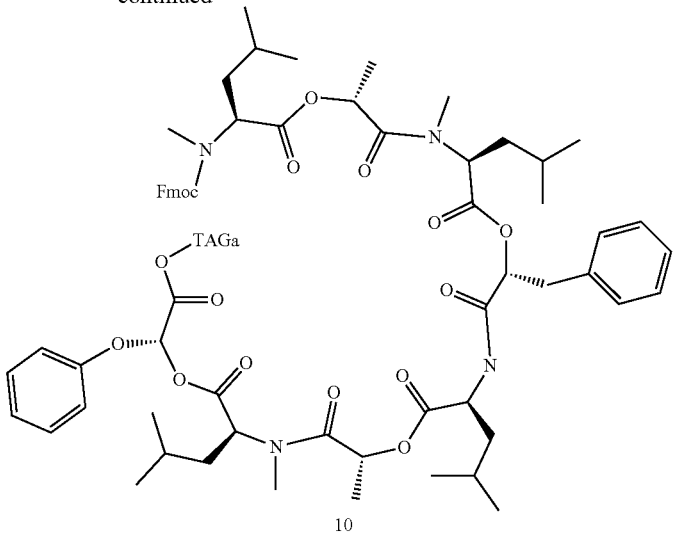

10

To a stirred solution of 9(155 mg, 96.2 μmol) in CH$_2$Cl$_2$ (1.9 mL) was added 8(103 mg, 0.144 mmol), N,N-diisopropylethylamine (73 μL, 0.434 mmol), and PyBroP (112 mg, 0.241 mmol) at room temperature. After stirring for 66 h, the reaction mixture was crystallized by the procedure described in synthesis of N-Fmoc-N-MeLeu-D-Lac-O-TAGa to afford 10 (201 mg, 100%) as a colorless powder.

mp: 47-48° C.

$[\alpha]_D^{27}$: −27.2 (c 1.1, CHCl$_3$)

$^1$H-NMR (500 MHz, CDCl$_3$) δ: 7.75 (m, 2H), 7.59 (m, 2H), 7.38 (n, 2H), 7.30-7.12 (complex m, 12H), 6.44 (m, 2H), 5.43-4.96 (complex m, 10H), 4.69-4.22 (complex m, 3H), 3.93 (m, 6H), 3.24-2.69 (complex m, 16H), 1.80-1.25 (complex m, 114H), 0.95-0.75 (complex m, 33H).

$^{13}$C-NMR (125 MHz, CDCl$_3$) δ: 174.1, 171.5, 171.4, 171.3, 171.2, 171.1 (×2), 170.9, 170.8, 170.7, 170.6, 170.5, 170.4, 170.0, 169.2, 157.0, 156.5, 153.3, 144.3, 144.2, 144.0 (×2), 141.4 (×2), 138.6, 138.4, 136.1, 136.0, 135.9 (×2), 135.7, 135.6, 135.3, 130.0, 129.8, 129.7, 129.6, 129.5, 129.3, 128.8, 128.7, 128.6, 128.4, 127.7, 127.4, 127.1 (×2), 127.0, 125.3, 125.2, 125.1, 125.0, 120.0, 107.5, 107.2, 107.1, 73.9, 73.5, 72.5, 71.3, 69.2, 68.0, 67.7, 57.5, 56.6 (×2), 55.1, 55.0, 54.9, 54.7, 54.4, 47.4, 47.3, 40.9, 40.6, 38.7, 37.6, 37.3, 37.2, 37.1, 32.0, 31.9, 31.7, 31.5, 31.3, 31.2, 31.0, 30.7, 30.6, 30.4, 30.3, 29.8 (×2), 29.6, 29.5 (×2), 25.0, 24.9, 24.8, 24.7, 24.5, 24.4 (×2), 23.4, 23.3, 23.1, 23.0, 22.9, 22.8, 22.3, 22.1, 22.0, 21.3, 21.2, 16.8, 16.6, 16.5, 14.2.

HRMS (FAB, NBA matrix) m/z: 2106.4910 [(M+Na)$^+$, calcd for C$_{128}$H$_{202}$N$_4$O$_{18}$Na: 2106.4912]

N-MeLeu-D-Lac-N-MeLeu-D-PhLac-N-MeLeu-D-Lac-N-MeLeu-D-PhLac-O-TAGa

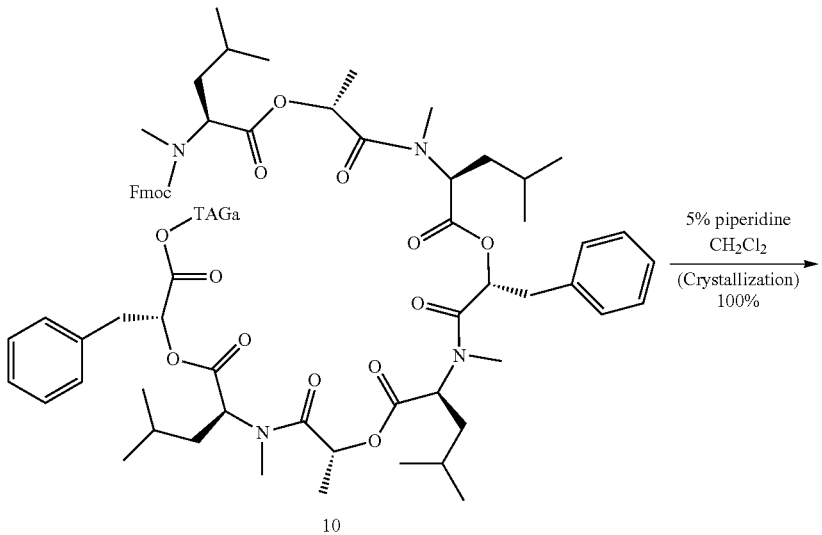

10

5% piperidine
CH$_2$Cl$_2$ (Crystallization)
100%

-continued

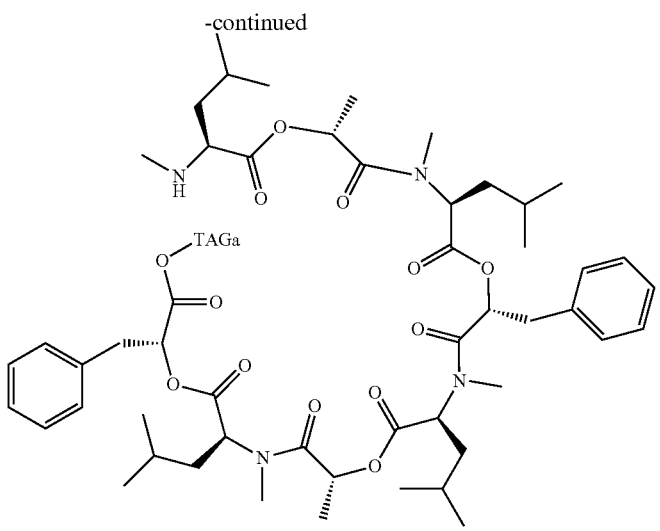

Following the procedure described for general procedure of Fmoc deprotection, 10 (181 mg, 86.8 μmol) was converted to the corresponding amine (163 mg, 100%) as a colorless powder.

mp: 47-48° C.

$[\alpha]_D^{27}$: −18.7 (c 1.3, CHCl$_3$)

$^1$H-NMR (500 MHz, CDCl$_3$) δ: 7.20 (m, 10H), 6.44 (s, 2H), 5.50-4.95 (complex m, 9H), 3.93 (m, 6H), 3.31-2.72 (complex m, 14H), 2.36 (m, 3H), 1.80-1.25 (complex m, 114H), 0.99-0.81 (complex m, 33H).

$^{13}$C-NMR (125 MHz, CDCl$_3$) δ: 171.4, 171.2, 171.0, 170.9, 170.6, 170.4, 153.3, 138.3, 136.1, 136.0, 135.9, 135.8, 130.0, 129.8 (×2), 129.7, 129.6 (×3), 129.5, 129.4, 129.2, 129.2 (×2), 128.8, 128.7, 128.6, 128.4, 127.4, 127.3, 127.2 (×2), 127.1, 127.0, 107.5, 107.2, 107.1, 73.9, 73.5, 72.3, 72.2, 71.3, 69.2, 68.0 (×2), 67.7, 67.4, 61.3, 55.2, 55.0, 54.8, 54.5, 54.4, 42.4, 40.6, 38.7, 37.7, 37.2, 37.1, 34.7 (×2), 32.0, 31.7, 31.5, 31.0, 30.4, 29.8 (×2), 29.6, 29.5 (×2), 26.2, 25.0, 24.9 (×2), 24.7, 23.5, 23.4 (×2), 23.3, 23.2, 23.0, 22.8, 22.4, 22.1, 21.9, 21.3 (×2), 16.9, 16.8 (×3), 16.7, 16.6, 16.5, 14.2.

HRMS (FAB, NBA matrix) m/z: 1862.4462 [(M+H)$^+$, calcd for C$_{113}$H$_{193}$N$_4$O$_{16}$: 1862.4412]

N-MeLeu-D-Lac-N-MeLeu-D-PhLac-N-MeLeu-D-Lac-N-MeLeu-D-PhLac-OH

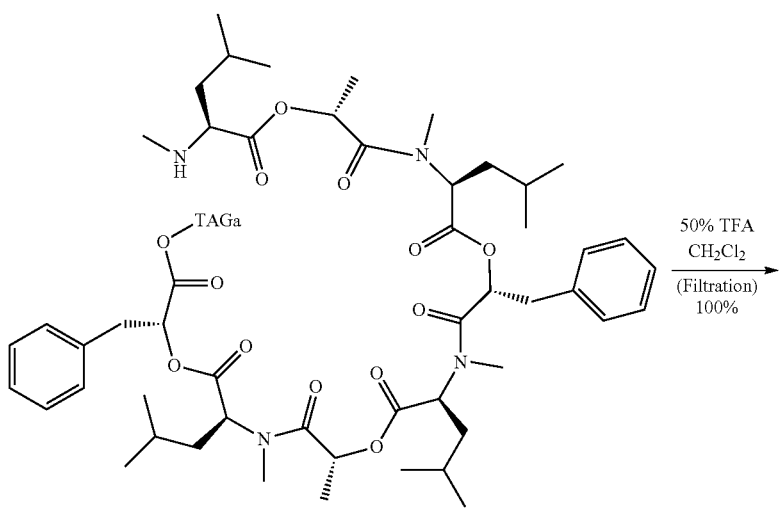

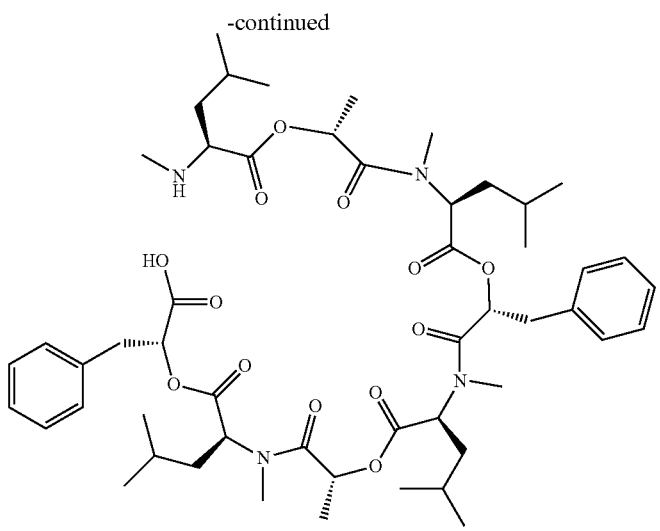
Following the procedure described for general procedure of TAGa cleavage, N-MeLeu-D-Lac-N-MeLeu-D-PhLac-N-MeLeu-D-Lac-N-MeLeu-D-PhLac-O-TAGa (143 mg, 0.768 mmol) was converted to the corresponding carboxylic acid (78 mg, 100%) as a yellow oil, which was used next reaction without further purification.
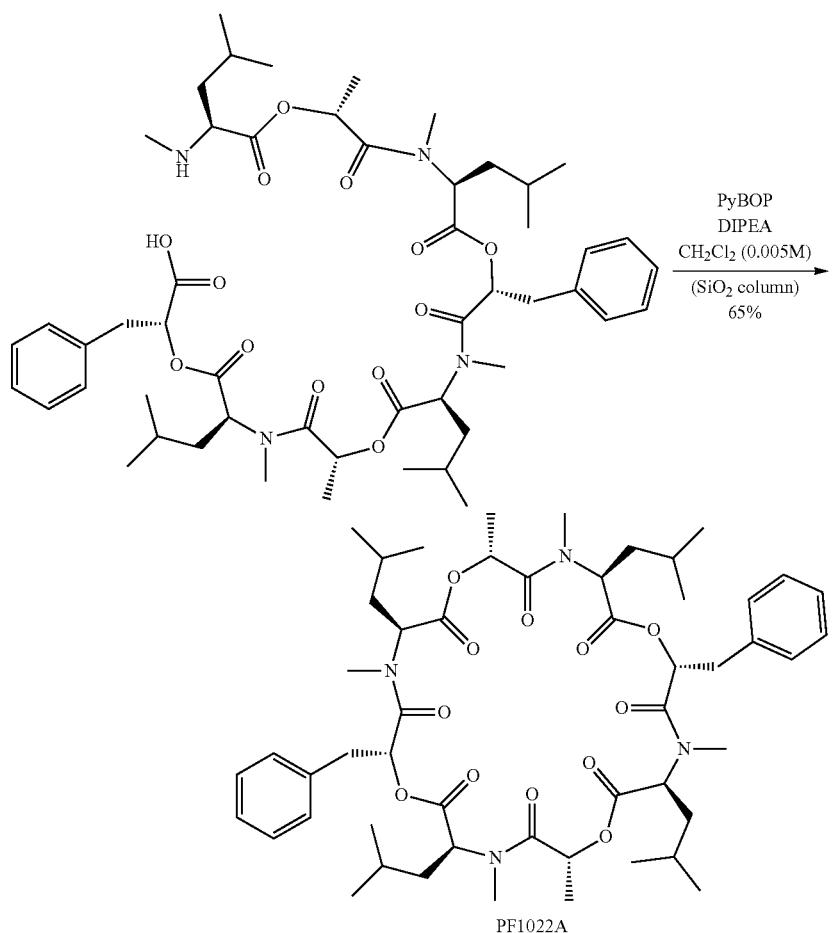
A crude of previous reaction (78 mg, 0.0777 mmol) was dissolved in CH$_2$C2 (16 mL, 0.005 M). The reaction mixture was added N,N-diisopropylethylamine (66 μL, 0.389 mmol) and PyBOP (81 mg, 0.155 mmol) at room temperature. After stirring for 48 h, the reaction mixture was quenched with saturated aqueous NaHCO$_3$ (16 mL) at 0° C. and this mixture was extracted with CHCl$_3$ (20 mL×2). The combined organic layers were washed with 10% aqueous NaHSO$_4$ (60 mL) and brine (60 mL), dried over Na$_2$SO$_4$, filtered and concentrated in vacuo. The crude was purified by column chromatography on silica gel (CHCl$_3$: MeOH=400:1 to 40:1) to provide PF1022A (48 mg, 65%) as a colorless solid.

All physical data for synthetic PF1022A matched with the data of authentic PF1022A.

Figure 7:
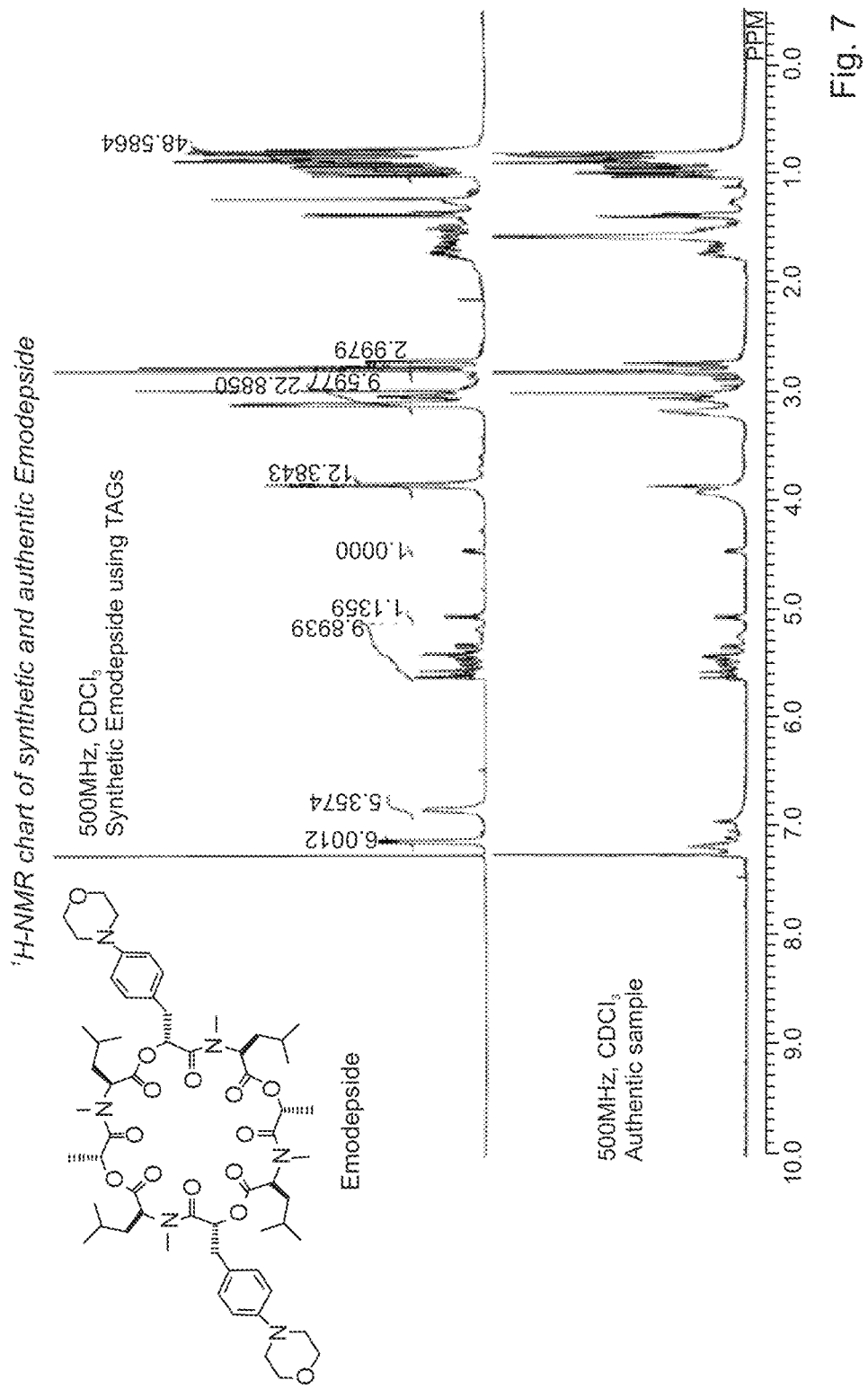
FIG. 7 $^1$H NMR spectra of Emodepside
Figure 8:
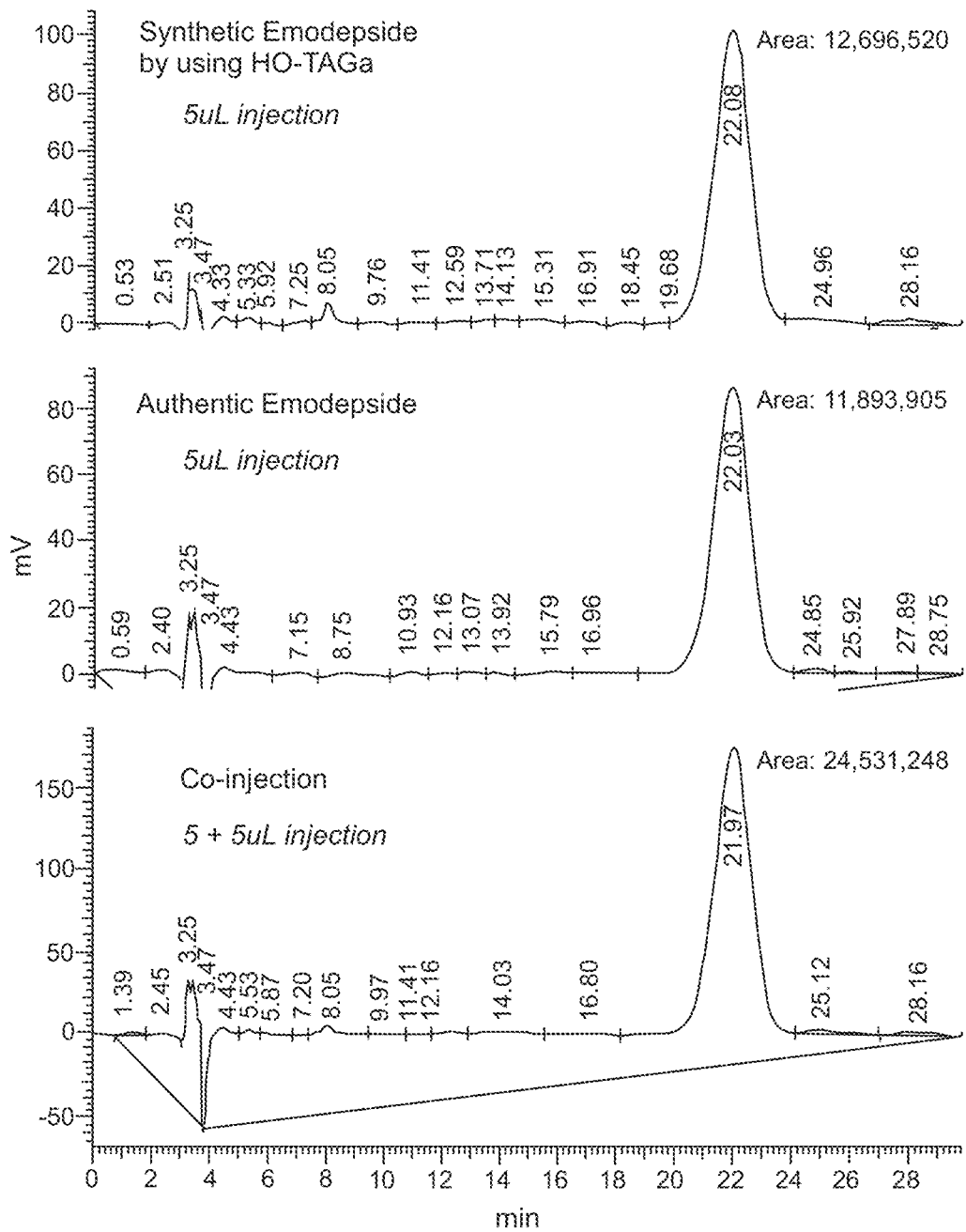
FIG. 8 LC-UV spectra of Emodepside

5. Preparation of Emodepside (Method 1; Cf. Reaction Schemes in FIGS. 6A, 6B, 6C and 6D, NMR Spectra in FIG. 7 and LC-UV Spectra in FIG. 8)

5-1. Synthetic Procedure

N-Fmoc-N-MeLeu-D-morphPhLac-N-MeLeu-D-Lac-O-TAGa

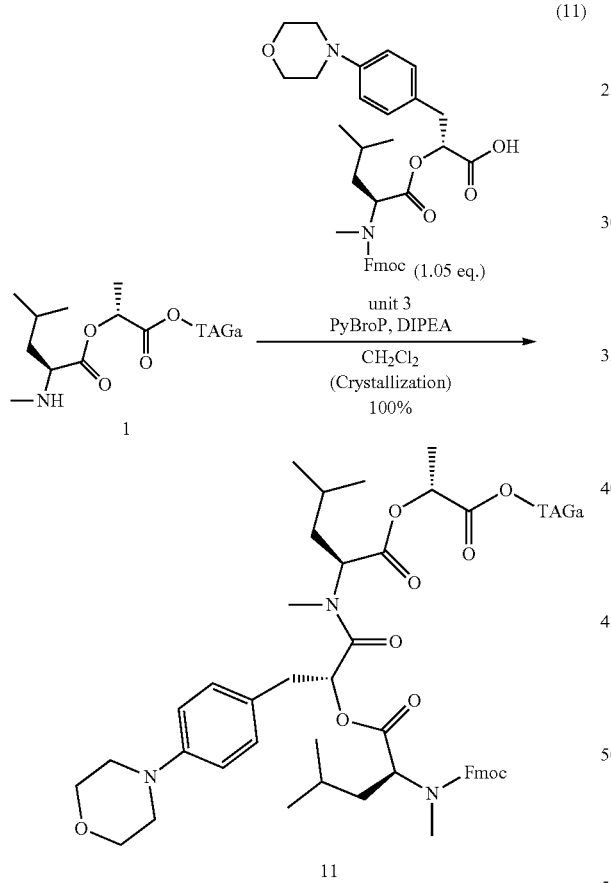

(11)

To a stirred solution of 1 (259 mg, 0.233 mmol) in CH$_2$C2 (4.7 mL) was added 0.2 M toluene solution of unit 3 (0.122 mL, 0.244 mmol), N,N-diisopropylethylamine (0.12 mL, 0.698 mmol), and PyBroP (163 mg, 0.349 mmol) at room temperature. After being stirred at 40 h, reaction mixture was crystallized by the procedure described in synthesis of N-Fmoc-N-MeLeu-D-Lac-O-TAGa to afford 11 (395 mg, 100%) as a colorless powder.

$^1$H-NMR (500 MHz, CDCl$_3$) δ: 7.74 (m, 2H), 7.57 (m, 2H), 7.42-7.27 (complex m, 4H), 7.05 (m, 2H), 6.70 (d, J=8.6 Hz, 2H), 6.48 (s, 2H), 5.40 (dd, J=6.9, 8.4 Hz, 3/10H, rotamer), 5.35-5.27 (complex m, 17/10H), 5.10-4.97 (complex m, 4H), 4.72-4.12 (complex m, 3H), 3.93 (m, 6H), 3.75 (m, 4H), 3.00-2.79 (complex m, 12H), 1.80-1.60 (complex m, 9H), 1.49-1.42 (complex m, 9H), 1.27 (complex m, 87H), 0.93-0.80 (complex m, 21H).

HRMS (FAB, NBA matrix) m/z: 1717.2701 [(M+Na)$^+$, calcd for C$_{106}$H$_{17}$N$_3$O$_{13}$Na: 1717.2710]

N-Fmoc-N-MeLeu-D-morphPhLac-N-MeLeu-D-Lac-OH (12)

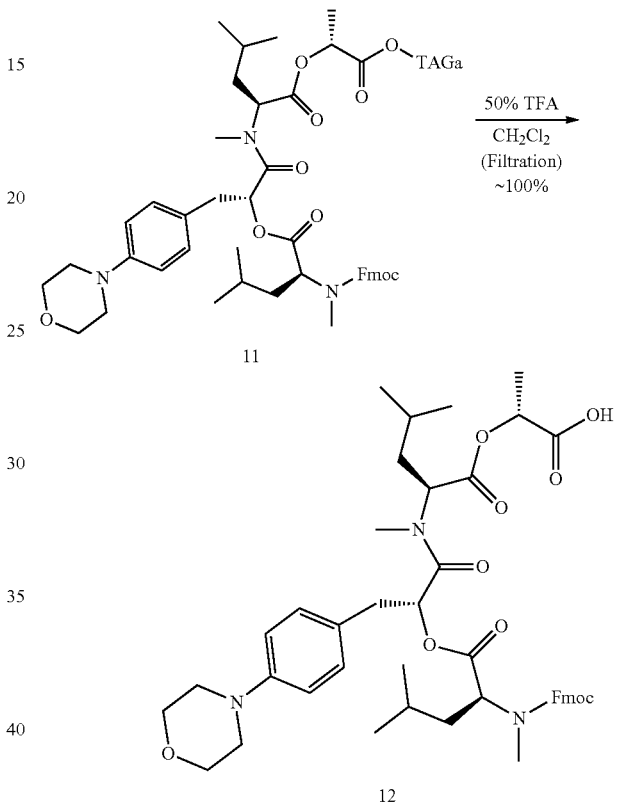

Following the procedure described for general procedure of TAGa cleavage, 11 (210 mg, 0.124 mmol) was converted to 12 (100 mg, 0.124 mmol) as a brown oil. This crude was used next reaction without further purification.

N-Fmoc-N-MeLeu-D-morphPhLac-N-MeLeu-D-Lac-OH (13)

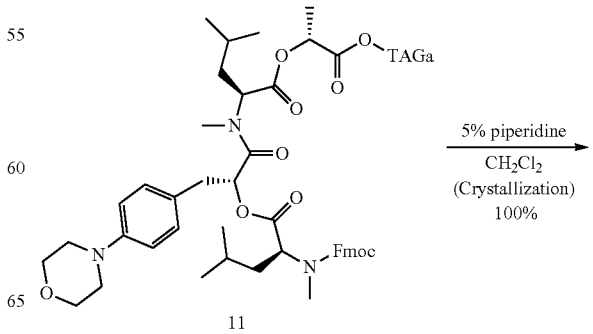

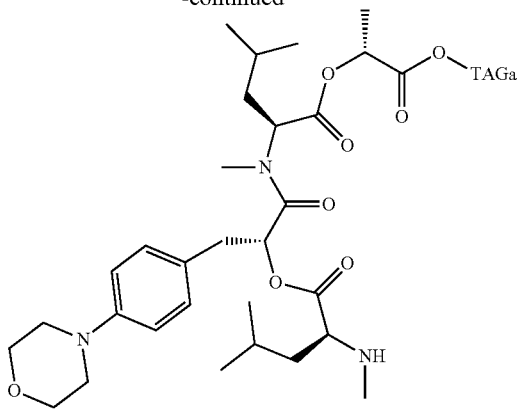

13

Following the procedure described for general procedure of Fmoc deprotection, 11 (158 mg, 0.0934 mmol) was converted to 13 (138 mg, 100%) as a colorless powder.

$^1$H-NMR (500 MHz, CDCl$_3$) δ: 7.15 (m, 2H), 6.83 (d, J=8.6 Hz, 2H), 6.49 (s, 2H), 5.47 (dd, J=6.9, 8.0 Hz, 1H), 5.32 (dd, J=4.9, 11.2 Hz, 1H), 5.09-5.00 (complex m, 3H), 3.94 (m, 6H), 3.85 (m, 4H), 3.27 (t, J=6.9 Hz, 1H), 3.13-2.79 (complex m, 9H), 2.29 (s, 3H), 1.81-1.25 (complex m, 105H), 1.01-0.78 (complex m, 21H).

HRMS (FAB, NBA matrix) m/z: 1473.2214 [(M+H)$^+$, calcd for C$_{91}$H$_{62}$N$_3$O$_{11}$: 1473.2209]

N-Fmoc-N-MeLeu-D-morphPhLac-N-MeLeu-D-Lac-N-MeLeu-D-morphPhLac-N-MeLeu-D-Lac-O-TAGa (14)

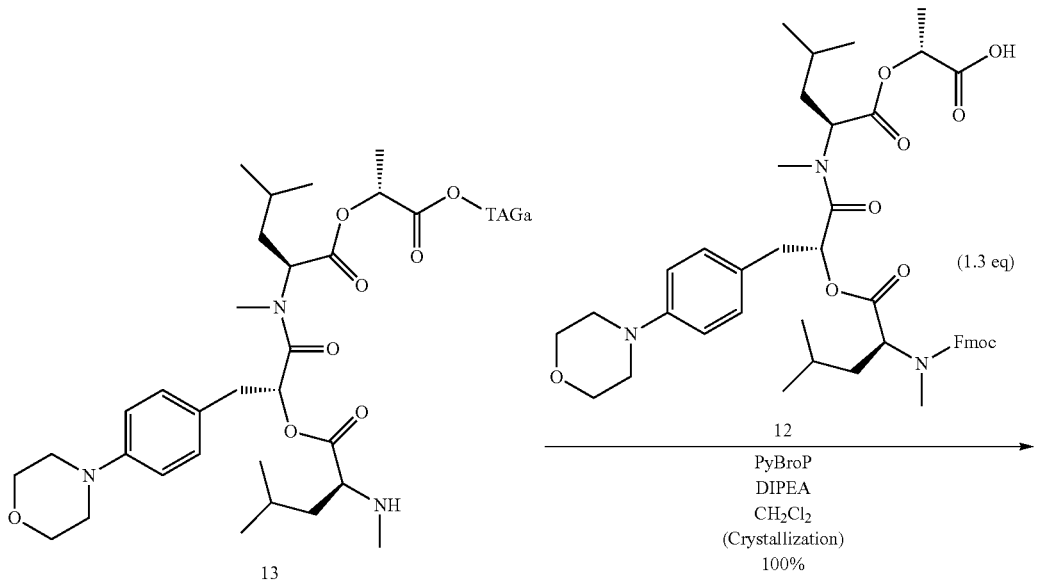

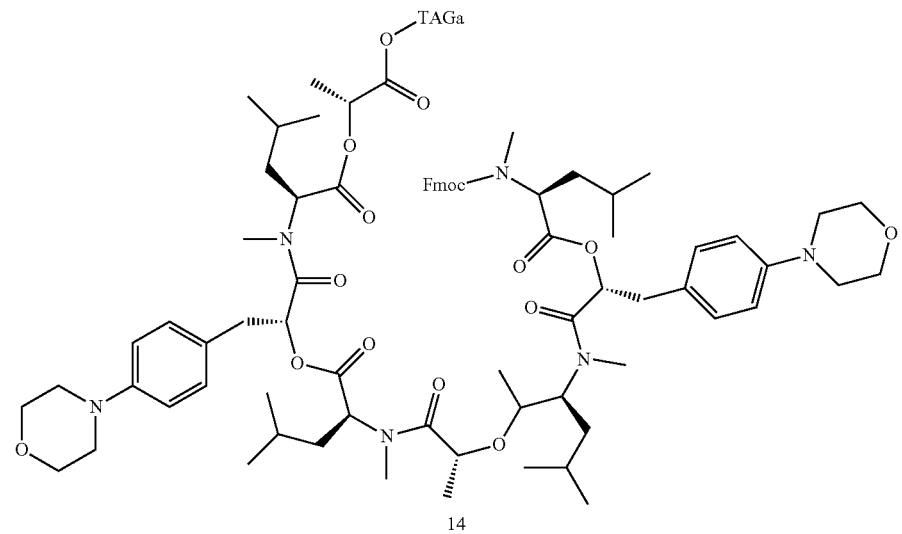

14

To a stirred solution of 13 (138 mg, 0.934 mmol) in CH$_2$C2 (1.9 mL) was added 12 (100 mg, ~0.124 mmol), N,N-diisopropylethylamine (48 μL, 0.280 mmol), and PyBroP (65 mg, 0.140 mmol) at room temperature. After stirring for 18 h, the reaction mixture was crystallized by the procedure described in synthesis of N-Fmoc-N-MeLeu-D-Lac-O-TAGa to afford 14 (211 mg, 100%) as a colorless powder.

$^1$H-NMR (500 MHz, CDCl$_3$) δ: 7.75 (m, 2H), 7.58 (m, 2H), 7.42-7.28 (complex m, 4H), 7.09 (m, 4H), 6.77 (m, 4H), 6.48 (s, 2H), 5.45-5.15 (complex m, 6H), 5.06-4.97 (complex m, 4H), 4.73-4.12 (complex m, 3H), 3.95-3.73 (complex m, 14H), 3.15-2.73 (complex m, 24H), 1.80-1.25 (complex m, 114H), 0.96-0.77 (complex m, 33H).

HRMS (FAB, NBA matrix) m/z: 2276.5962 [(M+Na)$^+$, calcd for C$_{136}$H$_{216}$N$_6$O$_{20}$Na: 2276.5967]

Following the procedure described for general procedure of Fmoc deprotection, 14 (211 mg, 0.0934 mmol) was converted to the corresponding amine (178 mg, 94%) as a colorless powder.

$^1$H-NMR (500 MHz, CDCl$_3$) δ: 7.15 (m, 4H), 6.82 (m, 4H), 6.49 (s, 2H), 5.14 (t, J=7.45 Hz, 1H), 5.44-5.09 (complex m, 5H), 5.07-5.00 (complex m, 3H), 3.93 (m, 6H), 3.85 (m, 8H), 3.32 (m, 1H), 3.17-2.74 (complex m, 21H), 2.33 (s, 3H), 1.81-1.64 (complex m, 12H), 1.55-1.25 (complex m, 102H), 1.03-0.77 (complex m, 33H).

HR-MS (FAB, NBA matrix+NaI) m/z: 2032.5488 [(M+H), calcd for C$_{121}$H$_{207}$N$_6$O$_{18}$: 2032.5467]

N-MeLeu-D-morphPhLac-N-MeLeu-D-Lac-N-MeLeu-D-morphPhLac-N-MeLeu-D-Lac-O-TAGa

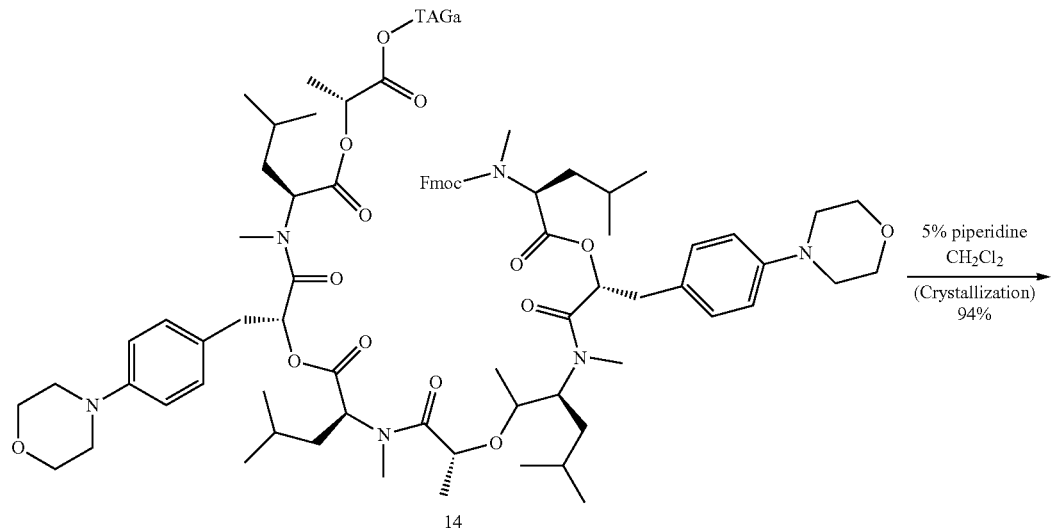

14

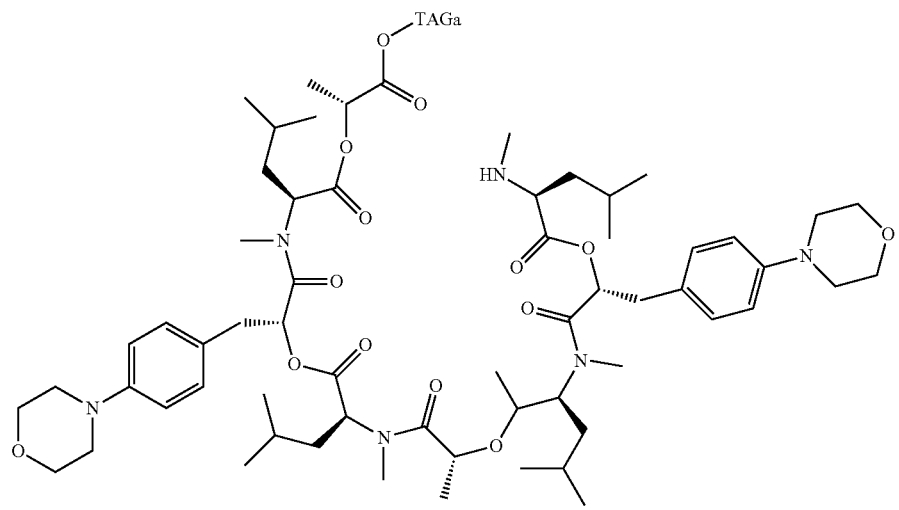

N-MeLeu-D-morphPhLac-N-MeLeu-D-Lac-N-MeLeu-D-morphPhLac-N-MeLeu-D-Lac-OH

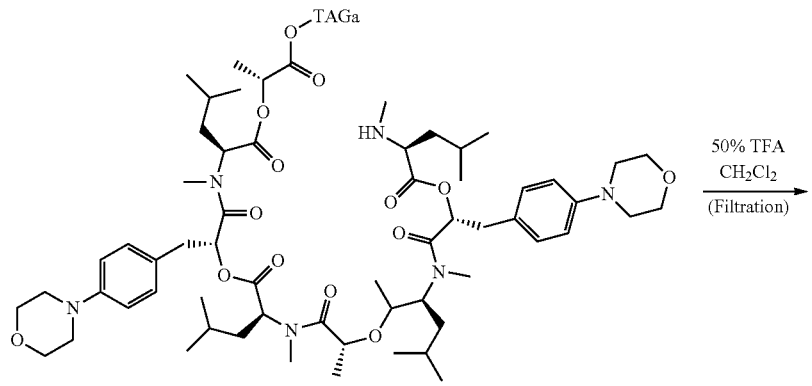

50% TFA
CH$_2$Cl$_2$
(Filtration)

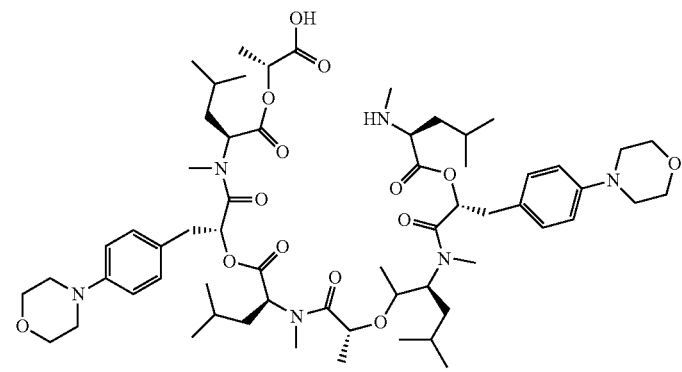

Following the procedure described for general procedure 40 of TAGa cleavage, N-MeLeu-D-morphPhLac-N-MeLeu-D-Lac-N-MeLeu-D-morphPhLac-N-MeLeu-D-LacO-TAGa (178 mg, 0.0876 mmol) was converted to the corresponding carboxylic acid (0.0876 mmol) as a crude oil, which was used next reaction without further purification.

Emodepside (Highly Diluted Condition Using PyBOP)

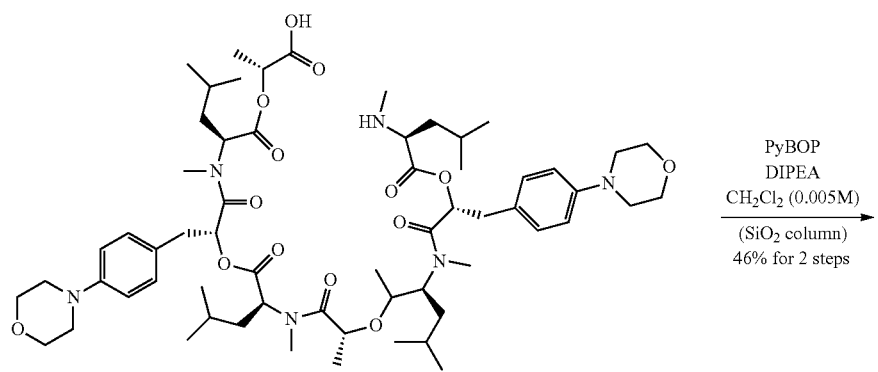

PyBOP
DIPEA
CH$_2$Cl$_2$ (0.005M)
(SiO$_2$ column)
46% for 2 steps

-continued

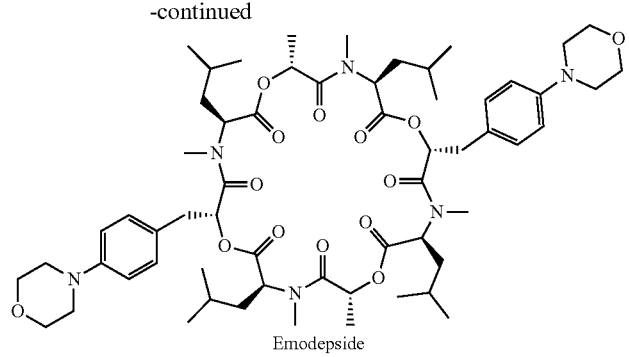

Emodepside
(8 steps for longest linear from HO-TAGa)
42% overall yield from HO-TAGa To a crude of carboxylic acid (0.0876 mmol) in $CH_2Cl_2$ (18 mL, 0.005 M) was added N,N-diisopropylethylamine (0.10 mL, 0.613 mmol) and PyBOP (91 mg, 0.175 mmol) at room temperature. After stirring for 19 h, the reaction mixture was quenched with saturated aqueous $NaHCO_3$ (18 mL) at 0° C. and this mixture was extracted with $CHCl_3$ (20 mL×3). The combined organic layers were washed with 10% aqueous $NaHSO_4$ (60 mL) and brine (60 mL), dried over $Na_2SO_4$, filtered and concentrated in vacuo. The crude was purified by column chromatography on silica gel ($CHCl_3$: MeOH=400:1 to 100:1) to provide Emodepside (45 mg, 46% for 2 steps) as a light yellow solid.

mp: 98-103° C.

$[\alpha]_D^{24}$: −40.3 (c 0.67, $CHCl_3$)

IR (neat) $\tilde{v}_{max}$: 2954, 2862, 1743, 1659, 1520, 1458, 1412, 1265, 1234, 1188, 1119, 1072, 1026, 926, 810.

$^1$H-NMR (500 MHz, $CDCl_3$) δ: 7.14-7.11 (complex m, 4H), 6.83-6.79 (complex m), 5.64-5.54 (complex m), 5.52-5.43, 5.43-5.39, 5.33, 5.18, 5.06 and 4.46 (5 m, 6H), 3.85 (apparently t, 8H), 3.15-3.04 (complex m, 8H), 3.04-2.92 (complex m, 4H), 3.00, 2.82, 2.79, 2.72 and 2.71 (5 s, 12H), 1.82-1.24 (complex m, 18H), 1.03-0.79 (complex m, 30H).

$^{13}$C-NMR (125 MHz, $CDCl_3$) δ: 171.6, 171.2, 171.0, 170.9, 170.3, 170.2, 170.1, 169.8, 169.7, 150.2, 130.4, 130.2, 115.7, 115.6, 71.2, 70.8, 68.5, 66.8, 66.7, 57.1, 54.0, 53.9, 49.3, 49.2, 38.0, 37.5, 37.1, 36.9, 36.8, 36.7, 36.6, 36.1, 31.1, 30.6, 30.4, 29.7, 29.6, 29.3, 25.0, 24.8, 24.6, 24.5, 24.5, 24.1, 23.6, 23.5, 23.4, 23.3, 23.3, 23.1, 22.6, 21.6, 21.5, 21.1, 21.1, 21.0, 20.8, 17.1, 15.7.

HRMS (ESI) m/z: 1141.6404 [(M+Na)$^+$, calcd for $C_{60}H_{90}N_6O_{14}Na$: 1141.6413]

*Literature (*Eur J. Org. Chem.*, 2012, 1546-1553)

$^1$H-NMR (400 MHz, $CDCl_3$) δ: 7.17-7.09 (m, 4H, Ar—H), 6.86-6.77 (m, 4H, Ar—H), 5.67-5.54 (m, 2H, CαH-Lac), 5.53-5.38, 5.34, 5.19, 5.08 and 4.47 (5 m, 6H, CαH-Leu, CαH-morphPhLac), 3.88-3.81 (pseudo-t, 8H, $OCH_2$ morpholine), 3.15-3.08 (m, 8H, N—$CH_2$-morpholine), 3.07-2.85 (m, 4H, $C\beta H_2$-morphPhLac), 3.00, 2.83, 2.80, 2.74 and 2.73 (5 s, 12H, $NCH_3$), 1.83-1.20 (m, 18H, $C\beta H_2$-Leu, C7H-Leu, $CH_3$-Lac), 1.05-0.77 (m, 30H, $C6H_3$-Leu, $C\beta H_3$-Lac).

$^{13}$C-NMR (100 MHz, $CDCl_3$) δ: 171.7, 171.2, 171.0, 170.6, 170.4, 170.2, 169.8, 141.7, 130.6, 130.4, 116.9, 116.1, 71.3, 70.8, 68.6, 66.9, 66.6, 66.5, 57.1, 54.0, 49.9, 38.1, 37.5, 37.2, 36.7, 36.2, 31.2, 30.5, 29.4, 24.9, 24.7, 24.2, 23.6, 23.5, 23.5, 23.4, 21.2, 21.1, 20.9, 17.1, 15.8.

Emodepside (Slow Addition Condition Using T3P)

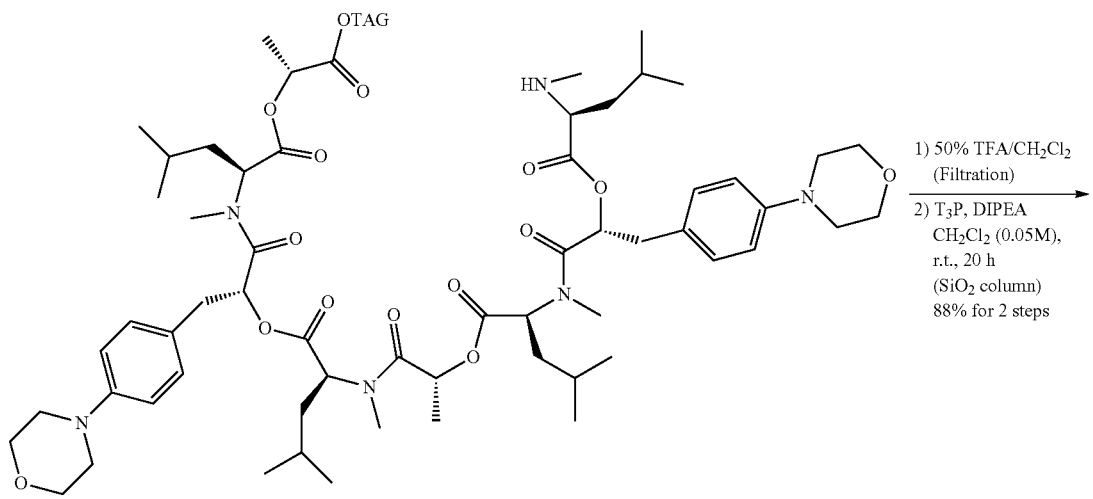

1) 50% TFA/$CH_2Cl_2$ (Filtration)

2) T$_3$P, DIPEA
$CH_2Cl_2$ (0.05M),
r.t., 20 h
(SiO$_2$ column)
88% for 2 steps -continued

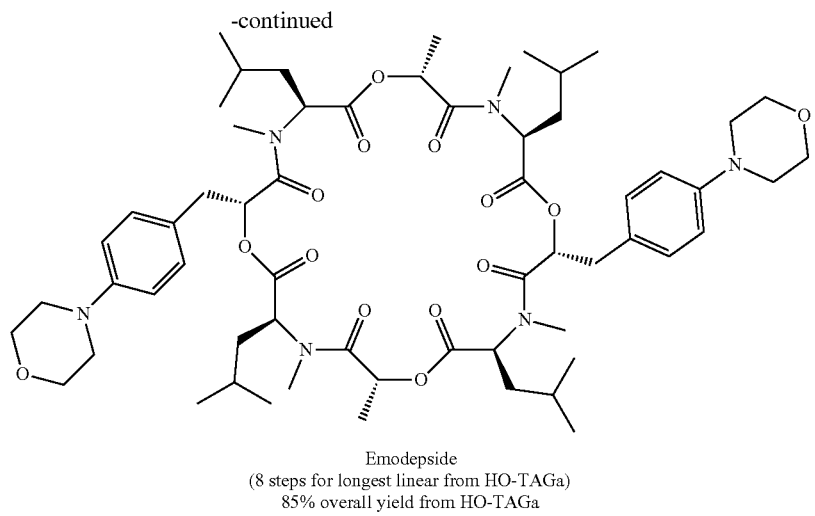

Emodepside
(8 steps for longest linear from HO-TAGa)
85% overall yield from HO-TAGa Cleavage of TAGa: To a stirring solution of linear compound on TAG (179.0 mg, 0.088 mmol) in DCM (1.8 mL) was added TFA (1.8 mL) at room temperature. After stirring for 6 h at room temperature, the solution was concentrated in vacuo. The resulting mixture was dissolved into toluene (10 mL) and concentrated under reducing pressure for 3 times to remove excess TFA. The crude residue was dissolved into $CH_2C2$ (1.0 mL), then recrystallized for the cleaved TAGa materials by the addition of MeOH (8.0 mL) at room temperature. The precipitates were filtered off through Celite® pad and washed with MeOH (20 mL). The combined filtrates were concentrated in vacuo. To the resulting product was added 4 M HC/Dioxane (0.05 M for product), followed by diluted with toluene (10 mL) and concentrated to afford the TFA salt free product. To remove excess HCl from a crude product, the product was dissolved again into toluene (10 mL) and concentrated under reducing pressure for 2 times.

Cyclization: To a stirring solution of T3P® (50% in EtOAc, 110 μL, 0.187 mmol) in DIPEA (110 μL, 0.187 mmol) was added dropwise a crude linear compound (0.088 mmol) in DCM (1.8 mL, 0.05 M including wash) over 2.5 h at room temperature. After stirring for 20 h at room temperature, the reaction mixture was quenched with sat. $NaHCO_3$ aq. (3.0 mL), extracted with $CHCl_3$ (2.0 mL×3). The combined organic layers were dried over sodium sulfate, filtered, and concentrated in vacuo. The crude residue was purified by silica gel column chromatography on silica gel ($CHCl_3$/MeOH=100/1) to provide Emodepside (86.4 mg, 88%) as an amorphous. The analytical data was identified by the authentic sample.

Figure 9A:
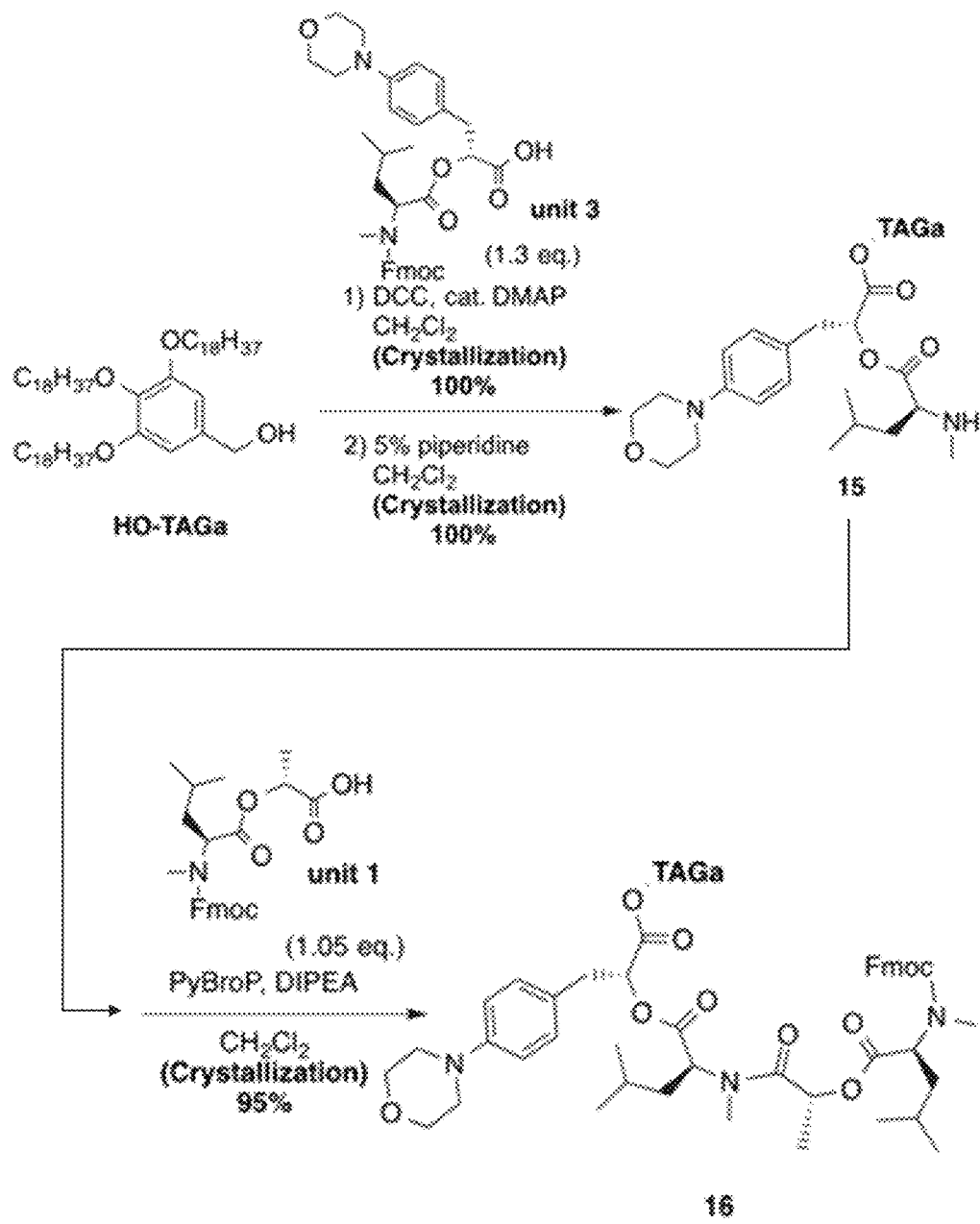
FIG. 9A Emodepside Synthesis (Method 2)-Preparation of 16
Figure 9B:
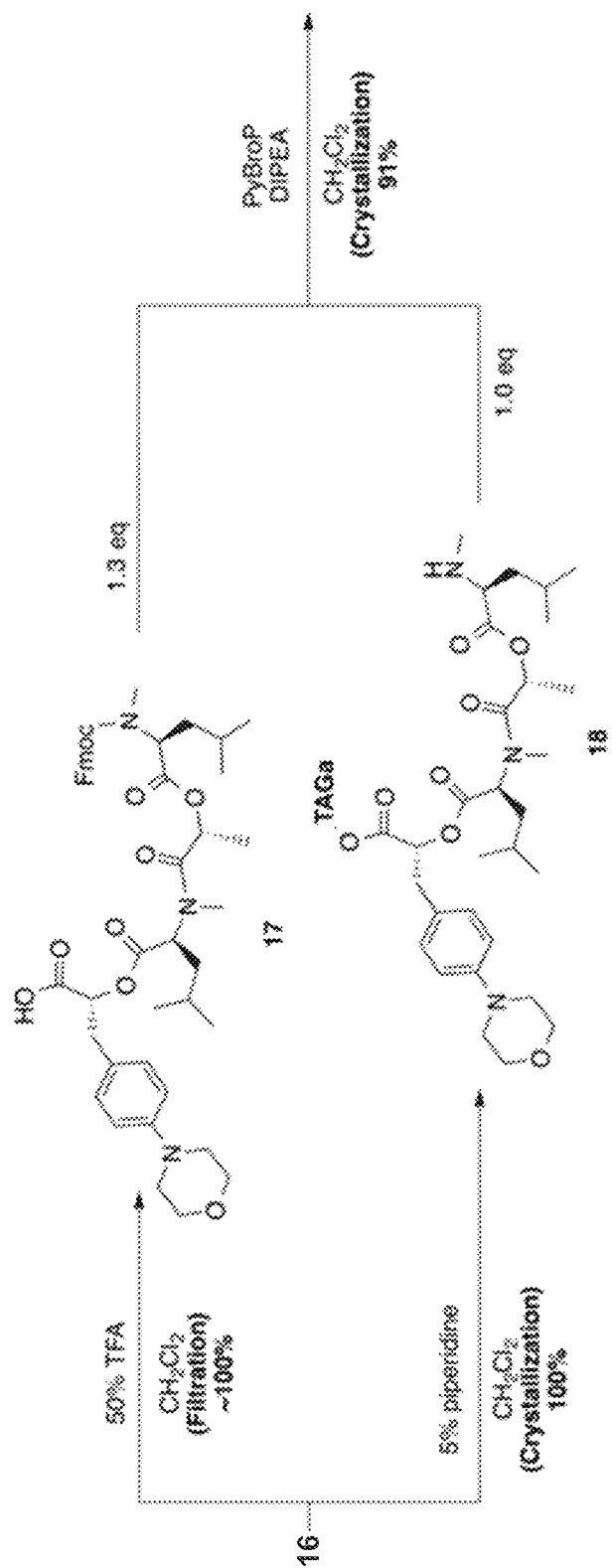
FIG. 9B Emodepside Synthesis (Method 2)-Preparation of 17 and 18 and reaction conditions for the preparation of 19
Figure 9C:
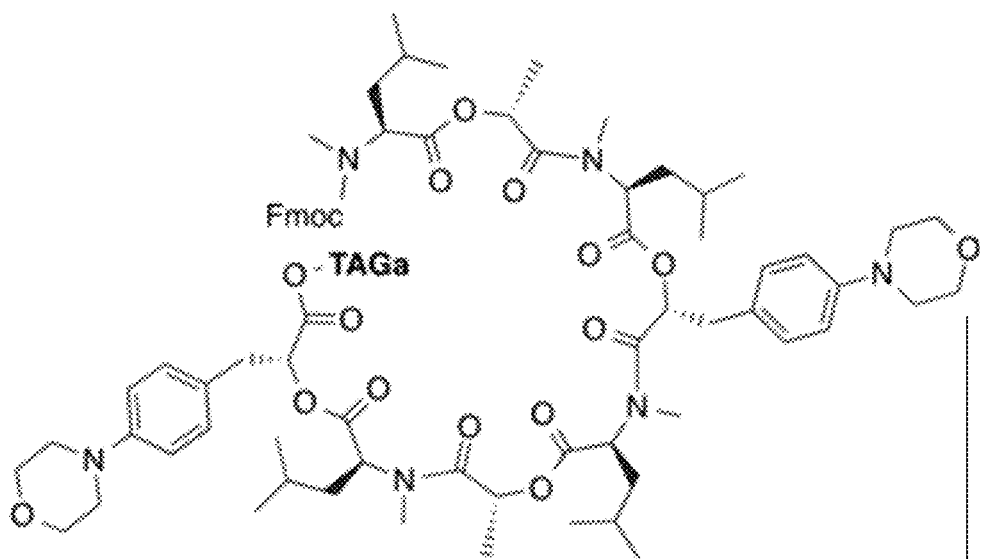
FIG. 9C Emodepside Synthesis (Method 2)-Preparation of Emodepside

6. Preparation of Emodepside (Method 2; Cf. Reaction Scheme in FIGS. 9A, 9B, and 9C)

N-Fmoc-N-MeLeu-D-morphPhLac-O-TAGa

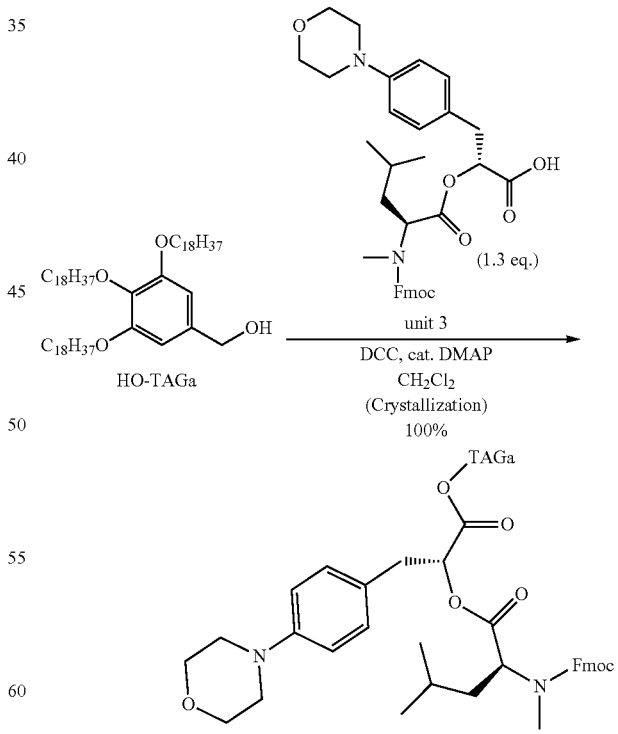

To a stirred solution of HO-TAGa (381 mg, 0.417 mmol) in $CH_2Cl_2$ (8.4 mL) was added 0.2 M toluene solution of unit 3 (2.71 mL, 0.542 mmol), 4-dimethylaminopyridine (2.5 mg, 20.8 mol), and N,N'-dicyclohexylcarbodiimide (129 mg, 0.626 mmol) at room temperature under N₂ atmosphere. After stirring for 1 h, the reaction mixture was crystallized by the procedure described in synthesis of N-Fmoc-N-MeLeu-D-Lac-O-TAGa to afford N-Fmoc-N-MeLeu-D-morphPhLac-O-TAGa (628 mg, 100%) as a colorless powder.

mp: 46-47° C.

$[\alpha]_D^{27}=-3.1$ (c 1.0, CHCl₃)

¹H-NMR (500 MHz, CDCl₃) δ: 7.78 (d, J=7.5 Hz, 1H), 7.74 (d, J=7.5 Hz, 1H), 7.57 (m, 2H), 7.39 (m, 2H), 7.27 (m, 2H), 6.98 (d, J=8.6 Hz, 1H), 6.96 (d, J=8.6 Hz, 1H), 6.67 (m, 2H), 6.49 (2 s, rotamer 4:3, 2H), 5.17 (2 dd, rotamer, J=4.0 Hz, 8.0 Hz, 1H), 5.08-4.98 (complex m, 3H), 4.67-4.13 (complex m, 3H), 3.93 (m, 6H), 3.73 (m, 4H), 3.08 (dd, J=4.0 Hz, 14.6 Hz, 1H), 3.07-2.95 (complex m, 5H), 2.80 (rotamer 4:3, 3H), 1.76 (m, 6H), 1.64-1.53 (complex m, 3H), 1.45 (m, 6H), 1.28 (complex m, 84H), 0.93-0.86 (complex m, 14H), 0.76 (d, J=6.3 Hz, 1H).

HRMS (FAB, NBA matrix) m/z: 1495.1583 (M⁺, calcd for $C_{96}H_{154}N_2O_{10}$: 1495.1604)

N-MeLeu-D-morphPhLac-O-TAGa (15)

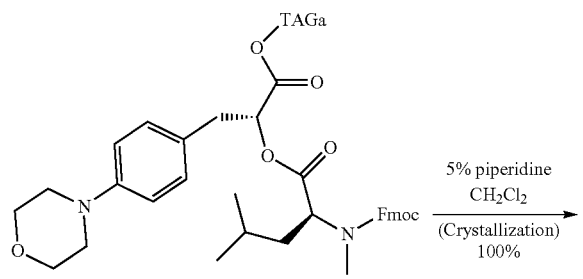

Following the procedure described for general procedure of Fmoc deprotection, N-Fmoc-N-MeLeu-D-morphPhLac-O-TAGa (628 mg, 0.417 mmol) was converted to 15 (530 mg, 100%) as a colorless powder.

mp: 49-50° C.

$[\alpha]_D^{27}=+5.7$ (c 1.0, CHCl₃)

¹H-NMR (500 MHz, CDCl₃) δ: 7.08 (d, J=8.6 Hz, 2H), 6.80 (d, J=8.6 Hz, 2H), 6.51 (s, 2H), 5.24 (dd, J=4.0, 9.7 Hz, 1H), 5.07 (q, J=12.0 Hz, 2H), 3.94 (m, 6H), 3.85 (m, 4H), 3.18 (m, 2H), 3.10 (m, 4H), 3.00 (d, J=10.3, 14.3 Hz, 1H), 2.21 (s, 3H), 1.76 (m, 6H), 1.47 (m, 6H), 1.34-1.25 (complex m, 87H), 0.88 (t, J=6.9 Hz, 9H), 0.80 (d, J=6.9 Hz, 3H), 0.79 (d, J=6.9 Hz, 3H).

HRMS (FAB, NBA matrix) m/z: 1274.0986 [(M+H)⁺, calcd for $C_{81}H_{145}N_2O_8$: 1274. 1001]

N-Fmoc-N-MeLeu-D-Lac-N-MeLeu-D-morphPhLac-O-TAGA (16)

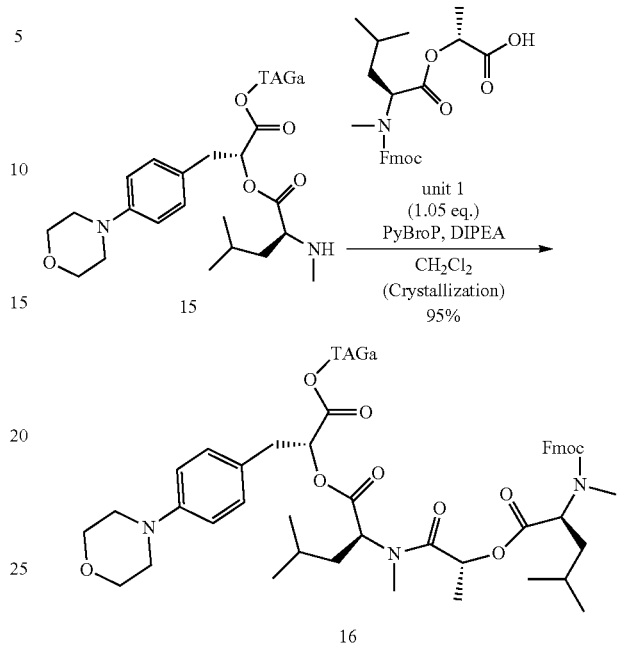

To a stirred solution of 15 (530 mg, 0.417 mmol) in CH₂Cl₂ (8.4 mL) was added 0.2 M toluene solution of unit 1 (0.22 mL, 0.44 mmol), N,N-diisopropylethylamine (0.212 mL, 1.25 mmol), and PyBroP (291 mg, 0.62 mmol) at room temperature. After stirring for 16 h, the reaction mixture was crystallized by the procedure described in synthesis of N-Fmoc-N-MeLeu-D-Lac-O-TAGa to afford 16 (670 mg, 95%) as a colorless powder.

mp: 48-49° C.

$[\alpha]_D^{27}=-12.4$ (c 1.0, CHCl₃)

¹H-NMR (500 MHz, CDCl₃) δ: 7.76 (m, 2H), 7.61 (m, 2H), 7.38 (m, 2H), 7.30 (m, 2H), 7.02 (m, 2H), 6.74 (m, 2H), 6.49 (2 s, rotamer, 2H), 5.38-5.22 (complex m, 2H), 5.15-4.98 (complex m, 4H), 4.47 (complex m, 3H), 3.94 (m, 6H), 3.81 (m, 4H), 3.12-2.78 (complex m, 12H), 1.82-1.56 (complex m, 9H), 1.53-1.40 (complex m, 8H), 1.34-1.26 (complex m, 88H), 0.98-0.75 (complex m, 21H).

HRMS (FAB, NBA matrix) m/z: 1694.2828 (M⁺, calcd for $C_{106}H_{171}N_3O_{13}$: 1694.2812)

N-Fmoc-N-MeLeu-D-Lac-N-MeLeu-D-morphPhLac-OH (17)

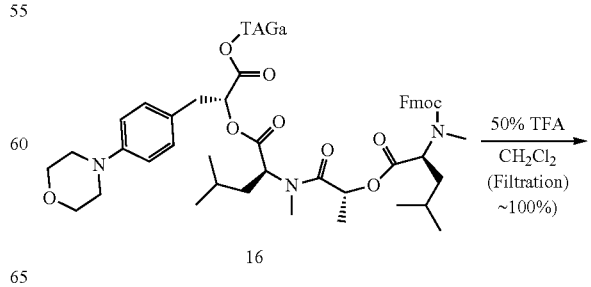

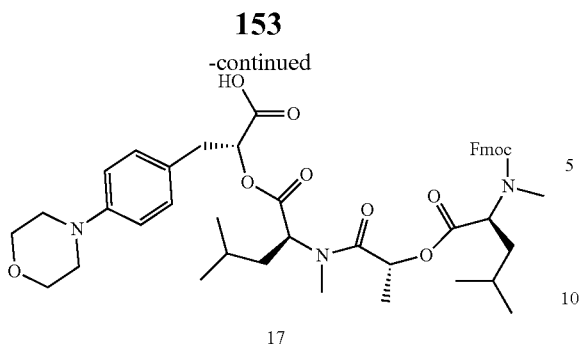

17

Following the procedure described for general procedure of TAGa cleavage, 16 (376 mg, 0.222 mmol) was converted to 17. In the case of this substrate, the reaction required longer time than that of the general condition of TAGa cleavage (ca. 1 h). The reaction of 16 in 50% TFA/CH$_2$Cl$_2$ at room temperature was needed to stir for 8 h to consume all of starting material, and gave product 17 (178 mg, 0.222 mmol) as a crude oil, which was used next action without further purification.

N-MeLeu-D-Lac-N-MeLeu-D-MorphPhLac-O-TAGa (18)

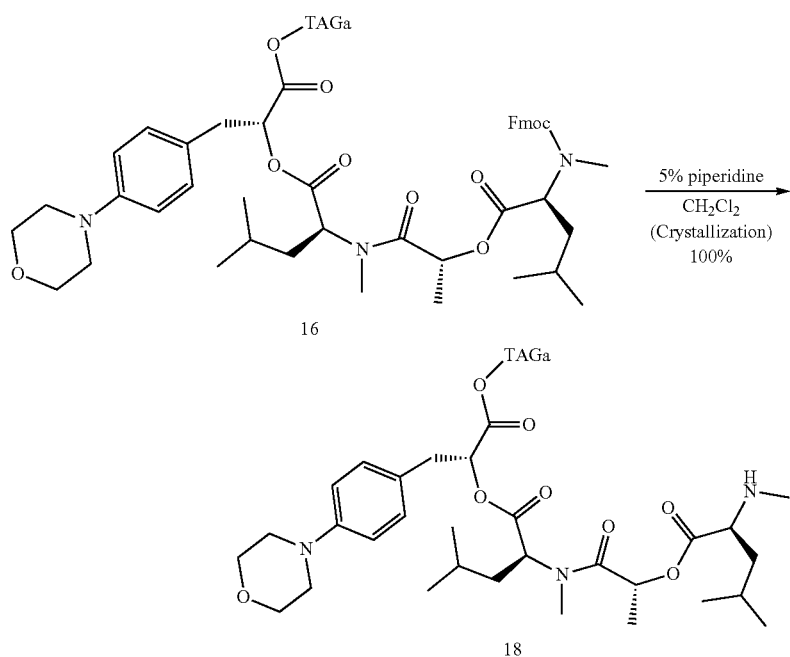

Following the procedure described for general procedure of Fmoc deprotection, 16 (290 mg, 0.171 mmol) was converted to 18 (251 mg, 100%) as a colorless powder.
mp: 43-45° C.
$[\alpha]_D^{25}$=−2.8 (c 1.0, CHCl$_3$)
$^1$H-NMR (500 MHz, CDCl$_3$) δ: 7.07 (d, J=8.6 Hz, 2H), 6.79 (d, J=8.6 Hz, 2H), 6.49 (s, 2H), 5.46 (q, J=6.9 Hz, 1H), 5.33 (dd, J=5.2, 10.9 Hz, 1H), 5.17 (dd, J=5.2, 7.5 Hz, 1H), 5.06 (m, 2H), 3.95 (m, 6H), 3.84 (m, 4H), 3.33 (t, J=7.5 Hz, 1H), 3.11-3.06 (complex m, 6H), 2.82 (2 s, rotamer 4:1, 3H), 2.40 (s, rotamer, 3H), 1.82-1.59 (complex m, 10H), 1.52-1.43 (complex m, 8H), 1.34-1.25 (complex m, 87H), 0.97-0.86 (complex m, 21H).
HRMS (FAB, NBA matrix+NaI) m/z: 1473.2222 [(M+H)$^+$, calcd for C$_{91}$H$_{162}$N$_3$O$_{11}$: 1473.2209]

N-Fmoc-N-MeLeu-D-Lac-N-MeLeu-D-morphPhLac-N-MeLeu-D-Lac-N-MeLeu-D-morphPhLac-O-TAGa (19)

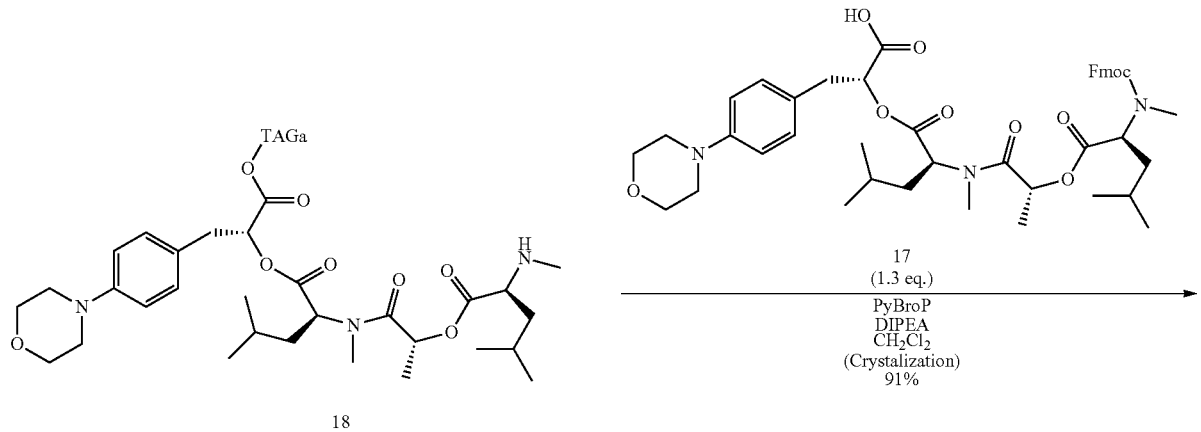

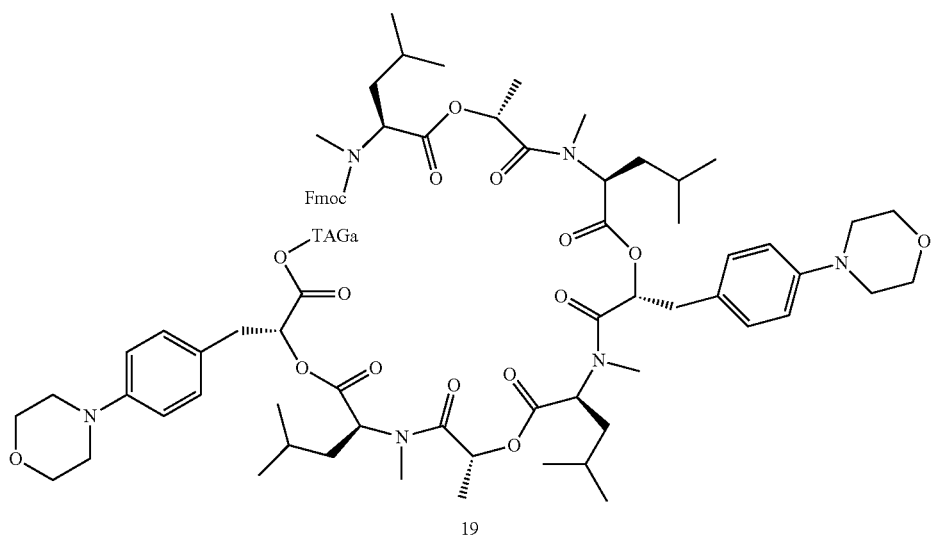

To a stirred solution of 18 (251 mg, 0.171 mmol) in CH$_2$Cl$_2$ (3.4 mL) was added 17 (178 mg, 0.222 mmol), N,N-diisopropylethylamine (87 μL, 0.513 mmol), and PyBroP (120 mg, 0.257 mmol) at room temperature. After stirring at 46 h, the reaction mixture was crystallized by the procedure described in synthesis of N-Fmoc-N-MeLeu-D-Lac-O-TAGa to afford 19 (350 mg, 91%) as a colorless powder.

mp: 50-52° C.

[α]$_D^{25}$=−25.5 (c 1.0, CHCl$_3$)

$^1$H-NMR (500 MHz, CDCl$_3$) δ: 7.75 (m, 2H), 7.62 (m, 2H), 7.38 (m, 2H), 7.30 (m, 2H), 7.06 (m, 4H), 6.77 (m, 4H), 6.49 (2 s, rotamer, 2H), 5.42-4.98 (complex m, 10H), 4.73-4.20 (complex m, 3H), 3.94 (m, 6H), 3.84 (m, 8H), 3.17-2.66 (complex m, 24H), 1.80-1.64 (complex m, 14H), 1.46-1.25 (complex m, 100H), 1.00-0.77 (complex m, 33H).

HRMS (FAB, NBA matrix) m/z: 2276.5940 [(M+Na)$^+$, calcd for C$_{136}$H$_{216}$N$_6$O$_{20}$Na: 2276.5967]

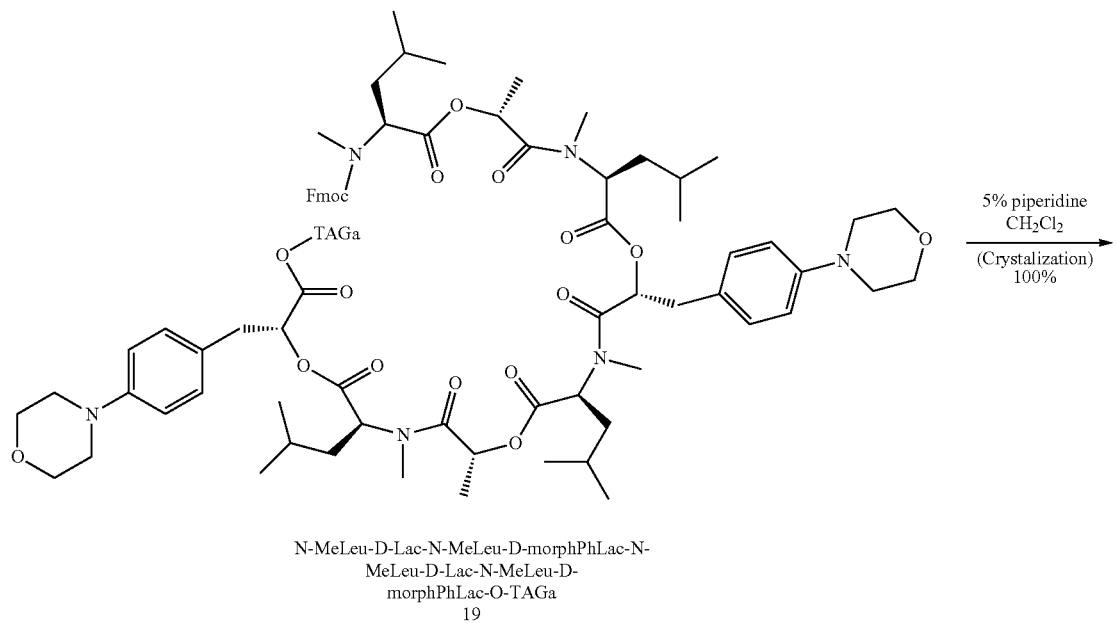

N-MeLeu-D-Lac-N-MeLeu-D-morphPhLac-N-
MeLeu-D-Lac-N-MeLeu-D-
morphPhLac-O-TAGa
19

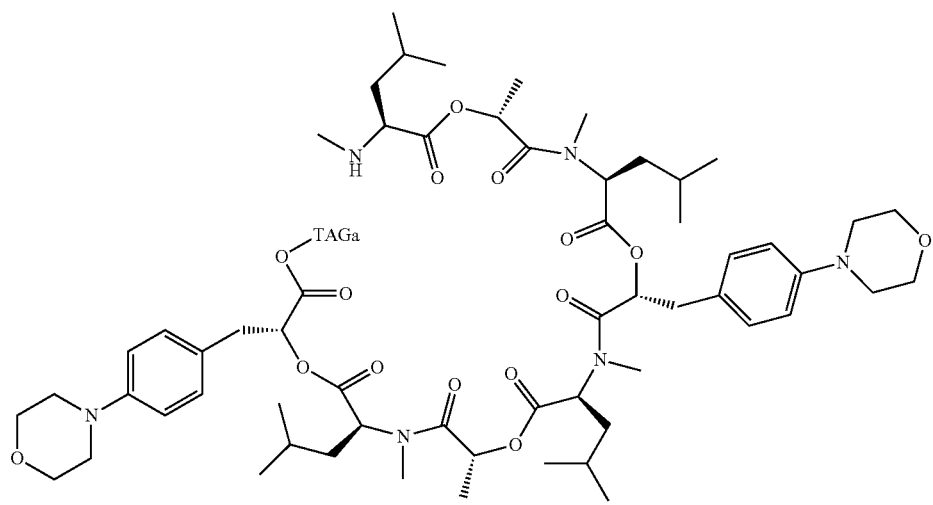

Following the procedure described for general procedure of Fmoc deprotection, 19 (114 mg, 0.0505 mmol) was converted to the corresponding amine (103 mg, 100%) as a colorless powder.

mp: 45-47° C.

$[\alpha]_D^{25}$=−19.6 (c 1.0, CHCl$_3$)

$^1$H-NMR (500 MHz, CDCl$_3$) δ: 7.76 (m, 4H), 6.79 (m, 4H), 6.48 (s, 2H), 5.50-4.96 (complex m, 9H), 3.94 (m, 6H), 3.83 (m, 8H), 3.30 (m, 1H), 3.16-2.74 (complex m, 21H), 2.38 (m, 3H), 1.80-1.55 (complex m, 9H), 1.47-1.24 (complex m, 105H), 1.00-0.81 (complex m, 33H).

HRMS (FAB, NBA matrix) m/z: 2032.5468 [(M+H)$^+$, calcd for C$_{12}$H$_{207}$N$_6$O$_{18}$: 2032.5467]

N-MeLeu-D-Lac-N-MeLeu-D-morphPhLac-N-MeLeu-D-Lac-N-MeLeu-D-morphPhLac-OH

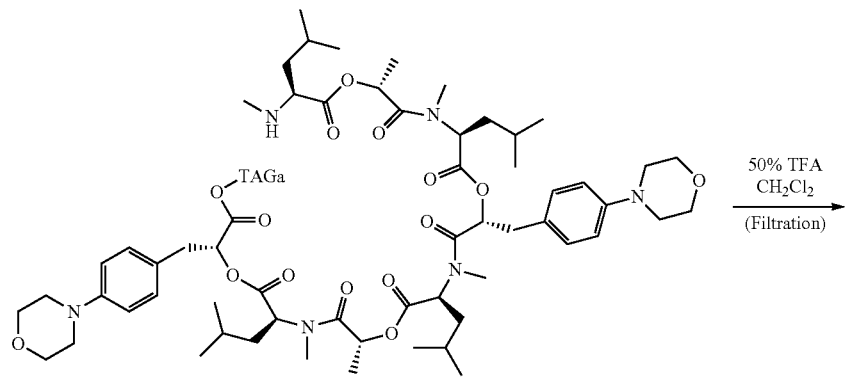

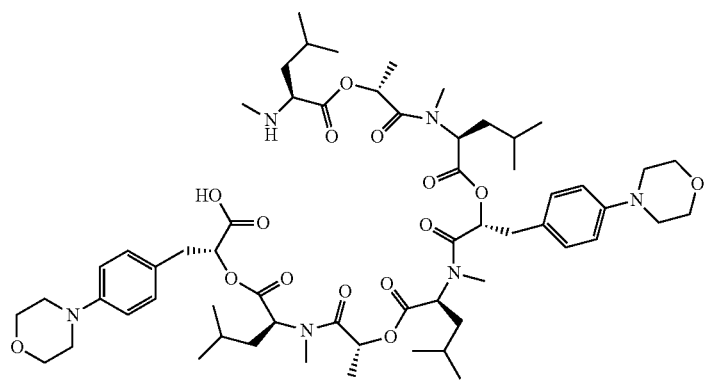

Following the procedure described for general procedure of TAGa cleavage, N-MeLeu-D-Lac-N-MeLeu-D-morphPhLac-N-MeLeu-D-Lac-N-MeLeu-D-morph-PhLac-O-TAGa (102 mg, 0.0502 mmol) was converted to the corresponding carboxylic acid. In the case of this substrate, the reaction required longer time than that of the general condition of TAGa cleavage (ca. 1 h). The reaction in 50% TFA/CH$_2$Cl$_2$ at room temperature was needed to stir for 5 h to consume all of starting material, and gave desired product (~0.0502 mmol) as a crude oil, which was used next reaction without further purification.

Emodepside

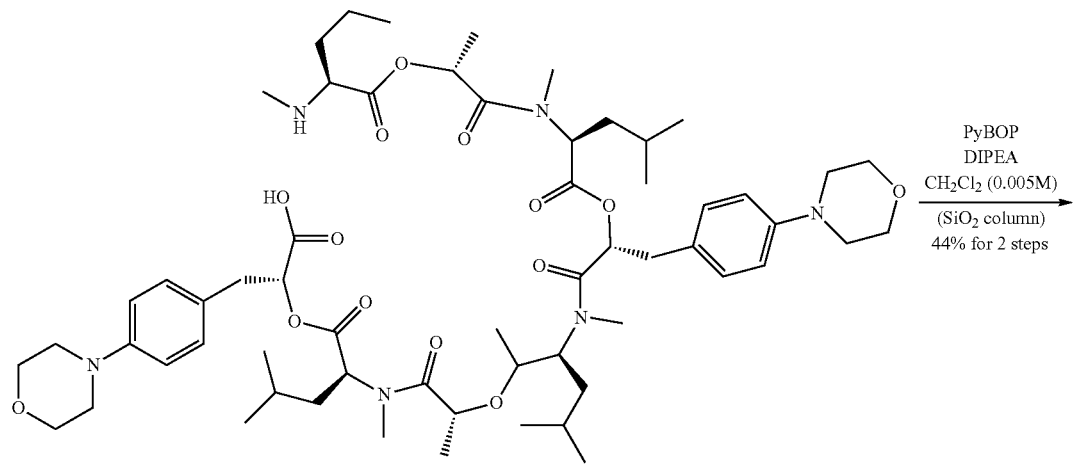

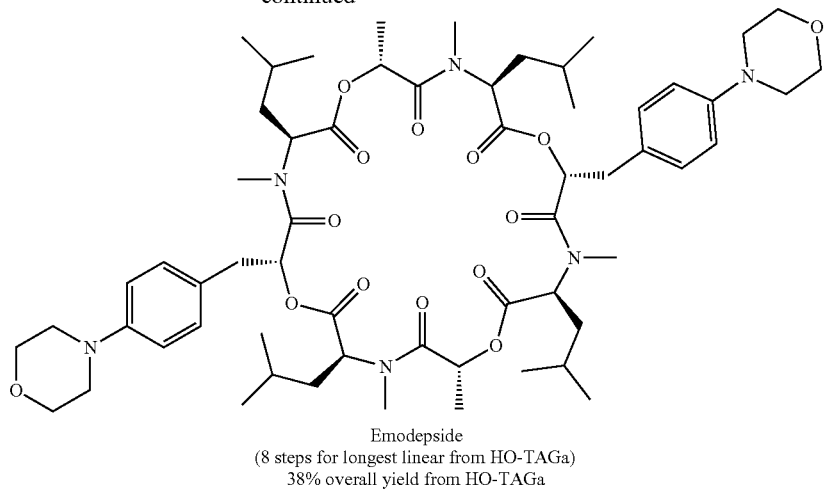

Emodepside
(8 steps for longest linear from HO-TAGa)
38% overall yield from HO-TAGa To a crude of carboxylic acid (0.0502 mmol) in $CH_2Cl_2$ (10 ml, 0.005 M) was added N,N-diisopropylethylamine (60 µL, 0.351 mmol) and PyBOP (52 mg, 0.175 mmol) at room temperature. After stirring for 44 h, the reaction mixture was quenched with saturated aqueous $NaHCO_3$ (10 mL) at 0° C. and this mixture was extracted with $CHCl_3$ (20 ml×3). The combined organic layers were washed with 10% aqueous $NaHSO_4$ (60 ml) and brine (60 ml), dried over $Na_2SO_4$, filtered and concentrated in vacuo. The crude was purified by column chromatography on silica gel ($CHCl_3$: MeOH=400:1 to 100:1) to provide Emodepside (25 mg, 44% for 2 steps) as alight brown solid.

All physical data for synthetic Emodepside matched with the data of authentic compound.

Comparative Example 1

A tag analogous to TAGa, but with $C_{12}$ instead of $C_{18}$ alkyl chains (C12-TAG), was prepared and coupled with N-Fmoc-N-MeLeu-D-Lac-OH (unit 1) according to the following reaction scheme:

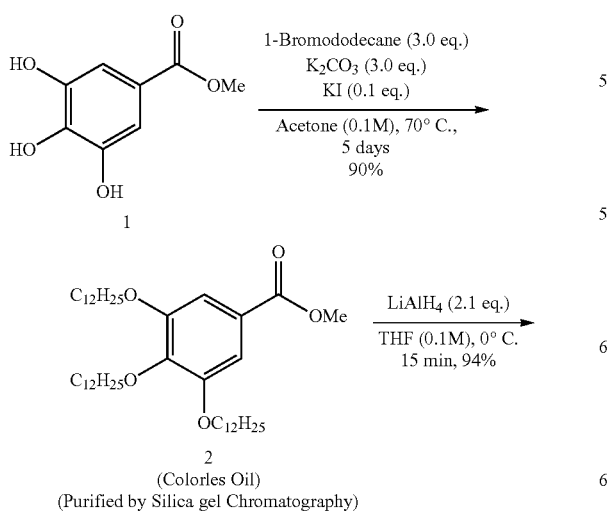

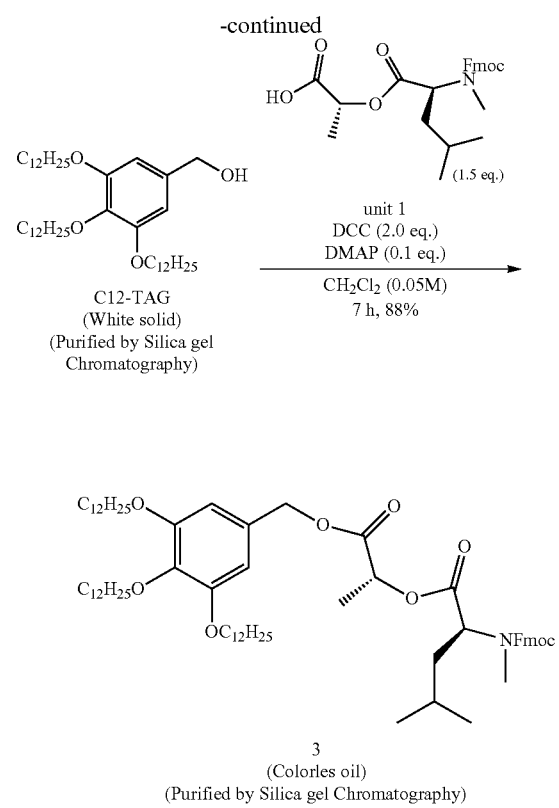

Purification via silica gel chromatography was necessary after each reaction step. The compounds 2, C12-TAG and 3 did not crystallize in methanol. This is in contrast to, for example, the synthetic procedure for N-Fmoc-N-MeLeu-D-Lac-O-TAGa (section 2.1 above). The C12-TAG in this comparative example was not suitable for the intended tag-assisted synthesis and the further functionalization of compound 3 was not investigated further.

Comparative Example 2

The commercially available C1-TAG was coupled with N-Fmoc-N-MeLeu-D-Lac-OH (unit 1) according to the following reaction scheme:

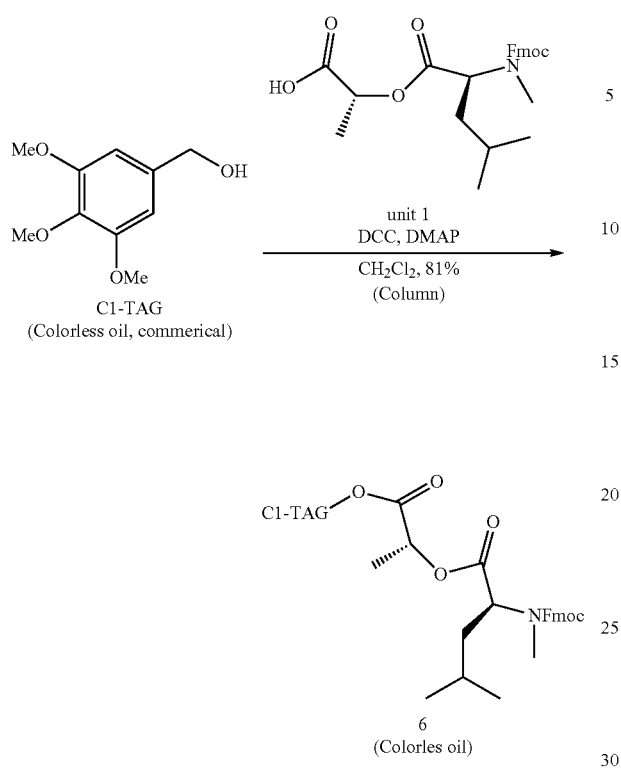

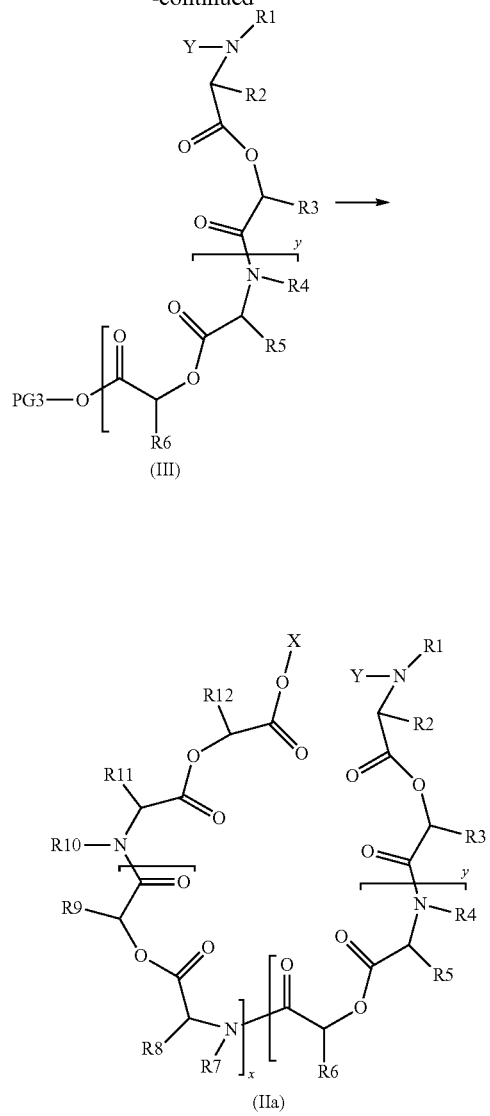

Purification via column chromatography was necessary after the reaction step. The compounds C1-TAG and 6 did not crystallize in methanol. The C1-TAG in this comparative example was not suitable for the intended tag-assisted synthesis and the further functionalization of compound 6 was not investigated further.

The invention claimed is:

1. A method of synthesizing a depsipeptide of formula (IIa) from formula (IV) and formula (III):

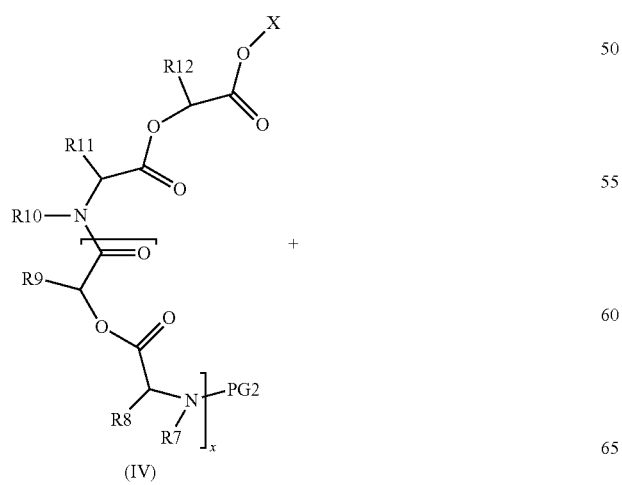

wherein PG2 is an amine protecting group and PG3 is a carboxylic acid protecting group, and by:

deprotecting the amine group that is protected by PG2 in the formula (IV) in the presence of a base to obtain a deprotected amine group;

deprotecting the carboxylic acid that is protected by the group PG3 in the formula (III) in the presence of an acid to obtain a deprotected carboxylic acid group; and condensing the deprotected amine group and the carboxylic acid group to obtain the depsipeptide of formula (IIa);

and further synthesizing a cyclic depsipeptide of formula (I) from the depsipeptide of formula (IIa):

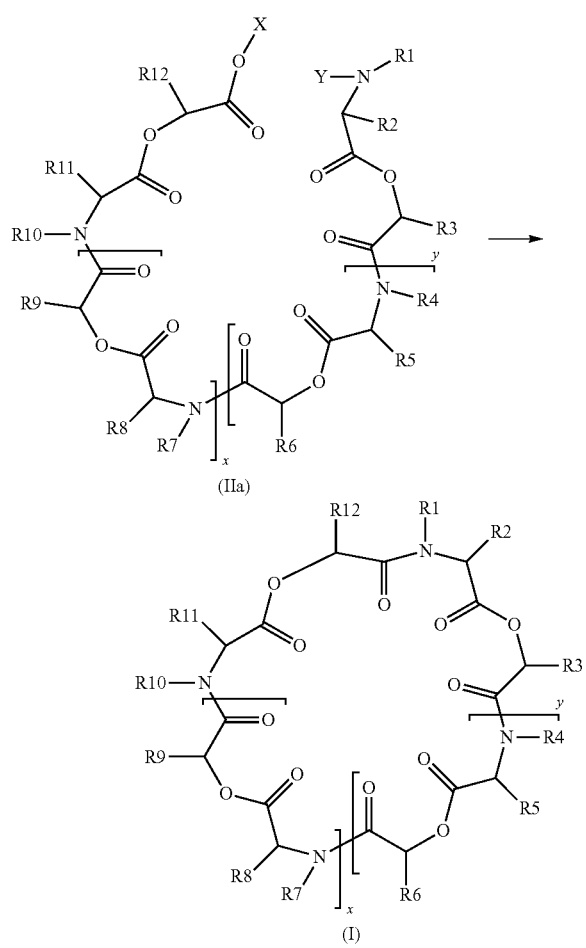

(IIa)

(I)

wherein Y is an amine protecting group and X is a carboxylic acid protecting group;

wherein

R2 and R8, are independently hydrogen, straight-chain or branched C1-C8-alkyl, straight-chain or branched halogenated C1-C8 alkyl, hydroxy-C1-C6-alkyl, C1-C4-alkanoyloxy-C1-C6-alkyl, C1-C4-alkoxy-C1-C6-alkyl, aryl-C1-C4-alkyloxy-C1-C6-alkyl, mercapto-C1-C6-alkyl, C1-C4-alkylthio-C1-C6-alkyl, C1-C4-alkylsulphinyl-C1-C6-alkyl, C1-C4-alkylsulphonyl-C1-C6-alkyl, carboxy-C1-C6-alkyl, C1-C4-alkoxycarbonyl-C1-C6-alkyl, C1-C4-arylalkoxycarbonyl-C1-C6-alkyl, carbamoyl-C1-C6-alkyl, amino-C1-C6-alkyl, C1-C4-alkylamino-C1-C6-alkyl, C1-C4-dialkylamino-C1-C6-alkyl, guanidino-C1-C6-alkyl, C1-C4-alkoxycarbonylamino-C1-C6-alkyl, 9-fluorenylmethoxycarbonyl(Fmoc)amino-C1-C6-alkyl, C2-C8-alkenyl, C3-C7-cycloalkyl, C3-C7-cycloalkyl-C1-C4-alkyl, benzyl, substituted benzyl, phenyl, or phenyl-C1-C4-alkyl which may optionally be substituted by halogen;

wherein x is 1, y is 1, R1, R4, R7 and R10 are each methyl, R6 and R12 are each methyl, R5 and R11 are each independently a straight-chain or branched C1-C4-alkyl or a straight-chain or branched halogenated C1-C4-alkyl, and R3 and R9 are each independently benzyl or substituted benzyl;

wherein synthesizing a cyclic depsipeptide of formula (I) from the depsipeptide of formula (IIa) comprises:

deprotecting the amine group that is protected by Y in the presence of an acid to obtain a deprotected amine group;

deprotecting the carboxylic acid that is protected by X via hydrogenolysis to obtain a deprotected carboxylic acid group; and condensing the deprotected amine group and the deprotected carboxylic acid group by a coupling agent to obtain the cyclic depsipeptide of formula (I), wherein the coupling agent is BOP ((Benzotriazol-1-yloxy)tris(dimethylamino)phosphonium hexafluorophosphate), EDCI (1-Ethyl-3-(3-dimethylaminopropyl)carbodiimide), DEPBT (3-(diethoxyphosphoryloxy)-1,2,3-benzotriazin-4(3H)-one), HATU (1-[Bis(dimethylamino)methylene]-1H-1,2,3-triazolo[4,5-b]pyridinium 3-oxid hexafluorophosphate), HBTU (2-(1H-benzotriazol-1-yl)-1, 1,3,3-tetramethyluronium hexafluorophosphate) or Propylphosphonic anhydride (2,4,6-Tripropyl-1,3,5, 2,4,6-trioxatriphosphorinane-2,4,6-trioxide, PPACA).

2. The method of claim 1, wherein one or both of R3 and R9 is p-morpholino substituted benzyl.

3. The method of claim 1, wherein X is a substituted or unsubstituted —CH$_2$-Aryl group.

4. The method of claim 1, wherein X is selected from the group consisting of benzoyl (Bn), 4-methoxy-benzoyl (PMB), 3,4-dimethoxybenzoyl (DPMB), 4-phenyl-benzoyl (PPB), 2-naphthylmethyl (Nap), and Benzyloxymethyl acetal (BOM).

5. The method of claim 1, wherein Y is t-Butyloxycarbonyl (BOC).

6. The method of claim 1, wherein the method further comprises obtaining the formula (IV) from formula (VI) and formula (V):

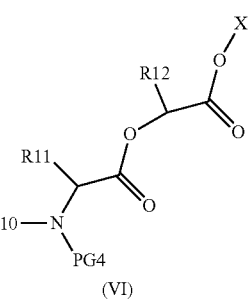

(VI)

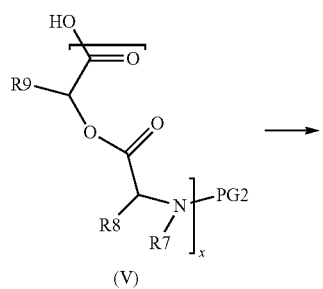

(V)

167

-continued

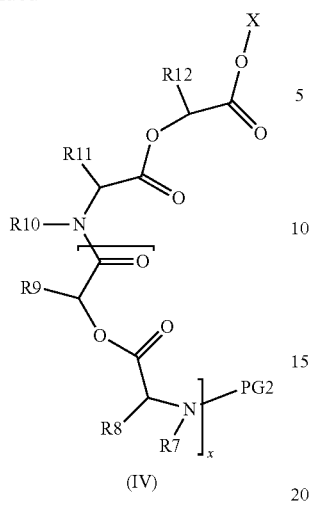
(IV)

wherein PG4 is an amine protecting group, by:

deprotecting the amine group that is protected by the group PG4 in the formula (VI) in the presence of a base to obtain a deprotected amine group; and condensing the deprotected amine group of the formula (VI) and the carboxylic acid group of the formula (V) to obtain the formula (IV).

7. The method of claim 1, wherein the method further comprises obtaining the formula (III) from formula (VIII) and formula (VII):

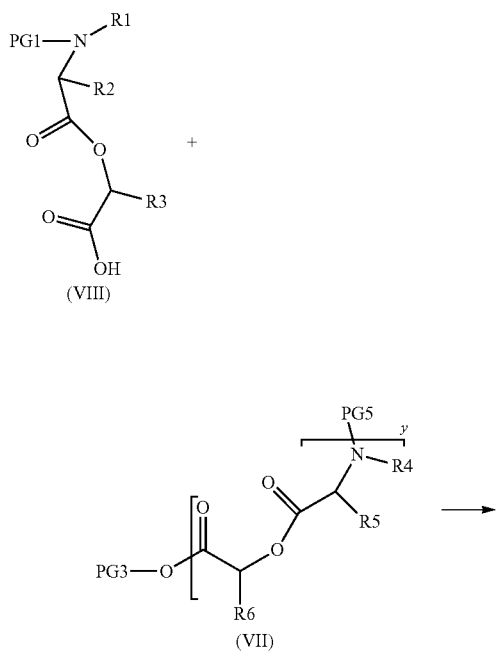
(VIII)

(VII)

168

-continued

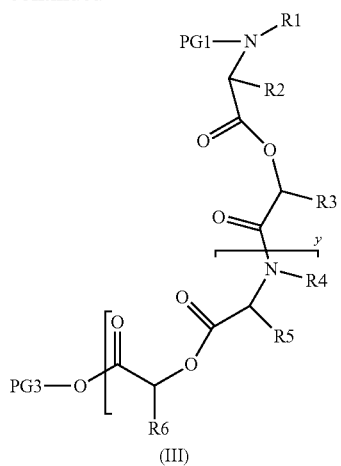
(III)

wherein PG1 is an amine protecting group and PG5 is an amine protecting group, by:

deprotecting the amine group that is protected by PG5 in the formula (VII) in the presence of a base to obtain a deprotected amine group; and condensing the deprotected amine group of the formula (VII) and the carboxylic acid group of the formula (VIII) to obtain the formula (III).

8. The method of claim 6, wherein the method further comprises obtaining the formula (VI) by esterifying a formula (IX) with X-LG:

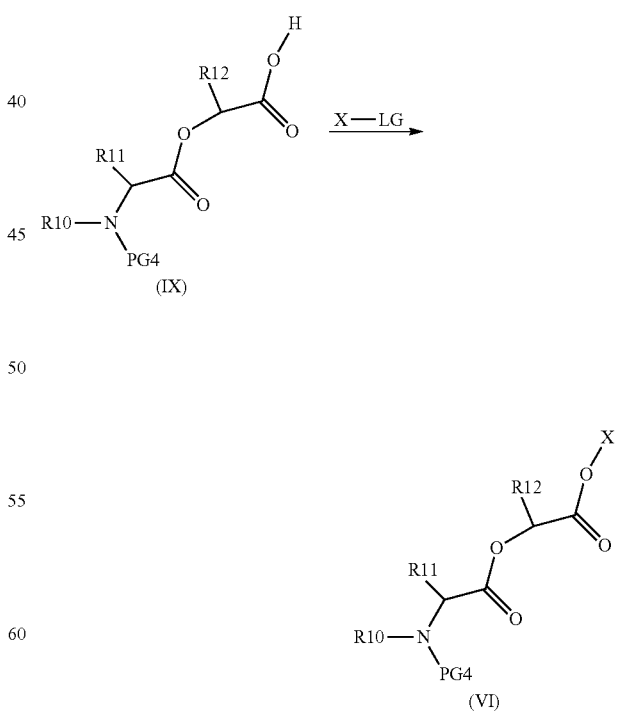
(IX)

(VI)

wherein LG is a leaving group.

9. The method of claim 7, wherein the method further comprises obtaining the formula (VII) by esterifying a formula (X) with PG3-OH:

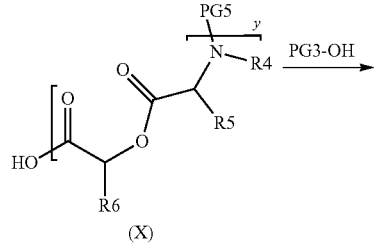

(X)

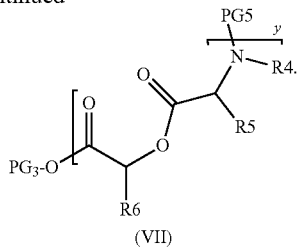

(VII)

10. The method of claim 9, wherein PG3 is X.
11. The method of claim 1, wherein the precursors of formulas (III) and (IV) are identical.
12. The method of claim 1, wherein R3 and R9 are identical, R2 and R8 are identical, and R5 and R11 are identical.
13. The method of claim 1, wherein the depsipeptide of formula (IIa) is selected from the group consisting of:

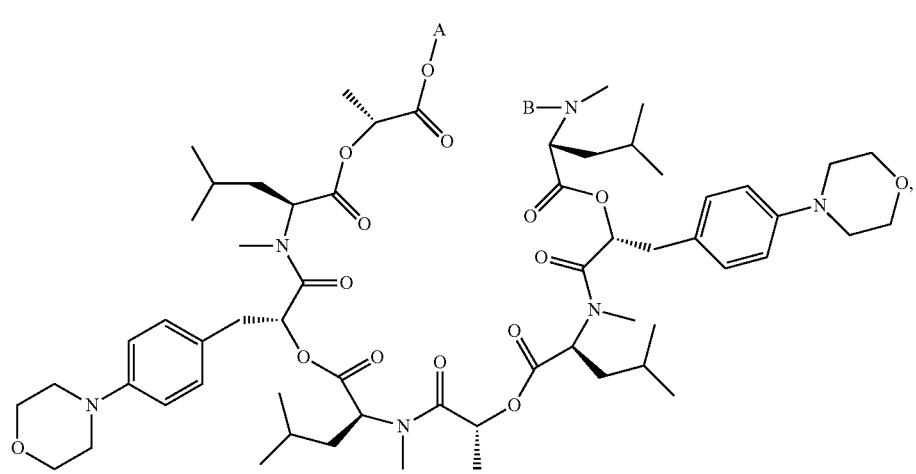

(II-1a)

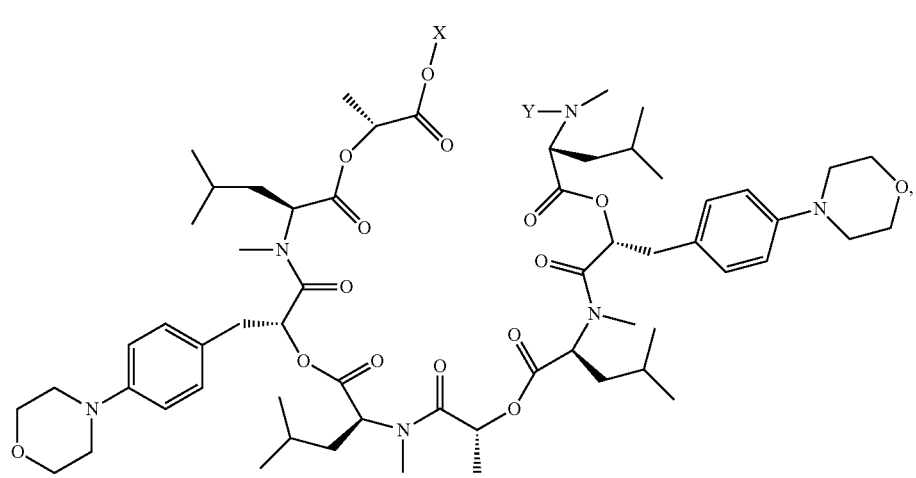

(II-1b)

-continued
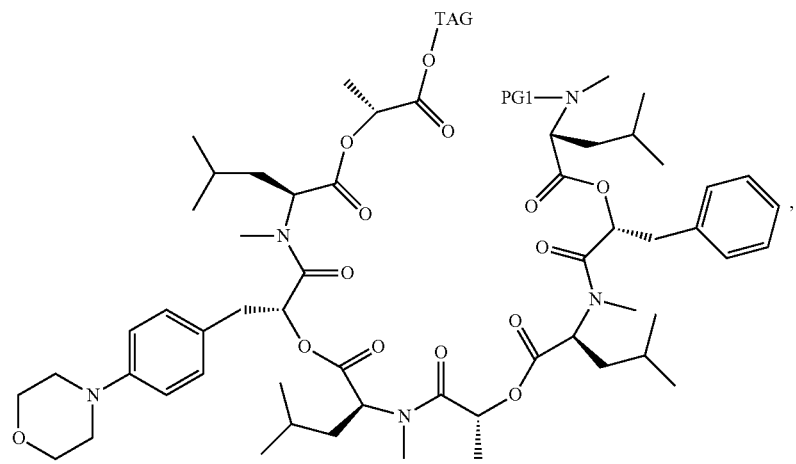
(II-2)
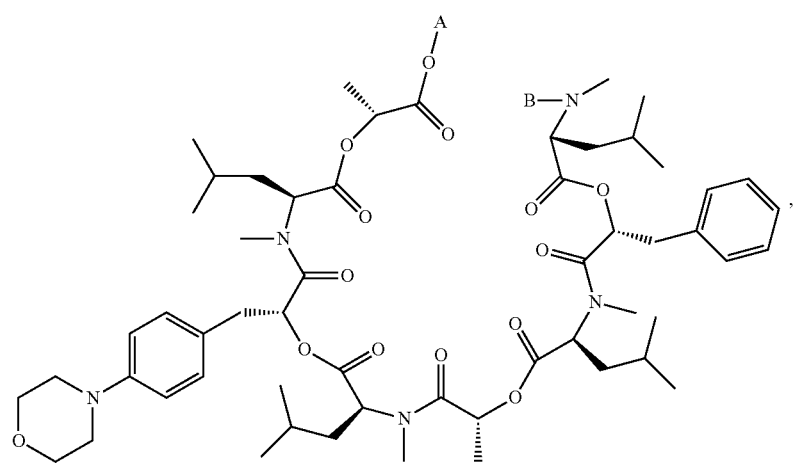
(II-2a)
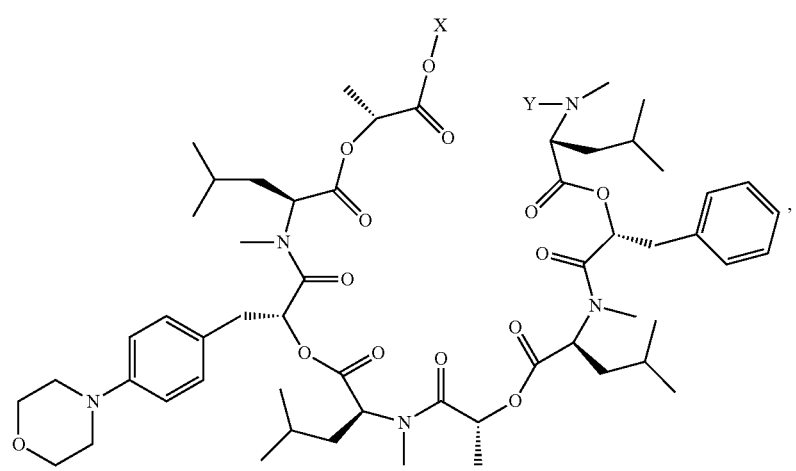
(II-2b)

-continued
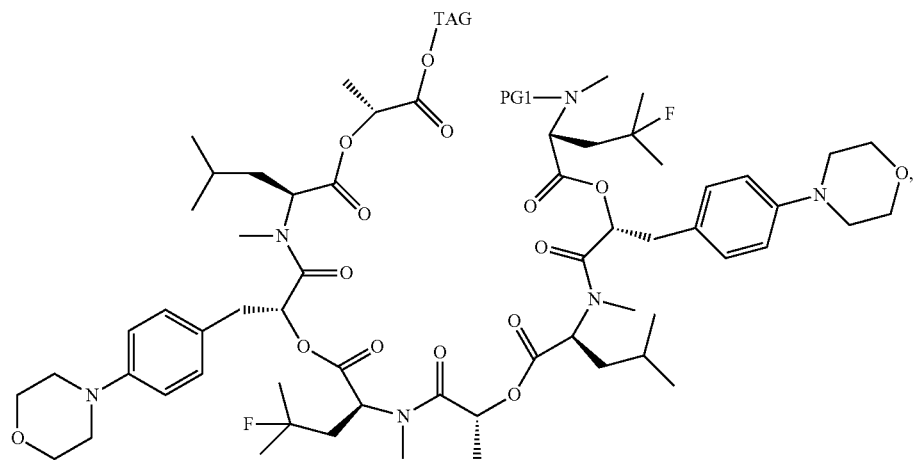
(II-3)
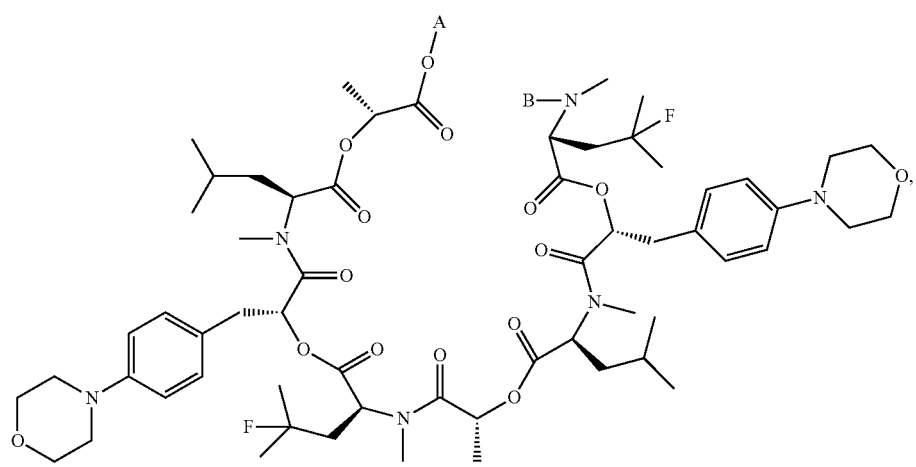
(II-3a)
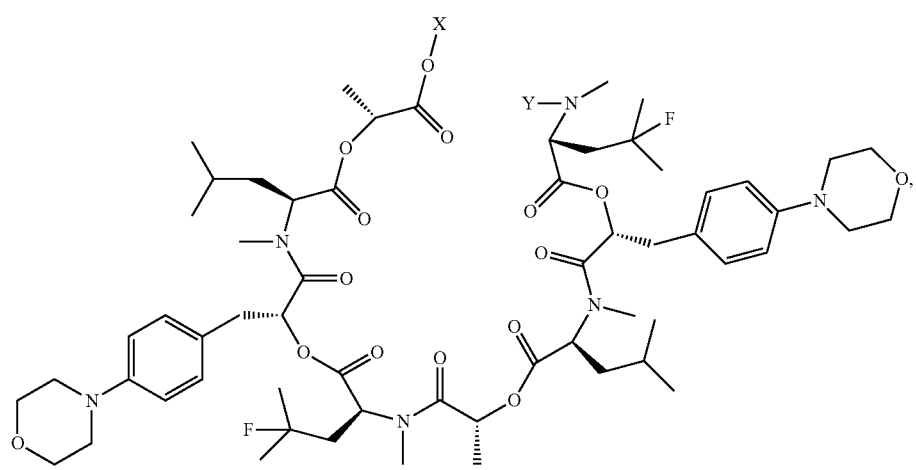
(II-3b)

(II-4)
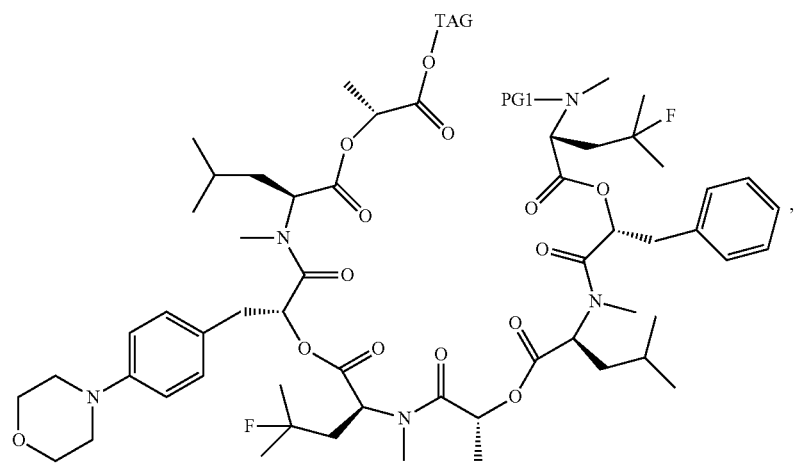
(II-4a)
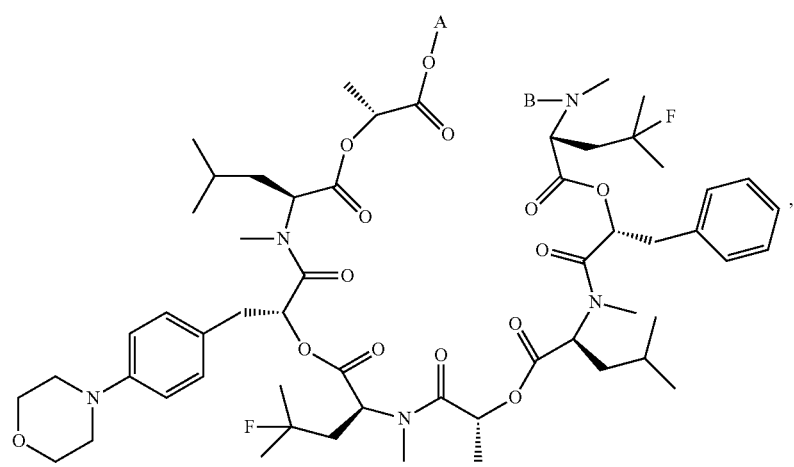
(II-4b)
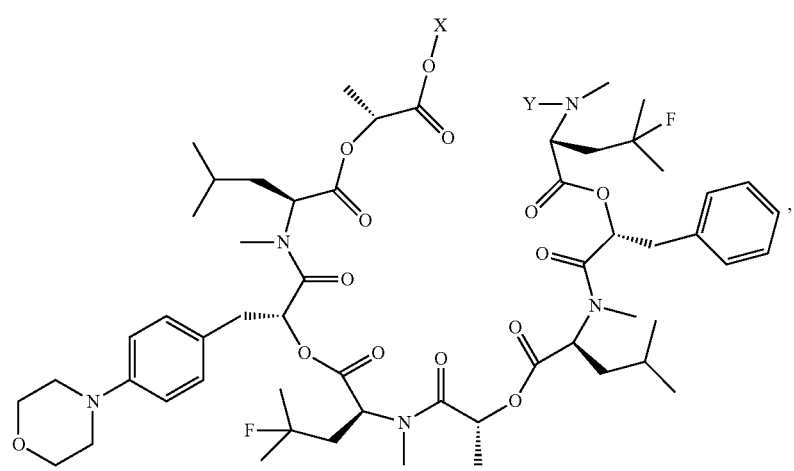

(II-5)
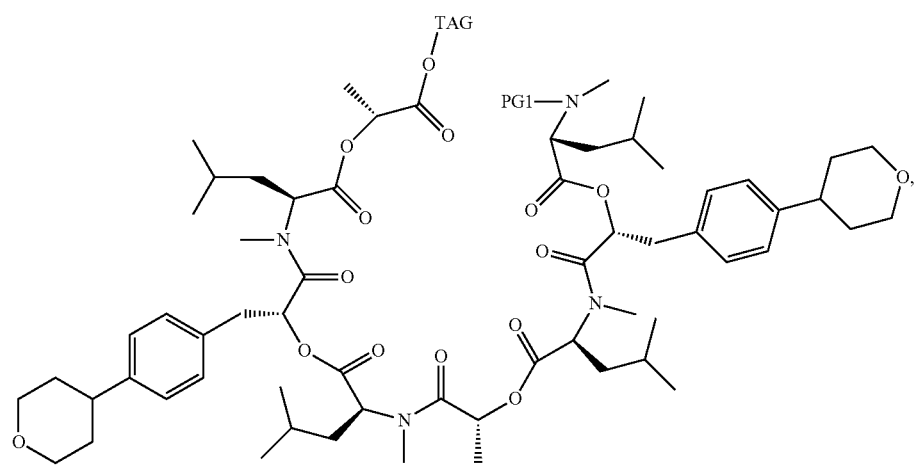
(II-5a)
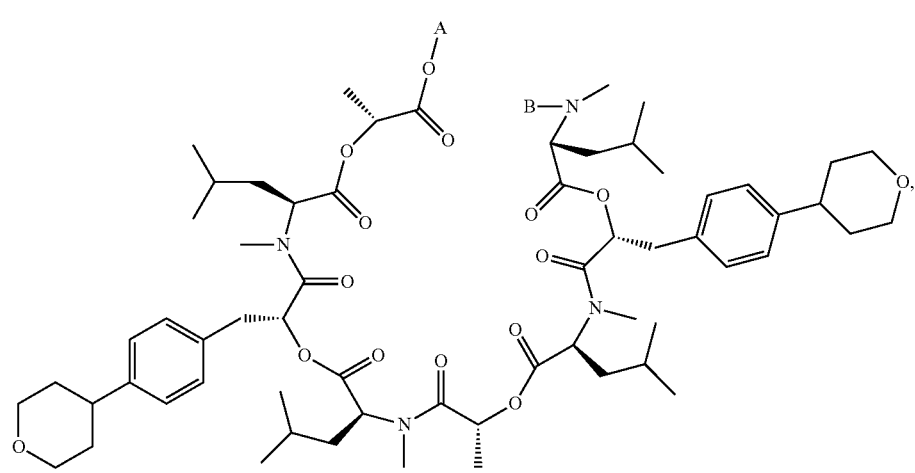
(II-5b)
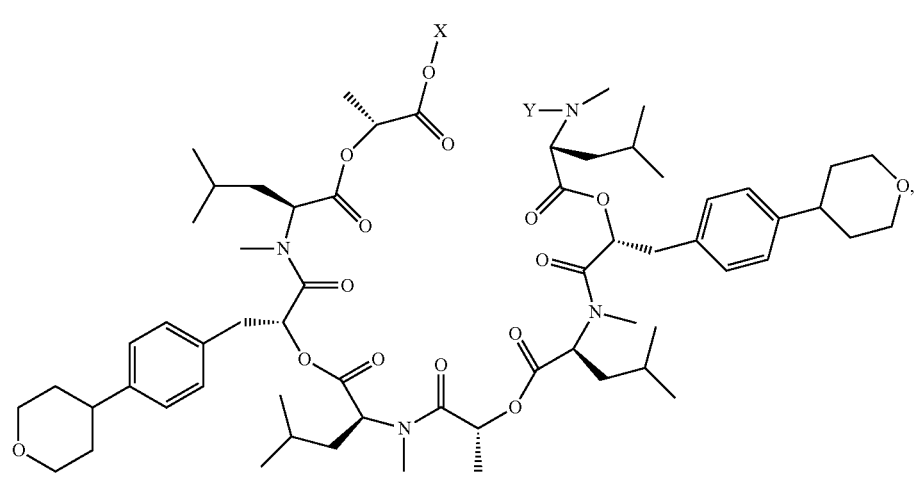

-continued
(II-6)
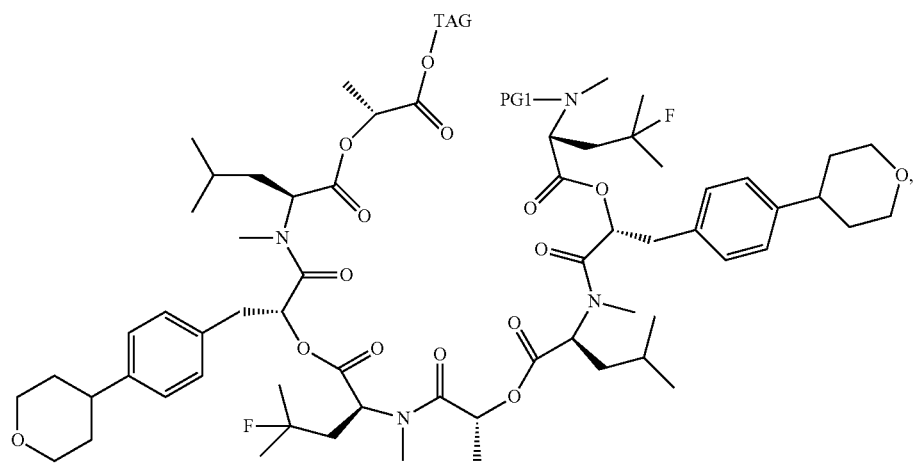
(II-6a)
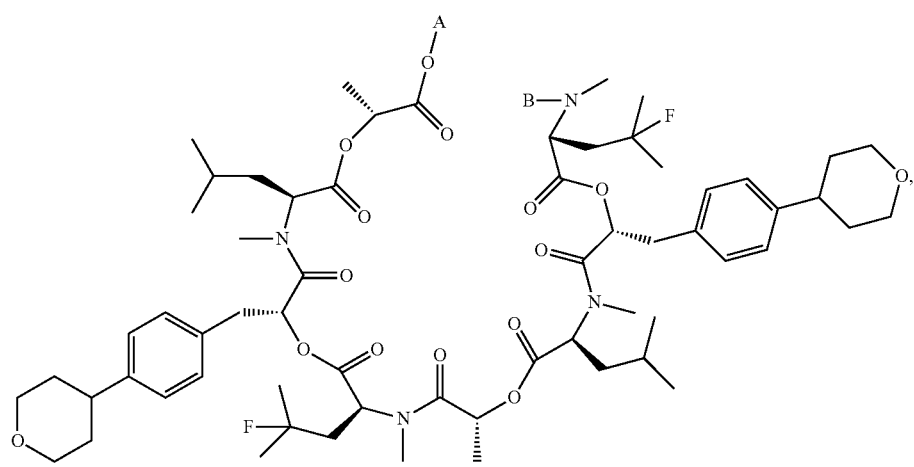
(II-6b)
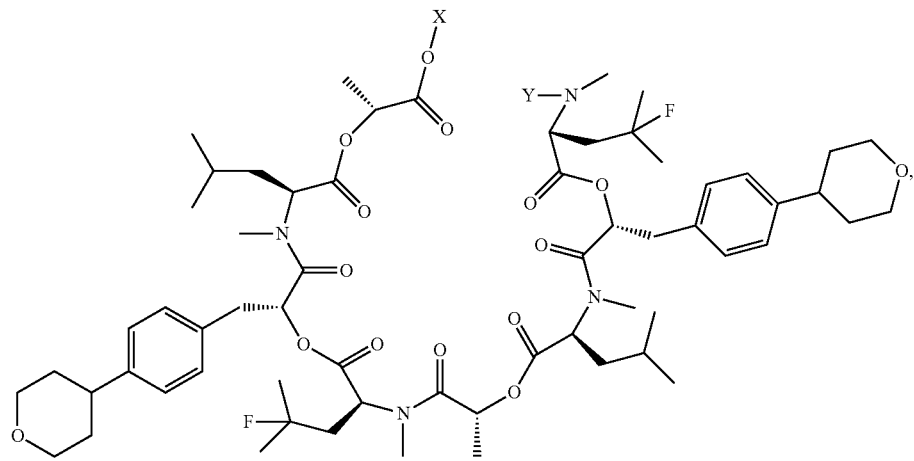

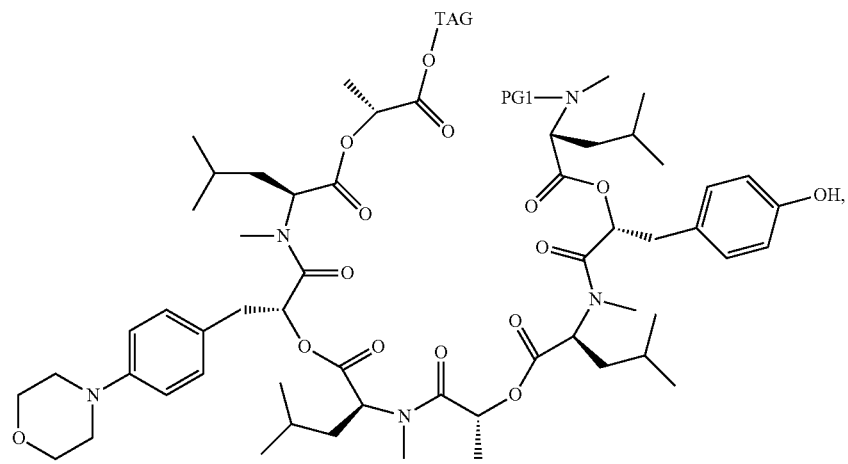
(II-7)
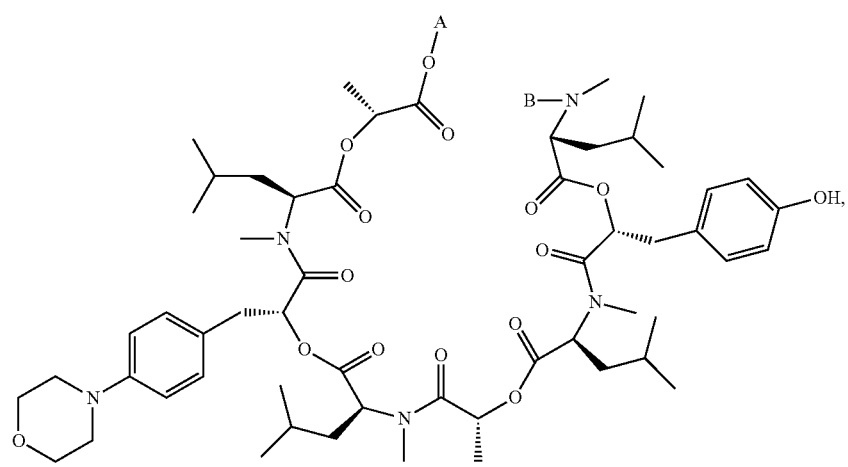
(II-7a)
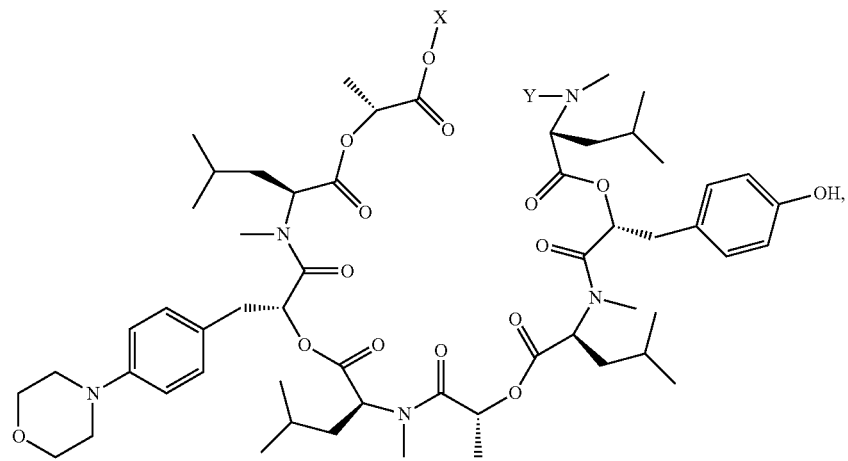
(II-7b)

(II-8)
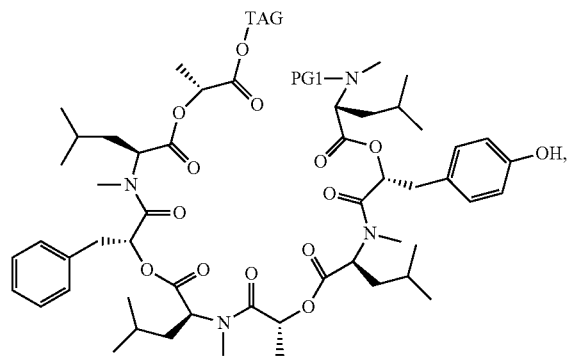
(II-8a)
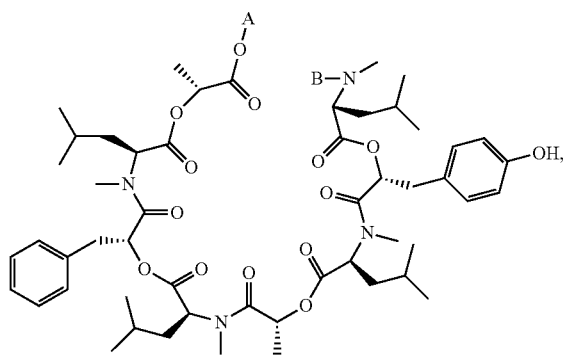
(II-8b)
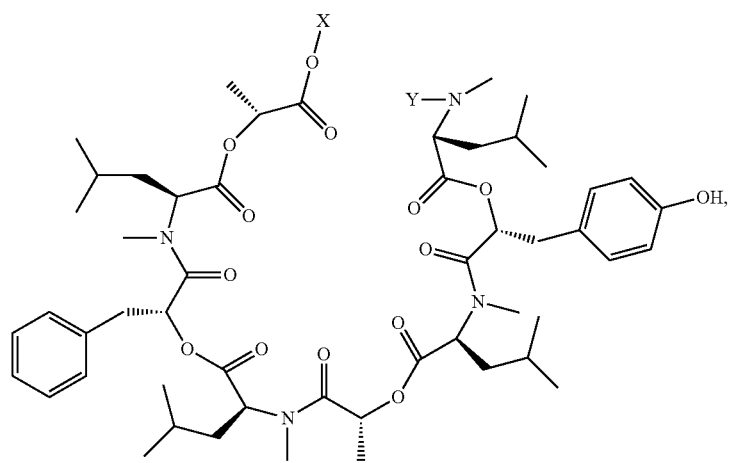
(II-9)
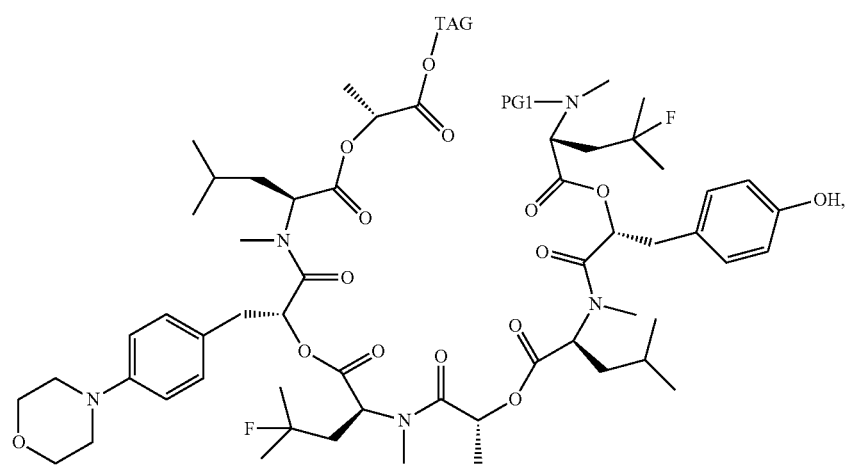

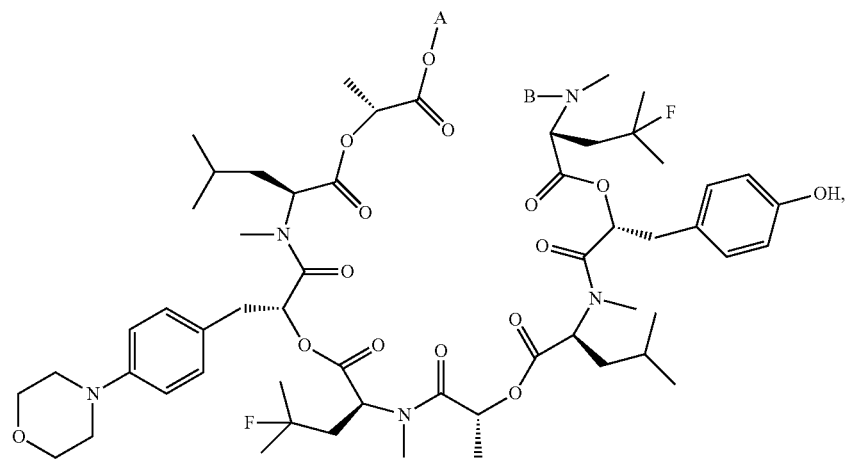
(II-9a)
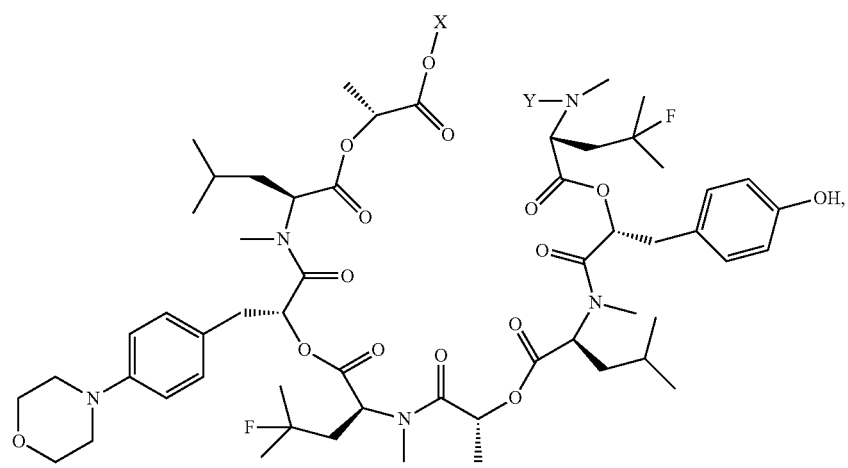
(II-9b)
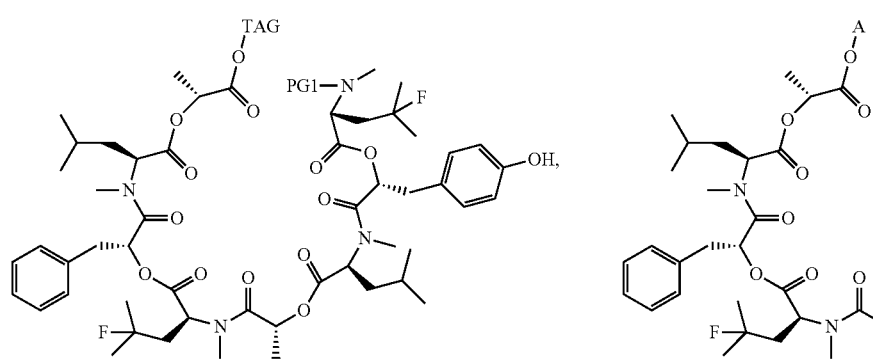
(II-10)
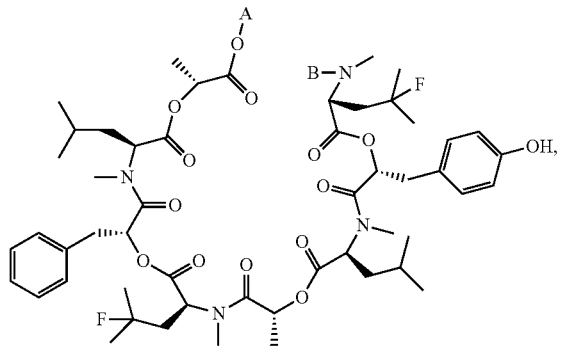
(II-10a)

-continued
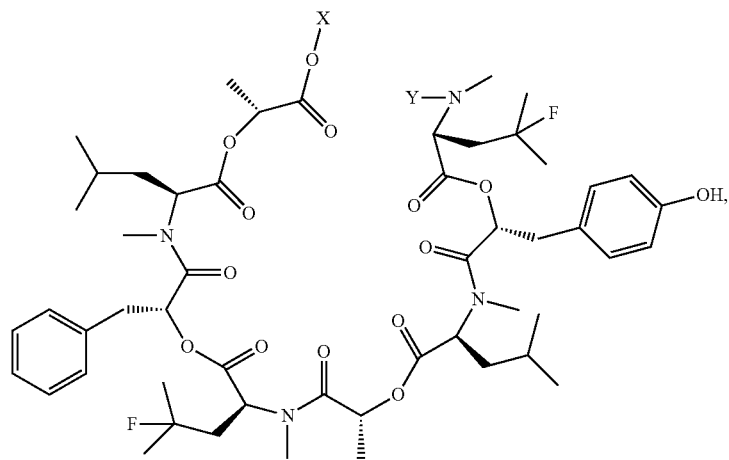
(II-10b)
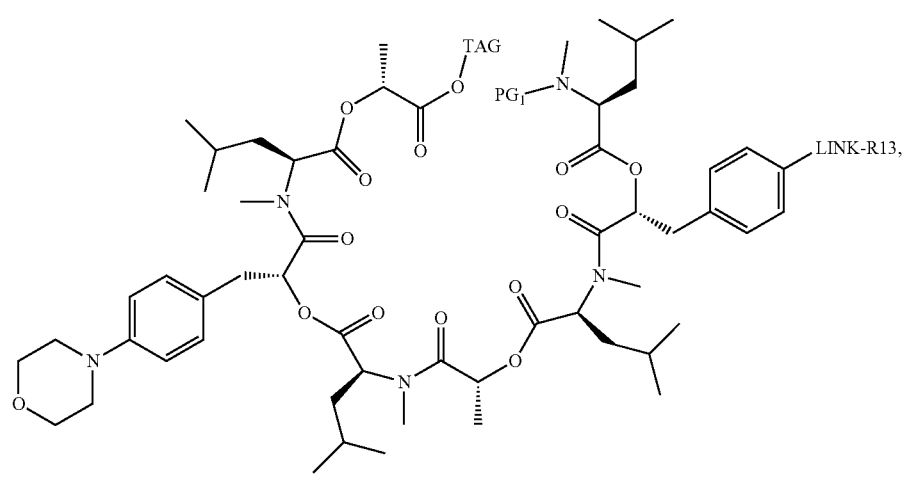
(II-11)
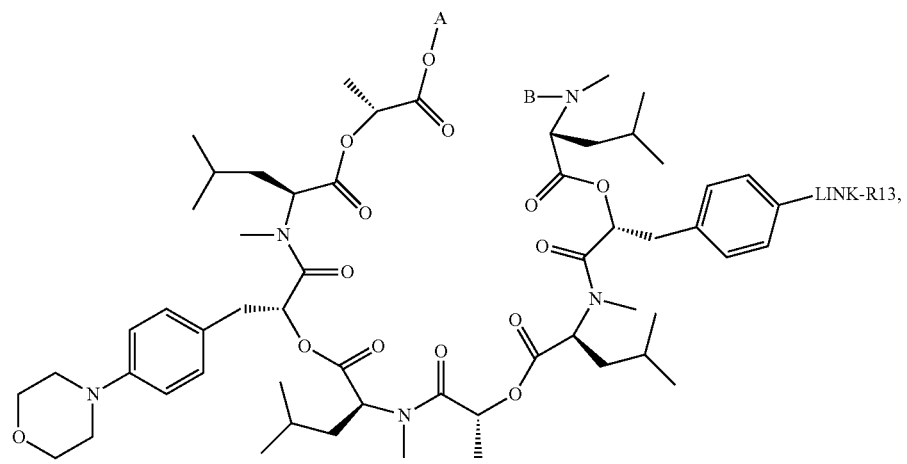
(II-11a)

-continued
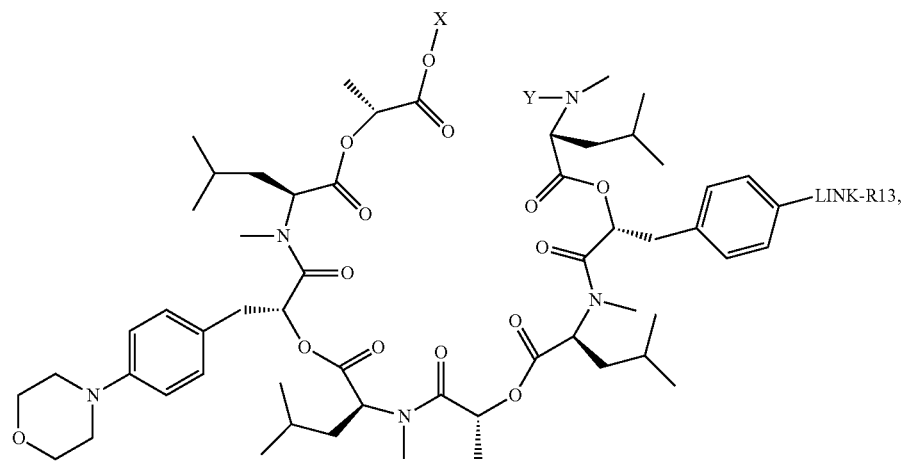
(II-11b)
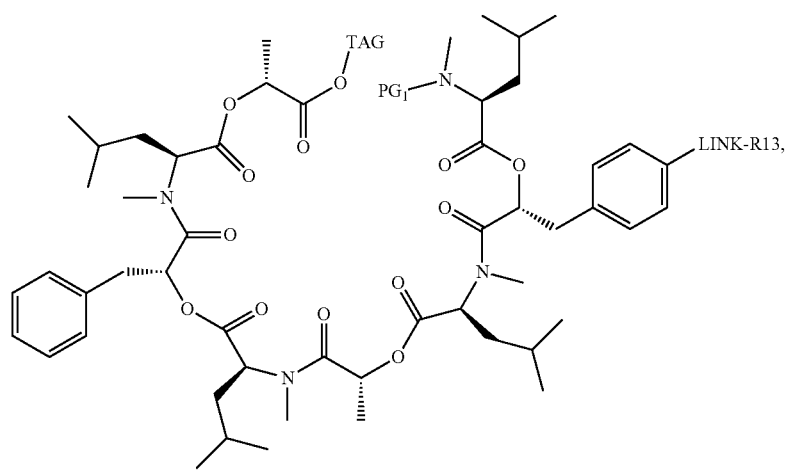
(II-12)
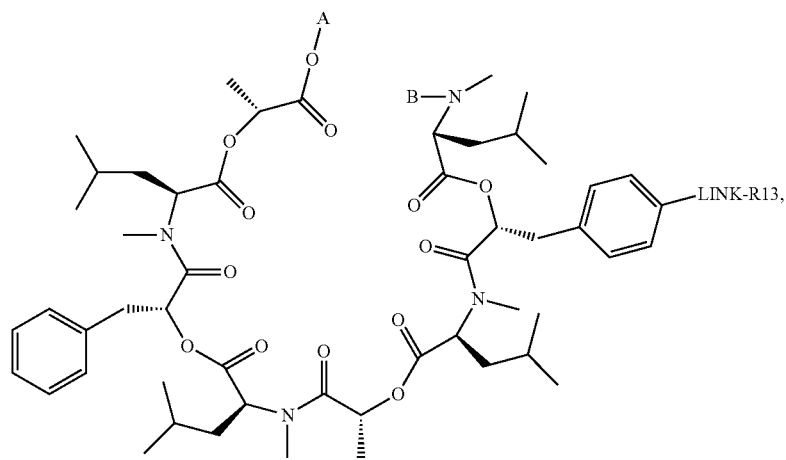
(II-12a)

(II-12b)
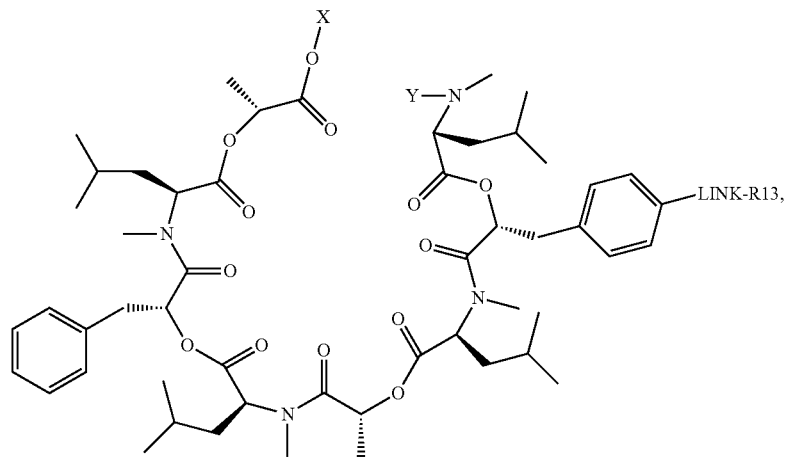
(II-13)
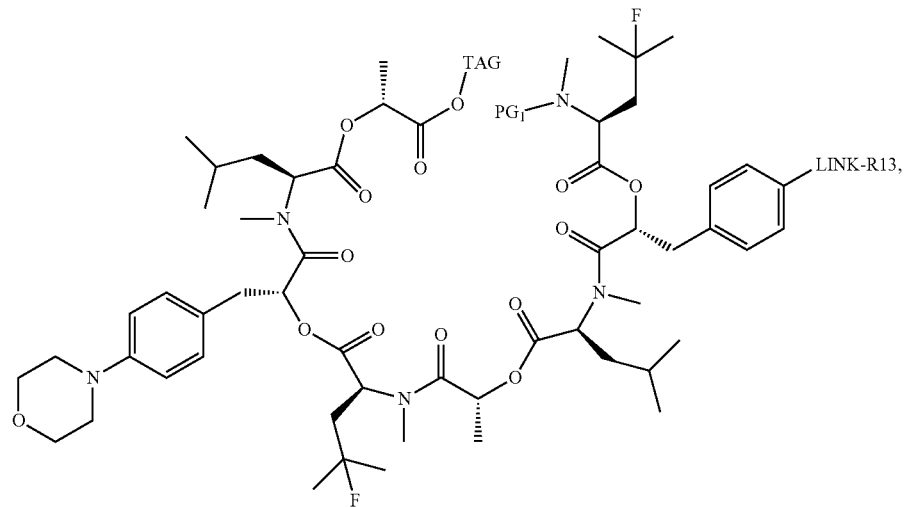
(II-13a)
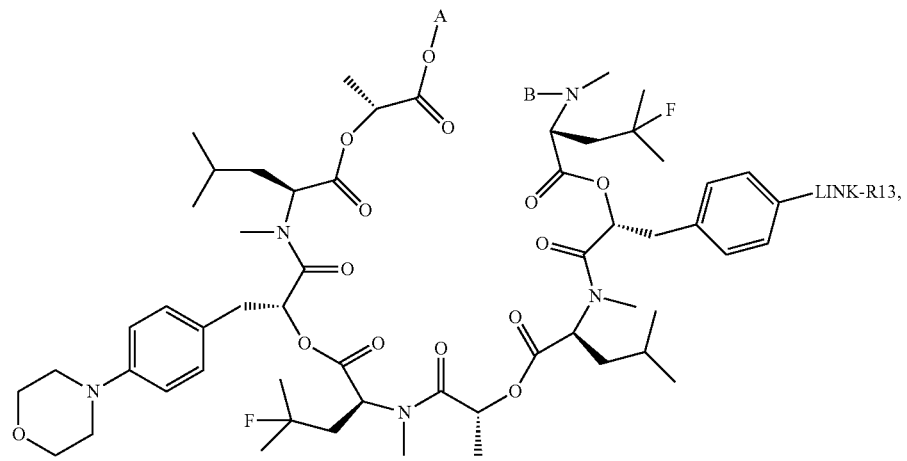

(II-13b)
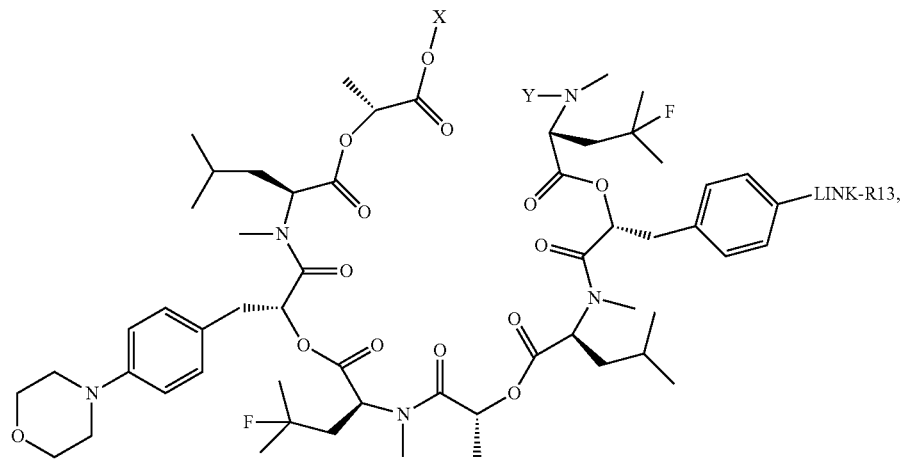
(II-14)
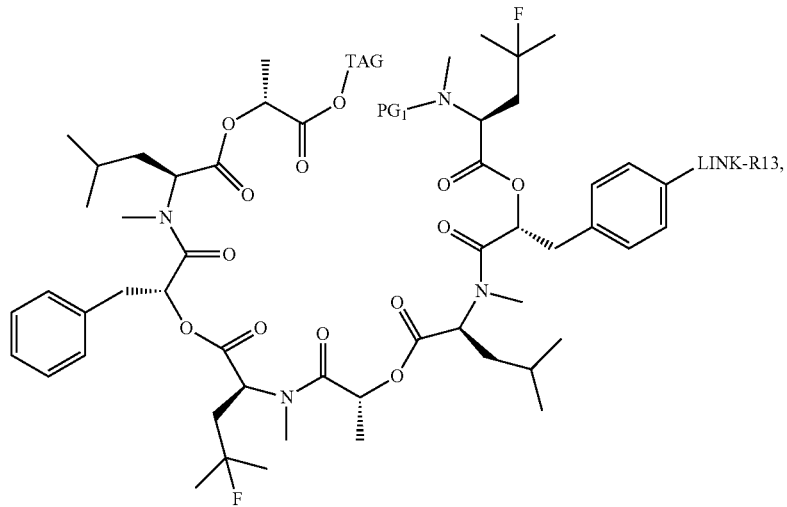
(II-14a)
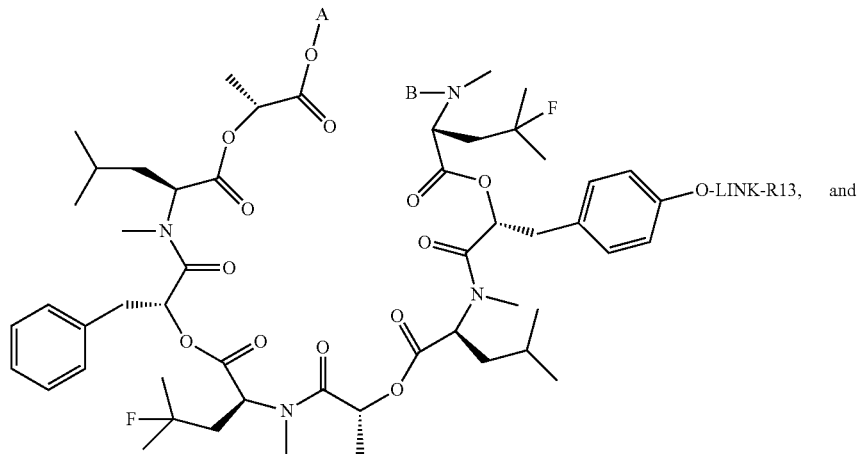
and (II-14b)

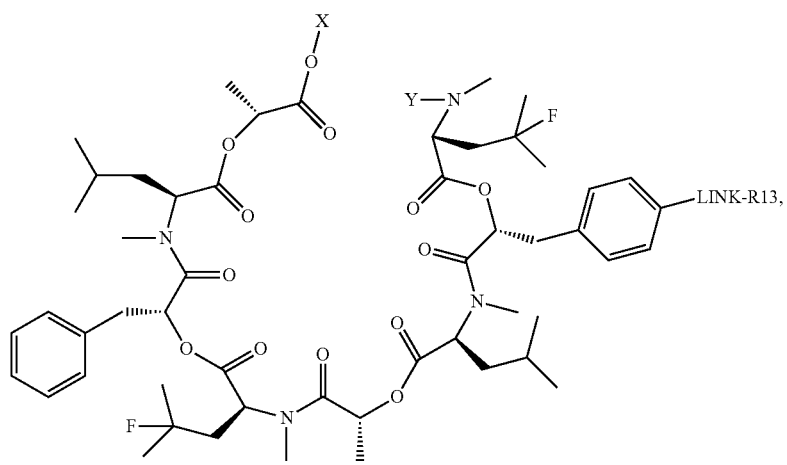

wherein in formulas (II-11a) to (II-14a), and (II-11b) to (II-14b) -LINK- is selected from the group consisting of:

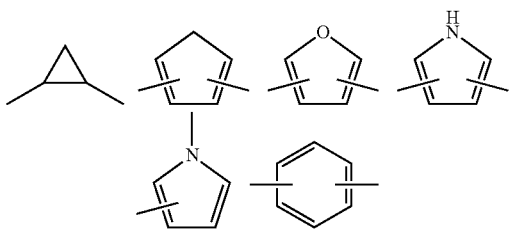

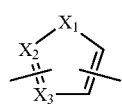

wherein X1 can be C, N, S, or O, X2 and X3 can be C or N;

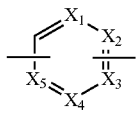

wherein X1 can be C, N, S, or O, X2, X3 and X4 can be C or N; and

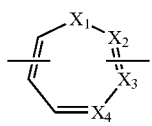

wherein X1, X2, X3 and X4 can be C or N;
and wherein R13 is selected from $SO_2NH(CH_3)$, $SO_2NH_2$, $OC(O)CH_3$, $CF_3$ or one the following lactone structures:

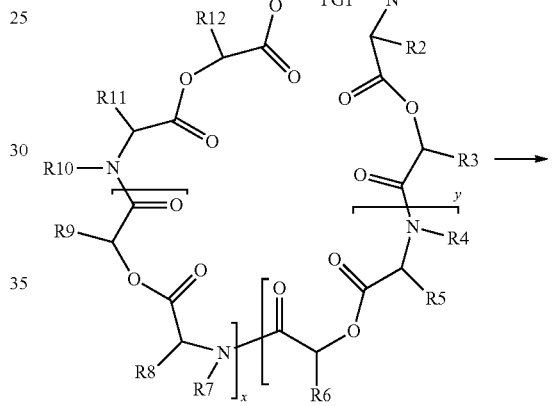

(IIb)

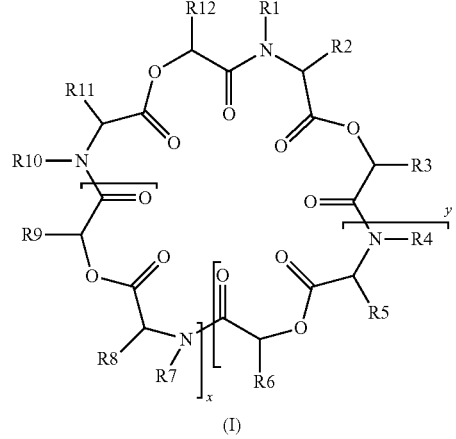

(I)

Y is an amine protecting group and X is a carboxylic acid protecting group;
B is an amine protecting group and A is a carboxylic acid protecting group;
PG1 is an amine protecting group and TAG is a carboxylic acid protecting group.

* * * * *